US011366114B2

(12) United States Patent
Hughes et al.

(10) Patent No.: US 11,366,114 B2
(45) Date of Patent: Jun. 21, 2022

(54) GENETICALLY ENCODED FLUORESCENT SENSORS FOR DETECTING LIGAND BIAS AND INTRACELLULAR SIGNALING THROUGH CAMP PATHWAYS

(71) Applicant: MONTANA MOLECULAR LLC, Bozeman, MT (US)

(72) Inventors: Thomas E. Hughes, Bozeman, MT (US); Paul H. Tewson, Bozeman, MT (US); Anne Marie Quinn, Bozemen, MT (US)

(73) Assignee: Montana Molecular LLC, Bozeman, MT (US)

( * ) Notice: Subject to any disclaimer, the term of this patent is extended or adjusted under 35 U.S.C. 154(b) by 1013 days.

(21) Appl. No.: 15/033,147

(22) PCT Filed: Nov. 4, 2014

(86) PCT No.: PCT/US2014/063916
§ 371 (c)(1),
(2) Date: Apr. 29, 2016

(87) PCT Pub. No.: WO2015/066706
PCT Pub. Date: May 7, 2015

(65) Prior Publication Data
US 2016/0274109 A1 Sep. 22, 2016

Related U.S. Application Data

(60) Provisional application No. 61/899,611, filed on Nov. 4, 2013.

(51) Int. Cl.
| *C12N 15/62* | (2006.01) |
| *A61K 38/16* | (2006.01) |
| *G01N 33/58* | (2006.01) |
| *G01N 33/566* | (2006.01) |
| *G01N 33/542* | (2006.01) |
| *C07K 14/00* | (2006.01) |

(52) U.S. Cl.
CPC ........... *G01N 33/566* (2013.01); *C07K 14/00* (2013.01); *G01N 33/542* (2013.01); *G01N 33/582* (2013.01); *C07K 2319/60* (2013.01)

(58) Field of Classification Search
CPC .......... C12N 9/12; C12Q 1/48; G01N 33/542; G01N 33/566
See application file for complete search history.

(56) References Cited

U.S. PATENT DOCUMENTS

| 5,519,163 | A | 5/1996 | Gibbs et al. |
| 6,469,154 | B1 | 10/2002 | Tsien et al. |
| 7,060,793 | B2 | 6/2006 | Tsien et al. |
| 2005/0026234 | A1 | 2/2005 | Violin et al. |
| 2007/0111270 | A1 | 5/2007 | Zhang et al. |
| 2007/0172850 | A1 | 7/2007 | Lukyanov et al. |
| 2010/0015701 | A1 | 1/2010 | Lukyanov et al. |
| 2012/0022092 | A1 | 1/2012 | Holland et al. |
| 2012/0034691 | A1 | 2/2012 | Looger et al. |
| 2016/0003854 | A1 | 1/2016 | Hughes et al. |
| 2017/0198364 | A1 | 7/2017 | Hughes et al. |
| 2017/0247769 | A1* | 8/2017 | Ast .................... C07K 14/4728 |

FOREIGN PATENT DOCUMENTS

| CA | 2286293 | 10/1998 |
| WO | WO 2006/054167 | 5/2006 |
| WO | WO 2009/142735 | 11/2009 |
| WO | WO 2013/138684 | 9/2013 |

OTHER PUBLICATIONS

UniProt database, Accession No. Q8WZA2, Jun. 2003.*
Adachi et al., "A technique for monitoring multiple signals with a combination of prism-based total internal reflection fluorescence microscopy and epifluorescence microscopy," Pflugers Arch—Eur. J. Physiol., 2009, vol. 459, pp. 227-234.
Akerboom et al., "Crystal Structures of the GCaMP Calcium Sensor Reveal the Mechanism of Fluorescence Signal Change and Aid Rational Design," The Journal of Biological Chemistry, 2009, vol. 284(10), pp. 6455-6464.
Akerboom et al., "Optimization of a GCaMP calcium indicator for neural activity imaging," J. Neuroscience, 2012, vol. 32(40), 43 pages.
Alford et al., "A Fluorogenic Red Fluorescent Protein Heterodimer," Chemical Biology, 2012, vol. 19(3), 16 pages.
Alford et al. "Dimerization-Dependent Green and Yellow Fluorescent Proteins," ACS Synthetic Biology, Dec. 2012, vol. 1, No. 12, pp. 569-575 (Abstract Only).
Almholt et al. "Changes in intracellular cAMP reported by a Redistribution@ assay using a cAMP-dependent protein kinase-green fluorescent protein chimera," Cellular Signalling, Aug. 2004, No. 16, No. 8, pp. 907-920 (Abstract Only).
Altschul et al., "Gapped BLAST and PSI-BLAST: a new generation of protein database search programs," Nucleic Acids Research, 1997, vol. 25(17), pp. 3389-3402.
Baird et al., "Circular permutation and receptor insertion within green fluorescent proteins," Proc. Natl. Acad. Sci. USA, 1999, vol. 96, pp. 11241-11246.
Barak et al. "Pharmacological Characterization of Membrane-Expressed Human Trace Amine-Associated Receptor 1 (TAAR1) by a Bioluminescence Resonance Energy Transfer cAMP Biosensor," Molecular Pharmacology, Sep. 2008, vol. 74, No. 3, pp. 585-594.
Barnett et al., "A Fluorescent, Genetically-Encoded Voltage Probe Capable of Resolving Action Potentials," PLOS ONE, 2012, vol. 7(9), 7 pages.
Berkner et al., "Abundant Expression of Polyomavirus Middle T Antigen and Dihydrofolate Reductase in an Adenovirus Recombinant," J. Virology, 1987, vol. 61(4), pp. 1213-1220.

(Continued)

*Primary Examiner* — Maryam Monshipouri
(74) *Attorney, Agent, or Firm* — Dechert LLP

(57) ABSTRACT

Described herein are novel fluorescent sensors for cyclic adenosine monophosphate (cAMP) that are based on single fluorescent proteins. These sensors use less visible spectrum than FRET-based sensors, produce robust changes in fluorescence, and can be combined with one another, or with other sensors, in a multiplex assay on standard fluorescent plate readers or live cell imaging systems.

12 Claims, 8 Drawing Sheets

Specification includes a Sequence Listing.

(56) References Cited

OTHER PUBLICATIONS

Binkowski et al. "A Luminescent Biosensor with Increased Dynamic Range for Intracellular cAMP." ACS Chemical Biology, Nov. 2011, vol. 6, No. 11, pp. 1193-1197 (Abstract Only).
Carlson et al., "Circularly permuted monomeric red fluorescent proteins with new termini in the β-sheet," Protein Science, 2010, vol. 19, pp. 1490-1499.
Cifuentes et al., "Proteolytic fragments of phosphoinositide-specific phospholipase C-delta 1. Catalytic and membrane binding properties," Journal of Biological Chemistry, 1993, vol. 268(16), pp. 11586-11593.
Davidson et al., "Overproduction of Polyomavirus Middle T Antigen in Mammalian Cells through the Use of an Adenovirus Vector," Journal of Virology, 1987, vol. 61(4), pp. 1226-1239.
Depry et al., "Multiplexed visualization of dynamic signaling networks using genetically encoded fluorescent protein-based biosensors," Pflugers Arch., 2013, vol. 465(3), 15 pages.
Falkenburger et al., "Kinetics of M1 muscarinic receptor and G protein signaling to phospholipase C in living cells," J. General Physiology, 2010, vol. 135(2), pp. 81-97.
Giorgione et al., "Increased Membrane Affinity of the C1 Domain of Protein Kinase Cδ Compensates for the Lack of Involvement of Its C2 Domain in Membrane Recruitment," The Journal of Biological Chemistry, 2006, vol. 281(3), pp. 1660-1669.
Haj-Ahmad et al., "Development of a Helper-Independent Human Adenovirus Vector and Its Use in the Transfer of the Herpes Simplex Virus Thymidine Kinase Gene," J. Virology, 1986, vol. 57(1), pp. 267-274.
Held et al. "Live Cell Imaging of GPCR Dependent Second-Messenger Systems Using the CytationTM 3 Cell Imaging Multi-Mode Reader to Image Genetically Encoded Gpcr Reactive Sensors in Real Time." BioTek Application note, 2014, 8 pages [retrieved from: www.biotek.com/assets/tech_resources/Montana%20Molecular_App_Note.pdf].
Hong et al. "Improved molecular toolkit for cAMP studies in live cells," BMC Research Notes, Jul. 2011, vol. 4, 241, 5 pages.
Jensen et al., "Fluorescence changes reveal kinetic steps of muscarinic receptor-mediated modulation of phosphoinositides and Kv7.2/7.3 K+ channels," J. General Physiology, 2009, vol. 133(4), pp. 347-359.
Jiang et al. "Use of a cAMP BRET sensor to characterize a novel regulation of cAMP by the sphingosine 1-phosphate/G13 pathway." The Journal of Biological Chemistry, Apr. 2007, vol. 282, No. 14, 10576-10584.
Kavran et al., "Specificity and Promiscuity in Phosphoinositide Binding by Pleckstrin Homology Domains," J. Biol. Chem., 1998, vol. 273(46), pp. 30497-30508.
Kenakin et al. "Signalling bias in new drug discovery: detection, quantification and therapeutic impact," Nature Reviews Drug Discovery, Mar. 2013, vol. 12, No. 3, pp. 205-216 (Abstract Only).
Kitaguchi et al. "Extracellular calcium influx activates adenylate cyclase 1 and potentiates insulin secretion in MIN6 cells," Biochemical Journal, Mar. 2013, vol. 450, No. 2, pp. 365-373.
Klarenbeek et al. "A mTurquoise-Based cAMP Sensor for Both Flim and Ratiometric Read-Out Has Improved Dynamic Range," PloS One, Apr. 2011, vol. 6, No. 4, e19170, 6 pages.
Kost et al. "Baculovirus as versatile vectors for protein expression in insect and mammalian cells," Nature Biotechnology, May, 2005, vol. 23, No. 5, 567-575 (Abstract Only).
Kredel et al. "Optimized and Far-Red-Emitting Variants of Fluorescent Protein eqFP611," Cell Chemical Biology, Mar. 2008, vol. 15, No. 3, pp. 224-233.
Kyte et al. "A simple method for displaying the hydropathic character of a protein," Journal of Molecular Biology, May, 1982, vol. 157, No. 1, pp. 105-132 (Abstract Only).
Lam et al., "Improving FRET dynamic range with bright green and red fluorescent proteins," Nature Methods, 2012, vol. 9(10), 26 pages.

Le Poul et al., "Adaption of Aequorin Functional Assay to High Throughput Screening," Journal of Biomolecular Screening, 2002, vol. 7(1), pp. 57-65.
Ledford "Bioengineers look beyond patents: Synthetic-biology company pushes open-source models," Nature, Jul. 2013, vol. 499, No. 7456, pp. 16-17.
Liu et al., "Biased signaling pathways in βB-adrenergic receptor characterized by 19F-NMR," Science, 2012, vol. 335(6072), 12 pages.
Massie et al., "Construction of a Helper-Free Recombinant Adenovirus That Expresses Polyomavirus Large T Antigen," Mol. Cell. Biol., 1986, vol. 6(8), pp. 2872-2883.
Nagai et al., "Circularly permuted green fluorescent proteins engineered to sense $Ca^2+$," Proceedings of the National Academy of Sciences, 2001, vol. 98(6), pp. 3197-3202.
Nakai et al., "A high signal-to-noise $Ca^2+$ probe composed of a single green fluorescent protein," Nature Biotechnology, 2001, vol. 19, pp. 137-141.
Nausch et al., "Differential patterning of cGMP in vascular smooth muscle cells revealed by single GFP-linked biosensors," Proceedings of the National Academy of Sciences, 2008, vol. 105(1), pp. 365-370.
Ni et al., "Signaling Diversity of PKA Achieved Via a Ca2+-cAMP-PKA Oscillatory Circuit," Nature Chemical Biology, 2011, vol. 7(1), 15 pages.
Oancea et al., "Green Fluorescent Protein (GFP)-tagged Cysteine-rich Domains from Protein Kinase C as Fluorescent Indicators for Diacylglycerol Signaling in Living Cells," The Journal of Cell Biology, 1998, vol. 140(3), pp. 485-498.
Okumoto et al., "Quantitative Imaging with Fluorescent Biosensors," Annu. Rev. Plant Biol., 2012, vo. 63, pp. 663-706.
Palmer et al., "Design and application of genetically encoded biosensors," Trends in Biotechnology, 2011, vol. 29(3), 18 pages.
Pletnev et al., "A Crystallographic Study of Bright Far-Red Fluorescent Protein mKate Reveals pH-induced cis-trans Isomerization of the Chromophore," The Journal of Biological Chemistry, 2008, vol. 283(43), pp. 28980-28987.
Ponsioen et al. "Detecting cAMP-induced Epac activation by fluorescence resonance energy transfer: Epac as a novel cAMP indicator," EMBO Reports, Dec. 2004, vol. 5, No. 12, pp. 1176-1180.
Prinz et al. "Novel, isotype-specific sensors for protein kinase a subunit interaction based on bioluminescence resonance energy transfer (BRET)." Cellular Signalling, Oct. 2006, vol. 18, No. 10, pp. 1616-1625 (Abstract Only).
Raehal et al., "Morphine Side Effects in β-Arrestin 2 Knockout Mice," The Journal of Pharmacology and Experimental Therapeutics, 2005, vol. 314(3), pp. 1195-1201.
Rajagopal et al., "Quantifying Ligand Bias at Seven-Transmembrane Receptors," Molecular Pharmacology, 2011, vol. 80(3), 28 pages.
Rajagopal et al., "Teaching old receptors new tricks: biasing seven-transmembrane receptors," Nature Reviews Drug Discovery, 2010, vol. 9(5), pp. 373-386.
Rehmann et al. "Structure of Epac2 in complex with a cyclic AMP analogue and RAP1B," Nature, Sep. 2008, vol. 455, No. 7209, pp. 124-127 (Abstract Only).
Rehmann et al. "Structure of the cyclic-AMP-responsive exchange factor Epac2 in its auto-inhibited state," Nature, Feb. 2006, vol. 439, No. 7076, pp. 625-628 (Abstract Only).
Salonikidis et al. "An Ion-insensitive cAMP Biosensor for Long Term Quantitative Ratiometric Fluorescence Resonance Energy Transfer (FRET) Measurements under Variable Physiological Conditions," Journal of Biological Chemistry, Jul. 2011, vol. 286, No. 26, pp. 23419-23431.
Schroeder et al., "FLIPR: A New Instrument for Accurate, High Throughput Optical Screening," Journal of Biomolecular Screening, 1996, vol. 1(2), pp. 75-80.
Shaner et al. "A guide to choosing fluorescent proteins," Nature Methods, Dec. 2005, vol. 2, No. 12, pp. 905-909.
Shaner et al. "Improving the photostability of bright monomeric orange and red fluorescent proteins," Nature Methods, Jun. 2008, vol. 5, No. 6, pp. 545-551 (Abstract Only).

(56) References Cited

OTHER PUBLICATIONS

Shaner et al. "A bright monomeric green fluorescent protein derived from Branchiostoma lanceolatum," Nature Methods, May 2013, vol. 10, No. 5, pp. 407-409 (Abstract Only).
Shaw et al., "Preferential transformation of human neuronal cells by human adenoviruses and the origin of HEK 293 cells," The FASEB Journal, 2002, vol. 16, pp. 869-871.
Shcherbo et al. "Practical and reliable FRET/FLIM pair of fluorescent proteins," BMC Biotechnology, Mar. 2009, vol. 9, 24, 6 pages.
Shui et al., "Circular Permutation of Red Fluorescent Proteins," PLoS ONE, 2011, vol. 6(5), e20505, 9 pages.
Subach et al. "Conversion of Red Fluorescent Protein into a Bright Blue Probe," Chemistry & Biology, Oct. 2008, vol. 15, No. 10, pp. 1116-1124.
Szymczak et al., "Correction of multi-gene deficiency in vivo using a single 'self-cleaving' 2A peptide-based retroviral vector," Nature Biotechnology, 2004, vol. 22(5), pp. 589-594.
Tewson et al., "Simultaneous Detection of $Ca^{2+}$ and Diacylglycerol Signaling in Living Cells," PLoS ONE, 2012, vol. 7(8), e42791, 6 pages.
Topell et al. "Circularly permuted variants of the green fluorescent protein," FEBS Letters, Aug. 1999, vol. 457, No. 2, pp. 283-289.
Tsutsui et al. "Improving membrane voltage measurements using FRET with new fluorescent proteins," Nature Methods, Aug. 2008, vol. 5, No. 8,683-685 (Abstract Only).
Van Der Wal et al., "Monitoring Agonist-induced Phospholipase C Activation in Live Cells by Fluorescence Resonance Energy Transfer," The Journal of Biological Chemistry, 2001, vol. 276(18), pp. 15337-15344.
White et al., "Characterization of a $Ca^{2+}$ Response to Both UTP and ATP at Human P2Y11 Receptors: Evidence for Agonist-Specific Signaling," Molecular Pharmacology, 2003, vol. 63(6), pp. 1356-1363.
Willoughby et al. "Live-cell imaging of cAMP dynamics," Nature Methods, Jan. 2008, vol. 5, No. 1, 29-36 (Abstract Only).
Woehler et al. "Signal/Noise Analysis of FRET-Based Sensors," Biophysical Journal, Oct. 2010, vol. 99, No. 7, pp. 2344-2354.
Xu et al. "A bioluminescence resonance energy transfer (BRET system: application to interacting circadian clock proteins," Proc. Natl. Acad. Sci. U.S.A., Jan. 1999, vol. 96, No. 1, pp. 151-156.
Zaccolo et al. "A genetically encoded, fluorescent indicator for cyclic AMP in living cells," Nature Cell Biology, Jan. 2000, vol. 2, No. 1, pp. 25-29 (Abstract Only).
Zaccolo et al. "Discrete microdomains with high concentration of cAMP in stimulated rat neonatal cardiac myocytes," Science, Mar. 2002, vol. 295, No. 5560, pp. 1711-1715 (Abstract Only).
Zhang et al. "Generation and identification of recombinant adenovirus by liposome-mediated transfection and PCR analysis," Biotechniques, Nov. 1993, vol. 15, No. 5, pp. 868-872 (Abstract Only).
Zhang et al., "A Sample Statistical Parameter for Use in Evaluation and Validation of High Throughput Screening Assays," Journal of Biomolecular Screening, 1999, vol. 4(2), pp. 67-73.
Zhang et al. "Genetically encoded reporters of protein kinase a activity reveal impact of substrate tethering," Proceedings of the National Academy of Sciences, Dec. 2001, vol. 98, No. 26, pp. 14997-15002.
Zhao et al., "An Expanded Palette of Genetically Encoded $Ca^{2+}$ Indicators," Science, 2011, vol. 333(6051), pp. 9 pages.
International Search Report and Written Opinion for International (PCT) Patent Application No. PCT/US14/63916, dated Apr. 15, 2015 14 pages.
International Preliminary Report on Patentability for International (PCT) Patent Application No. PCT/US2014/63916, dated May 19, 2016 10 pages.
Burns et al., "Protein Kinase C Contains Two Phorbol Ester Binding Domains," J. Biol. Chem., 1991, vol. 266(27), pp. 18330-8337.
Dries et al., "A Single Residue in the C1 Domain Sensitizes Novel Protein Kinase C Isoforms to Cellular Diacylglycerol Production," J. Biol. Chem., 2007, vol. 282(2), pp. 826-830.
Hurley et al., "Taxonomy and function of C1 protein kinase C homology domains," Protein Sci., 1997, vol. 6, pp. 477-480.
Nikolaev et al. "Novel Single Chain cAMP Sensors for Receptor-induced Signal Propagation," The Journal of Biological Chemistry, Sep. 2004, vol. 279, No. 36, pp. 37215-37218.
Extended Search Report for European Patent Application No. 14858784.3, dated Jun. 22, 2017 10 pages.
Official Action for European Patent Application No. 14858784.3, dated May 2, 2018 6 pages.
Official Action for European Patent Application No. 14858784.3, dated Mar. 29, 2019 5 pages.
Official Action for Canada Patent Application No. 2,929,392, dated Sep. 17, 2020 5 pages.
Extended Search Report for European Patent Application No. 20175471.0, dated Sep. 30, 2020 11 pages.
Alford, S. C., Ding, Y., Simmen, T., and Campbell, R. E. (2012b). Dimerization-Dependent Green and Yellow Fluorescent Proteins. ACS Synth. Biol. Dec. 2012, vol. 1, No. 12, pp. 569-575.
Almholt, K., Tullin, S., Skyggebjerg, O., and Scudder, K. (2004). Changes in intracellular cAMP reported by a Redistribution.RTM. assay using a cAMP-dependent protein kinase-green fluorescent protein chimera. Cellular Signalling, Aug. 2004, 16(8), 907-920.
Binkowski, B. F., Butler, B. L., Stecha, P. F., Eggers, C. T., Otto, P., Zimmerman, K., Vidugiris, G., Wood, M. G., Encell, L. P., Fan, F., et al. (2011). A Luminescent Biosensor with Increased Dynamic Range for Intracellular cAMP. ACS Chem. Biol. Nov. 2011, vol. 6, No. 11, pp. 1193-1197.
Kenakin, T., and Christopoulos, A. (2013). Signalling bias in new drug discovery: detection, quantification and therapeutic impact. Nat Rev Drug Discov, Mar. 2013, vol. 12, No. 3, pp. 205-216.
Kost, T. A., Condreay, J. P., and Jarvis, D. L. (2005). Baculovirus as versatile vectors for protein expression in insect and mammalian cells. Nature Biotechnology, May 2005, vol. 23, No. 5, 567-575.
Kyte, J., and Doolittle, R. F. (1982). A simple method for displaying the hydropathic character of a protein. Journal of Molecular Biology, May 1982, vol. 157, No. 1, pp. 105-132.
Nikolaev, V. O., B, M., and Imoto, K. (2001). A high signal-to-noise Ca(2+) probe composed of a single green fluorescent protein. Nature Biotechnology 19(2), 137-141, Feb. 19, 2001.
Prinz, A., Diskar, M., Erlbruch, A., and Herberg, F. W. (2006). Novel, isotype-specific sensors for protein kinase A subunit interaction based on bioluminescence resonance energy transfer (BRET). Cell. Signal. Vol. 18, No. 10, pp. 1616-1625.
Rehmann, H., Arias-Palomo, E., Hadders, M. A., and Schwede, F. (2008). Structure of Epac2 in complex with a cyclic AMP analogue and RAP1B. Nature, Sep. 2008, vol. 455, No. 7209, pp. 124-127.
Rehmann, H., Das, J., Knipscheer, P., and Wittinghofer, A. (2006). Structure of the cyclic-AMP-responsive exchange factor Epac2 in its auto-inhibited state. Nature, Feb. 2006, vol. 439, No. 7076, pp. 625-628.
Selvaratnam et al., PLoS One, 7(11): e48707 (Nov. 2012).
Shaner, N.C., Lin, M. Z., McKeown, M. R., Steinbach, P. A., Hazelwood, K. L., Davidson, M. W., and Tsien, R. Y. (2008). Improving the photostability of bright monomeric orange and red fluorescent proteins. Nature Methods, vol. 5, No. 6, pp. 545-551.
Shaner, N.C., Lambert, G. G., Chammas, A., Ni, Y., Cranfill, P. J., Baird, M. A., Sell, B. R., Allen, J. R., Day, R. N., Israelsson, M., et al. (2013). A bright monomeric green fluorescent protein derived from Branchiostoma lanceolatum. Nat Meth 10 (5), 407-409.
Tsalkova et al., JBC 284(35): 23644-23651 (Aug. 28, 2009).
Tsutsui, H., Karasawa, S., Okumura, Y., and Miyawaki, A. (2008). Improving membrane voltage measurements using FRET with new fluorescent proteins. Nature Methods 5(8), 683-685.
Willoughby, D., and Cooper, D. (2007). Live-cell imaging of cAMP dynamics. Nature Methods 5(1), 29-36.
Zaccolo, M., De Giorgi, F., Cho, C. Y., Feng, L., Knapp, T., Negulescu, P. A., Taylor, S. S., Tsien, R. Y., and Pozzan, T. (2000). A genetically encoded, fluorescent indicator for cyclic AMP in living cells. Nat. Cell Biol. 2(1), 25-29.
Zaccolo, M., and Pozzan, T. (2002). Discrete microdomains with high concentration of cAMP in stimulated rat neonatal cardiac myocytes. Science, 296(5560): 1711-1715.

(56) References Cited

OTHER PUBLICATIONS

Zhang, J., Ma, Y., Taylor, S. S., and Tsien, R. Y. Genetically encoded reporters of protein kinase A activity reveal impact of substrate tethering. Proceedings of the National Academy of Sciences, Dec. 2001, vol. 98, No. 26, pp. 14997-15002.

* cited by examiner

GENETICALLY ENCODED FLUORESCENT SENSORS FOR DETECTING LIGAND BIAS AND INTRACELLULAR SIGNALING THROUGH CAMP PATHWAYS

CROSS-REFERENCE TO RELATED APPLICATIONS

This application is a national stage application under 35 U.S.C. 371 of PCT Application No. PCT/US2014/063916, having an international date of Nov. 4, 2014, which designated the United States, which PCT application claimed the benefit of U.S. Provisional Patent Application No. 61/899,611, filed Nov. 4, 2013, both of which are incorporated by reference in their entirety.

GOVERNMENT SUPPORT

This invention was made with government support under NSF SBIR Phase I Proposal 1248138. The government has certain rights under this invention.

REFERENCE TO SEQUENCE LISTING

This application contains a Sequence Listing submitted as an electronic text file named "6666-3-PCT_Sequence_Listing_ST25.txt", having a size in bytes of 520 KB, and created on Nov. 4, 2014. The information contained in this electronic file is hereby incorporated by reference in its entirety pursuant to 37 CFR § 1.52(e)(5).

FIELD OF THE INVENTION

The field of the present invention is design and construction of fluorescent biological sensors for detection and measurement of intracellular analytes.

BACKGROUND OF THE INVENTION

For over a decade, several attempts have been made to create genetically encoded, fluorescent biosensors that can detect changes in cAMP and report these changes through alterations in fluorescence. Despite strenuous efforts, involving many different design strategies, over the course of more than fifteen years, these earlier attempts at cAMP sensors have not produced signals that are robust and/or reproducible enough for live cell assay on standard, automated fluorescence plate readers. Automated detection of cAMP is of considerable importance because cAMP is an essential signaling component of many drug targets, most notably, G-protein coupled receptors. As background to this invention, a summary of the various design strategies that are known in the art (FRET, Redistribution, BRET and Fluorescent Protein Complementation) are described in the following sections.

Fluorescence Resonance Energy Transfer (FRET)

Zaccolo and colleagues (Zaccolo, M., De Giorgi, F., Cho, C. Y., Feng, L., Knapp, T., Negulescu, P. A., Taylor, S. S., Tsien, R. Y., and Pozzan, T. (2000)). A genetically encoded, fluorescent indicator for cyclic AMP in living cells. Nat. Cell Biol. 2, 25 As baInitially described a cAMP biosensor in which changes in the distance and orientation between the regulatory and catalytic subunits of Protein Kinase A (PKA) could be detected through changes in the fluorescence energy transfer (FRET) between a donor and acceptor fluorescent protein. When cAMP rises in the cell, the regulatory subunit changes conformation and dissociates from the catalytic subunit. This dissociation increases the distance between the donor and acceptor pair of fluorescent proteins and lowers the fluorescence energy transfer efficiency, which can be detected as a change in the ratio of donor and acceptor emission. The initial sensor was created using a blue and green pair of fluorescent proteins, but other proteins with more favorable characteristics have been used since then including cyan and yellow (Zaccolo & Pozzan, 2002: Zhang et al., 2001).

Similar FRET-based biosensors, where donor and acceptor fluorescent proteins were fused to the regulatory and catalytic subunits of an Epac protein were reported simultaneously by three different groups over a decade ago (Reviewed in Willoughby and Cooper, 2007). Epac, unlike PKA, is a single protein composed of a large regulatory subunit tethered by a hinge region to the catalytic subunit. Donor or acceptor fluorescent proteins fused to the N terminus of Epac are effectively joined to the regulatory subunit, while fluorescent proteins fused to the C-terminus of Epac are connected to the catalytic subunit. When cAMP binds to the regulatory subunit, a conformational change occurs and the regulatory subunit swings away from the catalytic subunit, thereby freeing it to interact with its substrates. This dissociation of the two subunits produces a modest change in FRET. These FRET-based sensors were initially produced using the cyan and yellow fluorescent proteins (DiPilato et. al. 2004, Ponsioen et al., 2004 & Nikolaev, et. al. 2004), but a variety of other suitable pairs have been used in similar designs including GFP and mCherry (Hong et al., 2011), eCFP and mTurquoise (Klarenbeek et al., 2011) cerulean and citrine (Salonikidis et al., 2011).

While FRET based biosensors have the advantage of ratio metric measurements in living cells, there are disadvantages as well. The donor and acceptor fluorescent proteins use much of the visible spectrum, so they are difficult to combine with other sensors for multiplex measurements, thereby limiting the sensoratio metric measurements in living cells, there are disadvantages as well. The donor and acceptor fluorescent proteins use much of the visible spectrum, so they are difficult to combine with other signal to noise ratios (Woehler et al., 2010) that are only detectable with sophisticated research microscopes in limited applications.

Redistribution

The dissociation of the activated PKA subunits causes a redistribution of the catalytic subunit as it diffuses through the cell. This movement can be detected in an imaging microscope if a fluorescent protein is fused to the catalytic subunit. Activation of the PKA causes the fluorescence to move from small aggregates to a much more diffuse cytosolic labeling (Almholt, 2004). This assay requires sophisticated image analysis and instrumentation for detection and is incompatible with high throughput live cell assay. This method is also described in (patent publication number CA2286293 C).

BRET

Bioluminescence is similar to FRET in that it involves energy transfer from an enzyme and an acceptor fluorescent protein, a process that is sensitive to the distance between the two components (Xu et al., 1999). Accordingly, PKA based sensors have been created by replacing a donor fluorescent protein with a *Renilla* luciferase (Prinz et al., 2006; Binkowski et al., 2011; see also WO2009142735 A3). A similar strategy was used to create a BRET based Epac sensor in which the energy transfer occurs between the *Renilla* Luciferase and a YFP (Jiang et al., 2007).

Protein Complementation.

Protein complementation refers to the reconstitution of fluorescence by bringing together fragments of a fluorescent protein (Gosh et al., 2000; Magliery et al., 2005; Cabantous, 2005; Kerppola, 2006, Chu et al., 2009) or pairs of fluorescent proteins whose fluorescent properties depend upon a very specific dimerization (Alford, S. C., Abdelfattah, A. S., Ding, Y., and Campbell, R. E. (2012a). A Fluorogenic Red Fluorescent Protein Heterodimer. Chem. Biol. 19, 353 ementation refers to the reconstitution of fluorescence by bringing together fragments of a fluorescent protein (Gosh et al., 2000; Magliery et al., 2005; Cabantous, 2005; Kerppola, 2006, Chu et al., 2009) or pairs of fluorescent proependent fluorescent proteins can replace FRET or BRET pairs of fluorescent proteins to create analogous sensors. In the case of complementing fragments, two portions of the yellow fluorescent protein were fused to either end of a cAMP binding domain taken from the regulatory region of Epac (Kitaguchi et. al., 2013). In this sensor, cAMP binding causes a conformational change that disrupts the interactions of the complementing fragments, producing a decrease in fluorescence. In the case of dimerization dependent fluorescent proteins, the two different fluorescent proteins replace the FRET pairs typically used in PKA sensors to produce a sensor in which the dimerization dependent fluorescence decreases when the regulatory and catalytic subunits dissociate (Held et al., 2014).

A Different cAMP Sensor Design is Robust with Unprecedented Signal to Noise.

To date, the strategies for creating cAMP biosensors have involved placing fluorescent proteins, fluorescent protein fragments, and luciferases at the ends of cAMP binding proteins and subunits. Changes in the conformations of the cAMP binding proteins generate fluorescent signals as subunits dissociate from one another. The present invention describes how a more robust sensor can be created by inserting a single, circularly permuted fluorescent protein into the hinge region of Epac, a cAMP-regulated enzyme. The Epac hinge region connects the cAMP-binding, regulatory region with the catalytic region. Without wishing to be bound by theory, the large relative movements of the two regions can produce a change in the environmentally sensitive, circularly permuted fluorescent protein positioned in or near the interconnecting hinge Rehmann et al., 2006; 2008). In contrast to the prior art described above, the distance between the N- and C-termini of the Epac protein is irrelevant to producing the signal. Similarly, a single fluorescent protein inserted into a synthetic hinge between the catalytic region of Epac and its substrate, RAP1B (Rehmann et al., 2008), produces a fluorescent signal that is dependent upon movements of these regions. The large relative movements of the two subunits or proteins produce robust changes in the fluorescent protein which are either increases or decreases in fluorescence intensity.

SUMMARY OF THE INVENTION

The present disclosure provides cAMP sensor proteins comprising a first polypeptide linked to a single fluorescent protein. Within these cAMP sensor proteins, the first polypeptide comprises a cAMP-binding domain and the single fluorescent protein consists of an uninterrupted amino acid sequence. The binding of cAMP to the cAMP-binding site of these cAMP sensor proteins alters the level of fluorescence from the fluorescent protein.

In certain embodiments, the fluorescent protein comprises at least a portion of a protein selected from GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and synthetic non-*Aequorea* fluorescent proteins, which may include green fluorescent proteins.

In certain embodiments, the fluorescent protein comprises an amino acid sequence at least about 70%, or at least about 75%, or at least about 80%, or at least about 85%, or at least about 90%, or at least about 95% identical, or at least about 96% identical, or at least about 97% identical, or at least about 98% identical, or at least about 99% identical to a protein selected from GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-*Aequorea* fluorescent protein.

In certain embodiments, the first polypeptide comprises at least 100 contiguous amino acids from a sequence selected from SEQ ID NO:35, SEQ ID NO:74, SEQ ID NO:75 and SEQ ID NO:76. In related embodiments, the first polypeptide comprises an amino acid sequence at least 90% identical to a sequence selected from the group consisting of SEQ ID NO:35, SEQ ID NO:74, SEQ ID NO:75 and SEQ ID NO:76.

In certain embodiments, the cAMP sensor protein includes a linker between the first polypeptide and the fluorescent protein, or portion thereof.

In certain embodiments, the cAMP sensor protein comprises an amino acid sequence at least 90% identical to at least one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32 and SEQ ID NO:33.

In certain embodiments, the cAMP sensor protein includes a second polypeptide, wherein the second polypeptide is linked to the fluorescent protein, or portion thereof, such that the fluorescent protein is flanked by the first and second polypeptides. In specific embodiments, the amino acid sequence of the first polypeptide and the amino acid sequence of the second polypeptide are from different proteins. In other embodiments, the amino acid sequence of the first polypeptide and the amino acid sequence of the second polypeptide are from the same protein. In specific embodiments, the first and/or second polypeptide comprises an amino acid sequence from a protein selected from the group consisting of Epac1, Epac2, protein kinase A and RAP1b. In specific embodiments, the first and/or second polypeptide comprises an amino acid sequence at least 90% identical to a sequence selected from the group consisting of SEQ ID NO:35, SEQ ID NO:74, SEQ ID NO:75 and SEQ ID NO:76. In related embodiments, the first and second polypeptides are capable of interacting.

In certain embodiments, the sensor includes a first linker sequence between the fluorescent protein, or portion thereof, and the first or second polypeptide. In related embodiments, the sensor includes a first linker sequence between the first polypeptide and the fluorescent protein, or portion thereof, and a second linker sequence between the second polypeptide and the fluorescent protein, or portion thereof.

In certain embodiments, the fluorescent protein is circularly permuted.

In certain embodiments, the cAMP sensor protein comprises at least one amino acid sequence that is at least 70%, at least 80%, at least 85%, at least 90%, at least 95%, at least 97% or at least 99% identical to a sequence selected from SEQ ID NO:1, SEQ ID NO:2, SEQ ID NO:3, and SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32 and SEQ ID NO:33.

Another aspect of the disclosure provides nucleic acid sequences encoding these sensor proteins. Certain embodiments include a nucleic acid sequence encoding a cAMP sensor protein which includes a first polypeptide linked to a single fluorescent protein, wherein the encoded first polypeptide comprises a cAMP-binding domain and the encoded single fluorescent protein consists of an uninterrupted amino acid sequence and wherein binding of cAMP to the cAMP-binding site of the encoded protein alters a level of fluorescence from the fluorescent protein.

In certain embodiments, a cAMP sensor protein of the present invention is encoded by a nucleic acid molecule comprising a nucleic acid sequence at least 70%, at least 80%, at least 85%, at least 90%, at least 95%, at least 97% or at least 99% identical to a sequence selected from the group consisting of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72 and SEQ ID NO:73. In related embodiments, a cAMP sensor protein of the present invention is encoded by a nucleic acid molecule comprising a nucleic acid sequence selected from the group consisting of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72 and SEQ ID NO:73.

In related embodiments, the nucleic acid sequences encode a cAMP sensor protein in which a second polypeptide is linked to the fluorescent protein, or portion thereof, such that the fluorescent protein is flanked by the first and second polypeptides.

One aspect of the present invention is a method to detect changes in the intracellular level of cAMP, comprising expressing a cAMP sensor protein of the present invention in a cell, and detecting changes in the level of fluorescence from the sensor. In a related embodiment, the cell is treated with a compound (e.g., drug) to determine the effect of the compound on cAMP levels.

DETAILED DESCRIPTION OF THE INVENTION

Figure 1:
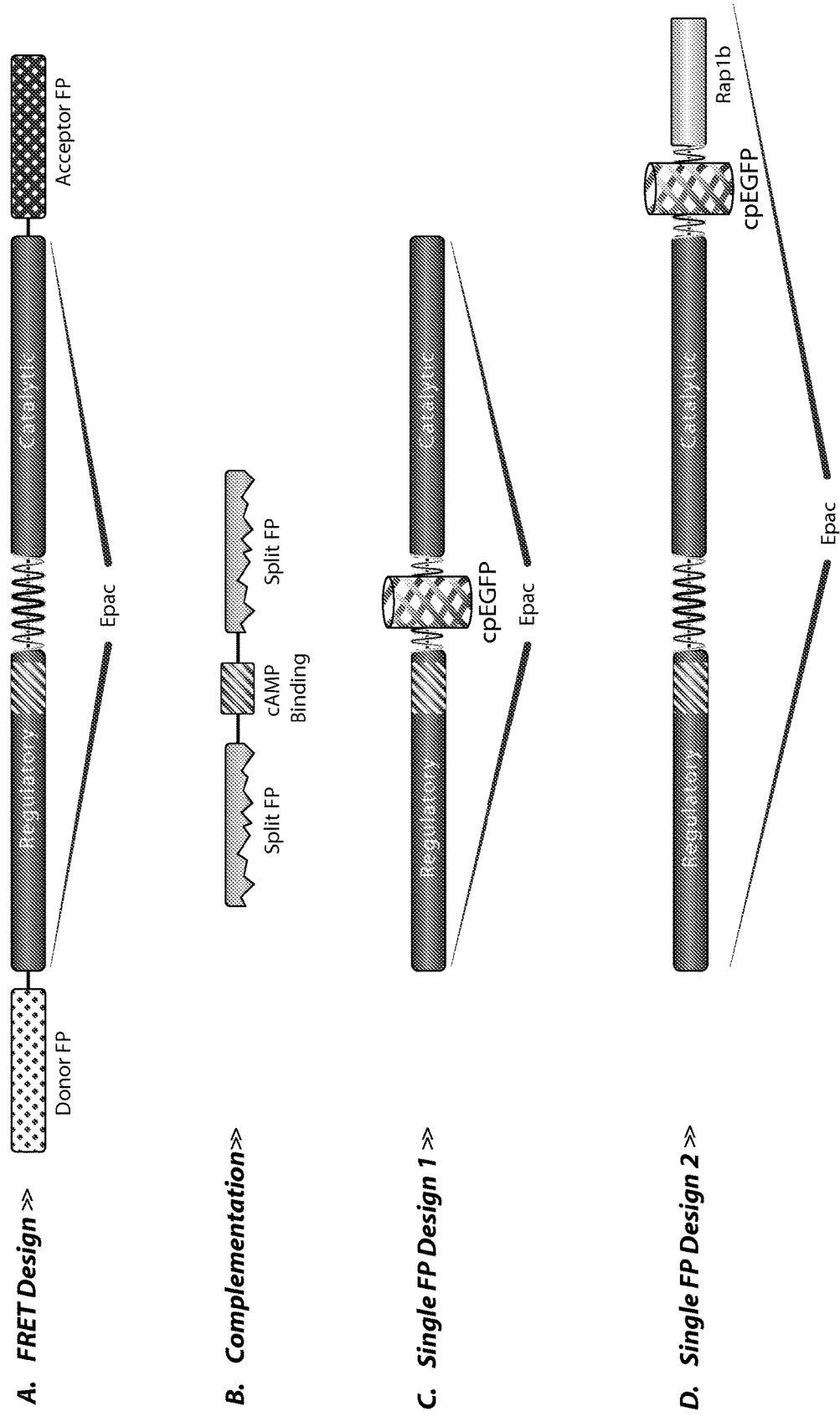
FIG. 1 Various designs for genetically-encoded cAMP sensors. (A) Forster Resonance Energy Transfer (FRET) design; (B) Complementation design; (C) Single FP design 1 of present invention (fluorescent protein flanked by sequences from same protein); (D) Single FP design 2 of present invention (fluorescent protein flanked by sequences from different protein).
Figure 2:
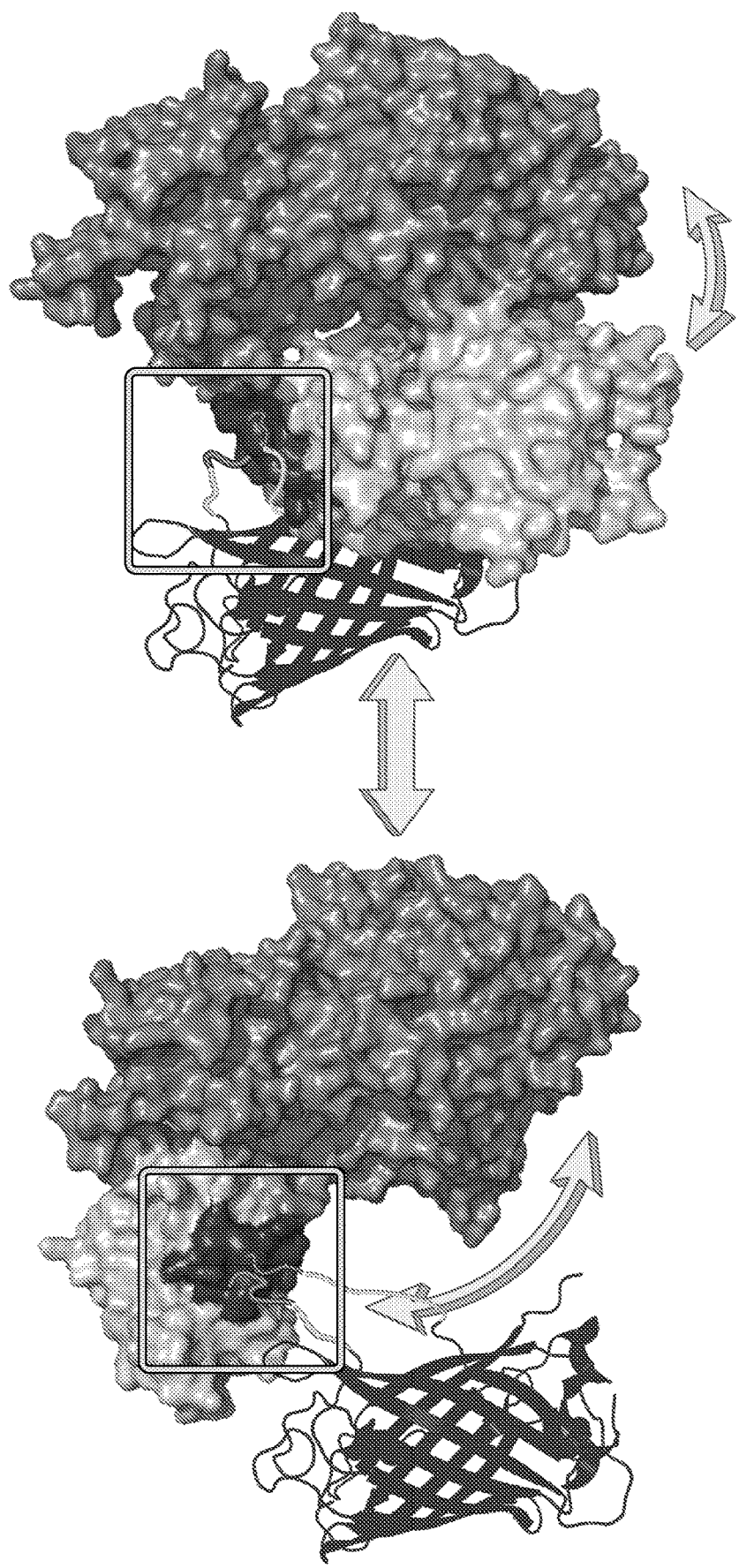
FIG. 2 Space filling model showing the approximate structure of an embodiment of the invention in both the cAMP unbound (left) and bound (right) states.

The present invention is directed to novel fluorescent sensors for the detection of cyclic adenosine monophosphate (cAMP), a second messenger of cell signaling. Described herein is the design and construction of novel, protein-based sensors that specifically detect cAMP, provide robust fluorescence signals in live cells, and can be used in live cell assays on standard fluorescent plate readers or live cell imaging systems. Combined with other sensors, such as a diacylglycerol (DAG) or a phosphatidylinositol 4,5-bisphosphate (PIP2) sensor made from a fluorescent protein with different excitation and emission spectra, such multiplex assays can detect whether the G protein pathways Gq, Gs, and Gi are activated individually or simultaneously.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly the terms "comprising", "including" and "having" can be used interchangeably. It is further noted that the claims may be drafted to exclude any optional element. As such, this statement is intended to serve as antecedent basis for use of such exclusive terminology as "solely," "only", "single" and the like in connection with the recitation of claim elements, or use of a "negative" limitation.

A novel cAMP sensor protein of the present invention can generally be produced by linking a protein comprising a cAMP-binding domain to a single fluorescent protein in such a way that the level of fluorescence emitted by the single fluorescent protein is dependent on the level of cAMP in the environment. Such proteins can be referred to as cAMP sensor proteins or simply as cAMP sensors. Thus, one embodiment of the present invention is a cAMP sensor protein comprising a first polypeptide linked to a single fluorescent protein, wherein the first polypeptide comprises a cAMP-binding domain, wherein the single fluorescent protein consists of an uninterrupted amino acid sequence, and wherein the fluorescence of the cAMP sensor changes upon binding cAMP.

As used herein, reference to a protein (or polypeptide) includes full-length proteins, fusion proteins, or any fragment, domain, conformational epitope, or homolog of such proteins. For example, an Epac protein refers o a full-length Epac protein as well as fragments, domains, conformational epitopes or homologs thereof. Any proteins or polypeptides can be used to construct cAMP sensors of the present invention as long as they have the characteristics and activities disclosed herein.

According to the present disclosure, any polypeptide can be used as the first polypeptide as long as that polypeptide is capable of comprising a cAMP-binding domain and as long as binding of cAMP to the resulting sensor protein construct causes a change in fluorescence of the cAMP sensor. First polypeptides used to construct sensors of the present invention comprise an amino acid sequence from a protein that may or may not naturally comprise a cAMP-binding domain. A protein that naturally comprises a cAMP-binding domain refers to a protein that has a cAMP-binding domain, as isolated from nature (i.e., not engineered by the hand of man). Thus, in one embodiment, the first polypeptide comprises an amino acid sequence from a protein that naturally comprises a cAMP-binding domain. Examples of such proteins are known to those skilled in the art and include, but are not limited to, Epac1, Epac2 and protein kinase A (PKA). AAS used herein, PKA (protein kinase A) refers to the cAMP-binding subunit of PKA (i.e., the regulatory subunit) Thus, in one embodiment the first polypeptide comprises an amino acid sequence from a protein selected from the group consisting of Epac1, Epac2 and protein kinase A (PKA). In one embodiment, the first polypeptide comprises at least 50 contiguous amino acids, at least 100 contiguous amino acids, at least 150 contiguous amino acids, at least 200 contiguous amino acids, or at least 250 contiguous amino acids from a PKA protein. In one embodiment, the first polypeptide comprises at least 50 contiguous amino acids, at least 100 contiguous amino acids, at least 150 contiguous amino acids, at least 200 contiguous amino acids, or at least 250 contiguous amino acids from SEQ ID NO:75. In one embodiment, the first polypeptide comprises at least 200 contiguous amino acids, at least 300 contiguous amino acids, at least 400 contiguous amino acids, at least 500 contiguous amino acids or at least 600 contiguous amino acids from an Epac1 or Epac2 protein. In one embodiment, the first polypeptide comprises at least 200 contiguous amino acids, at least 300 contiguous amino acids, at least 400 contiguous amino acids, at least 500 contiguous amino acids or at least 600 contiguous amino acids from SEQ ID NO:74 or SEQ ID NO:35. In one embodiment the first polypeptide comprises the amino acid sequence of a protein selected from the group consisting of Epac1, Epac2 and protein kinase A (PKA). In one embodiment the first polypeptide comprises an amino acid sequence selected from the group consisting of SEQ ID NO:75, SEQ ID NO:74 and SEQ ID NO:35.

Alternatively, the first polypeptide can comprise an amino acid sequence from a protein that does not naturally contain a cAMP-binding domain, as long as a cAMP-binding domain can be inserted into the first polypeptide and binding of cAMP to the cAMP sensor protein results in a change in fluorescene.

Before proceeding further, it should be appreciated that while exemplary amino acid and nucleic acid sequences useful for constructing cAMP sensors of the present invention are disclosed herein, variants (or homologs) of such sequences may also be used, as long as the variant sequences can function for its intended purpose (e.g., binding cAMP, fluorescing, etc.). As used herein, a variant (or homolog) refers to a protein, or nucleic acid molecule, the sequence of which is similar, but not identical, to a reference sequence (e.g., natural protein, wild type protein, etc.), wherein the activity of the variant protein (or the protein encoded by the variant nucleic acid molecule) is not significantly altered. These variations in sequence can be naturally occurring variations or they can be engineered through the use of genetic engineering technique know to those skilled in the art. Examples of such techniques are found in Sambrook J, Fritsch E F, Maniatis T et al., in Molecular Cloning—A Laboratory Manual, 2nd Edition, Cold Spring Harbor Laboratory Press, 1989, pp. 9.31-9.57), or in Current Protocols in Molecular Biology, John Wiley & Sons, N.Y. (1989), 6.3.1-6.3.6, both of which are incorporated herein by reference in their entirety.

With regard to variants, any type of alteration in the amino acid, or nucleic acid, sequence is permissible so long as the resulting variant sequence functions for its intended purpose. Examples of such variations include, but are not limited to, deletions, insertions, substitutions and combinations thereof. For example, with regard to proteins, it is well understood by those skilled in the art that one or more (e.g., 2, 3, 4, 5, 6, 7, 8, 9 or 10), amino acids can often be removed from the amino and/or carboxy terminal ends of a protein without significantly affecting the activity of that protein. Similarly, one or more (e.g., 2, 3, 4, 5, 6, 7, 8, 9 or 10) amino acids can often be inserted into a protein without significantly affecting the activity of the protein.

With specific regard to proteins, any amino acid substitution is permissible so long as the activity of the protein is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions.

Naturally occurring residues may be divided into classes based on common side chain properties:
1) hydrophobic: Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, conservative substitutions can involve the exchange of a member of one of these classes for a member from the same class. In contrast, non-conservative substitutions may involve the exchange of a member of one of these classes for a member from another class.

In making amino acid changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within nges, the hydropathic index of amino acids may be considered. Each amino acid has been assi It is also understood in the art that the substitution of like amino acids can be made effectively on the basis of hydrophilicity, particularly where the biologically functionally equivalent protein or peptide thereby created is intended for use in immunological invention. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity.

Desired amino acid substitutions (whether conservative or non-conservative) can be determined by those skilled in the art at the time such substitutions are desired. For example, amino acid substitutions can be used to identify important residues of a protein, or to increase or decrease the activity (e.g., cAMP-binding, fluorescence, etc.), solubility, flexibility or stability of a protein. Exemplary amino acid substitutions are shown in the following table:

| Amino Acid Substitutions | |
|---|---|
| Original Amino Acid | Exemplary Substitutions |
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala |
| Leu | Ile, Val, Met, Ala |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

As used herein, the phrase significantly affect a proteins activity refers to a decrease in the activity of a protein by at least 10%, at least 20%, at least 30% or at least 40%. With regard to the present invention, such an activity may be measured, for example, as the ability of a protein to elicit antibodies against the reference (i.e., non-mutated) protein, by measuring the ability of the protein to bind cAMP, or by measuring the fluorescence of the protein. Methods of making such measurements are known to those skilled in the art.

In addition to amino acid changes, substitutions and deletions, variants (or homologs) of proteins of the present invention include minor modifications to the finished protein, such as, for example, methylation, glycosylation, phosphorylation, acetylation, myristoylation, prenylation, palmitation, amidation.

In certain embodiments, the first polypeptide comprises a variant of a cAMP-binding protein. In one embodiment, the first polypeptide comprises an amino acid sequence at least about 45%, or at least about 50%, or at least about 55%, or at least about 60%, or at least about 65%, or at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to the amino acid sequence of a protein selected from the group consisting of Epac1, Epac2 and protein kinase A (PKA). In one embodiment, the first polypeptide comprises an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 75% and 99%, in whole integer increments), to a sequence selected from SEQ ID NO:35, SEQ ID NO:74 and SEQ ID NO:75.

As used herein, a cAMP-binding domain refers to a region of a protein that selectively binds to cAMP. cAMP-binding domains of the present invention include full length isoforms, or truncated or mutated versions of it that possess cAMP binding activity. It is well appreciated by those skilled in the art that such binding sites are part of the tertiary structure of a protein and are formed as a result of protein folding. A cAMP-binding domain of the present invention may be formed from a contiguous series of amino acids in a folded protein or it may be formed from amino acid residues that are not contiguous in the linear protein. Any cAMP-binding domain may be used to construct a cAMP sensor protein of the present invention, as long as the resulting protein sensor construct is capable of binding cAMP and such binding causes a change in fluorescence of the cAMP sensor. Without wishing to be bound by theory, it is believed that binding of cAMP to a cAMP sensor protein of the present invention, particularly at the cAMP-binding domain, leads to conformation changes in, at least, the first polypeptide, and such conformational changes alter the chromophore environment of the linked single, fluorescent protein, resulting in a change in fluorescence of the cAMP sensor protein. cAMP-binding domains of the present invention may have mutations to increase their affinity and/or specificity for cAMP. In one embodiment, the cAMP-binding domain comprises an amino acid sequence at least 80%, at least 85%, at least 90%, at least 95%, or at least 95% identical to SEQ ID NO:36 or SEQ ID NO:37, wherein the cAMP-binding domain is capable of binding cAMP. In one embodiment, the cAMP-binding domain comprises SEQ ID NO:36 or SEQ ID NO:37.

As used herein, and with regard to cAMP, selective binding refers to preferential binding of cAMP to a cAMP-binding domain or protein. Preferential binding refers to the fact that a cAMP-binding domain or protein will bind cAMP with an binding affinity greater than its binding affinity for an unrelated molecule (e.g., diacylglycerol, inisitol phosphate, calcium, etc).

As used herein, a fluorescent protein refers to a protein that emits light. Preferred fluorescent proteins are those that, upon absorption of light or other electromagnetic radiation, emit light of a same or different wavelength. Any fluorescent protein can be used to construct a cAMP sensor of the present invention, as long as upon binding of cAMP to the cAMP sensor, the level of fluorescence change. Examples of fluorescent proteins useful for producing cAMP sensor proteins of the present invention include, but are not limited to, green fluorescent protein (GFP), and its variants such as red fluorescent protein, yellow fluorescent protein, enhanced green fluorescent protein (eGFP), enhanced yellow fluorescent protein (eYFP), Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire. Such fluorescent proteins are discussed in Shaner et. al., (2005), and are expressly incorporated herein. Additional examples of fluorescent proteins include mKOK, mUKG (Tsutsui et al., 2008), Clover, Ruby (Lam et al., 2012), mKate (Pletnev et al., 2008), tagRFP, tagGFP (Shcherbo et al., 2009), mNEON green (Shaner et. al 2013), and a variety of synthetic non-*Aequorea* fluorescent proteins (DNA 2.0, Menlo Park, Calif. and Ledford, (2013). Thus, in one embodiment, a fluorescent protein of the present invention comprises at least a portion of a protein selected from the group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-*Aequorea* fluorescent protein. In one embodiment, a fluorescent protein of the present invention comprises at 50 contiguous amino acids, at least 100 contiguous amino acids, at least 150 contiguous amino acids, or at least 200 contiguous amino acids from a protein selected from the group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-*Aequorea* fluorescent protein. In one embodiment, a fluorescent protein of the present invention comprises at 50 contiguous amino acids, at least 100 contiguous amino acids, at least 150 contiguous amino acids, or at least 200 contiguous amino acids from a sequence selected from the group consisting of SEQ ID NO:38 and SEQ ID NO:77.

Fluorescent proteins useful for producing cAMP sensor proteins of the present invention can also be variants of the fluorescent proteins disclosed herein. Thus, in one embodiment, the single fluorescent protein comprises is a variant of a protein selected from the group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-*Aequorea* fluorescent protein. In one embodiment, a fluorescent protein of the present invention comprises an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical to a protein selected from the group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-*Aequorea* fluorescent protein. In one embodiment, a fluorescent protein of the present invention comprises an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical to a sequence selected from the group consisting of SEQ ID NO:38 and SEQ ID NO:77. In one embodiment, a fluorescent protein of the present invention comprises an amino acid sequence from a protein selected from the group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-*Aequorea* fluorescent protein. In one embodiment, a fluorescent protein of the present invention comprises an amino acid sequence selected from the group consisting of SEQ ID NO:38 and SEQ ID NO:77. It will be appreciated by those skilled in the art that truncated or variant forms of the fluorescent protein will include the amino acids necessary to form the chromophore.

It is understood by those skilled in the art that proteins can be circularly permuted. In a circularly permuted protein, the order of amino acids, or stretches of amino acids (e.g., domains), is changed compared to the order in the original protein. Further, it has been shown that circular permutation of a protein can alter the properties of a protein (for example, the activity or stability of a proteins). For example, when analyte sensing domains are fused to the original N- and C-termini of the fluorescent protein, movement of the termini may, but does not usually, produce changes in fluorescence. However, when the original N- and C-termini are fused, either with or without a short linker, and new N- and C-termini are introduced in the middle of one of the beta sheets of the barrel, a circularly permuted fluorescent protein is produced with new properties. Analyte sensing domains fused to these new termini can produce very large changes in fluorescence. Without wishing to be bound by theory, it is believed that the new N- and C-termini of the circularly permuted fluorescent protein, which are close to the chromophore, enable fusion partners to create a difference in the chromophore environment, thereby producing a change in fluorescence. Thus, for instance in the $Ca^{2+}$ sensor GCaMP3 (described in United States Patent Application 20120034691), the $Ca^{2+}$ binding domains are fused to the N- and C-termini adjacent to the chromophore of the circularly permuted green fluorescent protein. In one conformation, where $Ca^{2+}$ is at low concentrations and the binding domains are not interacting, there is an opening in the side of the beta barrel of the fluorescent protein and the chromophore is solvent accessible. When the $Ca^{2+}$ binding domains bind to one another in response to activation by $Ca^{2+}$, the hole is closed, and the new environment of the chromophore causes it to become fluorescent. Thus, in one embodiment, the single fluorescent protein is circularly permuted. In preferred embodiments, the N and the C termini of the protein are placed adjacent to the chromophore. For example, in one embodiment, the cAMP sensor protein comprises a circularly permuted green fluorescent protein described in Zhao and colleagues (2011), which is incorporated herein in its entirety. In one embodiment, the fluorescent protein is EGFP which has been circularly permuted around amino acids 149-144 [SEQ ID NO:38]. A number of fluorescent proteins are known in the art and may be circularly permuted to be used in the construction of the sensor of the present invention (Baird et al., 1999; Nagai et al., 2004; Nakai at al., 2001; Shui et al., 2011; Carlson et al., 2010; Topell et al., 1999).

In cAMP sensor proteins of the present invention, the first polypeptide is linked to a single fluorescent protein. As used herein, reference to a single fluorescent protein refers to the fact that the fluorescent protein portion of the sensor (i.e., the portion responsible for emitting light) consists of an uninterrupted amino acid sequence. In other words, when constructing cAMP sensor proteins of the present invention, the amino acid sequence of the fluorescent protein portion is a single, contiguous amino acid sequence and is not broken into two or more sequences located in separate regions of the overall cAMP sensor protein. For illustration purposes, the complementation design sensor shown in FIG. 1 represents a sensor construct in which the fluorescent protein has been split into two separate sequences, one of which is attached to one end of a cAMP binding domain, the other of which is attached to the opposite end of a cAMP binding domain. According to the present invention, such a construct does not contain a single fluorescent protein. In embodiments of the present invention, the single fluorescent protein is attached to one end or the other (e.g., either the N-terminal end or the C-terminal end) of the first polypeptide. It will be appreciated by those skilled in the art that in certain fluorescent proteins, the bonds of the amino acids that form the chromophore are broken following final folding of the protein. While such breaking of these bonds results in separation of the sequence of the fluorescent protein, the sequences remain close to one another and are not located in separate regions of the overall sensor protein. Thus, such photoconvertible fluorescent proteins can be used for constructing cAMP sensor proteins of the present invention.

As has been stated, binding of cAMP to the first polypeptide, and in particular to the cAMP-binding domain, causes an alteration in the level of fluorescence from the single fluorescent protein. Without wishing to be bound by theory, it is believed that the binding of cAMP leads to conformational changes in the first polypeptide, which changes the chromophore environment of the single fluorescent protein, thereby altering the level of fluorescence produced by the single fluorescent protein. As used herein an alteration in the level of fluorescence refers to an increase or decrease in the level of fluorescencey produced by the single fluorescent protein. Such alterations will be proportional to the level of cAMP that binds the sensor protein, which corresponds to the level of cAMP in the surrounding environment. In certain embodiments, binding of cAMP to the cAMP sensor protein will cause a change in the level of fluorescence of at least 5%, at least 6%, at least 7%, at least 8%, at least 9%, at least 10%, at least 15%, at least 20% or at least 30%. Methods of measuring changes in fluorescence are known to those skilled in the art.

As stated above, in cAMP sensor proteins of the present invention, the first polypeptide is linked to a single fluorescent protein. In one embodiment, the first polypeptide and the single fluorescent protein are directly linked. As used herein, direct linkage means that amino acids of the first polypeptide are covalently joined to amino acids of the single fluorescent protein. That is, there are no unrelated amino acid sequences between (covalently joining) an amino acid of the first polypeptide and an amino acid of the singe fluorescent protein. For example, if the first polypeptide consists of the amino acid sequence encoding a protein comprising a cAMP-binding domain, such as Epac2, covalently linkage of an amino acid (e.g., the N-terminal or C-terminal amino acid) with an amino acid of the single fluorescent protein represents direct joining of these two molecules.

Alternatively, the first polypeptide and the single fluorescent protein can be linked by a linker sequence. A linker sequence is a contiguous series of amino acid residues which may or may not be related to either the first polypeptide or the single fluorescent protein. Typically, linker sequences are short sequences, consisting of between 1 and about 10 amino acids and thus, while linker sequences may be related to either the first polypeptide or other single fluorescent protein, linker sequences do not comprise the activity (e.g., cAMP binding or fluorescence) of either. Preferred linker sequences are those that are unrelated to the sequence of either the first polypeptide or the single fluorescent protein. Linker sequences are used to join the N terminal, or the C-terminal, end of the single fluorescent protein with the N-terminal, or the C-terminal, end of the first polypeptide. It should be appreciated that in embodiments in which the single fluorescent protein is circularly permuted, the N- and C-terminal ends of the circularly permuted protein may not be the same as the N and C-terminal ends found in the native fluorescent protein from which the circularly permuted protein was derived. Linkers containing amino acids with side chains that give the linker ridged structure can be used to couple conformational changes in the cAMP binding domain to changes in the structure of the fluorescent protein barrel. Moreover, without being bound by theory, it is believed that, linkers with bulky amino acids that can form a surface/structure capable of occluding the hole in the side of the barrel produced by circular permutation are best capable of producing large changes in fluorescence by protecting the chromophore environment in one configuration and in another configuration producing a large hole in the side of the protein barrel that renders the chromophore less fluorescent. Examples of linkers useful for producing cAMP sensor proteins of the present invention include, but are not limited to, amino acid sequences such as LE, AI, PV, SH, TR, FN, LV, ENNHLS, LVSH, and FNNP.

Heretofore has been described a cAMP sensor protein, comprising a cAMP-binding domain, covalently joined at one end, either directly or indirectly, to a single fluorescent protein. Such cAMP sensor proteins can also comprise additional amino acid sequences. Thus, in one embodiment, the cAMP sensor protein comprises a second polypeptide, wherein the second polypeptide is linked to the single fluorescent protein such that the single fluorescent protein is flanked by the first and second polypeptide. In such an embodiment, each end of the single fluorescent protein (SFP) is covalently joined to a different polypeptide; either the first polypeptide (P1) or the second polypeptide (P2). The possible variations of such a construct can be illustrated as follows: P1-SFP-P2 and P2-SFP-P1. From such illustration, one skilled in the art will understand that in such a construct, the single fluorescent protein resides between the first and second polypeptides. It should further be appreciated that the N-terminal end of the single fluorescent protein can be joined to either the N- or C-terminal end of a polypeptide (first or second). Likewise, the C-terminal end of the single fluorescent protein can be joined to the N- or C-terminal end of the other polypeptide (first or second). Thus it can be seen that many variations are possible, with regard to orientation of the amino and carboxyl ends of the first polypeptide, the single fluorescent protein and the second polypeptide. All such variations are encompassed by the present invention, so long as the variant has the activities described herein. In one embodiment, the N-terminal amino acid of the single fluorescent protein is linked to the carboxyl end of the first polypeptide. In one embodiment, the N-terminal amino acid of the single fluorescent protein is linked to the amino end of the first polypeptide. In one embodiment, the N-terminal amino acid of the single fluorescent protein is linked to the carboxyl end of the second polypeptide. In one embodiment, the N-terminal amino acid of the single fluorescent protein is linked to the amino end of the first polypeptide.

Any polypeptide can be used as the second polypeptide, as long as the resulting cAMP sensor protein functions for the intended purpose described herein; that is, as long as the resulting construct binds cAMP and such binding causes a change in fluorescence of the cAMP sensor. The second polypeptide may or may not comprise an amino acid sequence derived from the same protein from which the amino acid sequence of the first polypeptide was derived. For example, if the first polypeptide comprises an amino acid sequences derived from EPAC1, the second polypeptide can, but need not, comprise an amino acid sequence from EPAC1. Thus, in one embodiment, the second polypeptide and the first polypeptide comprise amino acid sequence from the same protein. Alternatively, in one embodiment, the second polypeptide and the first polypeptide comprise amino acid sequence from unrelated (i.e., different) proteins. According to the present invention, two proteins are unrelated if their sequences differ by at least 35%, or if their structural relatedness differs by more than 50%. Methods of determining the relatedness of two proteins are known in the art.

In one embodiment, the second polypeptide comprises an amino acid sequence from a protein selected from the group consisting of Epac1, Epac2, protein kinase A (PKA) and RAP1B. In one embodiment, the second polypeptide comprises at least 50 contiguous amino acids, at least 100 contiguous amino acids, or at least 150 contiguous amino acids from a RAP1B protein. In one embodiment, the second polypeptide comprises at least 50 contiguous amino acids, at least 100 contiguous amino acids, or at least 150 contiguous amino acids from SEQ ID NO:76. In one embodiment, the second polypeptide comprises at least 50 contiguous amino acids, at least 100 contiguous amino acids, at least 150 contiguous amino acids, or at least 200 contiguous amino acids, or at least 250 contiguous amino acids from a PKA protein. In one embodiment, the second polypeptide comprises at least 50 contiguous amino acids, at least 100 contiguous amino acids, at least 150 contiguous amino acids, at least 200 contiguous amino acids, or at least 250 contiguous amino acids from SEQ ID NO:75. In one embodiment, the second polypeptide comprises at least 200 contiguous amino acids, at least 300 contiguous amino acids, at least 400 contiguous amino acids, at least 500 contiguous amino acids or at least 600 contiguous amino acids from an Epac1 or Epac2 protein. In one embodiment, the second polypeptide comprises at least 200 contiguous amino acids, at least 300 contiguous amino acids, at least 400 contiguous amino acids, at least 500 contiguous amino acids or at least 600 contiguous amino acids from SEQ ID NO:74 or SEQ ID NO:35.

In one embodiment, the second polypeptide comprises a variant of a protein disclosed herein. In one embodiment, the second polypeptide comprises an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 70% and 99%, in whole integer increments), to the amino acid sequence of a protein selected from the group consisting of Epac1, Epac2, protein kinase A (PKA) and RAP1B. In one embodiment, the second polypeptide comprises an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 75% and 99%, in whole integer increments), to a sequence selected from SEQ ID NO:35, SEQ ID NO:74, SEQ ID NO:75 and SEQ ID NO:76. In one embodiment, the second polypeptide comprises a sequence selected from the group consisting of SEQ ID NO:35, SEQ ID NO:74, SEQ ID NO:75 and SEQ ID NO:76.

As has been described for the linkage between the first polypeptide and the single fluorescent protein, the second polypeptide and the single fluorescent protein can be directly linked, or they can be linked by a linker sequence. In one embodiment, the second polypeptide and the single fluorescent protein are directly linked. In one embodiment, the second polypeptide and the single fluorescent protein can be linked by a linker sequence.

Because the first and second polypeptides can comprise amino acid sequences from the same protein, it should be appreciated that while the sequences comprised by the first and second polypeptides can come from the same portion of the same protein, they can also come from different portions (e.g., domains) from the same protein. Thus, the astute person skilled in the art will understand that a cAMP sensor protein can be constructed by dividing a cAMP-binding protein into two portions, one of which contains the cAMP-binding domain, and linking one portion to one end of a single fluorescent protein and the other portion to the other end of the single fluorescent protein. In essence, the single fluorescent portion is inserted into the cAMP-binding protein. It will be appreciated that such insertion can be anywhere within the amino acid sequence of the cAMP-binding protein, as long as the resulting construct can bind cAMP and such binding causes a change in fluorescence of the single fluorescent protein. Thus, in one embodiment, the amino acid sequences comprised by the first and second polypeptides are from different regions of the same protein. In one embodiment, the single fluorescent protein is inserted into a cAMP-binding domain. In certain embodiments, the single fluorescent protein is inserted into the cAMP-binding protein such that the portion of the cAMP binding protein upstream of the insertion site is coupled to the N-terminus of the single fluorescent protein and the portion of the cAMP binding protein downstream of the insertion site is coupled to the C-terminus of the FP. In certain embodiments, the single fluorescent protein is inserted into the cAMP-binding protein such that the portion of the cAMP binding protein upstream of the insertion site is coupled to the C-terminus of the single fluorescent protein and the portion of the cAMP binding protein downstream of the insertion site is coupled to the C-terminus of the FP.

To further illustrate such a construct, it is known that the EPAC1 protein contains a regulatory domain and a catalytic domain. In such case, if the amino acid sequences comprised by the first and second polypeptides are both from EPAC1, one polypeptide (the first or second) can comprise the regulatory domain while the other polypeptide (either the first or second) can comprise the catalytic domain. In one embodiment, the first and second polypeptides are capable of interacting. For example, the first and second polypeptide may bind to from a complex. In certain embodiments, such binding is non-covalent binding due to, for example, hydrogen, ionic, hydrophobic or Vander Waal interactions. In certain embodiments, one polypeptide comprises enzymatic activity and the other polypeptide is a substrate for the enzyme.

Insertion of single fluorescent protein into the sequence of a cAMP-binding protein can be done by such that the ends of the single fluorescent protein are linked to two amino acids that are normally adjoining in the cAMP-binding protein. For example, in a construct in which the single fluorescent protein is inserted between amino acids 100 and 101 of EPAC1, one end of the single fluorescent protein will be covalently linked to amino acid 100, while the other end of the single fluorescent protein will be covalently joined to amino acid 101. In such a construct, no amino acids are removed from the cAMP-binding protein. Thus, in certain embodiments the insertion region comprises the native amino acid sequence of the cAMP binding protein.

It is known in the art that some proteins contain regions between domains referred to as hinge regions. Such hinge regions allow movement of the domains relative to one another. Because it is believed that changes in fluorescence of sensors of the present invention results from changes in the environment of the chromophore due to relative movement of sequences flanking the fluorescent protein, such hinge regions can be used as sites of insertion of the fluorescent protein. Thus, in one embodiment, the fluorescent protein is inserted into the hinge region of a cAMP-binding protein. In one embodiment, the fluorescent protein is inserted into a sequence comprising SEQ ID NO:40.

In certain embodiments, insertion of the single fluorescent protein can comprise additions, deletions or alterations (e.g., substitutions) of amino acids that make the sequence deviate from the native sequence. For example, in various embodiments, the insertion region may comprise deletions of at least 1, 2, 3, 4, 5, 6, 7, 8, 9, 10, 11, 12, 13, 14, 15, 16, 17, 18, 19, or 20 amino acids to the native sequence. In various embodiments, the insertion region may comprise deletions of at least 1, 2, 3, 4, 5, 6, 7, 8, 9, 10, 11, 12, 13, 14, 15, 16, 17, 18, 19, 20, 21, or 22 amino acids from the native sequence. In some embodiments the insertion region may comprise one or more substitutions of the amino acids of the native sequence. In some embodiments, the insertion site may be after the last amino acid of a truncated cAMP binding protein. In this embodiment, the cAMP binding protein is coupled to the N-terminus of the single fluorescent protein. In some embodiments, the insertion site may be before the first amino acid of the cAMP binding protein such that the cAMP binding protein is coupled to the C-terminus of the single fluorescent protein.

Exemplary embodiments of the present are listed below in Table 1.

TABLE 1

Sequences of exemplary cAMP sensor proteins and related molecules

| Description | Name of Molecule | Description |
| --- | --- | --- |
| SEQID 1 | EcpG10G2-RasGEF-T2 | Best Upward Sensor amino acid, protein translation of SEQ ID NO: 41 |
| SEQID 2 | Library2-1 G12 | amino acid, protein translation of SEQ ID NO: 42 |
| SEQID 3 | Lib2-1 G12 RasGEF-T2 | amino acid, protein translation of SEQ ID NO: 43 |
| SEQID 4 | EcpG10 G2 | amino acid, protein translation of SEQ ID NO: 44 |
| SEQID 5 | Lib2-2 E7 | amino acid, protein translation of SEQ ID NO: 45 |
| SEQID 6 | Lib6-2 C1 T2 | Best Downward amino acid, protein translation of SEQ ID NO: 46 |
| SEQID 7 | Lib5-1 D2 | amino acid, protein translation of SEQ ID NO: 47 |
| SEQID 8 | Lib5-1 G12 | amino acid, protein translation of SEQ ID NO: 48 |
| SEQID 9 | Lib2-1 B12 | amino acid, protein translation of SEQ ID NO: 49 |
| SEQID 10 | Lib 1 C2 | amino acid, protein translation of SEQ ID NO: 50 |
| SEQID 11 | EcpG12 | amino acid, protein translation of SEQ ID NO: 51 |
| SEQID 12 | Lib2-2 F9 | amino acid, protein translation of SEQ ID NO: 52 |
| SEQID 13 | Lib2-2 G4 | amino acid, protein translation of SEQ ID NO: 53 |
| SEQID 14 | Lib2-1 C2 | amino acid, protein translation of SEQ ID NO: 54 |
| SEQID 15 | Lib5-1 E7 | amino acid, protein translation of SEQ ID NO: 55 |
| SEQID 16 | Library6-2 C1 | amino acid, protein translation of SEQ ID NO: 56 |
| SEQID 17 | EcpG15 | amino acid, protein translation of SEQ ID NO: 57 |
| SEQID 18 | Lib2-2 D1 | amino acid, protein translation of SEQ ID NO: 58 |
| SEQID 19 | Lib2-2 A11 | amino acid, protein translation of SEQ ID NO: 59 |

TABLE 1-continued

Sequences of exemplary cAMP sensor proteins and related molecules

| Description | Name of Molecule | Description |
|---|---|---|
| SEQID 20 | Lib2-2 A5 | amino acid, protein translation of SEQ ID NO: 60 |
| SEQID 21 | Lib2-1 D1 | amino acid, protein translation of SEQ ID NO: 61 |
| SEQID 22 | Lib 1 G2 | amino acid, protein translation of SEQ ID NO: 62 |
| SEQID 23 | Lib1 A6 | amino acid, protein translation of SEQ ID NO: 63 |
| SEQID 24 | Lib6-2 F1 | amino acid, protein translation of SEQ ID NO: 64 |
| SEQID 25 | EcpG10 | amino acid, protein translation of SEQ ID NO: 65 |
| SEQID 26 | EcpG10 G2N-G1C | amino acid, protein translation of SEQ ID NO: 66 |
| SEQID 27 | EPAC2-GFP-RAP1B | amino acid, protein translation of SEQ ID NO: 67 |
| SEQID 28 | EcpG13 | amino acid, protein translation of SEQ ID NO: 68 |
| SEQID 29 | EcpG23 | amino acid, protein translation of SEQ ID NO: 69 |
| SEQID 30 | EcpG9 | amino acid, protein translation of SEQ ID NO: 70 |
| SEQID 31 | EcpG22 | amino acid, protein translation of SEQ ID NO: 71 |
| SEQID 32 | EcpG18 | amino acid, protein translation of SEQ ID NO: 72 |
| SEQID 33 | EcpG24 | amino acid, protein translation of SEQ ID NO: 73 |
| SEQID 34 | Hinge | amino acid, protein translation of SEQ ID NO: 40 |
| SEQID 35 | Human EPAC2 from Genbank-translation | amino acid, protein translation of SEQ ID NO: 39 |
| SEQID 36 | cAMP binding domain A | amino acid, protein translation of SEQ ID NO: |
| SEQID 37 | cAMP binding domain B | amino acid, protein translation of SEQ ID NO: |
| SEQID 38 | cpEGFP | amino acid, protein translation of SEQ ID NO: |
| SEQID 39 | Human EPAC2 from Genbank | Nucleotide of SEQ ID NO: 35 |
| SEQID 40 | Hinge | Nucleotide of SEQ ID NO: 34 |
| SEQID 41 | EcpG10G2-RasGEF-T2 | Nucleotide of SEQ ID NO: 1 |
| SEQID 42 | Library2-1 G12 | Nucleotide of SEQ ID NO: 2 |
| SEQID 43 | Lib2-1 G12 RasGEF-T2 | Nucleotide of SEQ ID NO: 3 |
| SEQID 44 | EcpG10 G2 | Nucleotide of SEQ ID NO: 4 |
| SEQID 45 | Lib2-2 E7 | nucleotide of SEQ ID NO: 5 |
| SEQID 46 | Lib6-2 C1 T2 | nucleotide of SEQ ID NO: 6 |
| SEQID 47 | Lib5-1 D2 | nucleotide of SEQ ID NO: 7 |
| SEQID 48 | Lib5-1 G12 | nucleotide of SEQ ID NO: 8 |
| SEQID 49 | Lib2-1 B12 | nucleotide of SEQ ID NO: 9 |
| SEQID 50 | Lib 1 C2 | nucleotide of SEQ ID NO: 10 |
| SEQID 51 | EcpG12 | nucleotide of SEQ ID NO: 11 |
| SEQID 52 | Lib2-2 F9 | nucleotide of SEQ ID NO: 12 |
| SEQID 53 | Lib2-2 G4 | nucleotide of SEQ ID NO: 13 |
| SEQID 54 | Lib2-1 C2 | nucleotide of SEQ ID NO: 14 |
| SEQID 55 | Lib5-1 E7 | nucleotide of SEQ ID NO: 15 |
| SEQID 56 | Library6-2 C1 | nucleotide of SEQ ID NO: 16 |
| SEQID 57 | EcpG15 | nucleotide of SEQ ID NO: 17 |
| SEQID 58 | Lib2-2 D1 | nucleotide of SEQ ID NO: 18 |
| SEQID 59 | Lib2-2 A11 | nucleotide of SEQ ID NO: 19 |
| SEQID 60 | Lib2-2 A5 | nucleotide of SEQ ID NO: 20 |
| SEQID 61 | Lib2-1 D1 | nucleotide of SEQ ID NO: 21 |
| SEQID 62 | Lib 1 G2 | nucleotide of SEQ ID NO: 22 |
| SEQID 63 | Lib1 A6 | nucleotide of SEQ ID NO: 23 |
| SEQID 64 | Lib6-2 F1 | nucleotide of SEQ ID NO: 24 |
| SEQID 65 | EcpG10 | nucleotide of SEQ ID NO: 25 |
| SEQID 66 | EcpG10 G2N-G1C | nucleotide of SEQ ID NO: 26 |
| SEQID 67 | EPAC2-GFP-RAP1B | nucleotide of SEQ ID NO: 27 |
| SEQID 68 | EcpG13 | nucleotide of SEQ ID NO: 28 |
| SEQID 69 | EcpG23 | nucleotide of SEQ ID NO: 29 |
| SEQID 70 | EcpG9 | nucleotide of SEQ ID NO: 30 |
| SEQID 71 | EcpG22 | nucleotide of SEQ ID NO: 31 |
| SEQID 72 | EcpG18 | nucleotide of SEQ ID NO: 32 |
| SEQID 73 | EcpG24 | nucleotide of SEQ ID NO: 33 |
| SEQID74 | GenBank NP_001092002.1 (Epac1) | Amino acid sequence of Epac1 |
| SEQID 75 | GenBank NP_002725.1 (PKA) | Amino acid sequence of PKA |
| SEQID 76 | GenBank AAH95467.1 (Rap1B) | Amino acid sequence of Rap1B |
| SEQID 77 | EGFP | Enhanced fluorescent green protein |

In one embodiment, a cAMP sensor protein comprises an amino acid sequence at least 70%, at least 80%, at least 85%, at least 90%, at least 95%, at least 97% or at least 99% identical to a sequence in Table 1. In one embodiment, a cAMP sensor protein comprises a sequence in Table 1. In one embodiment, a cAMP sensor protein comprises an amino acid sequence at least 70%, at least 80%, at least 85%, at least 90%, at least 95%, at least 97% or at least 99% identical to a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32 and SEQ ID NO:33. In one embodiment, a cAMP sensor protein comprises an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32 and SEQ ID NO:33.

In one embodiment, a cAMP sensor protein of the present invention is encoded by a nucleic acid molecule comprising a nucleic acid sequence at least 70%, at least 80%, at least 85%, at least 90%, at least 95%, at least 97% or at least 99% identical to a sequence selected from the group consisting of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72 and SEQ ID NO:73. In one embodiment, a cAMP sensor protein of the present invention is encoded by a nucleic acid molecule comprising a nucleic acid sequence selected from the group consisting of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72 and SEQ ID NO:73.

cAMP sensor proteins of the present invention are encoded by recombinant nucleic acid molecules of the present invention. In accordance with the present invention, a recombinant nucleic acid molecule is one that has been created by the hand of man. As such, recombinant nucleic acid molecules of the present invention can be a combination of molecules obtained from a natural source, and molecules obtained through synthesis (e.g., cloning of genes or fragments thereof).

A recombinant nucleic acid molecule of the present invention can be produced using a number of methods known to those skilled in the art (see, for example, Sambrook et al., *Molecular Cloning: A Laboratory Manual, Third Edition*, 2001, which is incorporated herein by reference in its entirety). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule variants can be selected from a mixture of modified nucleic acids by screening for the function of the protein encoded by the nucleic acid (e.g., the ability to bind cAMP, the ability to fluoresce, etc.). Such screening methods have been described herein and are routinely performed by those skilled in the art.

One embodiment of the present invention is a nucleic acid molecule encoding a cAMP sensor protein of the present invention. One embodiment of the present invention is a nucleic acid molecule encoding a cAMP sensor protein comprising a first polypeptide linked to a single fluorescent protein, wherein the first polypeptide comprises a cAMP-binding domain, wherein the single fluorescent protein consists of an uninterrupted amino acid sequence, and wherein the fluorescence of the cAMP sensor changes upon binding cAMP. In one embodiment, the nucleic acid molecule encodes a cAMP sensor in which the first polypeptide comprises an amino acid sequence from a protein selected from the group consisting of Epac1, Epac2 and protein kinase A (PKA). In one embodiment, the nucleic acid molecule encodes a cAMP sensor in which the first polypeptide comprises at least 50 contiguous amino acids, at least 100 contiguous amino acids, at least 150 contiguous amino acids, at least 200 contiguous amino acids, or at least 250 contiguous amino acids from a PKA protein. In one embodiment, the nucleic acid molecule encodes a cAMP sensor in which the first polypeptide comprises at least 50 contiguous amino acids, at least 100 contiguous amino acids, at least 150 contiguous amino acids, at least 200 contiguous amino acids, or at least 250 contiguous amino acids from SEQ ID NO:75. In one embodiment, the nucleic acid molecule encodes a cAMP sensor in which the first polypeptide comprises at least 200 contiguous amino acids, at least 300 contiguous amino acids, at least 400 contiguous amino acids, at least 500 contiguous amino acids or at least 600 contiguous amino acids from an Epac1 or Epac2 protein. In one embodiment, the nucleic acid molecule encodes a cAMP sensor in which the first polypeptide comprises at least 200 contiguous amino acids, at least 300 contiguous amino acids, at least 400 contiguous amino acids, at least 500 contiguous amino acids or at least 600 contiguous amino acids from SEQ ID NO:74 or SEQ ID NO:35. In one embodiment, the nucleic acid molecule encodes a cAMP sensor in which the first polypeptide comprises the amino acid sequence of a protein selected from the group consisting of Epac1, Epac2 and protein kinase A (PKA). In one embodiment, the nucleic acid molecule encodes a cAMP sensor in which first polypeptide comprises an amino acid sequence selected from the group consisting of SEQ ID NO:35, SEQ ID NO:74 and SEQ ID NO:75.

One embodiment of the present invention is a nucleic acid molecule encoding a cAMP sensor protein comprising a first polypeptide linked to a single fluorescent protein, wherein the first polypeptide is capable of comprising a cAMP-binding domain, wherein the single fluorescent protein consists of an uninterrupted amino acid sequence, and wherein the fluorescence of the cAMP sensor changes upon binding cAMP. In one embodiment, the nucleic acid molecule encoded a cAMP sensor in which the first polypeptide comprises a sequence from a protein that does not naturally contain a cAMP-binding site. In one embodiment, the nucleic acid molecule encodes a cAMP sensor in which the first polypeptide comprises at least 50 contiguous amino acids, at least 100 contiguous amino acids, or at least 150 contiguous amino acids from a RAP1B protein. In one embodiment, the nucleic acid molecule encodes a cAMP sensor in which the first polypeptide comprises at least 50 contiguous amino acids, at least 100 contiguous amino acids, or at least 150 contiguous amino acids from SEQ ID NO:76.

In one embodiment, a nucleic acid molecule encodes a cAMP sensor protein comprising variant sequences. Thus, in one embodiment, the nucleic acid molecule encodes a cAMP sensor in which the first polypeptide comprises a variant of a cAMP-binding protein. In one embodiment, the nucleic acid molecule encodes a cAMP sensor in which the first polypeptide comprises an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to the amino acid sequence of a protein selected from the group consisting of Epac1, Epac2, protein kinase A (PKA) and RAP1B. In one embodiment, the nucleic acid molecule encodes a cAMP sensor in which the first polypeptide comprises an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 75% and 99%, in whole integer increments), to a sequence selected from SEQ ID NO:35, ID NO:74, SEQ ID NO:75 and SEQ ID NO:76.

One embodiment of the present invention is a nucleic acid molecule encoding a cAMP sensor of the present in invention in which the fluorescent protein comprises at least a portion of a protein selected from the group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-*Aequorea* fluorescent protein. In one embodiment, the nucleic acid molecule encodes a cAMP sensor in which the fluorescent protein comprises at least 50 contiguous amino acids, at least 100 contiguous amino acids, at least 150 contiguous amino acids, or at least 200 contiguous amino acids from a protein selected from the group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-*Aequorea* fluorescent protein. In one embodiment, the nucleic acid molecule encodes a cAMP sensor in which the fluorescent protein comprises the amino acid sequence of a protein selected from group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-*Aequorea* fluorescent protein. In one embodiment, the nucleic acid molecule encodes a cAMP sensor in which the fluorescent protein comprises at least 50 contiguous amino acids, at least 100 contiguous amino acids, at least 150 contiguous amino acids, or at least 200 contiguous amino acids from the group consisting of SEQ ID NO:38 and SEQ ID NO:77. In one embodiment, the nucleic acid molecule encodes a cAMP sensor in which the fluorescent protein comprises a sequence selected from the group consisting of SEQ ID NO:38 and SEQ ID NO:77.

One embodiment of the present invention is a nucleic acid molecule encoding a cAMP sensor protein of the present in invention in which the fluorescent protein comprises a variant of a fluorescent protein disclosed herein. In one embodiment, the nucleic acid molecule encodes a cAMP sensor in which the fluorescent protein comprises a variant of a protein selected from the group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-*Aequorea* fluorescent protein. In one embodiment, the nucleic acid molecule encodes a cAMP sensor in which the fluorescent protein comprises an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical to a protein selected from the group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-*Aequorea* fluorescent protein. In one embodiment, the nucleic acid molecule encodes a cAMP sensor in which the fluorescent protein comprises a fluorescent protein comprising an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical to a sequence selected from the group consisting of SEQ ID NO:38 and SEQ ID NO:77.

In one embodiment, the nucleic acid molecule encodes a cAMP sensor in which the fluorescent protein comprises an amino acid sequence from a protein selected from the group consisting of GFP, eGFP, eYFP Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire, mKOK, mUKG, Clover, mKate, tagRFP, tagGFP, mNEON green, and a synthetic non-*Aequorea* fluorescent protein. In one embodiment, the nucleic acid molecule encodes a cAMP sensor in which the fluorescent protein comprises an amino acid sequence selected from the group consisting of SEQ ID NO:38 and SEQ ID NO:77.

In one embodiment, the nucleic acid molecule encodes a cAMP sensor in which the fluorescent protein is circularly permuted. In preferred embodiments, the nucleic acid molecule encodes a cAMP sensor in which the fluorescent protein comprises N and the C termini of the protein placed adjacent to the chromophore. In one embodiment, the nucleic acid molecule encodes a cAMP sensor in which the s fluorescent protein is EGFP which has been circularly permuted around amino acids 149-144 [SEQ ID NO:39].

One embodiment of the present invention is a nucleic acid molecule encoding a cAMP sensor protein of the present invention comprising a second polypeptide, wherein the second polypeptide is linked to the single fluorescent protein such that the single fluorescent protein is flanked by the first and second polypeptide. In one embodiment, the nucleic acid molecule encodes a cAMP sensor in which the second polypeptide comprises an amino acid sequence from a protein selected from the group consisting of Epac1, Epac2, protein kinase A (PKA) and RAP1B. In one embodiment, the nucleic acid molecule encodes a cAMP sensor in which the second polypeptide comprises at least 50 contiguous amino acids, at least 100 contiguous amino acids, or at least 150 contiguous amino acids from a RAP1B protein. In one embodiment, the nucleic acid molecule encodes a cAMP sensor in which the second polypeptide comprises at least 50 contiguous amino acids, at least 100 contiguous amino acids, or at least 150 contiguous amino acids from SEQ ID NO:76. In one embodiment, the nucleic acid molecule encodes a cAMP sensor in which the second polypeptide comprises at least 50 contiguous amino acids, at least 100 contiguous amino acids, at least 150 contiguous amino acids, at least 200 contiguous amino acids, or at least 250 contiguous amino acids from a PKA protein. In one embodiment, the nucleic acid molecule encodes a cAMP sensor in which the second polypeptide comprises at least 50 contiguous amino acids, at least 100 contiguous amino acids, at least 150 contiguous amino acids, at least 200 contiguous amino acids, or at least 250 contiguous amino acids from SEQ ID NO:75. In one embodiment, the nucleic acid molecule encodes a cAMP sensor in which the second polypeptide comprises at least 200 contiguous amino acids, at least 300 contiguous amino acids, at least 400 contiguous amino acids, at least 500 contiguous amino acids or at least 600 contiguous amino acids from an Epac1 or Epac2 protein. In one embodiment, the nucleic acid molecule encodes a cAMP sensor in which the second polypeptide comprises at least 200 contiguous amino acids, at least 300 contiguous amino acids, at least 400 contiguous amino acids, at least 500 contiguous amino acids or at least 600 contiguous amino acids from SEQ ID NO:74 or SEQ ID NO:35.

In one embodiment, the nucleic acid molecule encodes a cAMP sensor in which the second polypeptide comprises a variant of a protein disclosed herein. In one embodiment, the nucleic acid molecule encodes a cAMP sensor in which the second polypeptide comprises an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 70% and 99%, in whole integer increments), to the amino acid sequence of a protein selected from the group consisting of Epac1, Epac2, protein kinase A (PKA) and RAP1B. In one embodiment, the nucleic acid molecule encodes a cAMP sensor in which the second polypeptide comprises an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 75% and 99%, in whole integer increments), to a sequence selected from SEQ ID NO:35, SEQ ID NO:74, SEQ ID NO:75 and SEQ ID NO:76.

In one embodiment, a nucleic acid molecule of the present invention encodes a cAMP sensor protein comprising an amino acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 75% and 99%, in whole integer increments), to a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32 and SEQ ID NO:33. In one embodiment, a nucleic acid molecule of the present invention encodes a cAMP sensor protein comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32 and SEQ ID NO:33. In one embodiment, a nucleic acid molecule of the present invention comprises a nucleic acid sequence at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 75% and 99%, in whole integer increments), to a sequence selected from the group consisting of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72 and SEQ ID NO:73. In one embodiment, a nucleic acid molecule of the present invention comprises a nucleic acid sequence selected from the group consisting of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72 and SEQ ID NO:73.

Also provided herein are vectors comprising the sensor-encoding nucleic acid sequences. Examples of suitable vectors include, but are not limited to, plasmids, artificial chromosomes, such as BACs, YACs, or PACs, and viral vectors. As used herein, vectors are agents that transport the disclosed nucleic acids into a cell without degradation and, optionally, include a promoter yielding expression of the nucleic acid molecule in the cells into which it is delivered.

Examples of viral vectors useful for practicing the present invention include, but are not limited to, Adenovirus, Adeno-associated virus, herpes virus, Vaccinia virus, Polio virus, Sindbis, and other RNA viruses, including these viruses with the HIV backbone. Any viral families which share the properties of these viruses which make them suitable for use as vectors are suitable. Retroviral vectors, in general are described by Coffin et al., 1997, which is incorporated by reference herein for the vectors and methods of making them. The construction of replication-defective adenoviruses has been described. (Berkner et al. 1987; Massie et al., 1986; Haj-Ahmad et al., 1986; Davidson et al., 1987; Zhang et al., 1993). Recombinant adenoviruses have been shown to achieve high efficiency after direct, in vivo delivery to airway epithelium, hepatocytes, vascular endothelium, CNS parenchyma, and a number of other tissue sites. Other useful systems include, for example, replicating and host-restricted non-replicating vaccinia virus vectors. Bacculovirus has also been demonstrated as a particularly useful vector for drug discovery applications (Kost et. al 2005)

Non-viral based vectors, can include expression vectors comprising nucleic acid molecules and nucleic acid sequences encoding polypeptides, wherein the nucleic acids are operably linked to an expression control sequence. Suitable vector backbones include, for example, those routinely used in the art such as plasmids, artificial chromosomes, BACs, YACs, or PACs. Numerous vectors and expression systems are commercially available from such corporations as Novagen (Madison, Wis.), Clonetech (Pal Alto, Calif.), Stratagene (La Jolla, Calif.), and Invitrogen/Life Technologies (Carlsbad, Calif.).

Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns. Preferred promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters, e.g. .beta.-actin promoter or EF1.alpha. promoter, or from hybrid or chimeric promoters (e.g., CMV promoter fused to the .beta.-actin promoter). Promoters from the host cell or related species are also useful herein. Enhancer generally refers to a sequence of DNA that functions at no fixed distance from the transcription start site and can be either 5' or 3' to the transcription unit. Enhancers usually function to increase transcription from nearby promoters. Enhancers can also contain response elements that mediate the regulation of transcription. Preferred examples are the SV40 enhancer on the late side of the replication origin, the cytomegalovirus early promoter enhancer, the polyoma enhancer on the late side of the replication origin, and adenovirus enhancers.

The promoter and/or the enhancer can be inducible (e.g. chemically or physically regulated). A chemically regulated promoter and/or enhancer can, for example, be regulated by the presence of alcohol, tetracycline, a steroid, or a metal. A physically regulated promoter and/or enhancer can, for example, be regulated by environmental factors, such as temperature and light. Optionally, the promoter and/or enhancer region can act as a constitutive promoter and/or enhancer to maximize the expression of the region of the transcription unit to be transcribed. In certain vectors, the promoter and/or enhancer region can be active in a cell type specific manner. Optionally, in certain vectors, the promoter and/or enhancer region can be active in all eukaryotic cells, independent of cell type. Preferred promoters of this type are the CMV promoter, the SV40 promoter, the beta.-actin promoter, the EF1.alpha. promoter, and the retroviral long terminal repeat (LTR).

Cells comprising the sensors of the present invention, the sensor-encoding nucleic acid sequences or vectors comprising the sensor-encoding nucleic acid sequence are provided. The cell can be, for example, a eukaryotic or prokaryotic cell. Suitable cells include, but are not limited to cells of *E. coli, Pseudomonas, Bacillus, Streptomyces*; fungi cells such as yeasts (*Saccharomyces*, and methylotrophic yeast such as *Pichia, Candida, Hansenula*, and *Torulopsis*); and animal cells, such as CHO, R1.1, B-W and LM cells, African Green Monkey kidney cells (for example, COS 1, COS 7, BSC1, BSC40, and BMT10), insect cells (for example, Sf9), human cells and plant cells. Suitable human cells include, for example, HeLa cells or human embryonic kidney (HEK) cells. Cells can be induced pluripotent stem cells (iPSC). Cells that can be used herein are commercially available from, for example, the American Type Culture Collection (ATCC), P.O. Box 1549, Manassas, Va. 20108. See also F. Ausubel et al., Current Protocols in Molecular Biology, John Wiley & Sons, New York, N.Y., (1998). Optionally, the sensor-encoding nucleic acid sequence may be located in the genome of the cell.

Methods of culturing the provided cells are known in the art and the method of transformation and choice of expression vector will depend on the host system selected. Transformation and transfection methods are described, e.g., in Ausubel et al. (1998), and, as described above, expression vectors may be chosen from examples known in the art. There are a number of compositions and methods which can be used to deliver the nucleic acid molecules and/or polypeptides to cells, either in vitro or in vivo via, for example, expression vectors. These methods and compositions can largely be broken down into two classes: viral based delivery systems and non-viral based delivery systems. Cells may be stable cell lines or transiently expressing the sensor. Such methods are well known in the art and readily adaptable for use with the compositions and methods described herein.

One embodiment of the present invention is a method of detecting cAMP levels comprising expressing a cAMP sensor protein of the present invention in a cell, and detecting the level of fluorescence from the sensor. In one embodiment, the cAMP sensor protein is expressed in the cell by inserting a nucleic acid molecule encoding the cAMP sensor into the cell. In one embodiment, changes in the level of cAMP are detected by detecting changes in the level of fluorescence from the cAMP sensor protein.

One embodiment of the present invention is a method of identifying a compound that affects cAMP levels in a cell, the method comprising expressing a cAMP sensor protein in a cell and detecting changes in the level of fluorescence from the cAMP sensor protein. In one embodiment, the cell is treated with a test compound and changes in fluorescence form the cAMP sensor protein measured.

As used herein, unless otherwise specified, reference to a percent (%) identity refers to an evaluation of homology which is performed using: (1) a BLAST Basic BLAST homology search using blastp for amino acid searches and blastn for nucleic acid searches with standard default parameters, wherein the query sequence is filtered for low complexity regions by default (described in Altschul et al., 1997); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, Methods of Enzymology, Vol. 194, Guthrie et al., eds., Cold Spring Harbor Laboratory Press (1990); Biology and activities of yeasts, Skinner, et al., eds., Academic Press (1980); Methods in yeast genetics: a laboratory course manual, Rose et al., Cold Spring Harbor Laboratory Press (1990); The Yeast *Saccharomyces*: Cell Cycle and Cell Biology, Pringle et al., eds., Cold Spring Harbor Laboratory Press (1997); The Yeast *Saccharomyces*: Gene Expression, Jones et al., eds., Cold Spring Harbor Laboratory Press (1993); The Yeast *Saccharomyces*: Genome Dynamics, Protein Synthesis, and Energetics, Broach et al., eds., Cold Spring Harbor Laboratory Press (1992); Molecular Cloning: A Laboratory Manual, second edition (Sambrook et al., 1989) and Molecular Cloning: A Laboratory Manual, third edition (Sambrook and Russel, 2001), (jointly referred to herein as "Sambrook" ambrooktice of the present invention will employ, unless otherwise indiCell Biology, Pringle et al., eds., Cold Spring Harbor Laboratory Press (1997); The Yeast *Saccharomyces*: Gene Expressioane (1988) Antibodies, A Laboratory Manual, Cold Spring Harbor Publications, New York; Harlow and Lane (1999) Using Antibodies: A Laboratory Manual Cold Spring Harbor Laboratory Press, Cold Spring Harbor, N.Y. (jointly referred to herein as "Harlow and Lane"), Beaucage et al. eds., Current Protocols in Nucleic Acid Chemistry John Wiley & Sons, Inc., New York, 2000); Casarett and Doull's Toxicology The Basic Science of Poisons, C. Klaassen, ed., 6th edition (2001), and Vaccines, S. Plotkin and W. Orenstein, eds., 3rd edition (1999).

EXAMPLES

Example 1

Design, Construction and Testing of the cAMP Sensor

A. An enhanced fluorescent green protein (EFGP) was circularly permuted using the methods described in Sambrook, Joseph, Edward F. Fritsch, and Tom Maniatis. Molecular cloning. Vol. 2. New York: Cold spring harbor laboratory press, 1989; and Baird et al., 1999. The sequence of the resulting circularly permuted green fluorescent protein (cpEGFP) is represented by SEQ ID NO:39. The sequence LE was then added to the N-terminal end of the cpEGFP and the sequence TR was added to the C-terminal end of the cpEGFP. The cpEGFP, obtaining the linker sequences, was then inserted at various locations within the sequence of an Epac2 protein (SEQ ID NO:36), resulting in 28 unique prototype sensors. Nucleic acid molecules encoding each construct were cloned into a modified CMV expression plasmid based on pcDNA3 (Life Technologies (Grand Island, N.Y.))

To test the functionality of these 28 prototype sensors, each construct was co-expressed with the beta adrenergic receptor, which couples to the Gs signaling pathway when activated by isoproteronol, in HEK 293 cells, and the fluorescence measured as described below. Briefly, 96-well glass-bottom plates were coated with Poly-D-Lysine (Fisher Scientific, Pittsburgh, Pa.) and HEK 293 were seeded and cultured in EMEM (ATCC, Manassas, Va.) supplemented with 10% fetal bovine serum and Penicillin-Streptomycin at 37 when activated by isoproteronol, in HEK 293 cells, and the fluorescence truct DNA and 30 ng of beta adrenergic receptor per well, using Lipofectamine 2000 Transfection Reagent (Life Technologies, Grand Island, N.Y.) according to the manufacturer's protocol, and incubated for 24-48 hours at 37° C. in 5% CO2.

Prior to screening transfected cells for fluorescence, he EMEM culture medium was removed and 1×DPBS added to each well. A Zeiss Axiovert S100TV inverted microscope equipped with computer controlled excitation/emission filter wheels, shutters, and a Qimaging Retiga Exi CCD camera (Surrey, BC Canada) was used to image cells at 25e A) supplemented with 10% fetal bovine serum and Penicillin-Streptomycin at 37hn filters were used to resolve the green fluorescence from the cAMP sensors. Cells were analyzed for increases or decreases in fluorescence intensity upon addition of isoproternol, DMSO, forskolin and IBMX. To analyze the image stacks, background fluorescence was defined as a region of the image that contained no cells. The average value of this region was subtracted frame by frame from the measurements of the mean pixel values of the fluorescent cells. Fluorescence intensity data was plotted and analyzed with IGOR (Wavemetrics, Oswego, Oreg.).

For transient expression and screening in an automated fluorescence plate reader, HEK 293T cells were cultured in Corning Co-Star Polystyrene 96-well plates coated with Poly-D-Lysine. HEK293T cells were plated at 35,000 cells/well in 100 µl growth medium per well without antibiotics so that the cells would be 90-95% confluent at the time of transfection (approximately 24 hours later). For each transfection (i.e. one well in a 96-well plate), 160 ng of plasmid DNA (120 ng sensor+40 ng receptor) was diluted in 25 HEK 293T cells were cultured in Corning Co-Star Polystyrene 96-well plates coated with Poly-D-Lysine. HEK293T cells were plated at 35,000 cells/well in 100 screening in an automated and then the mixture was replaced with fresh medium. Prior to scanning a plate on the Biotek Synergy Mx, EMEM culture medium was replaced with 250 µl of 1×DPBS per well. Plates were read at 25° C., using monochromators set to 488/20 nm excitation and 530/20 nm emission to resolve the green fluorescence from the cAMP sensor.

The results of these analyses are shown below in Table 2.

TABLE 2

Relative fluorescence response of various cAMP sensors to isoproternol

| Clone Name | dF/F | Fluorescent Protein insertion site |
|---|---|---|
| EcpG1 | no response | D449 |
| EcpG2 | no response | K450 |
| EcpG3 | no response | E451 |
| EcpG4 | no response | D452 |
| EcpG5 | no response | F453 |
| EcpG6 | no response | N454 |
| EcpG7 | no response | R455 |
| EcpG8 | no response | I456 |
| EcpG9 | 13 | L457 |
| EcpG10 | −30 | R458 |
| EcpG11 | no response | D459 |
| EcpG12 | −36 | V460 |
| EcpG13 | −22 | E461 |
| EcpG14 | no response | A462 |
| EcpG15 | 34 | N463 |
| EcpG16 | no response | E478 |
| EcpG18 | 12 | A486 |
| EcpG19 | no response | G490 |
| EcpG20 | no response | P494 |
| EcpG21 | no response | L648 |
| EcpG22 | −14% | V341 |
| EcpG23 | −16 | L518 |
| EcpG24 | −11 | A520 |
| EcpG25 | no response | Q557 |
| EcpG26 | no response | L592 |
| EcpG27 | no response | I616 |
| EcpG28 | no response | L619 |

As shown above in Table 2, of the 28 prototype sensors tested, nine produced detectable changes in fluorescence in response to drug application. Three of these produced greater than 30% change in fluorescence: EcpG10, EcpG12, and EcpG15. Some sensors increased fluorescence in response to drug and some sensors decreased fluorescence in response to drug. The three prototype sensors with the largest signal maintained their fluorescence and change in fluorescence when the N-terminus of Epac was truncated, removing all the amino acids upstream of P324.

B. Two variants of cpEGFP were created by using linkers other than LE and TR. In one variant, the sequence LVSH was added to the N-terminal end of the cpEGFP and the sequence FNNP added to the C-terminal end. In the second variant, the sequence SH was added to the N-terminal end and the sequence FN added to the C-terminal end. These two cpEGFP variants were inserted into three positions within Epac2, which were identified in part A as yielding the greatest change in fluorescence. These insertions resulted in six new sensors, which were tested as described in part A. The best of these produced a 60% change in fluorescence in response to drug.

C. Additional sensor variants were produced by mixing the N and C terminal portions of the variants described in part B. Briefly, the N-terminal half and C-terminal halves of each of the variant sensor constructs was amplified by using primers hybridizing to the middle of the cpEGFP and the ends of the sensor constructs. The different N-terminal halves were combined systematically with the C-terminal halves using In-Fusion cloning, resulting in six new sensors Some of these sensors, as well as some of the original 28 prototype sensors were used as templates to create more PCR products of the N-terminal and C-terminal halves of the sensors. All of these halves were put into an In-Fusion reaction to c create a library of randomly assembled sensors. This resulted in three new libraries (libraries 1-3), from which a total of 138 sensors were screened as described in part A. Two additional libraries (libraries 4 and 5) were created by applying the above-described shuffling method to the original templates as well as the best sensors from the first two libraries. Forty-three of these sensors were screened and several gave large changes in fluorescence, up to a 61% increase or 53% decrease.

D. Additional sensor variants were produced using a random mutagenesis technique. Briefly, purified PCR product amplified from cpEGFP, without linkers, were used as the template for a PCR reaction using degenerate primers. The degenerate primers added two amino acids to each end of cpEGFP. Since the primers were degenerate at those positions, the resulting population of PCR products contained differing amino acid combinations at each end of the cpEGFP. These PCR products were then inserted into position 10 of the Epac2 protein, resulting in another library of cAMP sensors, seven of which were screened. The best of these, Lib6-2 C1, produced a 30% change in fluorescence.

E. Additional cAMP sensors were created in which the first and second polypeptides were obtained from different (i.e., unrelated) proteins. Briefly, one end of cpEGFP was joined to Epac2 while the other end was joined to Rap1B. This design tethers a single circularly permuted green fluorescent protein between Epac2 and the small GTPase Rap1B (Rehmann et. al. 2008), such that the cAMP-dependent interaction between these two proteins produces a change in fluorescence. The general structure of such a sensor is illustrated in FIG. 1D. The best of these sensors had a 25% increase in fluorescence in response to drug.

Table 3 below lists the 34 best performing sensors identified from the studies described above n paragraphs 1A-1E:

TABLE 3

Relative Change in fluorescence in Response to Isoproternol

| Clone Name | Relative Change in Fluorescence | Sequence of Clone |
| --- | --- | --- |
| EcpG10 G2-RasGEF-T2 | 110% | SEQ ID NO: 1 |
| Library 2-1 G12 | 73% | SEQ ID NO: 2 |
| Lib2-1 G12-RasGEF-T2 | 74% | SEQ ID NO: 3 |
| Library 4-2 B1 | 61% | SEQ ID NO: 4 |
| EcpG10 G2 | 60% | SEQ ID NO: 5 |
| Library 2-2 E7 | −53% | SEQ ID NO: 6 |
| Lib6-2 C1-T2 | −40% | SEQ ID NO: 7 |
| Library 5-1 D2 | 39% | SEQ ID NO: 8 |

TABLE 3-continued

Relative Change in fluorescence in Response to Isoproternol

| Clone Name | Relative Change in Fluorescence | Sequence of Clone |
| --- | --- | --- |
| Library 5-1 G12 | −39% | SEQ ID NO: 9 |
| Library 2-1 B12 | −37% | SEQ ID NO: 10 |
| Library 1 C2 | 36% | SEQ ID NO: 11 |
| EcpG12 | −36% | SEQ ID NO: 12 |
| Library 2-2 F9 | −36% | SEQ ID NO: 13 |
| Library 2-2 G4 | −36% | SEQ ID NO: 14 |
| Library 2-1 C2 | 35% | SEQ ID NO: 15 |
| Library 5-1 E7 | −34% | SEQ ID NO: 16 |
| Library 6-2 C1 | −34% | SEQ ID NO: 17 |
| EcpG15 | 34% | SEQ ID NO: 18 |
| Library 2-2 D1 | −33% | SEQ ID NO: 19 |
| Library 2-2 A11 | 33% | SEQ ID NO: 20 |
| Library 2-2 A5 | −33% | SEQ ID NO: 21 |
| Library 2-1 D1 | 33% | SEQ ID NO: 22 |
| Library 1 G2 | 33% | SEQ ID NO: 23 |
| Library 1 A6 | −33% | SEQ ID NO: 24 |
| Library 6-2 F1 | 30% | SEQ ID NO: 25 |
| EcpG10 | −30% | SEQ ID NO: 26 |
| EcpG10 G2N-G1C | −28% | SEQ ID NO: 27 |
| EPAC2gfpRAP1B | 26% | SEQ ID NO: 28 |
| EcpG13 | −22% | SEQ ID NO: 29 |
| EcpG23 | −16% | SEQ ID NO: 30 |
| EcpG9 | 13% | SEQ ID NO: 31 |
| EcpG22 | −14% | SEQ ID NO: 32 |
| EcpG18 | 12% | SEQ ID NO: 33 |
| EcpG24 | −11% | SEQ ID NO: 34 |

Figure 3:
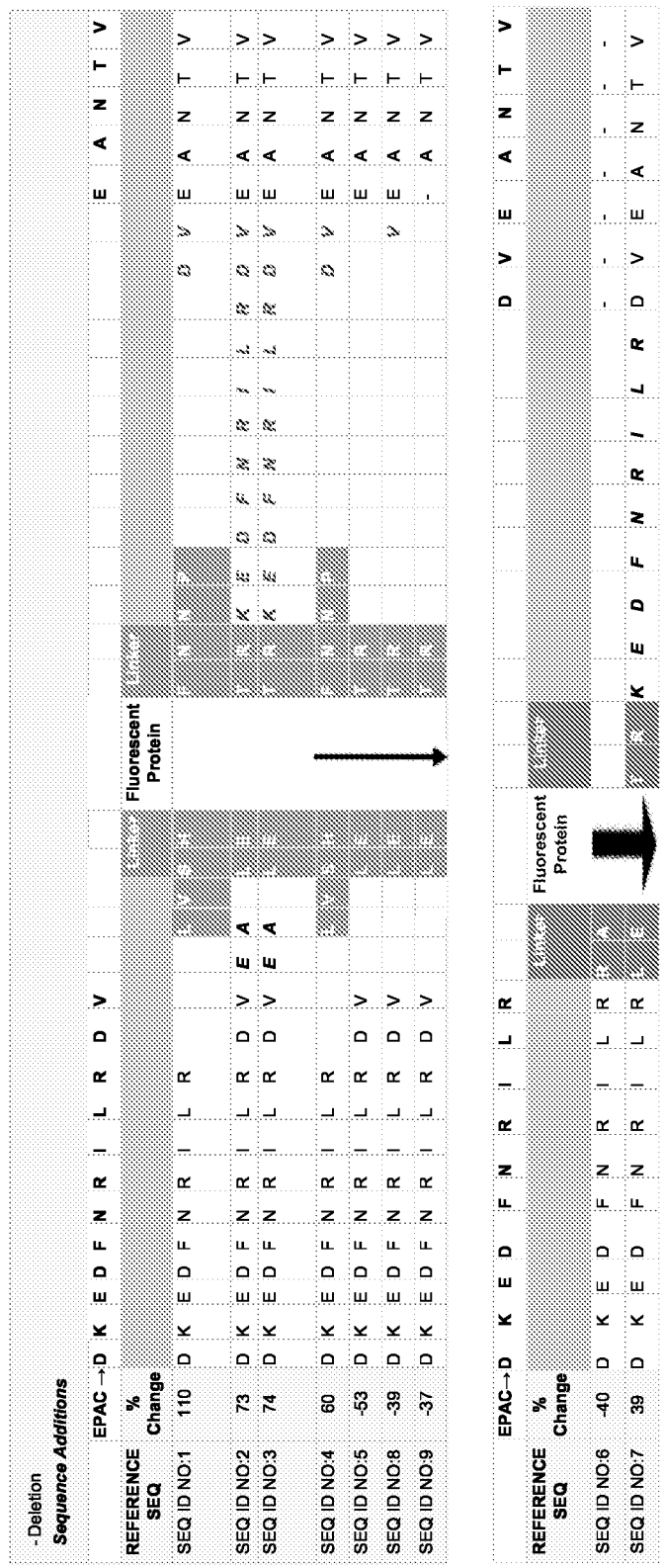
FIG. 3 Amino acid sequences surrounding the site of single FP insertion in nine embodiments. Column labeled ming cAMP sensors ding the average change in fluorescence relative to the baseline fluorescence observed prior to stimulation of the cells with drug.
Figure 4:
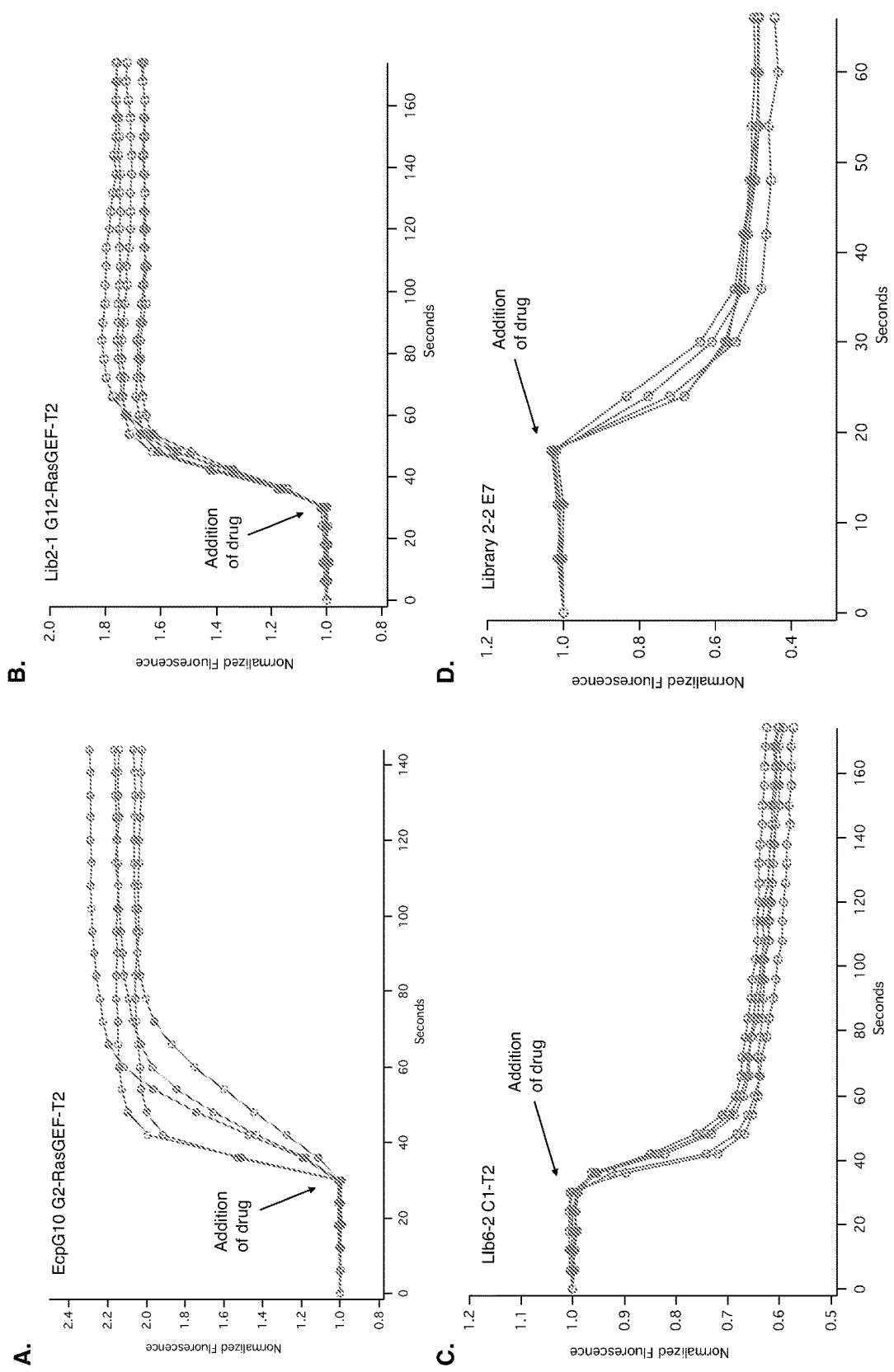
FIG. 4 Normalized response of four embodiments [(A) EcpG10 G2-RasGEF-T2 (SEQID_1); (B) Lib2-1 G12 RasGEF-T2 (SEQID 3); (C) Lib6-2 C1 T2 (SEQID 6); (D) Lib2-2 E7 (SEQID 5)] to 50 um isoproterenol. Cells transfected with an expression vector encoding each cAMP sensor protein constructed according to the disclosed methods, and then stimulated with isoproterenol, a specific ligand for the beta adrenergic GPCR. Receptor activation leads to increased cAMP production detected as a fluorescence change.
Figure 5:
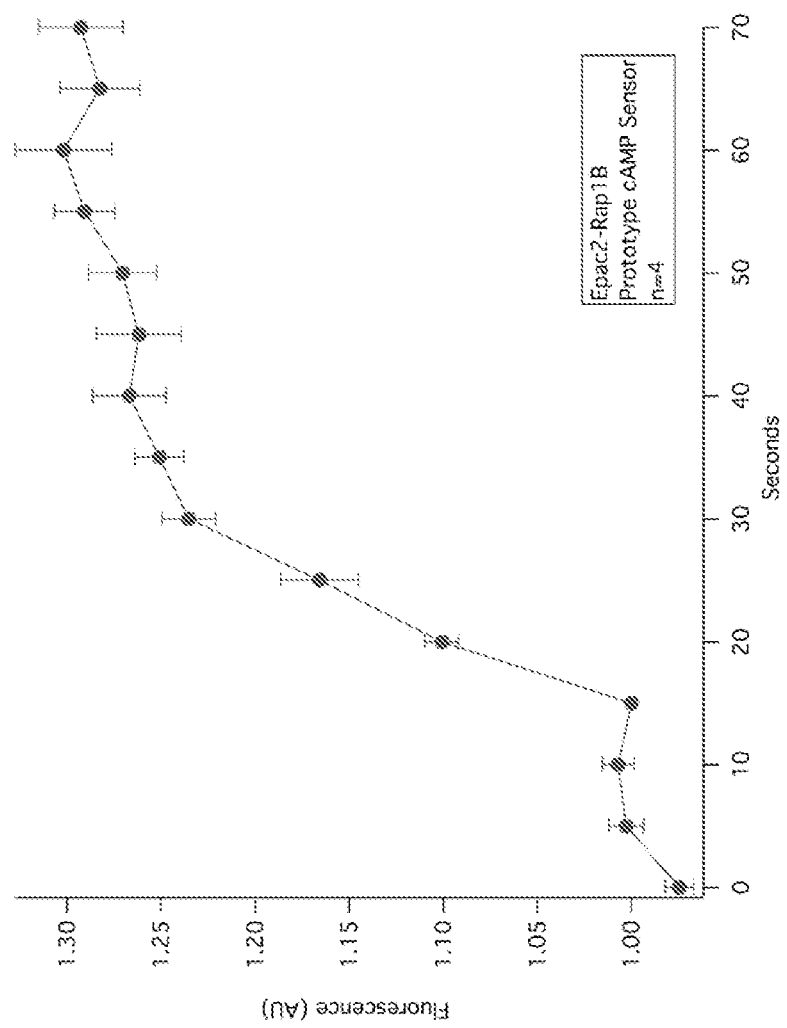
FIG. 5 Average response for a green cAMP Epac2-Rap1B sensor designed to detect pathway activation by way of the interaction between Epac2 and Rap1B. Response shown follows stimulation with 50 um isoproterenol, a specific ligand for the beta adrenergic GPCR.

F. Nine sensors identified in the studies described above were analyzed to determine the amino acid sequence of the site of insertion. The amino acid sequences around the insertion site in each sensor are listed in FIG. 3.

Example 2

Multiplexing of a cAMP Sensor Protein

The ability of cAMP sensor proteins of the present invention to be multiplexed with other fluorescence based sensors was tested. Briefly, cells were co-transfected with expression vector expressing a cAMP sensor protein of the present invention comprising a green fluorescent protein, and a DAG biosensor comprising a red fluorescent protein. The cells were cultured, treated with isoptroterenol and the resulting fluorescence measured as described in Example 1A. The results of this study are show in FIG. 6.

Figure 6:
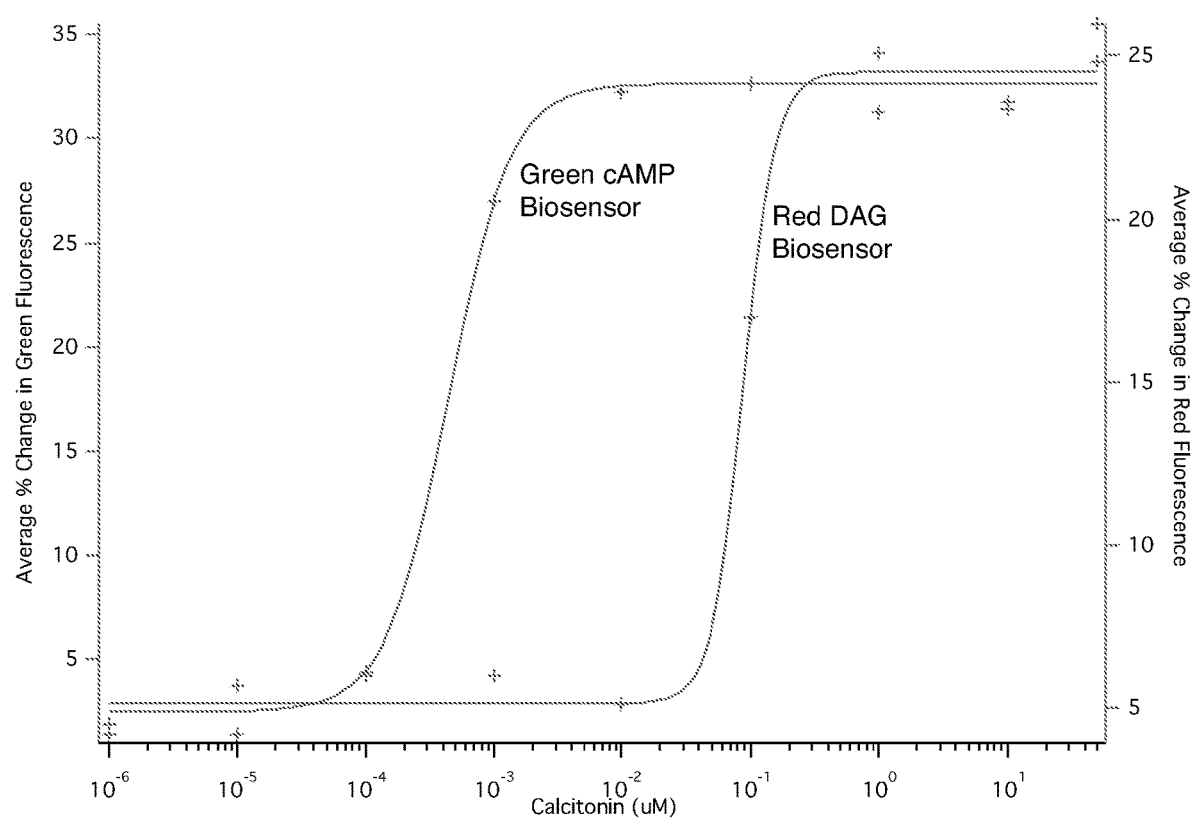
FIG. 6 Multiplexing of a cAMP biosensor based on a single fluorescent protein with a second biosensor of a different color. The G-protein coupled calcitonin receptor was stimulated with different amounts of calcitonin (shown on the X axis) to produce response curves for a red cAMP and a green DAG sensor. The Y axis on the right indicates cAMP response. The Y axis on the left indicates DAG response.

FIG. 6 illustrates how a pair of different colored sensors can be combined to detect the concentration dependent coupling of a receptor to one or more than one pathway. In this case the green cAMP sensor shows that low concentrations of calcitonin can stimulate just one G-protein pathway, while higher concentrations of the agonist produce changes in both cAMP sensor green fluorescence and DAG sensor red fluorescence in the same cells, indicating that two different G-protein pathways have been activated. The results demonstrate that cAMP sensor proteins of the present invention can be multiplexed with sensors comprised of fluorescent proteins with different spectral properties. Multiplexing enables the detection of multiple second messengers and can be used to detect pathway selectivity and agonist (ligand) bias.

Example 3

Multiplexing Using a PIP Sensor

Additional multiplexing studies were done using a red PIP2 sensor to indicate signaling of the Gq pathway. The studies were conducted as described in Example 2. The results of these studies are show in FIG. 7.

Figure 7:
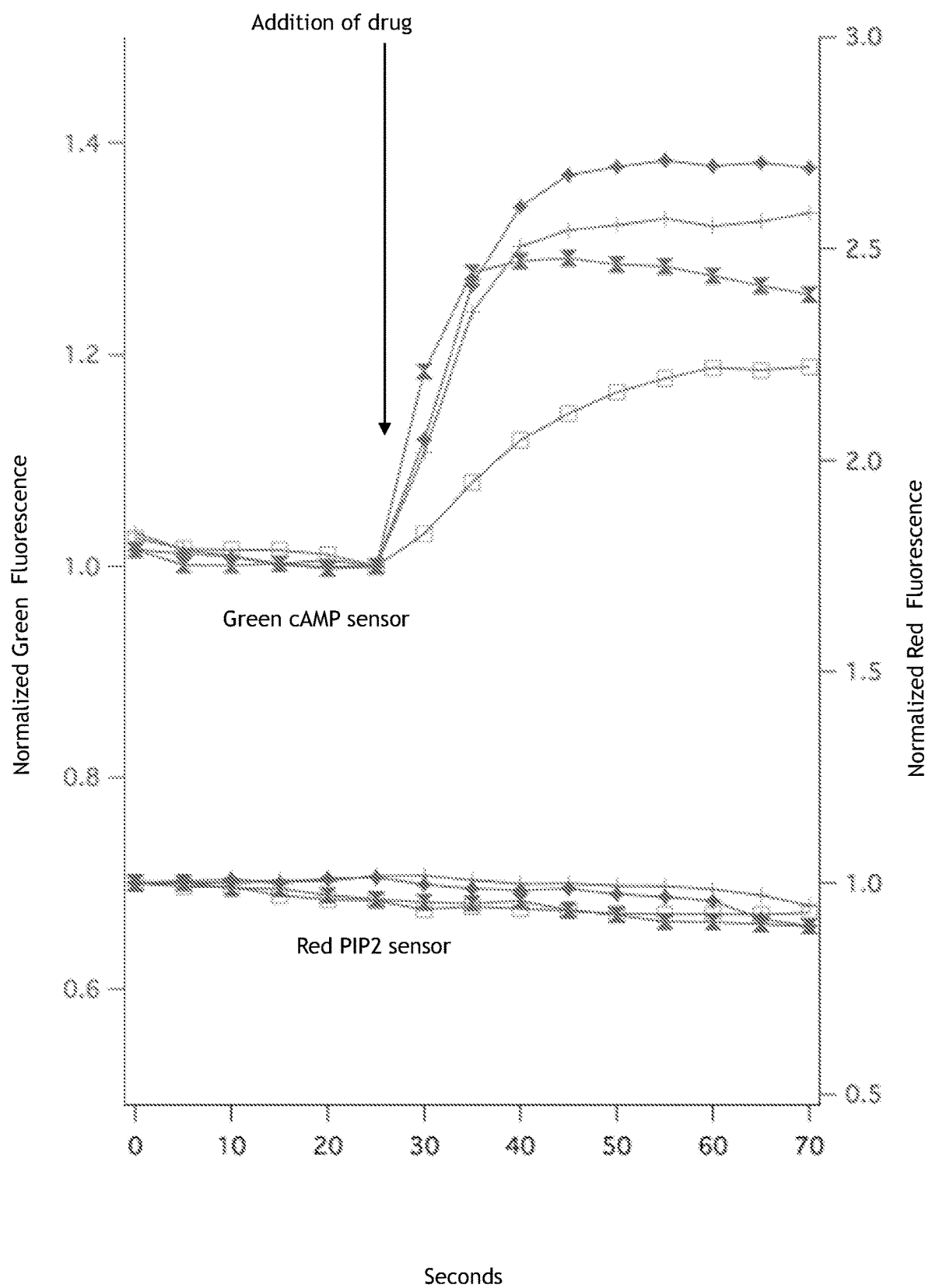
FIG. 7 Multiplexing a red PIP2 sensor (Gq signaling indicator) with the green cAMP sensor indicates a receptor and ligand that signal exclusively via the Gs pathway. The left hand Y axis is the cAMP green fluorescence normalized to the resting state of the cells before stimulation, the right hand axis is of the red fluorescence of the PIP2 sensor.

FIG. 7 illustrates that co-expression of two different colored sensors can be used to determine whether just one pathway is activated. The change in green fluorescence of the cAMP sensor indicates that stimulation of the Beta adrenergic receptor in these cells only produces a change in the activity of adenyl cyclase, presumably through Gs, and it does not signal through the Gq and phospholipase C pathway which can be seen in the red fluorescence.

Example 4

Use of the cAMP Sensor Protein in a Multiplate Assay

The ability of a cAMP sensor protein to be used in a multiplate, drug screening assay was tested. The results are shown in FIG. 8.

Figure 8:
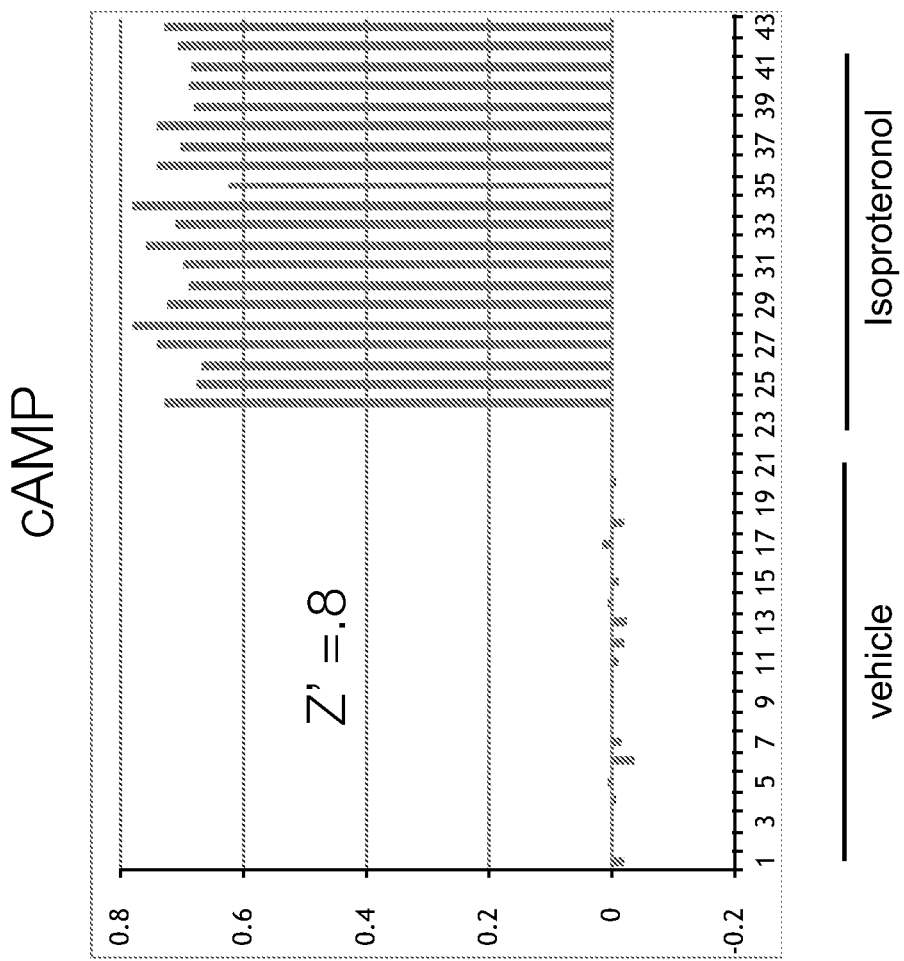
FIG. 8 Live cells expressing one of the fluorescent protein sensors for cAMP described in this invention. Change in fluorescence measured on a standard fluorescence plate reader (Biotek Synergy), five minutes after activating beta adrenergic receptors with 50 uM isoproteronol compared with PBS (vehicle).

FIG. 8 shows the response of one embodiment of the invention that decreases fluorescence in response to an increase in cAMP concentration, following activation of the Gs-coupled beta adrenergic receptor by isoproterenol. This data demonstrates that the cAMP sensor protein produces a consistent, reproducible signal (Z'>0.82) on a standard fluorescence plate reader. Thus, cAMP sensor proteins described herein are robust enough for automated drug screening using a fluorescent plate reader.

REFERENCES

Alford, S. C., Abdelfattah, A. S., Ding, Y., and Campbell, R. E. (2012a). A Fluorogenic Red Fluorescent Protein Heterodimer. Chem. Biol. 19, 353-360.

Alford, S. C., Ding, Y., Simmen, T., and Campbell, R. E. (2012b). Dimerization-Dependent Green and Yellow Fluorescent Proteins. ACS Synth. Biol. 1, 569 iment Almholt, K., Tullin, S., Skyggebjerg, O., and Scudder, K. (2004). Changes in intracellular cAMP reported by a Redistribution® assay using a cAMP-dependent protein kinase-green fluorescent protein chimera. Cellular Signalling 16, 907-920.

Altschul, S. F., Madden, T. L., Scherg, O., and Scudder, K. (2004). Changes in intracellular cAMP r(1997). Gapped BLAST and PSI-BLAST: a new generation of protein database search programs. Nucleic Acids Research 25, 3389ST: a Akerboom, J., Chen, T.-W., Wardill, T. J., Tian, L., Marvin, J. S., Mutlu, S., Calderellular cAMP r(1997). Gapped BLAST and PSI-BX. R., et al. (2012). Optimization of a GCaMP Calcium Indicator for Neural Activity Imaging. J. Neurosci. 32, 13819 Calciu Akerboom, J., Rivera, J. D. V., Guilbe, M. M. R., Malay Marvin, J. S., Mutlu, S., Calderellular cAMP r(1997). Gapped BLAST and PSI-BX.R., Schreiter, E. R. (2009). Crystal Structures of the GCaMP Calcium Sensor Reveal the Mechanism of Fluorescence Signal Change and Aid Rational Design. Journal of Biological Chemistry 284, 6455GCaMP Ausubel, F. et al., Current Protocols in Molecular Biology, John Wiley & Sons, New York, N.Y., (1998).

Baird, G. S., Zacharias, D. A., and Tsien, R. Y. (1999). Circular permutation and receptor insertion within green fluorescent proteins. Proceedings of the National Academy of Sciences 96, 11241Calcium Berkner, K. L., Schaffhausen, B. S., Roberts, T. M., and Sharp, P. A. (1987). Abundant expression of polyomavirus middle T antigen and dihydrofolate reductase in an adenovirus recombinant. J. Virol. 61, 1213 of po Binkowski, B. F., Butler, B. L., Stecha, P. F., Eggers, C. T., Otto, P., Zimmerman, K., Vidugiris, G., Wood, M. G., Encell, L. P., Fan, F., et al. (2011). A Luminescent Biosensor with Increased Dynamic Range for Intracellular cAMP. ACS Chem. Biol. 6, 1193od, M.

Carlson, H. J., Cotton, D. W., and Campbell, R. E. (2010). Circularly permuted monomeric red fluorescent proteins with new termini in the β-sheet. Protein Science 19, 1490 eric r Coffin, J. M., Hughes, S. H., Varmus, H. E., Coffin, J. M., Hughes, S. H., and Varmus, H. E. (1997). The Interactions of Retroviruses and their Hosts (Cold Spring Harbor (NY): Cold Spring Harbor Laboratory Press).

Chou, P. Y., and Fasman, G. D. (1978). Prediction of the secondary structure of proteins from their amino acid sequence. Adv. Enzymol. Relat. Areas Mol. Biol. 47, 45 (NY)

Davidson, D., and Hassell, J. A. (1987). Overproduction of polyomavirus middle T antigen in mammalian cells through the use of an adenovirus vector. J. Virol. 61, 1226 olyoma Haj-Ahmad, Y., and Graham, F. L. (1986). Development of a helper-independent human adenovirus vector and its use in the transfer of the herpes simplex virus thymidine kinase gene. J. Virol. 57, 267 elper Held, P., Banks, P., Tewson, P., Quinn, A. M., Hughes, T. (2014) Live Cell Imaging of GPCR Dependent Second-Messenger Systems Using the Cytation™ 3 Cell Imaging Multi-Mode Reader to Image Genetically Encoded GPCR Reactive Sensors in Real Time. BioTek Application note. http://www.biotek.com/assets/tech_resources/Montana %20Molecular_App_Note.pdf Hong, K., Spitzer, N.C., and Nicol, X. (2011). Improved molecular toolkit for cAMP studies in live cells. BMC Res Notes 4, 241.

Jiang, L. I., Collins, J., Davis, R., Lin, K.-M., DeCamp, D., Roach, T., Hsueh, R., Rebres, R. A., Ross, E. M., Taussig, R., et al. (2007). Use of a cAMP BRET sensor to characterize a novel regulation of cAMP by the sphingosine 1-phosphate/G13 pathway. J. Biol. Chem. 282, 10576., Ross Kenakin, T., and Christopoulos, A. (2013). Signalling bias in new drug discovery: detection, quantification and therapeutic impact. Nat Rev Drug Discov 12, 205 sor t Kitaguchi, T., Oya, M., Wada, Y., Tsuboi, T., and Miyawaki, A. (2013). Extracellular calcium influx activates adenylate cyclase 1 and potentiates insulin secretion in MING cells. Biochem. J. 450, 365f cAM Klarenbeek, J. B., Goedhart, J., Hink, M. A., Gadella, T. W. J., and Jalink, K. (2011). A mTurquoise-Based cAMP Sensor for Both FLIM and Ratiometric Read-Out Has Improved Dynamic Range. PloS One 6, e19170.

Kost, T. A., Condreay, J. P., and Jarvis, D. L. (2005). Baculovirus as versatile vectors for protein expression in insect and mammalian cells. Nature Biotechnology 23, 567 ors f Kredel, S., Nienhaus, K., Oswald, F., Wolff, M., Ivanchenko, S., Cymer, F., Jeromin, A., Michel, F. J., Spindler, K.-D., Heilker, R., et al. (2008). Optimized and Far-Red-Emitting Variants of Fluorescent Protein eqFP611. Chem. Biol. 15, 224-233.

Kyte, J., and Doolittle, R. F. (1982). A simple method for displaying the hydropathic character of a protein. Journal of Molecular Biology 157, 105. Opt Lam, A. J., St-Pierre, F., Gong, Y., Marshall, J. D., Cranfill, P. J., Baird, M. A., McKeown, M. R., Wiedenmann, J., Davidson, M. W., Schnitzer, M. J., et al. (2012). Improving FRET dynamic range with bright green and red fluorescent proteins. Nature Methods 9, 1005 range Ledford, H. (2013). Bioengineers look beyond patents Nature 499, 16-17.

Massie, B., Gluzman, Y., and Hassell, J. A. (1986). Construction of a helper-free recombinant adenovirus that expresses polyomavirus large T antigen. Molecular and Cellular Biology 6, 2872e with Nagai, T., Sawano, A., Park, E. S., and Miyawaki, A. (2001). Circularly permuted green fluorescent proteins engineered to sense Ca2. Proceedings of the National Academy of Sciences 98, 3197 with Nakai, J., Ohkura, M., and Imoto, K. (2001). A high signal-to-noise Ca(2+) probe composed of a single green fluorescent protein. Nature Biotechnology 19, 137137 or Nikolaev, V. O., B, M., and Imoto, K. (2001). A high signal-to-noise Ca(2+) probe composed of a single green fluorescent protein. Nature Biotechnology 19, 137-141.ademy of Sciences 97218.

Ormolaev, V. O., B, M., and Imoto, K. (2001). A high signal-to-noise Ca(2+) probe composed of a single green fluorescent protein. Nature Biotechnology 19, 137137 re Biotechnology 19, 13

Pletnev, S., Shcherbo, D., Chudakov, D. M., Pletneva, N., Merzlyak, E. M., Wlodawer, A., Dauter, Z., and Pletnev, V. (2008). A crystallographic study of bright far-red fluorescent protein mKate reveals pH-induced cis-trans isomerization of the chromophore. J. Biol. Chem. 283, 28980 merizat Ponsioen, B., Zhao, J., Riedl, J., Zwartkruis, F., van der Krogt, G., Zaccolo, M., Moolenaar, W. H., Bos, J. L., and Jalink, K. (2004). Detecting cAMP-induced Epac activation by fluorescence resonance energy transfer: Epac as a novel cAMP indicator. EMBO Rep. 5, 1176-1180.

Prinz, A., Diskar, M., Erlbruch, A., and Herberg, F. W. (2006). Novel, isotype-specific sensors for protein kinase A subunit interaction based on bioluminescence resonance energy transfer (BRET). Cell. Signal. 18, 1616 pac as Rehmann, H., Arias-Palomo, E., Hadders, M. A., and Schwede, F. (2008). Structure of Epac2 in complex with a cyclic AMP analogue and RAP1B. Nature.

Rehmann, H., Das, J., Knipscheer, P., and Wittinghofer, A. (2006). Structure of the cyclic-AMP-responsive exchange factor Epac2 in its auto-inhibited state. Nature.

Salonikidis, P. S., Niebert, M., Ullrich, T., Bao, G., Zeug, A., and Richter, D. W. (2011). An Ion-insensitive cAMP Biosensor for Long Term Quantitative Ratiometric Fluorescence Resonance Energy Transfer (FRET) Measurements under Variable Physiological Conditions. Journal of Biological Chemistry 286, 23419Term Qu Shcherbo, D., Souslova, E. A., Goedhart, J., Chepurnykh, T. V., Gaintzeva, A., Shemiakina, L I., Gadella, T. W., Lukyanov, S., and Chudakov, D. M. (2009). Practical and reliable FRET/FLIM pair of fluorescent proteins. BMC Biotechnology 9, 24.

Shaner, N.C., Steinbach, P. A., and Tsien, R. Y. (2005). A guide to choosing fluorescent proteins. Nature Methods 2, 905, S., Shaner, N.C., Lin, M. Z., McKeown, M. R., Steinbach, P. A., Hazelwood, K. L., Davidson, M. W., and Tsien, R. Y. (2008). Improving the photostability of bright monomeric orange and red fluorescent proteins. Nature Methods 5, 545 bilit Shaner, N.C., Lambert, G. G., Chammas, A., Ni, Y., Cranfill, P. J., Baird, M. A., Sell, B. R., Allen, J. R., Day, R. N., Israelsson, M., et al. (2013). A bright monomeric green fluorescent protein derived from *Branchiostoma lanceolatum*. Nat Meth 10, 407-409.

Shui, B., Wang, Q., Lee, F., Byrnes, L. J., Chudakov, D. M., Lukyanov, S. A., Sondermann, H., and Kotlikoff, M. I. (2011). Circular Permutation of Red Fluorescent Proteins. PloS One 6, e20505.

Subach, O. M., Gundorov, I. S., Yoshimura, M., Subach, F. V., Zhang, J., Gr., Sondermann, H., and Kotlikoff, M. I. (2011). Circular Permutation of ReConversion of Red Fluorescent Protein into a Bright Blue Probe. Chem. Biol. 15, 1116 of ReC Tewson, P., Westenberg, M., Zhao, Y., Campbell, R. E., Quinn, A. M., and Hughes, T. E. (2012). Simultaneous Detection of Ca2+ and Diacylglycerol Signaling in Living Cells. PloS One 7, e42791.

Topell, S., Hennecke, J., and Glockshuber, R. (1999). Circularly permuted variants of the green fluorescent protein. FEBS Lett. 457, 283 cerol Tsutsui, H., Karasawa, S., Okamura, Y., and Miyawaki, A. (2008). Improving membrane voltage measurements using FRET with new fluorescent proteins. Nature Methods 5, 683-685.

Willoughby, D., and Cooper, D. (2007). Live-cell imaging of cAMP dynamics. Nature Methods 5, 29-36.

Woehler, A., Wlodarczyk, J., and Neher, E. (2010). Signal/Noise Analysis of FRET-Based Sensors. Biophysical Journal 99, 2344ET-Bas Xu, Y., Piston, D. W., and Johnson, C. H. (1999). A bioluminescence resonance energy transfer (BRET) system: application to interacting circadian clock proteins. Proc. Natl. Acad. Sci. U.S.a. 96, 151Blue Zaccolo, M., De Giorgi, F., Cho, C. Y., Feng, L., Knapp, T., Negulescu, P. A., Taylor, S. S., Tsien, R. Y., and Pozzan, T. (2000). A genetically encoded, fluorescent indicator for cyclic AMP in living cells. Nat. Cell Biol. 2, 251116

Zaccolo, M., and Pozzan, T. (2002). Discrete microdomains with high concentration of cAMP in stimulated rat neonatal cardiac myocytes. Science.

Zhao, Y., Araki, S., Wu, J., Teramoto, T., Chang, Y. F., Nakano, M., Abdelfattah, A. S., Fujiwara, M., Ishihara, T., Nagai, T., et al. (2011). An Expanded Palette of Genetically Encoded Ca2+ Indicators. Science 333, 1888e of G Zhang, W. W., Fang, X., Branch, C. D., Mazur, W., French, B. A., and Roth, J. A. (1993). Generation and identification of recombinant adenovirus by liposome-mediated transfection and PCR analysis.

Zhang, J., Ma, Y., Taylor, S. S., and Tsien, R. Y. Genetically encoded reporters of protein kinase A activity reveal impact of substrate tethering. Proceedings of the National Academy of Sciences 98, 14997 ience 3.

What is claimed is:

1. A nucleic acid molecule encoding a cyclic adenosine monophosphate (cAMP) sensor protein comprising a first polypeptide linked to a second polypeptide, wherein the first polypeptide comprises an amino acid sequence at least 95% identical to amino acids 1-292 of SEQ ID NO: 6; and the second polypeptide comprises a circularly permuted, fluorescent protein, wherein the fluorescent protein is selected from the group consisting of GFP, eGFP, eYFP, Emerald, mApple, mPlum, mCherry, tdTomato, mStrawberry, J-Red, DsRed-monomer, mOrange, MKO, mCitrine, Venus, YPet, CyPet, mCFPm, Cerulean, T-Sapphire, mKOK, mUKG, Clover, mKate, tagRFP, tagGFP, and mNEON green, wherein binding of cAMP to the first polypeptide alters the level of fluorescence from the second polypeptide, wherein the C-terminal amino acid of the amino acid sequence at least 95% identical to amino acids 1-292 of SEQ ID NO: 6 is covalently bound to a linker of 1-10 amino acids, and wherein the C-terminal amino acid of the linker is covalently bound to the N-terminal amino acid of the circularly permuted, fluorescent protein.

2. A method of detecting changes in the intracellular level of cAMP, comprising:

a. introducing into a cell a nucleic acid molecule encoding a cAMP sensor protein comprising a first polypeptide linked to a second polypeptide, wherein the first polypeptide comprises an amino acid sequence at least 95% identical to amino acids 1-292 of SEQ ID NO: 6; and the second polypeptide comprises a circularly permuted, fluorescent protein, wherein the fluorescent protein is selected from the group consisting of GFP, eGFP, eYFP, Emerald, mApple, mPlum, mCherry, tdTomato, mStrawberry, J-Red, DsRed-monomer, mOrange, MKO, mCitrine, Venus, YPet, CyPet, mCFPm, Cerulean, T-Sapphire, mKOK, mUKG, Clover, mKate, tagRFP, tagGFP, and mNEON green, wherein binding of cAMP to the first polypeptide alters the level of fluorescence from the second polypeptide, wherein the C-terminal amino acid of the amino acid sequence at least 95% identical to amino acids 1-292 of SEQ ID NO: 6 is covalently bound to a linker of 1-10 amino acids, and wherein the C-terminal amino acid of the linker is covalently bound to the N-terminal amino acid of the circularly permuted, fluorescent protein; and b. detecting changes in the intracellular level of fluorescence produced by the fluorescent protein.

3. The nucleic acid molecule of claim 1, wherein the first polypeptide comprises an amino acid sequence at least 90% identical to the amino acid sequence of SEQ ID NO:37.

4. The method of claim 2, wherein the first polypeptide comprises an amino acid sequence at least 90% identical to the amino acid sequence of SEQ ID NO:37.

5. The nucleic acid molecule of claim 1, wherein the first polypeptide comprises an amino acid sequence at least 99% identical to amino acids 1-292 of SEQ ID NO: 6.

6. The nucleic acid molecule of claim 1, wherein the first polypeptide comprises amino acids 1-292 of SEQ ID NO: 6.

7. The nucleic acid molecule of claim 1, wherein the second polypeptide comprises mNEON green.

8. The nucleic acid molecule of claim 5, wherein the second polypeptide comprises mNEON green.

9. The method of claim 2, wherein the first polypeptide comprises an amino acid sequence at least 99% identical to amino acids 1-292 of SEQ ID NO: 6.

10. The method of claim 2, wherein the first polypeptide comprises amino acids 1-292 of SEQ ID NO: 6.

11. The method of claim 2, wherein the second polypeptide comprises mNEON green.

12. The method of claim 9, wherein the second polypeptide comprises mNEON green.

* * * * *

SEQUENCE LISTING

<160> NUMBER OF SEQ ID NOS: 77

<210> SEQ ID NO 1
<211> LENGTH: 739
<212> TYPE: PRT
<213> ORGANISM: Artificial Sequence
<220> FEATURE:
<223> OTHER INFORMATION: Synthetic
<400> SEQUENCE: 1

```
Met Gly Ser Asn Asn Asp Arg Ile Pro Asp Lys Glu Asn Thr Pro Leu
1               5                   10                  15

Ile Glu Pro His Val Pro Leu Arg Pro Ala Asn Thr Ile Thr Lys Val
            20                  25                  30

Pro Ser Glu Lys Ile Leu Arg Ala Gly Lys Ile Leu Arg Asn Ala Ile
        35                  40                  45

Leu Ser Arg Ala Pro His Met Ile Arg Asp Arg Lys Tyr His Leu Lys
    50                  55                  60

Thr Tyr Arg Gln Cys Cys Val Gly Thr Glu Leu Val Asp Trp Met Met
65                  70                  75                  80

Gln Gln Thr Pro Cys Val His Ser Arg Thr Gln Ala Val Gly Met Trp
                85                  90                  95

Gln Val Leu Leu Glu Asp Gly Val Leu Asn His Val Asp Gln Glu His
            100                 105                 110

His Phe Gln Asp Lys Tyr Leu Phe Tyr Arg Phe Leu Asp Asp Glu His
        115                 120                 125

Glu Asp Ala Pro Leu Pro Thr Glu Glu Lys Lys Glu Cys Asp Glu
    130                 135                 140

Glu Leu Gln Asp Thr Met Leu Leu Leu Ser Gln Met Gly Pro Asp Ala
145                 150                 155                 160

His Met Arg Met Ile Leu Arg Lys Pro Pro Gly Gln Arg Thr Val Asp
                165                 170                 175

Asp Leu Glu Ile Ile Tyr Glu Glu Leu Leu His Ile Lys Ala Leu Ser
            180                 185                 190

His Leu Ser Thr Thr Val Lys Arg Glu Leu Ala Gly Val Leu Ile Phe
        195                 200                 205

Glu Ser His Ala Lys Gly Gly Thr Val Leu Phe Asn Gln Gly Glu Glu
    210                 215                 220

Gly Thr Ser Trp Tyr Ile Ile Leu Lys Gly Ser Val Asn Val Val Ile
225                 230                 235                 240

Tyr Gly Lys Gly Val Val Cys Thr Leu His Glu Gly Asp Asp Phe Gly
                245                 250                 255

Lys Leu Ala Leu Val Asn Asp Ala Pro Arg Ala Ala Ser Ile Val Leu
            260                 265                 270

Arg Glu Asp Asn Cys His Phe Leu Arg Val Asp Lys Glu Asp Phe Asn
        275                 280                 285

Arg Ile Leu Arg Leu Val Ser His Asn Val Tyr Ile Lys Ala Asp Lys
    290                 295                 300

Gln Lys Asn Gly Ile Lys Ala Asn Phe Lys Ile Arg His Asn Ile Glu
305                 310                 315                 320

Asp Gly Gly Val Gln Leu Ala Tyr His Tyr Gln Gln Asn Thr Pro Ile
                325                 330                 335

Gly Asp Gly Pro Val Leu Leu Pro Asp Asn His Tyr Leu Ser Val Gln
            340                 345                 350

Ser Ile Leu Ser Lys Asp Pro Asn Glu Lys Arg Asp His Met Val Leu
```

```
                355                 360                 365
Leu Glu Phe Val Thr Ala Ala Gly Ile Thr Leu Gly Met Asp Glu Leu
            370                 375                 380
Tyr Lys Gly Gly Thr Gly Gly Ser Met Val Ser Lys Gly Glu Glu Leu
385                 390                 395                 400
Phe Thr Gly Val Val Pro Ile Gln Val Glu Leu Asp Gly Asp Val Asn
                405                 410                 415
Gly His Lys Phe Ser Val Ser Gly Glu Gly Glu Gly Asp Ala Thr Tyr
            420                 425                 430
Gly Lys Leu Thr Leu Lys Phe Ile Cys Thr Thr Gly Lys Leu Pro Val
        435                 440                 445
Pro Trp Pro Thr Leu Val Thr Thr Leu Thr Tyr Gly Val Gln Cys Phe
        450                 455                 460
Ser Arg Tyr Pro Asp His Met Lys Gln His Asp Phe Phe Lys Ser Ala
465                 470                 475                 480
Met Pro Glu Gly Tyr Ile Gln Glu Arg Thr Ile Phe Phe Lys Asp Asp
                485                 490                 495
Gly Asn Tyr Lys Thr Arg Ala Glu Val Lys Phe Glu Gly Asp Thr Leu
            500                 505                 510
Val Asn Arg Ile Glu Leu Lys Gly Ile Asp Phe Lys Glu Asp Gly Asn
        515                 520                 525
Ile Leu Gly His Lys Leu Glu Tyr Asn Phe Asn Asn Pro Asp Val Glu
        530                 535                 540
Ala Asn Thr Val Arg Leu Lys Glu His Asp Gln Asp Val Leu Val Leu
545                 550                 555                 560
Glu Lys Val Pro Ala Gly Asn Arg Ala Ser Asn Gln Gly Asn Ser Gln
                565                 570                 575
Pro Gln Gln Lys Tyr Thr Val Met Ser Gly Thr Pro Glu Lys Ile Leu
            580                 585                 590
Glu His Phe Leu Glu Thr Ile Arg Leu Glu Ala Thr Leu Asn Glu Ala
        595                 600                 605
Thr Asp Ser Val Leu Asn Asp Phe Ile Met Met His Cys Val Phe Met
610                 615                 620
Pro Asn Thr Gln Leu Cys Pro Ala Leu Val Ala His Tyr His Ala Gln
625                 630                 635                 640
Pro Ser Gln Gly Thr Glu Gln Glu Lys Met Asp Tyr Ala Leu Asn Asn
                645                 650                 655
Lys Arg Arg Val Ile Arg Leu Val Leu Gln Trp Ala Ala Met Tyr Gly
            660                 665                 670
Asp Leu Leu Gln Glu Asp Asp Val Ser Met Ala Phe Leu Glu Glu Phe
        675                 680                 685
Tyr Val Ser Val Ser Asp Asp Ala Arg Met Ile Ala Ala Leu Lys Glu
        690                 695                 700
Gln Leu Pro Glu Leu Glu Lys Ile Val Lys Gln Ile Ser Glu Asp Ala
705                 710                 715                 720
Lys Ala Pro Gln Lys Lys His Lys Val Leu Leu Gln Gln Phe Asn Thr
                725                 730                 735
Gly Asp Glu

<210> SEQ ID NO 2
<211> LENGTH: 1269
<212> TYPE: PRT
<213> ORGANISM: Artificial Sequence
<220> FEATURE:
```

<223> OTHER INFORMATION: Synthetic

<400> SEQUENCE: 2

| Met | Val | Ala | Ala | His | Ala | Ala | His | Ser | Ser | Ser | Ala | Glu | Trp | Ile |
|---|---|---|---|---|---|---|---|---|---|---|---|---|---|---|
| 1 | | | | 5 | | | | | 10 | | | | | 15 |

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Thr Val Leu
    370                 375                 380

Phe Asn Gln Gly Glu Glu Gly Thr Ser Trp Tyr Ile Ile Leu Lys Gly
385                 390                 395                 400

-continued

```
Ser Val Asn Val Val Ile Tyr Gly Lys Gly Val Cys Thr Leu His
            405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
            435                 440                 445

Asp Lys Glu Asp Phe Asn Arg Ile Leu Arg Asp Val Glu Ala Leu Glu
            450                 455                 460

Asn Val Tyr Ile Lys Ala Asp Lys Gln Lys Asn Gly Ile Lys Ala Asn
465                 470                 475                 480

Phe Lys Ile Arg His Asn Ile Glu Asp Gly Gly Val Gln Leu Ala Tyr
            485                 490                 495

His Tyr Gln Gln Asn Thr Pro Ile Gly Asp Gly Pro Val Leu Leu Pro
            500                 505                 510

Asp Asn His Tyr Leu Ser Val Gln Ser Ile Leu Ser Lys Asp Pro Asn
            515                 520                 525

Glu Lys Arg Asp His Met Val Leu Leu Glu Phe Val Thr Ala Ala Gly
            530                 535                 540

Ile Thr Leu Gly Met Asp Glu Leu Tyr Lys Gly Gly Thr Gly Gly Ser
545                 550                 555                 560

Met Val Ser Lys Gly Glu Glu Leu Phe Thr Gly Val Val Pro Ile Gln
            565                 570                 575

Val Glu Leu Asp Gly Asp Val Asn Gly His Lys Phe Ser Val Ser Gly
            580                 585                 590

Glu Gly Glu Gly Asp Ala Thr Tyr Gly Lys Leu Thr Leu Lys Phe Ile
            595                 600                 605

Cys Thr Thr Gly Lys Leu Pro Val Pro Trp Pro Thr Leu Val Thr Thr
            610                 615                 620

Leu Thr Tyr Gly Val Gln Cys Phe Ser Arg Tyr Pro Asp His Met Lys
625                 630                 635                 640

Gln His Asp Phe Phe Lys Ser Ala Met Pro Glu Gly Tyr Ile Gln Glu
            645                 650                 655

Arg Thr Ile Phe Phe Lys Asp Asp Gly Asn Tyr Lys Thr Arg Ala Glu
            660                 665                 670

Val Lys Phe Glu Gly Asp Thr Leu Val Asn Arg Ile Glu Leu Lys Gly
            675                 680                 685

Ile Asp Phe Lys Glu Asp Gly Asn Ile Leu Gly His Lys Leu Glu Tyr
            690                 695                 700

Asn Thr Arg Lys Glu Asp Phe Asn Arg Ile Leu Arg Asp Val Glu Ala
705                 710                 715                 720

Asn Thr Val Arg Leu Lys Glu His Asp Gln Asp Val Leu Val Leu Glu
            725                 730                 735

Lys Val Pro Ala Gly Asn Arg Ala Ser Asn Gln Gly Asn Ser Gln Pro
            740                 745                 750

Gln Gln Lys Tyr Thr Val Met Ser Gly Thr Pro Glu Lys Ile Leu Glu
            755                 760                 765

His Phe Leu Glu Thr Ile Arg Leu Glu Ala Thr Leu Asn Glu Ala Thr
            770                 775                 780

Asp Ser Val Leu Asn Asp Phe Ile Met Met His Cys Val Phe Met Pro
785                 790                 795                 800

Asn Thr Gln Leu Cys Pro Ala Leu Val Ala His Tyr His Ala Gln Pro
            805                 810                 815

Ser Gln Gly Thr Glu Gln Glu Lys Met Asp Tyr Ala Leu Asn Asn Lys
```

-continued

```
               820                 825                 830
Arg Arg Val Ile Arg Leu Val Leu Gln Trp Ala Ala Met Tyr Gly Asp
            835                 840                 845
Leu Leu Gln Glu Asp Asp Val Ser Met Ala Phe Leu Glu Glu Phe Tyr
        850                 855                 860
Val Ser Val Ser Asp Asp Ala Arg Met Ile Ala Ala Leu Lys Glu Gln
865                 870                 875                 880
Leu Pro Glu Leu Glu Lys Ile Val Lys Gln Ile Ser Glu Asp Ala Lys
                885                 890                 895
Ala Pro Gln Lys Lys His Lys Val Leu Leu Gln Gln Phe Asn Thr Gly
            900                 905                 910
Asp Glu Arg Ala Gln Lys Arg Gln Pro Ile Arg Gly Ser Asp Glu Val
        915                 920                 925
Leu Phe Lys Val Tyr Cys Met Asp Pro Thr Tyr Thr Thr Ile Arg Val
        930                 935                 940
Pro Val Ala Thr Ser Val Lys Glu Val Ile Ser Ala Val Ala Asp Lys
945                 950                 955                 960
Leu Gly Ser Gly Glu Gly Leu Ile Ile Val Lys Met Ser Ser Gly Gly
                965                 970                 975
Glu Lys Val Val Leu Lys Pro Asn Asp Val Ser Val Phe Met Thr Leu
            980                 985                 990
Thr Ile Asn Gly Arg Leu Phe Ala Cys Pro Arg Glu Gln Phe Asp Ser
            995                 1000                1005
Leu Thr Pro Leu Pro Glu Gln Glu Gly Pro Thr Val Gly Thr Val
        1010                1015                1020
Gly Thr Phe Glu Leu Met Ser Ser Lys Asp Leu Ala Tyr Gln Met
        1025                1030                1035
Thr Ile Tyr Asp Trp Glu Leu Phe Asn Cys Val His Glu Leu Glu
        1040                1045                1050
Leu Ile Tyr His Thr Phe Gly Arg His Asn Phe Lys Lys Thr Thr
        1055                1060                1065
Ala Asn Leu Asp Leu Phe Leu Arg Arg Phe Asn Glu Ile Gln Phe
        1070                1075                1080
Trp Val Val Thr Glu Ile Cys Leu Cys Ser Gln Leu Ser Lys Arg
        1085                1090                1095
Val Gln Leu Leu Lys Lys Phe Ile Lys Ile Ala Ala His Cys Lys
        1100                1105                1110
Glu Tyr Lys Asn Leu Asn Ser Phe Phe Ala Ile Val Met Gly Leu
        1115                1120                1125
Ser Asn Val Ala Val Ser Arg Leu Ala Leu Thr Trp Glu Lys Leu
        1130                1135                1140
Pro Ser Lys Phe Lys Lys Phe Tyr Ala Glu Phe Glu Ser Leu Met
        1145                1150                1155
Asp Pro Ser Arg Asn His Arg Ala Tyr Arg Leu Thr Val Ala Lys
        1160                1165                1170
Leu Glu Pro Pro Leu Ile Pro Phe Met Pro Leu Leu Ile Lys Asp
        1175                1180                1185
Met Thr Phe Thr His Glu Gly Asn Lys Thr Phe Ile Asp Asn Leu
        1190                1195                1200
Val Asn Phe Glu Lys Met Arg Met Ile Ala Asn Thr Ala Arg Thr
        1205                1210                1215
Val Arg Tyr Tyr Arg Ser Gln Pro Phe Asn Pro Asp Ala Ala Gln
        1220                1225                1230
```

```
Ala Asn Lys Asn His Gln Asp  Val Arg Ser Tyr Val  Arg Gln Leu
    1235            1240                 1245

Asn Val Ile Asp Asn Gln Arg  Thr Leu Ser Gln Met  Ser His Arg
    1250            1255                 1260

Leu Glu  Pro Arg Arg Pro
    1265

<210> SEQ ID NO 3
<211> LENGTH: 748
<212> TYPE: PRT
<213> ORGANISM: Artificial Sequence
<220> FEATURE:
<223> OTHER INFORMATION: Synthetic

<400> SEQUENCE: 3

Met Gly Ser Asn Asn Asp Arg Ile Pro Asp Lys Glu Asn Thr Pro Leu
1               5                   10                  15

Ile Glu Pro His Val Pro Leu Arg Pro Ala Asn Thr Ile Thr Lys Val
            20                  25                  30

Pro Ser Glu Lys Ile Leu Arg Ala Gly Lys Ile Leu Arg Asn Ala Ile
        35                  40                  45

Leu Ser Arg Ala Pro His Met Ile Arg Asp Arg Lys Tyr His Leu Lys
    50                  55                  60

Thr Tyr Arg Gln Cys Cys Val Gly Thr Glu Leu Val Asp Trp Met Met
65                  70                  75                  80

Gln Gln Thr Pro Cys Val His Ser Arg Thr Gln Ala Val Gly Met Trp
                85                  90                  95

Gln Val Leu Leu Glu Asp Gly Val Leu Asn His Val Asp Gln Glu His
            100                 105                 110

His Phe Gln Asp Lys Tyr Leu Phe Tyr Arg Phe Leu Asp Asp Glu His
        115                 120                 125

Glu Asp Ala Pro Leu Pro Thr Glu Glu Lys Lys Glu Cys Asp Glu
    130                 135                 140

Glu Leu Gln Asp Thr Met Leu Leu Ser Gln Met Gly Pro Asp Ala
145                 150                 155                 160

His Met Arg Met Ile Leu Arg Lys Pro Pro Gly Gln Arg Thr Val Asp
                165                 170                 175

Asp Leu Glu Ile Ile Tyr Glu Glu Leu Leu His Ile Lys Ala Leu Ser
            180                 185                 190

His Leu Ser Thr Thr Val Lys Arg Glu Leu Ala Gly Val Leu Ile Phe
        195                 200                 205

Glu Ser His Ala Lys Gly Gly Thr Val Leu Phe Asn Gln Gly Glu Glu
    210                 215                 220

Gly Thr Ser Trp Tyr Ile Ile Leu Lys Gly Ser Val Asn Val Val Ile
225                 230                 235                 240

Tyr Gly Lys Gly Val Val Cys Thr Leu His Glu Gly Asp Asp Phe Gly
                245                 250                 255

Lys Leu Ala Leu Val Asn Asp Ala Pro Arg Ala Ala Ser Ile Val Leu
            260                 265                 270

Arg Glu Asp Asn Cys His Phe Leu Arg Val Asp Lys Glu Asp Phe Asn
        275                 280                 285

Arg Ile Leu Arg Asp Val Glu Ala Leu Glu Asn Val Tyr Ile Lys Ala
    290                 295                 300

Asp Lys Gln Lys Asn Gly Ile Lys Ala Asn Phe Lys Ile Arg His Asn
305                 310                 315                 320
```

```
Ile Glu Asp Gly Gly Val Gln Leu Ala Tyr His Tyr Gln Gln Asn Thr
                325                 330                 335

Pro Ile Gly Asp Gly Pro Val Leu Leu Pro Asp Asn His Tyr Leu Ser
            340                 345                 350

Val Gln Ser Ile Leu Ser Lys Asp Pro Asn Glu Lys Arg Asp His Met
        355                 360                 365

Val Leu Leu Glu Phe Val Thr Ala Ala Gly Ile Thr Leu Gly Met Asp
    370                 375                 380

Glu Leu Tyr Lys Gly Gly Thr Gly Gly Ser Met Val Ser Lys Gly Glu
385                 390                 395                 400

Glu Leu Phe Thr Gly Val Val Pro Ile Gln Val Glu Leu Asp Gly Asp
            405                 410                 415

Val Asn Gly His Lys Phe Ser Val Ser Gly Glu Gly Glu Gly Asp Ala
        420                 425                 430

Thr Tyr Gly Lys Leu Thr Leu Lys Phe Ile Cys Thr Thr Gly Lys Leu
    435                 440                 445

Pro Val Pro Trp Pro Thr Leu Val Thr Thr Leu Thr Tyr Gly Val Gln
450                 455                 460

Cys Phe Ser Arg Tyr Pro Asp His Met Lys Gln His Asp Phe Phe Lys
465                 470                 475                 480

Ser Ala Met Pro Glu Gly Tyr Ile Gln Glu Arg Thr Ile Phe Phe Lys
            485                 490                 495

Asp Asp Gly Asn Tyr Lys Thr Arg Ala Glu Val Lys Phe Glu Gly Asp
        500                 505                 510

Thr Leu Val Asn Arg Ile Glu Leu Lys Gly Ile Asp Phe Lys Glu Asp
    515                 520                 525

Gly Asn Ile Leu Gly His Lys Leu Glu Tyr Asn Thr Arg Lys Glu Asp
530                 535                 540

Phe Asn Arg Ile Leu Arg Asp Val Glu Ala Asn Thr Val Arg Leu Lys
545                 550                 555                 560

Glu His Asp Gln Asp Val Leu Val Leu Glu Lys Val Pro Ala Gly Asn
            565                 570                 575

Arg Ala Ser Asn Gln Gly Asn Ser Gln Pro Gln Gln Lys Tyr Thr Val
        580                 585                 590

Met Ser Gly Thr Pro Glu Lys Ile Leu Glu His Phe Leu Glu Thr Ile
    595                 600                 605

Arg Leu Glu Ala Thr Leu Asn Glu Ala Thr Asp Ser Val Leu Asn Asp
610                 615                 620

Phe Ile Met Met His Cys Val Phe Met Pro Asn Thr Gln Leu Cys Pro
625                 630                 635                 640

Ala Leu Val Ala His Tyr His Ala Gln Pro Ser Gln Gly Thr Glu Gln
            645                 650                 655

Glu Lys Met Asp Tyr Ala Leu Asn Asn Lys Arg Arg Val Ile Arg Leu
        660                 665                 670

Val Leu Gln Trp Ala Ala Met Tyr Gly Asp Leu Leu Gln Glu Asp Asp
    675                 680                 685

Val Ser Met Ala Phe Leu Glu Glu Phe Tyr Val Ser Val Ser Asp Asp
690                 695                 700

Ala Arg Met Ile Ala Ala Leu Lys Glu Gln Leu Pro Glu Leu Glu Lys
705                 710                 715                 720

Ile Val Lys Gln Ile Ser Glu Asp Ala Lys Ala Pro Gln Lys Lys His
            725                 730                 735
```

```
Lys Val Leu Gln Gln Phe Asn Thr Gly Asp Glu
        740                 745

<210> SEQ ID NO 4
<211> LENGTH: 1260
<212> TYPE: PRT
<213> ORGANISM: Artificial Sequence
<220> FEATURE:
<223> OTHER INFORMATION: Synthetic

<400> SEQUENCE: 4

Met Val Ala Ala His Ala Ala His Ser Ser Ser Ala Glu Trp Ile
1               5                   10                  15

Ala Cys Leu Asp Lys Arg Pro Leu Glu Arg Ser Ser Glu Asp Val Asp
                20                  25                  30

Ile Ile Phe Thr Arg Leu Lys Glu Val Lys Ala Phe Glu Lys Phe His
            35                  40                  45

Pro Asn Leu Leu His Gln Ile Cys Leu Cys Gly Tyr Tyr Glu Asn Leu
        50                  55                  60

Glu Lys Gly Ile Thr Leu Phe Arg Gln Gly Asp Ile Gly Thr Asn Trp
65              70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
        290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350
```

```
His Ile Lys Ala Leu Ser His Leu Ser Thr Thr Val Lys Arg Glu Leu
            355                 360                 365

Ala Gly Val Leu Ile Phe Glu Ser His Ala Lys Gly Gly Thr Val Leu
        370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Leu Val Ser His Asn Val
    450                 455                 460

Tyr Ile Lys Ala Asp Lys Gln Lys Asn Gly Ile Lys Ala Asn Phe Lys
465                 470                 475                 480

Ile Arg His Asn Ile Glu Asp Gly Gly Val Gln Leu Ala Tyr His Tyr
                485                 490                 495

Gln Gln Asn Thr Pro Ile Gly Asp Gly Pro Val Leu Leu Pro Asp Asn
            500                 505                 510

His Tyr Leu Ser Val Gln Ser Ile Leu Ser Lys Asp Pro Asn Glu Lys
        515                 520                 525

Arg Asp His Met Val Leu Leu Glu Phe Val Thr Ala Ala Gly Ile Thr
    530                 535                 540

Leu Gly Met Asp Glu Leu Tyr Lys Gly Gly Thr Gly Gly Ser Met Val
545                 550                 555                 560

Ser Lys Gly Glu Glu Leu Phe Thr Gly Val Val Pro Ile Gln Val Glu
                565                 570                 575

Leu Asp Gly Asp Val Asn Gly His Lys Phe Ser Val Ser Gly Glu Gly
            580                 585                 590

Glu Gly Asp Ala Thr Tyr Gly Lys Leu Thr Leu Lys Phe Ile Cys Thr
        595                 600                 605

Thr Gly Lys Leu Pro Val Pro Trp Pro Thr Leu Val Thr Thr Leu Thr
    610                 615                 620

Tyr Gly Val Gln Cys Phe Ser Arg Tyr Pro Asp His Met Lys Gln His
625                 630                 635                 640

Asp Phe Phe Lys Ser Ala Met Pro Glu Gly Tyr Ile Gln Glu Arg Thr
                645                 650                 655

Ile Phe Phe Lys Asp Asp Gly Asn Tyr Lys Thr Arg Ala Glu Val Lys
            660                 665                 670

Phe Glu Gly Asp Thr Leu Val Asn Arg Ile Glu Leu Lys Gly Ile Asp
        675                 680                 685

Phe Lys Glu Asp Gly Asn Ile Leu Gly His Lys Leu Glu Tyr Asn Phe
    690                 695                 700

Asn Asn Pro Asp Val Glu Ala Asn Thr Val Arg Leu Lys Glu His Asp
705                 710                 715                 720

Gln Asp Val Leu Val Leu Glu Lys Val Pro Ala Gly Asn Arg Ala Ser
                725                 730                 735

Asn Gln Gly Asn Ser Gln Pro Gln Lys Tyr Thr Val Met Ser Gly
            740                 745                 750

Thr Pro Glu Lys Ile Leu Glu His Phe Leu Glu Thr Ile Arg Leu Glu
        755                 760                 765

Ala Thr Leu Asn Glu Ala Thr Asp Ser Val Leu Asn Asp Phe Ile Met
```

-continued

```
            770             775             780
Met His Cys Val Phe Met Pro Asn Thr Gln Leu Cys Pro Ala Leu Val
785             790             795             800

Ala His Tyr His Ala Gln Pro Ser Gln Gly Thr Glu Gln Glu Lys Met
            805             810             815

Asp Tyr Ala Leu Asn Asn Lys Arg Arg Val Ile Arg Leu Val Leu Gln
            820             825             830

Trp Ala Ala Met Tyr Gly Asp Leu Leu Gln Glu Asp Val Ser Met
            835             840             845

Ala Phe Leu Glu Glu Phe Tyr Val Ser Val Ser Asp Asp Ala Arg Met
850             855             860

Ile Ala Ala Leu Lys Glu Gln Leu Pro Glu Leu Glu Lys Ile Val Lys
865             870             875             880

Gln Ile Ser Glu Asp Ala Lys Ala Pro Gln Lys Lys His Lys Val Leu
            885             890             895

Leu Gln Gln Phe Asn Thr Gly Asp Glu Arg Ala Gln Lys Arg Gln Pro
            900             905             910

Ile Arg Gly Ser Asp Glu Val Leu Phe Lys Val Tyr Cys Met Asp Pro
            915             920             925

Thr Tyr Thr Thr Ile Arg Val Pro Val Ala Thr Ser Val Lys Glu Val
            930             935             940

Ile Ser Ala Val Ala Asp Lys Leu Gly Ser Gly Glu Gly Leu Ile Ile
945             950             955             960

Val Lys Met Ser Ser Gly Gly Glu Lys Val Val Leu Lys Pro Asn Asp
            965             970             975

Val Ser Val Phe Met Thr Leu Thr Ile Asn Gly Arg Leu Phe Ala Cys
            980             985             990

Pro Arg Glu Gln Phe Asp Ser Leu  Thr Pro Leu Pro Glu  Gln Glu Gly
            995            1000            1005

Pro Thr  Val Gly Thr Val Gly  Thr Phe Glu Leu Met  Ser Ser Lys
           1010            1015            1020

Asp Leu  Ala Tyr Gln Met Thr  Ile Tyr Asp Trp Glu  Leu Phe Asn
           1025            1030            1035

Cys Val  His Glu Leu Glu Leu  Ile Tyr His Thr Phe  Gly Arg His
           1040            1045            1050

Asn Phe  Lys Lys Thr Thr Ala  Asn Leu Asp Leu Phe  Leu Arg Arg
           1055            1060            1065

Phe Asn  Glu Ile Gln Phe Trp  Val Val Thr Glu Ile  Cys Leu Cys
           1070            1075            1080

Ser Gln  Leu Ser Lys Arg Val  Gln Leu Leu Lys Lys  Phe Ile Lys
           1085            1090            1095

Ile Ala  Ala His Cys Lys Glu  Tyr Lys Asn Leu Asn  Ser Phe Phe
           1100            1105            1110

Ala Ile  Val Met Gly Leu Ser  Asn Val Ala Val Ser  Arg Leu Ala
           1115            1120            1125

Leu Thr  Trp Glu Lys Leu Pro  Ser Lys Phe Lys Lys  Phe Tyr Ala
           1130            1135            1140

Glu Phe  Glu Ser Leu Met Asp  Pro Ser Arg Asn His  Arg Ala Tyr
           1145            1150            1155

Arg Leu  Thr Val Ala Lys Leu  Glu Pro Pro Leu Ile  Pro Phe Met
           1160            1165            1170

Pro Leu  Leu Ile Lys Asp Met  Thr Phe Thr His Glu  Gly Asn Lys
           1175            1180            1185
```

-continued

```
Thr Phe Ile Asp Asn Leu Val Asn Phe Glu Lys Met Arg Met Ile
    1190                1195                1200

Ala Asn Thr Ala Arg Thr Val Arg Tyr Tyr Arg Ser Gln Pro Phe
    1205                1210                1215

Asn Pro Asp Ala Ala Gln Ala Asn Lys Asn His Gln Asp Val Arg
    1220                1225                1230

Ser Tyr Val Arg Gln Leu Asn Val Ile Asp Asn Gln Arg Thr Leu
    1235                1240                1245

Ser Gln Met Ser His Arg Leu Glu Pro Arg Arg Pro
    1250                1255                1260

<210> SEQ ID NO 5
<211> LENGTH: 1256
<212> TYPE: PRT
<213> ORGANISM: Artificial Sequence
<220> FEATURE:
<223> OTHER INFORMATION: Synthetic

<400> SEQUENCE: 5

Met Val Ala Ala His Ala Ala His Ser Ser Ser Ala Glu Trp Ile
1               5                   10                  15

Ala Cys Leu Asp Lys Arg Pro Leu Glu Arg Ser Ser Glu Asp Val Asp
                20                  25                  30

Ile Ile Phe Thr Arg Leu Lys Glu Val Lys Ala Phe Glu Lys Phe His
            35                  40                  45

Pro Asn Leu Leu His Gln Ile Cys Leu Cys Gly Tyr Tyr Glu Asn Leu
        50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285
```

```
Phe Leu Asp Asp Glu His Glu Asp Ala Pro Leu Pro Thr Glu Glu Glu
    290                 295                 300

Lys Lys Glu Cys Asp Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Asp Val Leu Glu Asn Val
    450                 455                 460

Tyr Ile Lys Ala Asp Lys Gln Lys Asn Gly Ile Lys Ala Asn Phe Lys
465                 470                 475                 480

Ile Arg His Asn Ile Glu Asp Gly Gly Val Gln Leu Ala Tyr His Tyr
                485                 490                 495

Gln Gln Asn Thr Pro Ile Gly Asp Gly Pro Val Leu Leu Pro Asp Asn
            500                 505                 510

His Tyr Leu Ser Val Gln Ser Ile Leu Ser Lys Asp Pro Asn Glu Lys
        515                 520                 525

Arg Asp His Met Val Leu Leu Glu Phe Val Thr Ala Ala Gly Ile Thr
    530                 535                 540

Leu Gly Met Asp Glu Leu Tyr Lys Gly Gly Thr Gly Gly Ser Met Val
545                 550                 555                 560

Ser Lys Gly Glu Glu Leu Phe Thr Gly Val Val Pro Ile Gln Val Glu
                565                 570                 575

Leu Asp Gly Asp Val Asn Gly His Lys Phe Ser Val Ser Gly Glu Gly
            580                 585                 590

Glu Gly Asp Ala Thr Tyr Gly Lys Leu Thr Leu Lys Phe Ile Cys Thr
        595                 600                 605

Thr Gly Lys Leu Pro Val Pro Trp Pro Thr Leu Val Thr Thr Leu Thr
    610                 615                 620

Tyr Gly Val Gln Cys Phe Ser Arg Tyr Pro Asp His Met Lys Gln His
625                 630                 635                 640

Asp Phe Phe Lys Ser Ala Met Pro Glu Gly Tyr Ile Gln Glu Arg Thr
                645                 650                 655

Ile Phe Phe Lys Asp Asp Gly Asn Tyr Lys Thr Arg Ala Glu Val Lys
            660                 665                 670

Phe Glu Gly Asp Thr Leu Val Asn Arg Ile Glu Leu Lys Gly Ile Asp
        675                 680                 685

Phe Lys Glu Asp Gly Asn Ile Leu Gly His Lys Leu Glu Tyr Asn Thr
    690                 695                 700
```

```
Arg Glu Ala Asn Thr Val Arg Leu Lys Glu His Asp Gln Asp Val Leu
705                 710                 715                 720

Val Leu Glu Lys Val Pro Ala Gly Asn Arg Ala Ser Asn Gln Gly Asn
            725                 730                 735

Ser Gln Pro Gln Gln Lys Tyr Thr Val Met Ser Gly Thr Pro Glu Lys
            740                 745                 750

Ile Leu Glu His Phe Leu Glu Thr Ile Arg Leu Glu Ala Thr Leu Asn
            755                 760                 765

Glu Ala Thr Asp Ser Val Leu Asn Asp Phe Ile Met Met His Cys Val
770                 775                 780

Phe Met Pro Asn Thr Gln Leu Cys Pro Ala Leu Val Ala His Tyr His
785                 790                 795                 800

Ala Gln Pro Ser Gln Gly Thr Glu Gln Glu Lys Met Asp Tyr Ala Leu
            805                 810                 815

Asn Asn Lys Arg Arg Val Ile Arg Leu Val Leu Gln Trp Ala Ala Met
            820                 825                 830

Tyr Gly Asp Leu Leu Gln Glu Asp Val Ser Met Ala Phe Leu Glu
            835                 840                 845

Glu Phe Tyr Val Ser Val Ser Asp Asp Ala Arg Met Ile Ala Ala Leu
850                 855                 860

Lys Glu Gln Leu Pro Glu Leu Glu Lys Ile Val Lys Gln Ile Ser Glu
865                 870                 875                 880

Asp Ala Lys Ala Pro Gln Lys Lys His Lys Val Leu Leu Gln Gln Phe
            885                 890                 895

Asn Thr Gly Asp Glu Arg Ala Gln Lys Arg Gln Pro Ile Arg Gly Ser
            900                 905                 910

Asp Glu Val Leu Phe Lys Val Tyr Cys Met Asp Pro Thr Tyr Thr Thr
            915                 920                 925

Ile Arg Val Pro Val Ala Thr Ser Val Lys Glu Val Ile Ser Ala Val
            930                 935                 940

Ala Asp Lys Leu Gly Ser Gly Glu Gly Leu Ile Ile Val Lys Met Ser
945                 950                 955                 960

Ser Gly Gly Glu Lys Val Val Leu Lys Pro Asn Asp Val Ser Val Phe
            965                 970                 975

Met Thr Leu Thr Ile Asn Gly Arg Leu Phe Ala Cys Pro Arg Glu Gln
            980                 985                 990

Phe Asp Ser Leu Thr Pro Leu Pro Glu Gln Glu Gly Pro Thr Val Gly
            995                 1000                1005

Thr Val Gly Thr Phe Glu Leu Met Ser Ser Lys Asp Leu Ala Tyr
    1010                1015                1020

Gln Met Thr Ile Tyr Asp Trp Glu Leu Phe Asn Cys Val His Glu
    1025                1030                1035

Leu Glu Leu Ile Tyr His Thr Phe Gly Arg His Asn Phe Lys Lys
    1040                1045                1050

Thr Thr Ala Asn Leu Asp Leu Phe Leu Arg Arg Phe Asn Glu Ile
    1055                1060                1065

Gln Phe Trp Val Val Thr Glu Ile Cys Leu Cys Ser Gln Leu Ser
    1070                1075                1080

Lys Arg Val Gln Leu Leu Lys Lys Phe Ile Lys Ile Ala Ala His
    1085                1090                1095

Cys Lys Glu Tyr Lys Asn Leu Asn Ser Phe Phe Ala Ile Val Met
    1100                1105                1110

Gly Leu Ser Asn Val Ala Val Ser Arg Leu Ala Leu Thr Trp Glu
```

```
                    1115                1120                1125

Lys Leu Pro Ser Lys Phe Lys Phe Tyr Ala Glu Phe Glu Ser
            1130                1135                1140

Leu Met Asp Pro Ser Arg Asn His Arg Ala Tyr Arg Leu Thr Val
1145                1150                1155

Ala Lys Leu Glu Pro Pro Leu Ile Pro Phe Met Pro Leu Leu Ile
        1160                1165                1170

Lys Asp Met Thr Phe Thr His Glu Gly Asn Lys Thr Phe Ile Asp
    1175                1180                1185

Asn Leu Val Asn Phe Glu Lys Met Arg Met Ile Ala Asn Thr Ala
        1190                1195                1200

Arg Thr Val Arg Tyr Tyr Arg Ser Gln Pro Phe Asn Pro Asp Ala
    1205                1210                1215

Ala Gln Ala Asn Lys Asn His Gln Asp Val Arg Ser Tyr Val Arg
        1220                1225                1230

Gln Leu Asn Val Ile Asp Asn Gln Arg Thr Leu Ser Gln Met Ser
    1235                1240                1245

His Arg Leu Glu Pro Arg Arg Pro
        1250                1255

<210> SEQ ID NO 6
<211> LENGTH: 535
<212> TYPE: PRT
<213> ORGANISM: Artificial Sequence
<220> FEATURE:
<223> OTHER INFORMATION: Synthetic

<400> SEQUENCE: 6

Met Gly Ser Asn Asn Asp Arg Ile Pro Asp Lys Glu Asn Thr Pro Leu
1               5                   10                  15

Ile Glu Pro His Val Pro Leu Arg Pro Ala Asn Thr Ile Thr Lys Val
            20                  25                  30

Pro Ser Glu Lys Ile Leu Arg Ala Gly Lys Ile Leu Arg Asn Ala Ile
        35                  40                  45

Leu Ser Arg Ala Pro His Met Ile Arg Asp Arg Lys Tyr His Leu Lys
    50                  55                  60

Thr Tyr Arg Gln Cys Cys Val Gly Thr Glu Leu Val Asp Trp Met Met
65                  70                  75                  80

Gln Gln Thr Pro Cys Val His Ser Arg Thr Gln Ala Val Gly Met Trp
                85                  90                  95

Gln Val Leu Leu Glu Asp Gly Val Leu Asn His Val Asp Gln Glu His
            100                 105                 110

His Phe Gln Asp Lys Tyr Leu Phe Tyr Arg Phe Leu Asp Asp Glu His
        115                 120                 125

Glu Asp Ala Pro Leu Pro Thr Glu Glu Glu Lys Lys Glu Cys Asp Glu
    130                 135                 140

Glu Leu Gln Asp Thr Met Leu Leu Leu Ser Gln Met Gly Pro Asp Ala
145                 150                 155                 160

His Met Arg Met Ile Leu Arg Lys Pro Pro Gly Gln Arg Thr Val Asp
                165                 170                 175

Asp Leu Glu Ile Ile Tyr Glu Glu Leu Leu His Ile Lys Ala Leu Ser
            180                 185                 190

His Leu Ser Thr Thr Val Lys Arg Glu Leu Ala Gly Val Leu Ile Phe
        195                 200                 205

Glu Ser His Ala Lys Gly Gly Thr Val Leu Phe Asn Gln Gly Glu Glu
```

```
                210                 215                 220
Gly Thr Ser Trp Tyr Ile Ile Leu Lys Gly Ser Val Asn Val Val Ile
225                 230                 235                 240

Tyr Gly Lys Gly Val Val Cys Thr Leu His Glu Gly Asp Asp Phe Gly
                245                 250                 255

Lys Leu Ala Leu Val Asn Asp Ala Pro Arg Ala Ala Ser Ile Val Leu
                260                 265                 270

Arg Glu Asp Asn Cys His Phe Leu Arg Val Asp Lys Glu Asp Phe Asn
            275                 280                 285

Arg Ile Leu Arg Arg Ala Asn Val Tyr Ile Lys Ala Asp Lys Gln Lys
        290                 295                 300

Asn Gly Ile Lys Ala Asn Phe Lys Ile Arg His Asn Ile Glu Asp Gly
305                 310                 315                 320

Gly Val Gln Leu Ala Tyr His Tyr Gln Gln Asn Thr Pro Ile Gly Asp
                325                 330                 335

Gly Pro Val Leu Leu Pro Asp Asn His Tyr Leu Ser Val Gln Ser Ile
                340                 345                 350

Leu Ser Lys Asp Pro Asn Glu Lys Arg Asp His Met Val Leu Leu Glu
            355                 360                 365

Phe Val Thr Ala Ala Gly Ile Thr Leu Gly Met Asp Glu Leu Tyr Lys
        370                 375                 380

Gly Gly Thr Gly Gly Ser Met Val Ser Lys Gly Glu Glu Leu Phe Thr
385                 390                 395                 400

Gly Val Val Pro Ile Gln Val Glu Leu Asp Gly Asp Val Asn Gly His
                405                 410                 415

Lys Phe Ser Val Ser Gly Glu Gly Glu Gly Asp Ala Thr Tyr Gly Lys
                420                 425                 430

Leu Thr Leu Lys Phe Ile Cys Thr Thr Gly Lys Leu Pro Val Pro Trp
            435                 440                 445

Pro Thr Leu Val Thr Thr Leu Thr Tyr Gly Val Gln Cys Phe Ser Arg
        450                 455                 460

Tyr Pro Asp His Met Lys Gln His Asp Phe Phe Lys Ser Ala Met Pro
465                 470                 475                 480

Glu Gly Tyr Ile Gln Glu Arg Thr Ile Phe Phe Lys Asp Asp Gly Asn
                485                 490                 495

Tyr Lys Thr Arg Ala Glu Val Lys Phe Glu Gly Asp Thr Leu Val Asn
                500                 505                 510

Arg Ile Glu Leu Lys Gly Ile Asp Phe Lys Glu Asp Gly Asn Ile Leu
            515                 520                 525

Gly His Lys Leu Glu Tyr Asn
        530                 535

<210> SEQ ID NO 7
<211> LENGTH: 1265
<212> TYPE: PRT
<213> ORGANISM: Artificial Sequence
<220> FEATURE:
<223> OTHER INFORMATION: Synthetic

<400> SEQUENCE: 7

Met Val Ala Ala His Ala His Ser Ser Ser Ser Ala Glu Trp Ile
1               5                   10                  15

Ala Cys Leu Asp Lys Arg Pro Leu Glu Arg Ser Ser Glu Asp Val Asp
                20                  25                  30

Ile Ile Phe Thr Arg Leu Lys Glu Val Lys Ala Phe Glu Lys Phe His
```

-continued

|  |  |  | 35 |  |  |  | 40 |  |  |  | 45 |  |  |
|---|---|---|---|---|---|---|---|---|---|---|---|---|---|

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Leu Glu Asn Val Tyr Ile
    450                 455                 460

-continued

```
Lys Ala Asp Lys Gln Lys Asn Gly Ile Lys Ala Asn Phe Lys Ile Arg
465                 470                 475                 480

His Asn Ile Glu Asp Gly Gly Val Gln Leu Ala Tyr His Tyr Gln Gln
                485                 490                 495

Asn Thr Pro Ile Gly Asp Gly Pro Val Leu Leu Pro Asp Asn His Tyr
            500                 505                 510

Leu Ser Val Gln Ser Ile Leu Ser Lys Asp Pro Asn Glu Lys Arg Asp
        515                 520                 525

His Met Val Leu Leu Glu Phe Val Thr Ala Ala Gly Ile Thr Leu Gly
    530                 535                 540

Met Asp Glu Leu Tyr Lys Gly Gly Thr Gly Gly Ser Met Val Ser Lys
545                 550                 555                 560

Gly Glu Glu Leu Phe Thr Gly Val Val Pro Ile Gln Val Glu Leu Asp
                565                 570                 575

Gly Asp Val Asn Gly His Lys Phe Ser Val Ser Gly Glu Gly Glu Gly
            580                 585                 590

Asp Ala Thr Tyr Gly Lys Leu Thr Leu Lys Phe Ile Cys Thr Thr Gly
        595                 600                 605

Lys Leu Pro Val Pro Trp Pro Thr Leu Val Thr Thr Leu Thr Tyr Gly
    610                 615                 620

Val Gln Cys Phe Ser Arg Tyr Pro Asp His Met Lys Gln His Asp Phe
625                 630                 635                 640

Phe Lys Ser Ala Met Pro Glu Gly Tyr Ile Gln Glu Arg Thr Ile Phe
                645                 650                 655

Phe Lys Asp Asp Gly Asn Tyr Lys Thr Arg Ala Glu Val Lys Phe Glu
            660                 665                 670

Gly Asp Thr Leu Val Asn Arg Ile Glu Leu Lys Gly Ile Asp Phe Lys
        675                 680                 685

Glu Asp Gly Asn Ile Leu Gly His Lys Leu Glu Tyr Asn Thr Arg Lys
    690                 695                 700

Glu Asp Phe Asn Arg Ile Leu Arg Asp Val Glu Ala Asn Thr Val Arg
705                 710                 715                 720

Leu Lys Glu His Asp Gln Asp Val Leu Val Leu Glu Lys Val Pro Ala
                725                 730                 735

Gly Asn Arg Ala Ser Asn Gln Gly Asn Ser Gln Pro Gln Gln Lys Tyr
            740                 745                 750

Thr Val Met Ser Gly Thr Pro Glu Lys Ile Leu Glu His Phe Leu Glu
        755                 760                 765

Thr Ile Arg Leu Glu Ala Thr Leu Asn Glu Ala Thr Asp Ser Val Leu
    770                 775                 780

Asn Asp Phe Ile Met Met His Cys Val Phe Met Pro Asn Thr Gln Leu
785                 790                 795                 800

Cys Pro Ala Leu Val Ala His Tyr His Ala Gln Pro Ser Gln Gly Thr
                805                 810                 815

Glu Gln Glu Lys Met Asp Tyr Ala Leu Asn Asn Lys Arg Arg Val Ile
            820                 825                 830

Arg Leu Val Leu Gln Trp Ala Ala Met Tyr Gly Asp Leu Leu Gln Glu
        835                 840                 845

Asp Asp Val Ser Met Ala Phe Leu Glu Glu Phe Tyr Val Ser Val Ser
    850                 855                 860

Asp Asp Ala Arg Met Ile Ala Ala Leu Lys Glu Gln Leu Pro Glu Leu
865                 870                 875                 880
```

-continued

```
Glu Lys Ile Val Lys Gln Ile Ser Glu Asp Ala Lys Ala Pro Gln Lys
                885                 890                 895
Lys His Lys Val Leu Leu Gln Gln Phe Asn Thr Gly Asp Glu Arg Ala
            900                 905                 910
Gln Lys Arg Gln Pro Ile Arg Gly Ser Asp Glu Val Leu Phe Lys Val
            915                 920                 925
Tyr Cys Met Asp Pro Thr Tyr Thr Thr Ile Arg Val Pro Val Ala Thr
            930                 935                 940
Ser Val Lys Glu Val Ile Ser Ala Val Ala Asp Lys Leu Gly Ser Gly
945                 950                 955                 960
Glu Gly Leu Ile Ile Val Lys Met Ser Ser Gly Gly Glu Lys Val Val
                965                 970                 975
Leu Lys Pro Asn Asp Val Ser Val Phe Met Thr Leu Thr Ile Asn Gly
                980                 985                 990
Arg Leu Phe Ala Cys Pro Arg Glu Gln Phe Asp Ser Leu Thr Pro Leu
                995                1000                1005
Pro Glu Gln Glu Gly Pro Thr Val Gly Thr Val Gly Thr Phe Glu
            1010                1015                1020
Leu Met Ser Ser Lys Asp Leu Ala Tyr Gln Met Thr Ile Tyr Asp
            1025                1030                1035
Trp Glu Leu Phe Asn Cys Val His Glu Leu Glu Leu Ile Tyr His
            1040                1045                1050
Thr Phe Gly Arg His Asn Phe Lys Lys Thr Thr Ala Asn Leu Asp
            1055                1060                1065
Leu Phe Leu Arg Arg Phe Asn Glu Ile Gln Phe Trp Val Val Thr
            1070                1075                1080
Glu Ile Cys Leu Cys Ser Gln Leu Ser Lys Arg Val Gln Leu Leu
            1085                1090                1095
Lys Lys Phe Ile Lys Ile Ala Ala His Cys Lys Glu Tyr Lys Asn
            1100                1105                1110
Leu Asn Ser Phe Phe Ala Ile Val Met Gly Leu Ser Asn Val Ala
            1115                1120                1125
Val Ser Arg Leu Ala Leu Thr Trp Glu Lys Leu Pro Ser Lys Phe
            1130                1135                1140
Lys Lys Phe Tyr Ala Glu Phe Glu Ser Leu Met Asp Pro Ser Arg
            1145                1150                1155
Asn His Arg Ala Tyr Arg Leu Thr Val Ala Lys Leu Glu Pro Pro
            1160                1165                1170
Leu Ile Pro Phe Met Pro Leu Leu Ile Lys Asp Met Thr Phe Thr
            1175                1180                1185
His Glu Gly Asn Lys Thr Phe Ile Asp Asn Leu Val Asn Phe Glu
            1190                1195                1200
Lys Met Arg Met Ile Ala Asn Thr Ala Arg Thr Val Arg Tyr Tyr
            1205                1210                1215
Arg Ser Gln Pro Phe Asn Pro Asp Ala Ala Gln Ala Asn Lys Asn
            1220                1225                1230
His Gln Asp Val Arg Ser Tyr Val Arg Gln Leu Asn Val Ile Asp
            1235                1240                1245
Asn Gln Arg Thr Leu Ser Gln Met Ser His Arg Leu Glu Pro Arg
            1250                1255                1260
Arg Pro
1265
```

```
<210> SEQ ID NO 8
<211> LENGTH: 1257
<212> TYPE: PRT
<213> ORGANISM: Artificial Sequence
<220> FEATURE:
<223> OTHER INFORMATION: Synthetic

<400> SEQUENCE: 8
```

Met Val Ala Ala His Ala Ala His Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
            35                  40                  45

Pro Asn Leu Leu His Gln Ile Cys Leu Cys Gly Tyr Tyr Glu Asn Leu
50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu

```
            370                 375                 380
Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
                420                 425                 430

Ala Ala Ser Ile Val Leu Arg Glu Asp Asn Cys His Phe Leu Arg Val
            435                 440                 445

Asp Lys Glu Asp Phe Asn Arg Ile Leu Arg Asp Val Leu Glu Asn Val
        450                 455                 460

Tyr Ile Lys Ala Asp Lys Gln Lys Asn Gly Ile Lys Ala Asn Phe Lys
465                 470                 475                 480

Ile Arg His Asn Ile Glu Asp Gly Gly Val Gln Leu Ala Tyr His Tyr
                485                 490                 495

Gln Gln Asn Thr Pro Ile Gly Asp Gly Pro Val Leu Leu Pro Asp Asn
                500                 505                 510

His Tyr Leu Ser Val Gln Ser Ile Leu Ser Lys Asp Pro Asn Glu Lys
            515                 520                 525

Arg Asp His Met Val Leu Leu Glu Phe Val Thr Ala Ala Gly Ile Thr
        530                 535                 540

Leu Gly Met Asp Glu Leu Tyr Lys Gly Gly Thr Gly Gly Ser Met Val
545                 550                 555                 560

Ser Lys Gly Glu Glu Val Ser Ser Gly Gly Val Pro Ile Gln Val Glu
                565                 570                 575

Leu Asp Gly Asp Val Asn Gly His Lys Phe Ser Val Ser Gly Glu Gly
                580                 585                 590

Glu Gly Asp Ala Thr Tyr Gly Lys Leu Thr Leu Lys Phe Ile Cys Thr
            595                 600                 605

Thr Gly Lys Leu Pro Val Pro Trp Pro Thr Leu Val Thr Thr Leu Thr
        610                 615                 620

Tyr Gly Val Gln Cys Phe Ser Arg Tyr Pro Asp His Met Lys Gln His
625                 630                 635                 640

Asp Phe Phe Lys Ser Ala Met Pro Glu Gly Tyr Ile Gln Glu Arg Thr
                645                 650                 655

Ile Phe Phe Lys Asp Asp Gly Asn Tyr Lys Thr Arg Ala Glu Val Lys
                660                 665                 670

Phe Glu Gly Asp Thr Leu Val Asn Arg Ile Glu Leu Lys Gly Ile Asp
            675                 680                 685

Phe Lys Glu Asp Gly Asn Ile Leu Gly His Lys Leu Glu Tyr Asn Thr
        690                 695                 700

Arg Val Glu Ala Asn Thr Val Arg Leu Lys His Asp Gln Asp Val
705                 710                 715                 720

Leu Val Leu Glu Lys Val Pro Ala Gly Asn Arg Ala Ser Asn Gln Gly
                725                 730                 735

Asn Ser Gln Pro Gln Gln Lys Tyr Thr Val Met Ser Gly Thr Pro Glu
                740                 745                 750

Lys Ile Leu Glu His Phe Leu Gly Thr Ile Arg Leu Glu Ala Thr Leu
            755                 760                 765

Asn Glu Ala Thr Asp Ser Val Leu Asn Asp Phe Ile Met Met His Cys
        770                 775                 780

Val Phe Met Pro Asn Thr Gln Leu Cys Pro Ala Leu Val Ala His Tyr
785                 790                 795                 800
```

```
His Ala Gln Pro Ser Gln Gly Thr Glu Gln Glu Lys Met Asp Tyr Ala
                805                 810                 815

Leu Asn Asn Lys Arg Arg Val Ile Arg Leu Val Leu Gln Trp Ala Ala
                820                 825                 830

Met Tyr Gly Asp Leu Leu Gln Glu Asp Val Ser Met Ala Phe Leu
                835                 840                 845

Glu Glu Phe Tyr Val Ser Val Ser Asp Asp Ala Arg Met Ile Ala Ala
                850                 855                 860

Leu Lys Glu Gln Leu Pro Glu Leu Glu Lys Ile Val Lys Gln Ile Ser
865                 870                 875                 880

Glu Asp Ala Lys Ala Pro Gln Lys Lys His Lys Val Leu Leu Gln Gln
                885                 890                 895

Phe Asn Thr Gly Asp Glu Arg Ala Gln Lys Arg Gln Pro Ile Arg Gly
                900                 905                 910

Ser Asp Glu Val Leu Phe Lys Val Tyr Cys Met Asp Pro Thr Tyr Thr
                915                 920                 925

Thr Ile Arg Val Pro Val Ala Thr Ser Val Lys Glu Val Ile Ser Ala
                930                 935                 940

Val Ala Asp Lys Leu Gly Ser Gly Glu Gly Leu Ile Ile Val Lys Met
945                 950                 955                 960

Ser Ser Gly Gly Glu Lys Val Val Leu Lys Pro Asn Asp Val Ser Val
                965                 970                 975

Phe Met Thr Leu Thr Ile Asn Gly Arg Leu Phe Ala Cys Pro Arg Glu
                980                 985                 990

Gln Phe Asp Ser Leu Thr Pro Leu Pro Glu Gln Glu Gly Pro Thr Val
                995                 1000                1005

Gly Thr Val Gly Thr Phe Glu Leu Met Ser Ser Lys Asp Leu Ala
        1010                1015                1020

Tyr Gln Met Thr Ile Tyr Asp Trp Glu Leu Phe Asn Cys Val His
        1025                1030                1035

Glu Leu Glu Leu Ile Tyr His Thr Phe Gly Arg His Asn Phe Lys
        1040                1045                1050

Lys Thr Thr Ala Asn Leu Asp Leu Phe Leu Arg Arg Phe Asn Glu
        1055                1060                1065

Ile Gln Phe Trp Val Val Thr Glu Ile Cys Leu Cys Ser Gln Leu
        1070                1075                1080

Ser Lys Arg Val Gln Leu Leu Lys Lys Phe Ile Lys Ile Ala Ala
        1085                1090                1095

His Cys Lys Glu Tyr Lys Asn Leu Asn Ser Phe Phe Ala Ile Val
        1100                1105                1110

Met Gly Leu Ser Asn Val Ala Val Ser Arg Leu Ala Leu Thr Trp
        1115                1120                1125

Glu Lys Leu Pro Ser Lys Phe Lys Lys Phe Tyr Ala Glu Phe Glu
        1130                1135                1140

Ser Leu Met Asp Pro Ser Arg Asn His Arg Ala Tyr Arg Leu Thr
        1145                1150                1155

Val Ala Lys Leu Glu Pro Pro Leu Ile Pro Phe Met Pro Leu Leu
        1160                1165                1170

Ile Lys Asp Met Thr Phe Thr His Glu Gly Asn Lys Thr Phe Ile
        1175                1180                1185

Asp Asn Leu Val Asn Phe Glu Lys Met Arg Met Ile Ala Asn Thr
        1190                1195                1200
```

Ala Arg Thr Val Arg Tyr Tyr Arg Ser Gln Pro Phe Asn Pro Asp
1205                1210                     1215

Ala Ala Gln Ala Asn Lys Asn His Gln Asp Val Arg Ser Tyr Val
1220                1225                     1230

Arg Gln Leu Asn Val Ile Asp Asn Gln Arg Thr Leu Ser Gln Met
1235                1240                     1245

Ser His Arg Leu Glu Pro Arg Arg Pro
1250                1255

<210> SEQ ID NO 9
<211> LENGTH: 1255
<212> TYPE: PRT
<213> ORGANISM: Artificial Sequence
<220> FEATURE:
<223> OTHER INFORMATION: Synthetic

<400> SEQUENCE: 9

Met Val Ala Ala His Ala Ala His Ser Ser Ser Ser Ala Glu Trp Ile
1                5                   10                  15

Ala Cys Leu Asp Lys Arg Pro Leu Glu Arg Ser Ser Glu Asp Val Asp
                20                  25                  30

Ile Ile Phe Thr Arg Leu Lys Glu Val Lys Ala Phe Glu Lys Phe His
            35                  40                  45

Pro Asn Leu Leu His Gln Ile Cys Leu Cys Gly Tyr Tyr Glu Asn Leu
        50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
        290                 295                 300

-continued

Lys Lys Glu Cys Asp Glu Leu Gln Asp Thr Met Leu Leu Ser
305                 310                 315                 320

Gln Met Gly Pro Asp Ala His Met Arg Met Ile Leu Arg Lys Pro Pro
            325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Val Lys Arg Glu Leu
            355                 360                 365

Ala Gly Val Leu Ile Phe Glu Ser His Ala Lys Gly Thr Val Leu
            370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
            435                 440                 445

Asp Lys Glu Asp Phe Asn Arg Ile Leu Arg Asp Val Leu Glu Asn Val
450                 455                 460

Tyr Ile Lys Ala Asp Lys Gln Lys Asn Gly Ile Lys Ala Asn Phe Lys
465                 470                 475                 480

Ile Arg His Asn Ile Glu Asp Gly Gly Val Gln Leu Ala Tyr His Tyr
                485                 490                 495

Gln Gln Asn Thr Pro Ile Gly Asp Gly Pro Val Leu Leu Pro Asp Asn
            500                 505                 510

His Tyr Leu Ser Val Gln Ser Ile Leu Ser Lys Asp Pro Asn Glu Lys
            515                 520                 525

Arg Asp His Met Val Leu Leu Glu Phe Val Thr Ala Ala Gly Ile Thr
530                 535                 540

Leu Gly Met Asp Glu Leu Tyr Lys Gly Gly Thr Gly Gly Ser Met Val
545                 550                 555                 560

Ser Lys Gly Glu Glu Leu Phe Thr Gly Val Val Pro Ile Gln Val Glu
                565                 570                 575

Leu Asp Gly Asp Val Asn Gly His Lys Phe Ser Val Ser Gly Glu Gly
            580                 585                 590

Glu Gly Asp Ala Thr Tyr Gly Lys Leu Thr Leu Lys Phe Ile Cys Thr
            595                 600                 605

Thr Gly Lys Leu Pro Val Pro Trp Pro Thr Leu Val Thr Thr Leu Thr
610                 615                 620

Tyr Gly Val Gln Cys Phe Ser Arg Tyr Pro Asp His Met Lys Gln His
625                 630                 635                 640

Asp Phe Phe Lys Ser Ala Met Pro Glu Gly Tyr Ile Gln Glu Arg Thr
                645                 650                 655

Ile Phe Phe Lys Asp Asp Gly Asn Tyr Lys Thr Arg Ala Glu Val Lys
            660                 665                 670

Phe Glu Gly Asp Thr Leu Val Asn Arg Ile Glu Leu Lys Gly Ile Asp
            675                 680                 685

Phe Lys Glu Asp Gly Asn Ile Leu Gly His Lys Leu Glu Tyr Asn Thr
            690                 695                 700

Arg Ala Asn Thr Val Arg Leu Lys Glu His Asp Gln Asp Val Leu Val
705                 710                 715                 720

Leu Glu Lys Val Pro Ala Gly Asn Arg Ala Ser Asn Gln Gly Asn Ser

```
                725                 730                 735
Gln Pro Gln Gln Lys Tyr Thr Val Met Ser Gly Thr Pro Glu Lys Ile
            740                 745                 750
Leu Glu His Phe Leu Glu Thr Ile Arg Leu Glu Ala Thr Leu Asn Glu
            755                 760                 765
Ala Thr Asp Ser Val Leu Asn Asp Phe Ile Met Met His Cys Val Phe
            770                 775                 780
Met Pro Asn Thr Gln Leu Cys Pro Ala Leu Val Ala His Tyr His Ala
785                 790                 795                 800
Gln Pro Ser Gln Gly Thr Glu Gln Lys Met Asp Tyr Ala Leu Asn
            805                 810                 815
Asn Lys Arg Arg Val Ile Arg Leu Val Leu Gln Trp Ala Ala Met Tyr
            820                 825                 830
Gly Asp Leu Leu Gln Glu Asp Val Ser Met Ala Phe Leu Glu Glu
            835                 840                 845
Phe Tyr Val Ser Val Ser Asp Asp Ala Arg Met Ile Ala Ala Leu Lys
        850                 855                 860
Glu Gln Leu Pro Glu Leu Glu Lys Ile Val Lys Gln Ile Ser Glu Asp
865                 870                 875                 880
Ala Lys Ala Pro Gln Lys Lys His Lys Val Leu Leu Gln Gln Phe Asn
                885                 890                 895
Thr Gly Asp Glu Arg Ala Gln Lys Arg Gln Pro Ile Arg Gly Ser Asp
            900                 905                 910
Glu Val Leu Phe Lys Val Tyr Cys Met Asp Pro Thr Tyr Thr Thr Ile
            915                 920                 925
Arg Val Pro Val Ala Thr Ser Val Lys Glu Val Ile Ser Ala Val Ala
            930                 935                 940
Asp Lys Leu Gly Ser Gly Glu Gly Leu Ile Ile Val Lys Met Ser Ser
945                 950                 955                 960
Gly Gly Glu Lys Val Val Leu Lys Pro Asn Asp Val Ser Val Phe Met
                965                 970                 975
Thr Leu Thr Ile Asn Gly Arg Leu Phe Ala Cys Pro Arg Glu Gln Phe
            980                 985                 990
Asp Ser Leu Thr Pro Leu Pro Glu Gln Glu Gly Pro Thr Val Gly Thr
            995                 1000                1005
Val Gly Thr Phe Glu Leu Met Ser Ser Lys Asp Leu Ala Tyr Gln
        1010                1015                1020
Met Thr Ile Tyr Asp Trp Glu Leu Phe Asn Cys Val His Glu Leu
        1025                1030                1035
Glu Leu Ile Tyr His Thr Phe Gly Arg His Asn Phe Lys Lys Thr
        1040                1045                1050
Thr Ala Asn Leu Asp Leu Phe Leu Arg Arg Phe Asn Glu Ile Gln
        1055                1060                1065
Phe Trp Val Val Thr Glu Ile Cys Leu Cys Ser Gln Leu Ser Lys
        1070                1075                1080
Arg Val Gln Leu Leu Lys Lys Phe Ile Lys Ile Ala Ala His Cys
        1085                1090                1095
Lys Glu Tyr Lys Asn Leu Asn Ser Phe Phe Ala Ile Val Met Gly
        1100                1105                1110
Leu Ser Asn Val Ala Val Ser Arg Leu Ala Leu Thr Trp Glu Lys
        1115                1120                1125
Leu Pro Ser Lys Phe Lys Lys Phe Tyr Ala Glu Phe Glu Ser Leu
        1130                1135                1140
```

```
Met Asp Pro Ser Arg Asn His Arg Ala Tyr Arg Leu Thr Val Ala
    1145                1150                1155

Lys Leu Glu Pro Pro Leu Ile Pro Phe Met Pro Leu Leu Ile Lys
    1160                1165                1170

Asp Met Thr Phe Thr His Glu Gly Asn Lys Thr Phe Ile Asp Asn
    1175                1180                1185

Leu Val Asn Phe Glu Lys Met Arg Met Ile Ala Asn Thr Ala Arg
    1190                1195                1200

Thr Val Arg Tyr Tyr Arg Ser Gln Pro Phe Asn Pro Asp Ala Ala
    1205                1210                1215

Gln Ala Asn Lys Asn His Gln Asp Val Arg Ser Tyr Val Arg Gln
    1220                1225                1230

Leu Asn Val Ile Asp Asn Gln Arg Thr Leu Ser Gln Met Ser His
    1235                1240                1245

Arg Leu Glu Pro Arg Arg Pro
    1250                1255

<210> SEQ ID NO 10
<211> LENGTH: 1260
<212> TYPE: PRT
<213> ORGANISM: Artificial Sequence
<220> FEATURE:
<223> OTHER INFORMATION: Synthetic

<400> SEQUENCE: 10

Met Val Ala Ala His Ala Ala His Ser Ser Ser Ala Glu Trp Ile
1               5                   10                  15

Ala Cys Leu Asp Lys Arg Pro Leu Glu Arg Ser Ser Glu Asp Val Asp
                20                  25                  30

Ile Ile Phe Thr Arg Leu Lys Glu Val Lys Ala Phe Glu Lys Phe His
                35                  40                  45

Pro Asn Leu Leu His Gln Ile Cys Leu Cys Gly Tyr Tyr Glu Asn Leu
            50                  55                      60

Glu Lys Gly Ile Thr Leu Phe Arg Gln Gly Asp Ile Gly Thr Asn Trp
65              70                      75                  80

Tyr Ala Val Leu Ala Gly Ser Leu Asp Val Lys Val Ser Glu Thr Ser
                    85                  90                  95

Ser His Gln Asp Ala Val Thr Ile Cys Thr Leu Gly Ile Gly Thr Ala
                100                 105                 110

Phe Gly Glu Ser Ile Leu Asp Asn Thr Pro Arg His Ala Thr Ile Val
            115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
                180                 185                 190

Asn Thr Ile Thr Lys Val Pro Ser Glu Lys Ile Leu Arg Ala Gly Lys
            195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240
```

-continued

```
Leu Val Asp Trp Met Met Gln Gln Thr Pro Cys Val His Ser Arg Thr
            245                 250                 255
Gln Ala Val Gly Met Trp Gln Val Leu Leu Glu Asp Gly Val Leu Asn
        260                 265                 270
His Val Asp Gln Glu His His Phe Gln Asp Lys Tyr Leu Phe Tyr Arg
    275                 280                 285
Phe Leu Asp Asp Glu His Glu Asp Ala Pro Leu Pro Thr Glu Glu Glu
290                 295                 300
Lys Lys Glu Cys Asp Glu Leu Gln Asp Thr Met Leu Leu Leu Ser
305                 310                 315                 320
Gln Met Gly Pro Asp Ala His Met Arg Met Ile Leu Arg Lys Pro Pro
            325                 330                 335
Gly Gln Arg Thr Val Asp Asp Leu Glu Ile Ile Tyr Glu Glu Leu Leu
        340                 345                 350
His Ile Lys Ala Leu Ser His Leu Ser Thr Thr Val Lys Arg Glu Leu
    355                 360                 365
Ala Gly Val Leu Ile Phe Glu Ser His Ala Lys Gly Gly Thr Val Leu
370                 375                 380
Phe Asn Gln Gly Glu Glu Gly Thr Ser Trp Tyr Ile Ile Leu Lys Gly
385                 390                 395                 400
Ser Val Asn Val Val Ile Tyr Gly Lys Gly Val Val Cys Thr Leu His
            405                 410                 415
Glu Gly Asp Asp Phe Gly Lys Leu Ala Leu Val Asn Asp Ala Pro Arg
        420                 425                 430
Ala Ala Ser Ile Val Leu Arg Glu Asp Asn Cys His Phe Leu Arg Val
    435                 440                 445
Asp Lys Glu Asp Phe Asn Arg Ile Leu Arg Leu Glu Asn Val Tyr Ile
450                 455                 460
Lys Ala Asp Lys Gln Lys Asn Gly Ile Lys Ala Asn Phe Lys Ile Arg
465                 470                 475                 480
His Asn Ile Glu Asp Gly Gly Val Gln Leu Ala Tyr His Tyr Gln Gln
            485                 490                 495
Asn Thr Pro Ile Gly Asp Gly Pro Val Leu Leu Pro Asp Asn His Tyr
        500                 505                 510
Leu Ser Val Gln Ser Ile Leu Ser Lys Asp Pro Asn Glu Lys Arg Asp
    515                 520                 525
His Met Val Leu Leu Glu Phe Val Thr Ala Ala Gly Ile Thr Leu Gly
530                 535                 540
Met Asp Glu Leu Tyr Lys Gly Gly Thr Gly Gly Ser Met Val Ser Lys
545                 550                 555                 560
Gly Glu Glu Leu Phe Thr Gly Val Val Pro Ile Gln Val Glu Leu Asp
            565                 570                 575
Gly Asp Val Asn Gly His Lys Phe Ser Val Ser Gly Glu Gly Glu Gly
        580                 585                 590
Asp Ala Thr Tyr Gly Lys Leu Thr Leu Lys Phe Ile Cys Thr Thr Gly
    595                 600                 605
Lys Leu Pro Val Pro Trp Pro Thr Leu Val Thr Thr Leu Thr Tyr Gly
610                 615                 620
Val Gln Cys Phe Ser Arg Tyr Pro Asp His Met Lys Gln His Asp Phe
625                 630                 635                 640
Phe Lys Ser Ala Met Pro Glu Gly Tyr Ile Gln Glu Arg Thr Ile Phe
            645                 650                 655
```

```
Phe Lys Asp Asp Gly Asn Tyr Lys Thr Arg Ala Glu Val Lys Phe Glu
        660                 665                 670

Gly Asp Thr Leu Val Asn Arg Ile Glu Leu Lys Gly Ile Asp Phe Lys
        675                 680                 685

Glu Asp Gly Asn Ile Leu Gly His Lys Leu Glu Tyr Asn Thr Arg Arg
        690                 695                 700

Ile Leu Arg Asp Val Glu Ala Asn Thr Val Arg Leu Lys Glu His Asp
705                 710                 715                 720

Gln Asp Val Leu Val Leu Glu Lys Val Pro Ala Gly Asn Arg Ala Ser
                725                 730                 735

Asn Gln Gly Asn Ser Gln Pro Gln Gln Lys Tyr Thr Val Met Ser Gly
        740                 745                 750

Thr Pro Glu Lys Ile Leu Glu His Phe Leu Glu Thr Ile Arg Leu Glu
        755                 760                 765

Ala Thr Leu Asn Glu Ala Thr Asp Ser Val Leu Asn Asp Phe Ile Met
        770                 775                 780

Met His Cys Val Phe Met Pro Asn Thr Gln Leu Cys Pro Ala Leu Val
785                 790                 795                 800

Ala His Tyr His Ala Gln Pro Ser Gln Gly Thr Glu Gln Lys Met
        805                 810                 815

Asp Tyr Ala Leu Asn Asn Lys Arg Arg Val Ile Arg Leu Val Leu Gln
        820                 825                 830

Trp Ala Ala Met Tyr Gly Asp Leu Leu Gln Glu Asp Val Ser Met
        835                 840                 845

Ala Phe Leu Glu Glu Phe Tyr Val Ser Val Ser Asp Asp Ala Arg Met
850                 855                 860

Ile Ala Ala Leu Lys Glu Gln Leu Pro Glu Leu Glu Lys Ile Val Lys
865                 870                 875                 880

Gln Ile Ser Glu Asp Ala Lys Ala Pro Gln Lys Lys His Lys Val Leu
                885                 890                 895

Leu Gln Gln Phe Asn Thr Gly Asp Glu Arg Ala Gln Lys Arg Gln Pro
        900                 905                 910

Ile Arg Gly Ser Asp Glu Val Leu Phe Lys Val Tyr Cys Met Asp Pro
        915                 920                 925

Thr Tyr Thr Thr Ile Arg Val Pro Val Ala Thr Ser Val Lys Glu Val
        930                 935                 940

Ile Ser Ala Val Ala Asp Lys Leu Gly Ser Gly Gly Leu Ile Ile
945                 950                 955                 960

Val Lys Met Ser Ser Gly Gly Glu Lys Val Val Leu Lys Pro Asn Asp
                965                 970                 975

Val Ser Val Phe Met Thr Leu Thr Ile Asn Gly Arg Leu Phe Ala Cys
        980                 985                 990

Pro Arg Glu Gln Phe Asp Ser Leu Thr Pro Leu Pro Glu Gln Glu Gly
        995                 1000                1005

Pro Thr Val Gly Thr Val Gly Thr Phe Glu Leu Met Ser Ser Lys
        1010                1015                1020

Asp Leu Ala Tyr Gln Met Thr Ile Tyr Asp Trp Glu Leu Phe Asn
        1025                1030                1035

Cys Val His Glu Leu Glu Leu Ile Tyr His Thr Phe Gly Arg His
        1040                1045                1050

Asn Phe Lys Lys Thr Thr Ala Asn Leu Asp Leu Phe Leu Arg Arg
        1055                1060                1065

Phe Asn Glu Ile Gln Phe Trp Val Val Thr Glu Ile Cys Leu Cys
```

```
                    1070                1075                1080

Ser  Gln  Leu  Ser  Lys  Arg  Val  Gln  Leu  Leu  Lys  Lys  Phe  Ile  Lys
              1085                1090                1095

Ile  Ala  Ala  His  Cys  Lys  Glu  Tyr  Lys  Asn  Leu  Asn  Ser  Phe  Phe
         1100                1105                1110

Ala  Ile  Val  Met  Gly  Leu  Ser  Asn  Val  Ala  Val  Ser  Arg  Leu  Ala
    1115                1120                1125

Leu  Thr  Trp  Glu  Lys  Leu  Pro  Ser  Lys  Phe  Lys  Phe  Tyr  Ala
1130                1135                1140

Glu  Phe  Glu  Ser  Leu  Met  Asp  Pro  Ser  Arg  Asn  His  Arg  Ala  Tyr
    1145                1150                1155

Arg  Leu  Thr  Val  Ala  Lys  Leu  Glu  Pro  Pro  Leu  Ile  Pro  Phe  Met
         1160                1165                1170

Pro  Leu  Leu  Ile  Lys  Asp  Met  Thr  Phe  Thr  His  Glu  Gly  Asn  Lys
              1175                1180                1185

Thr  Phe  Ile  Asp  Asn  Leu  Val  Asn  Phe  Glu  Lys  Met  Arg  Met  Ile
                   1190                1195                1200

Ala  Asn  Thr  Ala  Arg  Thr  Val  Arg  Tyr  Tyr  Arg  Ser  Gln  Pro  Phe
                        1205                1210                1215

Asn  Pro  Asp  Ala  Ala  Gln  Ala  Asn  Lys  Asn  His  Gln  Asp  Val  Arg
    1220                1225                1230

Ser  Tyr  Val  Arg  Gln  Leu  Asn  Val  Ile  Asp  Asn  Gln  Arg  Thr  Leu
         1235                1240                1245

Ser  Gln  Met  Ser  His  Arg  Leu  Glu  Pro  Arg  Arg  Pro
              1250                1255                1260

<210> SEQ ID NO 11
<211> LENGTH: 1256
<212> TYPE: PRT
<213> ORGANISM: Artificial Sequence
<220> FEATURE:
<223> OTHER INFORMATION: Synthetic

<400> SEQUENCE: 11

Met  Val  Ala  Ala  His  Ala  Ala  His  Ser  Ser  Ser  Ala  Glu  Trp  Ile
1                 5                  10                  15

Ala  Cys  Leu  Asp  Lys  Arg  Pro  Leu  Glu  Arg  Ser  Ser  Glu  Asp  Val  Asp
              20                  25                  30

Ile  Ile  Phe  Thr  Arg  Leu  Lys  Glu  Val  Lys  Ala  Phe  Glu  Lys  Phe  His
                 35                  40                  45

Pro  Asn  Leu  Leu  His  Gln  Ile  Cys  Leu  Cys  Gly  Tyr  Tyr  Glu  Asn  Leu
    50                  55                  60

Glu  Lys  Gly  Ile  Thr  Leu  Phe  Arg  Gln  Gly  Asp  Ile  Gly  Thr  Asn  Trp
65                  70                  75                  80

Tyr  Ala  Val  Leu  Ala  Gly  Ser  Leu  Asp  Val  Lys  Val  Ser  Glu  Thr  Ser
                    85                  90                  95

Ser  His  Gln  Asp  Ala  Val  Thr  Ile  Cys  Thr  Leu  Gly  Ile  Gly  Thr  Ala
                100                 105                 110

Phe  Gly  Glu  Ser  Ile  Leu  Asp  Asn  Thr  Pro  Arg  His  Ala  Thr  Ile  Val
            115                 120                 125

Thr  Arg  Glu  Ser  Ser  Glu  Leu  Leu  Arg  Ile  Glu  Gln  Lys  Asp  Phe  Lys
        130                 135                 140

Ala  Leu  Trp  Glu  Lys  Tyr  Arg  Gln  Tyr  Met  Ala  Gly  Leu  Leu  Ala  Pro
145                 150                 155                 160

Pro  Tyr  Gly  Val  Met  Glu  Thr  Gly  Ser  Asn  Asn  Asp  Arg  Ile  Pro  Asp
```

```
                    165                 170                 175
Lys Glu Asn Thr Pro Leu Ile Glu Pro His Val Pro Leu Arg Pro Ala
                180                 185                 190

Asn Thr Ile Thr Lys Val Pro Ser Glu Lys Ile Leu Arg Ala Gly Lys
            195                 200                 205

Ile Leu Arg Asn Ala Ile Leu Ser Arg Ala Pro His Met Ile Arg Asp
210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
                260                 265                 270

His Val Asp Gln Glu His His Phe Gln Asp Lys Tyr Leu Phe Tyr Arg
                275                 280                 285

Phe Leu Asp Asp Glu His Glu Asp Ala Pro Leu Pro Thr Glu Glu Glu
            290                 295                 300

Lys Lys Glu Cys Asp Glu Leu Gln Asp Thr Met Leu Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
                340                 345                 350

His Ile Lys Ala Leu Ser His Leu Ser Thr Thr Val Lys Arg Glu Leu
            355                 360                 365

Ala Gly Val Leu Ile Phe Glu Ser His Ala Lys Gly Gly Thr Val Leu
370                 375                 380

Phe Asn Gln Gly Glu Gly Thr Ser Trp Tyr Ile Ile Leu Lys Gly Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
                420                 425                 430

Ala Ala Ser Ile Val Leu Arg Glu Asp Asn Cys His Phe Leu Arg Val
            435                 440                 445

Asp Lys Glu Asp Phe Asn Arg Ile Leu Arg Asp Val Leu Glu Asn Val
450                 455                 460

Tyr Ile Lys Ala Asp Lys Gln Lys Asn Gly Ile Lys Ala Asn Phe Lys
465                 470                 475                 480

Ile Arg His Asn Ile Glu Asp Gly Gly Val Gln Leu Ala Tyr His Tyr
                485                 490                 495

Gln Gln Asn Thr Pro Ile Gly Asp Gly Pro Val Leu Leu Pro Asp Asn
                500                 505                 510

His Tyr Leu Ser Val Gln Ser Ile Leu Ser Lys Asp Pro Asn Glu Lys
            515                 520                 525

Arg Asp His Met Val Leu Leu Glu Phe Val Thr Ala Ala Gly Ile Thr
530                 535                 540

Leu Gly Met Asp Glu Leu Tyr Lys Gly Gly Thr Gly Gly Ser Met Val
545                 550                 555                 560

Ser Lys Gly Glu Glu Leu Phe Thr Gly Val Val Pro Ile Gln Val Glu
                565                 570                 575

Leu Asp Gly Asp Val Asn Gly His Lys Phe Ser Val Ser Gly Glu Gly
                580                 585                 590
```

```
Glu Gly Asp Ala Thr Tyr Gly Lys Leu Thr Leu Lys Phe Ile Cys Thr
        595                 600                 605

Thr Gly Lys Leu Pro Val Pro Trp Pro Thr Leu Val Thr Thr Leu Thr
        610                 615                 620

Tyr Gly Val Gln Cys Phe Ser Arg Tyr Pro Asp His Met Lys Gln His
625                 630                 635                 640

Asp Phe Phe Lys Ser Ala Met Pro Glu Gly Tyr Ile Gln Glu Arg Thr
                645                 650                 655

Ile Phe Phe Lys Asp Asp Gly Asn Tyr Lys Thr Arg Ala Glu Val Lys
                660                 665                 670

Phe Glu Gly Asp Thr Leu Val Asn Arg Ile Glu Leu Lys Gly Ile Asp
        675                 680                 685

Phe Lys Glu Asp Gly Asn Ile Leu Gly His Lys Leu Glu Tyr Asn Thr
        690                 695                 700

Arg Glu Ala Asn Thr Val Arg Leu Lys Glu His Asp Gln Asp Val Leu
705                 710                 715                 720

Val Leu Glu Lys Val Pro Ala Gly Asn Arg Ala Ser Asn Gln Gly Asn
                725                 730                 735

Ser Gln Pro Gln Gln Lys Tyr Thr Val Met Ser Gly Thr Pro Glu Lys
        740                 745                 750

Ile Leu Glu His Phe Leu Glu Thr Ile Arg Leu Glu Ala Thr Leu Asn
        755                 760                 765

Glu Ala Thr Asp Ser Val Leu Asn Asp Phe Ile Met Met His Cys Val
770                 775                 780

Phe Met Pro Asn Thr Gln Leu Cys Pro Ala Leu Val Ala His Tyr His
785                 790                 795                 800

Ala Gln Pro Ser Gln Gly Thr Glu Gln Glu Lys Met Asp Tyr Ala Leu
                805                 810                 815

Asn Asn Lys Arg Arg Val Ile Arg Leu Val Leu Gln Trp Ala Ala Met
        820                 825                 830

Tyr Gly Asp Leu Leu Gln Glu Asp Asp Val Ser Met Ala Phe Leu Glu
        835                 840                 845

Glu Phe Tyr Val Ser Val Ser Asp Asp Ala Arg Met Ile Ala Ala Leu
        850                 855                 860

Lys Glu Gln Leu Pro Glu Leu Glu Lys Ile Val Lys Gln Ile Ser Glu
865                 870                 875                 880

Asp Ala Lys Ala Pro Gln Lys Lys His Lys Val Leu Leu Gln Gln Phe
                885                 890                 895

Asn Thr Gly Asp Glu Arg Ala Gln Lys Arg Gln Pro Ile Arg Gly Ser
        900                 905                 910

Asp Glu Val Leu Phe Lys Val Tyr Cys Met Asp Pro Thr Tyr Thr Thr
        915                 920                 925

Ile Arg Val Pro Val Ala Thr Ser Val Lys Glu Val Ile Ser Ala Val
        930                 935                 940

Ala Asp Lys Leu Gly Ser Gly Glu Gly Leu Ile Ile Val Lys Met Ser
945                 950                 955                 960

Ser Gly Gly Glu Lys Val Val Leu Lys Pro Asn Asp Val Ser Val Phe
                965                 970                 975

Met Thr Leu Thr Ile Asn Gly Arg Leu Phe Ala Cys Pro Arg Glu Gln
        980                 985                 990

Phe Asp Ser Leu Thr Pro Leu Pro  Glu Gln Glu Gly Pro  Thr Val Gly
        995                 1000                1005
```

Thr Val Gly Thr Phe Glu Leu Met Ser Ser Lys Asp Leu Ala Tyr
1010                1015                1020

Gln Met Thr Ile Tyr Asp Trp Glu Leu Phe Asn Cys Val His Glu
    1025                1030                1035

Leu Glu Leu Ile Tyr His Thr Phe Gly Arg His Asn Phe Lys Lys
    1040                1045                1050

Thr Thr Ala Asn Leu Asp Leu Phe Leu Arg Arg Phe Asn Glu Ile
    1055                1060                1065

Gln Phe Trp Val Val Thr Glu Ile Cys Leu Cys Ser Gln Leu Ser
    1070                1075                1080

Lys Arg Val Gln Leu Leu Lys Lys Phe Ile Lys Ile Ala Ala His
    1085                1090                1095

Cys Lys Glu Tyr Lys Asn Leu Asn Ser Phe Phe Ala Ile Val Met
    1100                1105                1110

Gly Leu Ser Asn Val Ala Val Ser Arg Leu Ala Leu Thr Trp Glu
    1115                1120                1125

Lys Leu Pro Ser Lys Phe Lys Lys Phe Tyr Ala Glu Phe Glu Ser
    1130                1135                1140

Leu Met Asp Pro Ser Arg Asn His Arg Ala Tyr Arg Leu Thr Val
    1145                1150                1155

Ala Lys Leu Glu Pro Pro Leu Ile Pro Phe Met Pro Leu Leu Ile
    1160                1165                1170

Lys Asp Met Thr Phe Thr His Glu Gly Asn Lys Thr Phe Ile Asp
    1175                1180                1185

Asn Leu Val Asn Phe Glu Lys Met Arg Met Ile Ala Asn Thr Ala
    1190                1195                1200

Arg Thr Val Arg Tyr Tyr Arg Ser Gln Pro Phe Asn Pro Asp Ala
    1205                1210                1215

Ala Gln Ala Asn Lys Asn His Gln Asp Val Arg Ser Tyr Val Arg
    1220                1225                1230

Gln Leu Asn Val Ile Asp Asn Gln Arg Thr Leu Ser Gln Met Ser
    1235                1240                1245

His Arg Leu Glu Pro Arg Arg Pro
    1250                1255

<210> SEQ ID NO 12
<211> LENGTH: 1263
<212> TYPE: PRT
<213> ORGANISM: Artificial Sequence
<220> FEATURE:
<223> OTHER INFORMATION: Synthetic

<400> SEQUENCE: 12

Met Val Ala Ala His Ala Ala His Ser Ser Ser Ala Glu Trp Ile
1               5                   10                  15

Ala Cys Leu Asp Lys Arg Pro Leu Glu Arg Ser Ser Glu Asp Val Asp
                20                  25                  30

Ile Ile Phe Thr Arg Leu Lys Glu Val Lys Ala Phe Glu Lys Phe His
                35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

```
Ser His Gln Asp Ala Val Thr Ile Cys Thr Leu Gly Ile Gly Thr Ala
                100                 105                 110

Phe Gly Glu Ser Ile Leu Asp Asn Thr Pro Arg His Ala Thr Ile Val
            115                 120                 125

Thr Arg Glu Ser Ser Glu Leu Leu Arg Ile Glu Gln Lys Asp Phe Lys
        130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
        290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
        370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Asp Leu Glu Asn Val Tyr
        450                 455                 460

Ile Lys Ala Asp Lys Gln Lys Asn Gly Ile Lys Ala Asn Phe Lys Ile
465                 470                 475                 480

Arg His Asn Ile Glu Asp Gly Gly Val Gln Leu Ala Tyr His Tyr Gln
                485                 490                 495

Gln Asn Thr Pro Ile Gly Asp Gly Pro Val Leu Leu Pro Asp Asn His
            500                 505                 510

Tyr Leu Ser Val Gln Ser Ile Leu Ser Lys Asp Pro Asn Glu Lys Arg
```

-continued

```
            515                 520                 525
Asp His Met Val Leu Glu Phe Val Thr Ala Ala Gly Ile Thr Leu
            530                 535                 540
Gly Met Asp Glu Leu Tyr Lys Gly Gly Thr Gly Gly Ser Met Val Ser
545                 550                 555                 560
Lys Gly Glu Glu Leu Phe Thr Gly Val Val Pro Ile Gln Val Glu Leu
                    565                 570                 575
Asp Gly Asp Val Asn Gly His Lys Phe Ser Val Ser Gly Glu Gly Glu
                580                 585                 590
Gly Asp Ala Thr Tyr Gly Lys Leu Thr Leu Lys Phe Ile Cys Thr Thr
                595                 600                 605
Gly Lys Leu Pro Val Pro Trp Pro Thr Leu Val Thr Thr Leu Thr Tyr
            610                 615                 620
Gly Val Gln Cys Phe Ser Arg Tyr Pro Asp His Met Lys Gln His Asp
625                 630                 635                 640
Phe Phe Lys Ser Ala Met Pro Glu Gly Tyr Ile Gln Glu Arg Thr Ile
                    645                 650                 655
Phe Phe Lys Asp Asp Gly Asn Tyr Lys Thr Arg Ala Glu Val Lys Phe
                660                 665                 670
Glu Gly Asp Thr Leu Val Asn Arg Ile Glu Leu Lys Gly Ile Asp Phe
                675                 680                 685
Lys Glu Asp Gly Asn Ile Leu Gly His Lys Leu Glu Tyr Asn Thr Arg
690                 695                 700
Phe Asn Arg Ile Leu Arg Asp Val Glu Ala Asn Thr Val Arg Leu Lys
705                 710                 715                 720
Glu His Asp Gln Asp Val Leu Val Leu Glu Lys Val Pro Ala Gly Asn
                    725                 730                 735
Arg Ala Ser Asn Gln Gly Asn Ser Gln Pro Gln Lys Tyr Thr Val
                740                 745                 750
Met Ser Gly Thr Pro Glu Lys Ile Leu Glu His Phe Leu Glu Thr Ile
            755                 760                 765
Arg Leu Glu Ala Thr Leu Asn Glu Ala Thr Asp Ser Val Leu Asn Asp
770                 775                 780
Phe Ile Met Met His Cys Val Phe Met Pro Asn Thr Gln Leu Cys Pro
785                 790                 795                 800
Ala Leu Val Ala His Tyr His Ala Gln Pro Ser Gln Gly Thr Glu Gln
                    805                 810                 815
Glu Lys Met Asp Tyr Ala Leu Asn Asn Lys Arg Arg Val Ile Arg Leu
                820                 825                 830
Val Leu Gln Trp Ala Ala Met Tyr Gly Asp Leu Leu Gln Glu Asp Asp
            835                 840                 845
Val Ser Met Ala Phe Leu Glu Glu Phe Tyr Val Ser Val Ser Asp Asp
            850                 855                 860
Ala Arg Met Ile Ala Ala Leu Lys Glu Gln Leu Pro Glu Leu Glu Lys
865                 870                 875                 880
Ile Val Lys Gln Ile Ser Glu Asp Ala Lys Ala Pro Gln Lys Lys His
                    885                 890                 895
Lys Val Leu Leu Gln Gln Phe Asn Thr Gly Asp Glu Arg Ala Gln Lys
                900                 905                 910
Arg Gln Pro Ile Arg Gly Ser Asp Glu Val Leu Phe Lys Val Tyr Cys
            915                 920                 925
Met Asp Pro Thr Tyr Thr Thr Ile Arg Val Pro Val Ala Thr Ser Val
            930                 935                 940
```

Lys Glu Val Ile Ser Ala Val Ala Asp Lys Leu Gly Ser Gly Glu Gly
945                 950                 955                 960

Leu Ile Ile Val Lys Met Ser Gly Gly Glu Lys Val Val Leu Lys
            965                 970                 975

Pro Asn Asp Val Ser Val Phe Met Thr Leu Thr Ile Asn Gly Arg Leu
            980                 985                 990

Phe Ala Cys Pro Arg Glu Gln Phe Asp Ser Leu Thr Pro Leu Pro Glu
            995                 1000                1005

Gln Glu Gly Pro Thr Val Gly Thr Val Gly Thr Phe Glu Leu Met
    1010                1015                1020

Ser Ser Lys Asp Leu Ala Tyr Gln Met Thr Ile Tyr Asp Trp Glu
    1025                1030                1035

Leu Phe Asn Cys Val His Glu Leu Glu Leu Ile Tyr His Thr Phe
    1040                1045                1050

Gly Arg His Asn Phe Lys Lys Thr Thr Ala Asn Leu Asp Leu Phe
    1055                1060                1065

Leu Arg Arg Phe Asn Glu Ile Gln Phe Trp Val Val Thr Glu Ile
    1070                1075                1080

Cys Leu Cys Ser Gln Leu Ser Lys Arg Val Gln Leu Leu Lys Lys
    1085                1090                1095

Phe Ile Lys Ile Ala Ala His Cys Lys Glu Tyr Lys Asn Leu Asn
    1100                1105                1110

Ser Phe Phe Ala Ile Val Met Gly Leu Ser Asn Val Ala Val Ser
    1115                1120                1125

Arg Leu Ala Leu Thr Trp Glu Lys Leu Pro Ser Lys Phe Lys Lys
    1130                1135                1140

Phe Tyr Ala Glu Phe Glu Ser Leu Met Asp Pro Ser Arg Asn His
    1145                1150                1155

Arg Ala Tyr Arg Leu Thr Val Ala Lys Leu Glu Pro Pro Leu Ile
    1160                1165                1170

Pro Phe Met Pro Leu Leu Ile Lys Asp Met Thr Phe Thr His Glu
    1175                1180                1185

Gly Asn Lys Thr Phe Ile Asp Asn Leu Val Asn Phe Glu Lys Met
    1190                1195                1200

Arg Met Ile Ala Asn Thr Ala Arg Thr Val Arg Tyr Tyr Arg Ser
    1205                1210                1215

Gln Pro Phe Asn Pro Asp Ala Ala Gln Ala Asn Lys Asn His Gln
    1220                1225                1230

Asp Val Arg Ser Tyr Val Arg Gln Leu Asn Val Ile Asp Asn Gln
    1235                1240                1245

Arg Thr Leu Ser Gln Met Ser His Arg Leu Glu Pro Arg Arg Pro
    1250                1255                1260

<210> SEQ ID NO 13
<211> LENGTH: 1255
<212> TYPE: PRT
<213> ORGANISM: Artificial Sequence
<220> FEATURE:
<223> OTHER INFORMATION: Synthetic

<400> SEQUENCE: 13

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

```
Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
 50                      55                  60

Glu Lys Gly Ile Thr Leu Phe Arg Gln Gly Asp Ile Gly Thr Asn Trp
 65                  70                  75                  80

Tyr Ala Val Leu Ala Gly Ser Leu Asp Val Lys Val Ser Glu Thr Ser
                 85                  90                  95

Ser His Gln Asp Ala Val Thr Ile Cys Thr Leu Gly Ile Gly Thr Ala
                100                 105                 110

Phe Gly Glu Ser Ile Leu Asp Asn Thr Pro Arg His Ala Thr Ile Val
            115                 120                 125

Thr Arg Glu Ser Ser Glu Leu Leu Arg Ile Glu Gln Lys Asp Phe Lys
        130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445
```

```
Asp Lys Glu Asp Phe Asn Arg Ile Leu Arg Asp Val Leu Glu Asn Val
450                 455                 460
Tyr Ile Lys Ala Asp Lys Gln Lys Asn Gly Ile Lys Ala Asn Phe Lys
465                 470                 475                 480
Ile Arg His Asn Ile Glu Asp Gly Gly Val Gln Leu Ala Tyr His Tyr
                485                 490                 495
Gln Gln Asn Thr Pro Ile Gly Asp Gly Pro Val Leu Leu Pro Asp Asn
                500                 505                 510
His Tyr Leu Ser Val Gln Ser Ile Leu Ser Lys Asp Pro Asn Glu Lys
            515                 520                 525
Arg Asp His Met Val Leu Leu Glu Phe Val Thr Ala Ala Gly Ile Thr
530                 535                 540
Leu Gly Met Asp Glu Leu Tyr Lys Gly Gly Thr Gly Gly Ser Met Val
545                 550                 555                 560
Ser Lys Gly Glu Glu Leu Phe Thr Arg Gly Val Val Pro Ile Gln Val
                565                 570                 575
Glu Leu Asp Gly Asp Val Asn Gly His Lys Phe Ser Val Ser Gly Glu
                580                 585                 590
Gly Glu Gly Asp Ala Thr Tyr Gly Lys Leu Thr Leu Lys Phe Ile Cys
            595                 600                 605
Thr Thr Gly Lys Leu Pro Val Pro Trp Pro Thr Leu Val Thr Thr Leu
            610                 615                 620
Thr Tyr Gly Val Gln Cys Phe Ser Arg Tyr Pro Asp His Met Lys Gln
625                 630                 635                 640
His Asp Phe Phe Lys Ser Ala Met Pro Glu Gly Tyr Ile Gln Glu Arg
                645                 650                 655
Thr Ile Phe Phe Lys Asp Asp Gly Asn Tyr Lys Thr Arg Ala Glu Val
                660                 665                 670
Lys Phe Glu Gly Asp Thr Leu Val Asn Arg Ile Glu Leu Lys Gly Ile
            675                 680                 685
Asp Phe Lys Glu Asp Gly Asn Ile Leu Gly His Lys Leu Glu Tyr Asn
            690                 695                 700
Thr Arg Asn Thr Val Arg Leu Lys Glu His Asp Gln Asp Val Leu Val
705                 710                 715                 720
Leu Glu Lys Val Pro Ala Gly Asn Arg Ala Ser Asn Gln Gly Asn Ser
                725                 730                 735
Gln Pro Gln Gln Lys Tyr Thr Val Met Ser Gly Thr Pro Glu Lys Ile
                740                 745                 750
Leu Glu His Phe Leu Glu Thr Ile Arg Leu Glu Ala Thr Leu Asn Glu
            755                 760                 765
Ala Thr Asp Ser Val Leu Asn Asp Phe Ile Met Met His Cys Val Phe
770                 775                 780
Met Pro Asn Thr Gln Leu Cys Pro Ala Leu Val Ala His Tyr His Ala
785                 790                 795                 800
Gln Pro Ser Gln Gly Thr Glu Gln Glu Lys Met Asp Tyr Ala Leu Asn
                805                 810                 815
Asn Lys Arg Arg Val Ile Arg Leu Val Leu Gln Trp Ala Ala Met Tyr
                820                 825                 830
Gly Asp Leu Leu Gln Glu Asp Asp Val Ser Met Ala Phe Leu Glu Glu
            835                 840                 845
Phe Tyr Val Ser Val Ser Asp Asp Ala Arg Met Ile Ala Ala Leu Lys
            850                 855                 860
Glu Gln Leu Pro Glu Leu Glu Lys Ile Val Lys Gln Ile Ser Glu Asp
```

```
              865                 870                 875                 880
Ala Lys Ala Pro Gln Lys Lys His Lys Val Leu Leu Gln Gln Phe Asn
                        885                 890                 895
Thr Gly Asp Glu Arg Ala Gln Lys Arg Gln Pro Ile Arg Gly Ser Asp
            900                 905                 910
Glu Val Leu Phe Lys Val Tyr Cys Met Asp Pro Thr Tyr Thr Thr Ile
            915                 920                 925
Arg Val Pro Val Ala Thr Ser Val Lys Glu Val Ile Ser Ala Val Ala
            930                 935                 940
Asp Lys Leu Gly Ser Gly Glu Gly Leu Ile Ile Val Lys Met Ser Ser
945                 950                 955                 960
Gly Gly Glu Lys Val Val Leu Lys Pro Asn Asp Val Ser Val Phe Met
                        965                 970                 975
Thr Leu Thr Ile Asn Gly Arg Leu Phe Ala Cys Pro Arg Glu Gln Phe
                980                 985                 990
Asp Ser Leu Thr Pro Leu Pro Glu Gln Glu Gly Pro Thr Val Gly Thr
                995                 1000                1005
Val Gly Thr Phe Glu Leu Met Ser Ser Lys Asp Leu Ala Tyr Gln
    1010                1015                1020
Met Thr Ile Tyr Asp Trp Glu Leu Phe Asn Cys Val His Glu Leu
    1025                1030                1035
Glu Leu Ile Tyr His Thr Phe Gly Arg His Asn Phe Lys Lys Thr
    1040                1045                1050
Thr Ala Asn Leu Asp Leu Phe Leu Arg Arg Phe Asn Glu Ile Gln
    1055                1060                1065
Phe Trp Val Val Thr Glu Ile Cys Leu Cys Ser Gln Leu Ser Lys
    1070                1075                1080
Arg Val Gln Leu Leu Lys Lys Phe Ile Lys Ile Ala Ala His Cys
    1085                1090                1095
Lys Glu Tyr Lys Asn Leu Asn Ser Phe Phe Ala Ile Val Met Gly
    1100                1105                1110
Leu Ser Asn Val Ala Val Ser Arg Leu Ala Leu Thr Trp Glu Lys
    1115                1120                1125
Leu Pro Ser Lys Phe Lys Lys Phe Tyr Ala Glu Phe Glu Ser Leu
    1130                1135                1140
Met Asp Pro Ser Arg Asn His Arg Ala Tyr Arg Leu Thr Val Ala
    1145                1150                1155
Lys Leu Glu Pro Pro Leu Ile Pro Phe Met Pro Leu Leu Ile Lys
    1160                1165                1170
Asp Met Thr Phe Thr His Glu Gly Asn Lys Thr Phe Ile Asp Asn
    1175                1180                1185
Leu Val Asn Phe Glu Lys Met Arg Met Ile Ala Asn Thr Ala Arg
    1190                1195                1200
Thr Val Arg Tyr Tyr Arg Ser Gln Pro Phe Asn Pro Asp Ala Ala
    1205                1210                1215
Gln Ala Asn Lys Asn His Gln Asp Val Arg Ser Tyr Val Arg Gln
    1220                1225                1230
Leu Asn Val Ile Asp Asn Gln Arg Thr Leu Ser Gln Met Ser His
    1235                1240                1245
Arg Leu Glu Pro Arg Arg Pro
    1250                1255

<210> SEQ ID NO 14
```

```
<211> LENGTH: 1255
<212> TYPE: PRT
<213> ORGANISM: Artificial Sequence
<220> FEATURE:
<223> OTHER INFORMATION: Synthetic

<400> SEQUENCE: 14

Met Val Ala Ala His Ala Ala His Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Gly Lys Ile Leu Arg Ala Gly Lys
        195                 200                 205

Ile Leu Arg Asn Ala Ile Leu Ser Arg Ala Pro His Met Ile Arg Asp
210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
370                 375                 380
```

```
Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
            405                 410                 415

Glu Gly Asp Asp Phe Gly Lys Leu Ala Leu Val Asn Asp Ala Pro Arg
        420                 425                 430

Ala Ala Ser Ile Val Leu Arg Glu Asp Asn Cys His Phe Leu Arg Val
            435                 440                 445

Asp Lys Glu Asp Phe Asn Arg Ile Leu Arg Leu Glu Asn Val Tyr Ile
        450                 455                 460

Lys Ala Asp Lys Gln Lys Asn Gly Ile Lys Ala Asn Phe Lys Ile Arg
465                 470                 475                 480

His Asn Ile Glu Asp Gly Gly Val Gln Leu Ala Tyr His Tyr Gln Gln
            485                 490                 495

Asn Thr Pro Ile Gly Asp Gly Pro Val Leu Leu Pro Asp Asn His Tyr
            500                 505                 510

Leu Ser Val Gln Ser Ile Leu Ser Lys Asp Pro Asn Glu Lys Arg Asp
            515                 520                 525

His Met Val Leu Leu Glu Phe Val Thr Ala Ala Gly Ile Thr Leu Gly
            530                 535                 540

Met Asp Glu Leu Phe Lys Gly Thr Gly Gly Ser Met Val Ser Lys
545                 550                 555                 560

Gly Glu Glu Leu Phe Thr Gly Val Val Pro Ile Gln Val Glu Leu Asp
                565                 570                 575

Gly Asp Val Asn Gly His Lys Phe Ser Val Ser Gly Glu Gly Glu Gly
            580                 585                 590

Asp Ala Thr Tyr Gly Lys Leu Thr Leu Lys Phe Ile Cys Thr Thr Gly
            595                 600                 605

Lys Leu Pro Val Pro Trp Pro Thr Leu Val Thr Thr Leu Thr Tyr Gly
            610                 615                 620

Val Gln Cys Phe Ser Arg Tyr Pro Asp His Met Lys Gln His Asp Phe
625                 630                 635                 640

Phe Lys Ser Ala Met Pro Glu Gly Tyr Ile Gln Glu Arg Thr Ile Phe
                645                 650                 655

Phe Lys Asp Asp Gly Asn Tyr Lys Thr Arg Ala Glu Val Lys Phe Glu
            660                 665                 670

Gly Asp Thr Leu Val Asn Arg Ile Glu Leu Lys Gly Ile Asp Phe Lys
            675                 680                 685

Glu Asp Gly Asn Ile Leu Gly His Lys Leu Glu Tyr Asn Thr Arg Val
            690                 695                 700

Glu Ala Asn Thr Val Arg Leu Lys Glu His Asp Gln Asp Val Leu Val
705                 710                 715                 720

Leu Glu Lys Val Pro Ala Gly Asn Arg Ala Ser Asn Gln Gly Asn Ser
                725                 730                 735

Gln Pro Gln Gln Lys Tyr Thr Val Met Ser Gly Thr Pro Glu Lys Ile
            740                 745                 750

Leu Glu His Phe Leu Glu Thr Ile Arg Leu Glu Ala Thr Leu Asn Glu
            755                 760                 765

Ala Thr Asp Ser Val Leu Asn Asp Phe Ile Met Met His Cys Val Phe
            770                 775                 780

Met Pro Asn Thr Gln Leu Cys Pro Ala Leu Val Ala His Tyr His Ala
785                 790                 795                 800
```

```
Gln Pro Ser Gln Gly Thr Glu Gln Glu Lys Met Asp Tyr Ala Leu Asn
            805                 810                 815

Asn Lys Arg Arg Val Ile Arg Leu Val Leu Gln Trp Ala Ala Met Tyr
        820                 825                 830

Gly Asp Leu Leu Gln Glu Asp Val Ser Met Ala Phe Leu Glu Glu
            835                 840                 845

Phe Tyr Val Ser Val Ser Asp Asp Ala Arg Met Ile Ala Ala Leu Lys
    850                 855                 860

Glu Gln Leu Pro Glu Leu Glu Lys Ile Val Lys Gln Ile Ser Glu Asp
865                 870                 875                 880

Ala Lys Ala Pro Gln Lys Lys His Lys Val Leu Leu Gln Gln Phe Asn
                885                 890                 895

Thr Gly Asp Glu Arg Ala Gln Lys Arg Gln Pro Ile Arg Gly Ser Asp
        900                 905                 910

Glu Val Leu Phe Lys Val Tyr Cys Met Asp Pro Thr Tyr Thr Thr Ile
            915                 920                 925

Arg Val Pro Val Ala Thr Ser Val Lys Glu Val Ile Ser Ala Val Ala
        930                 935                 940

Asp Lys Leu Gly Ser Gly Glu Gly Leu Ile Ile Val Lys Met Ser Ser
945                 950                 955                 960

Gly Gly Glu Lys Val Val Leu Lys Pro Asn Asp Val Ser Val Phe Met
                965                 970                 975

Thr Leu Thr Ile Asn Gly Arg Leu Phe Ala Cys Pro Arg Glu Gln Phe
            980                 985                 990

Asp Ser Leu Thr Pro Leu Pro Glu Gln Glu Gly Pro Thr Val Gly Thr
            995                 1000                1005

Val Gly Thr Phe Glu Leu Met Ser Ser Lys Asp Leu Ala Tyr Gln
        1010                1015                1020

Met Thr Ile Tyr Asp Trp Glu Leu Phe Asn Cys Val His Glu Leu
        1025                1030                1035

Glu Leu Ile Tyr His Thr Phe Gly Arg His Asn Phe Lys Lys Thr
        1040                1045                1050

Thr Ala Asn Leu Asp Leu Phe Leu Arg Arg Phe Asn Glu Ile Gln
        1055                1060                1065

Phe Trp Val Val Thr Glu Ile Cys Leu Cys Ser Gln Leu Ser Lys
        1070                1075                1080

Arg Val Gln Leu Leu Lys Lys Phe Ile Lys Ile Ala Ala His Cys
        1085                1090                1095

Lys Glu Tyr Lys Asn Leu Asn Ser Phe Phe Ala Ile Val Met Gly
        1100                1105                1110

Leu Ser Asn Val Ala Val Ser Arg Leu Ala Leu Thr Trp Glu Lys
        1115                1120                1125

Leu Pro Ser Lys Phe Lys Lys Phe Tyr Ala Glu Phe Glu Ser Leu
        1130                1135                1140

Met Asp Pro Ser Arg Asn His Arg Ala Tyr Arg Leu Thr Val Ala
        1145                1150                1155

Lys Leu Glu Pro Pro Leu Ile Pro Phe Met Pro Leu Leu Ile Lys
        1160                1165                1170

Asp Met Thr Phe Thr His Glu Gly Asn Lys Thr Phe Ile Asp Asn
        1175                1180                1185

Leu Val Asn Phe Glu Lys Met Arg Met Ile Ala Asn Thr Ala Arg
        1190                1195                1200

Thr Val Arg Tyr Tyr Arg Ser Gln Pro Phe Asn Pro Asp Ala Ala
```

```
                    1205                1210                1215

Gln Ala  Asn Lys Asn His  Gln Asp Val Arg Ser  Tyr Val Arg Gln
         1220                1225                1230

Leu Asn  Val Ile Asp Asn  Gln Arg Thr Leu Ser  Gln Met Ser His
         1235                1240                1245

Arg Leu  Glu Pro Arg Pro
         1250                1255

<210> SEQ ID NO 15
<211> LENGTH: 1261
<212> TYPE: PRT
<213> ORGANISM: Artificial Sequence
<220> FEATURE:
<223> OTHER INFORMATION: Synthetic

<400> SEQUENCE: 15

Met Val Ala Ala His Ala Ala His Ser Ser Ser Ala Glu Trp Ile
1               5                   10                  15

Ala Cys Leu Asp Lys Arg Pro Leu Glu Arg Ser Ser Glu Asp Val Asp
                20                  25                  30

Ile Ile Phe Thr Arg Leu Lys Glu Val Lys Ala Phe Glu Lys Phe His
                35                  40                  45

Pro Asn Leu Leu His Gln Ile Cys Leu Cys Gly Tyr Tyr Glu Asn Leu
            50                  55                  60

Glu Lys Gly Ile Thr Leu Phe Arg Gln Gly Asp Ile Gly Thr Asn Trp
65              70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
                100                 105                 110

Phe Gly Glu Ser Ile Leu Asp Asn Thr Pro Arg His Ala Thr Ile Val
            115                 120                 125

Thr Arg Glu Ser Ser Glu Leu Leu Arg Ile Glu Gln Lys Asp Phe Lys
        130                 135                 140

Ala Leu Trp Glu Lys Tyr Arg Gln Tyr Met Ala Gly Leu Leu Ala Pro
145             150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225             230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
```

-continued

```
            305                 310                 315                 320
        Gln Met Gly Pro Asp Ala His Met Arg Met Ile Leu Arg Lys Pro Pro
                        325                 330                 335
        Gly Gln Arg Thr Val Asp Asp Leu Glu Ile Ile Tyr Glu Glu Leu Leu
                        340                 345                 350
        His Ile Lys Ala Leu Ser His Leu Ser Thr Thr Val Lys Arg Glu Leu
                        355                 360                 365
        Ala Gly Val Leu Ile Phe Glu Ser His Ala Lys Gly Gly Thr Val Leu
                        370                 375                 380
        Phe Asn Gln Gly Glu Glu Gly Thr Ser Trp Tyr Ile Ile Leu Lys Gly
        385                 390                 395                 400
        Ser Val Asn Val Val Ile Tyr Gly Lys Gly Val Val Cys Thr Leu His
                        405                 410                 415
        Glu Gly Asp Asp Phe Gly Lys Leu Ala Leu Val Asn Asp Ala Pro Arg
                        420                 425                 430
        Ala Ala Ser Ile Val Leu Arg Glu Asp Asn Cys His Phe Leu Arg Val
                        435                 440                 445
        Asp Lys Glu Asp Phe Asn Arg Ile Leu Arg Asp Val Leu Glu Asn Val
                        450                 455                 460
        Tyr Ile Lys Ala Asp Lys Gln Lys Asn Gly Ile Lys Ala Asn Phe Lys
        465                 470                 475                 480
        Ile Arg His Asn Ile Glu Asp Gly Gly Val Gln Leu Ala Tyr His Tyr
                        485                 490                 495
        Gln Gln Asn Thr Pro Ile Gly Asp Gly Pro Val Leu Leu Pro Asp Asn
                        500                 505                 510
        His Tyr Leu Ser Val Gln Ser Ile Leu Ser Lys Asp Pro Asn Glu Lys
                        515                 520                 525
        Arg Asp His Met Val Leu Leu Glu Phe Val Thr Ala Pro Gly Ile Thr
                        530                 535                 540
        Leu Gly Met Asp Glu Leu Tyr Lys Gly Gly Thr Gly Gly Ser Met Val
        545                 550                 555                 560
        Ser Lys Gly Glu Glu Leu Phe Thr Gly Val Val Pro Ile Gln Val Glu
                        565                 570                 575
        Leu Asp Gly Asp Val Asn Gly His Lys Phe Ser Val Ser Gly Glu Gly
                        580                 585                 590
        Glu Gly Asp Ala Thr Tyr Gly Lys Leu Thr Leu Lys Phe Ile Cys Thr
                        595                 600                 605
        Thr Gly Lys Leu Pro Val Pro Trp Pro Thr Leu Val Thr Thr Leu Thr
                        610                 615                 620
        Tyr Gly Val Gln Cys Phe Ser Arg Tyr Pro Asp His Met Lys Gln His
        625                 630                 635                 640
        Asp Phe Phe Lys Ser Ala Met Pro Glu Gly Tyr Ile Gln Glu Arg Thr
                        645                 650                 655
        Ile Phe Phe Lys Asp Asp Gly Asn Tyr Lys Thr Arg Ala Glu Val Lys
                        660                 665                 670
        Phe Glu Gly Asp Thr Leu Val Asn Arg Ile Glu Leu Lys Gly Ile Asp
                        675                 680                 685
        Phe Lys Glu Asp Gly Asn Ile Leu Gly His Lys Leu Glu Tyr Asn Thr
                        690                 695                 700
        Arg Ile Leu Arg Asp Val Glu Ala Asn Thr Val Arg Leu Lys Glu His
        705                 710                 715                 720
        Asp Gln Asp Val Leu Val Leu Glu Lys Val Pro Ala Gly Asn Arg Ala
                        725                 730                 735
```

-continued

```
Ser Asn Gln Gly Asn Ser Gln Pro Gln Gln Lys Tyr Thr Val Met Ser
            740                 745                 750

Gly Thr Pro Glu Lys Ile Leu Glu His Phe Leu Glu Thr Ile Arg Leu
            755                 760                 765

Glu Ala Thr Leu Asn Glu Ala Thr Asp Ser Val Leu Asn Asp Phe Ile
770                 775                 780

Met Met His Cys Val Phe Met Pro Asn Thr Gln Leu Cys Pro Ala Leu
785                 790                 795                 800

Val Ala His Tyr His Ala Gln Pro Ser Gln Gly Thr Glu Gln Glu Lys
                805                 810                 815

Met Asp Tyr Ala Leu Asn Asn Lys Arg Arg Val Ile Arg Leu Val Leu
            820                 825                 830

Gln Trp Ala Ala Met Tyr Gly Asp Leu Leu Gln Glu Asp Asp Val Ser
            835                 840                 845

Met Ala Phe Leu Glu Glu Phe Tyr Val Ser Val Ser Asp Asp Ala Arg
    850                 855                 860

Met Ile Ala Ala Leu Lys Glu Gln Leu Pro Glu Leu Glu Lys Ile Val
865                 870                 875                 880

Lys Gln Ile Ser Glu Asp Ala Lys Ala Pro Gln Lys Lys His Lys Val
                885                 890                 895

Leu Leu Gln Gln Phe Asn Thr Gly Asp Glu Arg Ala Gln Lys Arg Gln
            900                 905                 910

Pro Ile Arg Gly Ser Asp Glu Val Leu Phe Lys Val Tyr Cys Met Asp
            915                 920                 925

Pro Thr Tyr Thr Thr Ile Arg Val Pro Val Ala Thr Ser Val Lys Glu
    930                 935                 940

Val Ile Ser Ala Val Ala Asp Lys Leu Gly Ser Gly Glu Gly Leu Ile
945                 950                 955                 960

Ile Val Lys Met Ser Ser Gly Glu Lys Val Val Leu Lys Pro Asn
                965                 970                 975

Asp Val Ser Val Phe Met Thr Leu Thr Ile Asn Gly Arg Leu Phe Ala
            980                 985                 990

Cys Pro Arg Glu Gln Phe Asp Ser  Leu Thr Pro Leu  Glu Gln Glu
            995                 1000                 1005

Gly Pro  Thr Val Gly Thr Val  Gly Thr Phe Glu Leu  Met Ser Ser
            1010                 1015                 1020

Lys Asp  Leu Ala Tyr Gln Met  Thr Ile Tyr Asp Trp  Glu Leu Phe
            1025                 1030                 1035

Asn Cys  Val His Glu Leu Glu  Leu Ile Tyr His Thr  Phe Gly Arg
            1040                 1045                 1050

His Asn  Phe Lys Lys Thr Thr  Ala Asn Leu Asp Leu  Phe Leu Arg
            1055                 1060                 1065

Arg Phe  Asn Glu Ile Gln Phe  Trp Val Val Thr Glu  Ile Cys Leu
            1070                 1075                 1080

Cys Ser  Gln Leu Ser Lys Arg  Val Gln Leu Leu Lys  Lys Phe Ile
            1085                 1090                 1095

Lys Ile  Ala Ala His Cys Lys  Glu Tyr Lys Asn Leu  Asn Ser Phe
            1100                 1105                 1110

Phe Ala  Ile Val Met Gly Leu  Ser Asn Val Ala Val  Ser Arg Leu
            1115                 1120                 1125

Ala Leu  Thr Trp Glu Lys Leu  Pro Ser Lys Phe Lys  Lys Phe Tyr
            1130                 1135                 1140
```

-continued

Ala Glu Phe Glu Ser Leu Met Asp Pro Ser Arg Asn His Arg Ala
    1145                1150                1155

Tyr Arg Leu Thr Val Ala Lys Leu Glu Pro Pro Leu Ile Pro Phe
    1160                1165                1170

Met Pro Leu Leu Ile Lys Asp Met Thr Phe Thr His Glu Gly Asn
    1175                1180                1185

Lys Thr Phe Ile Asp Asn Leu Val Asn Phe Glu Lys Met Arg Met
    1190                1195                1200

Ile Ala Asn Thr Ala Arg Thr Val Arg Tyr Tyr Arg Ser Gln Pro
    1205                1210                1215

Phe Asn Pro Asp Ala Ala Gln Ala Asn Lys Asn His Gln Asp Val
    1220                1225                1230

Arg Ser Tyr Val Arg Gln Leu Asn Val Ile Asp Asn Gln Arg Thr
    1235                1240                1245

Leu Ser Gln Met Ser His Arg Leu Glu Pro Arg Arg Pro
    1250                1255                1260

<210> SEQ ID NO 16
<211> LENGTH: 700
<212> TYPE: PRT
<213> ORGANISM: Artificial Sequence
<220> FEATURE:
<223> OTHER INFORMATION: Synthetic

<400> SEQUENCE: 16

Met Val Ala Ala His Ala Ala His Ser Ser Ser Ser Ala Glu Trp Ile
1                5                   10                  15

Ala Cys Leu Asp Lys Arg Pro Leu Glu Arg Ser Ser Glu Asp Val Asp
                20                  25                  30

Ile Ile Phe Thr Arg Leu Lys Glu Val Lys Ala Phe Glu Lys Phe His
            35                  40                  45

Pro Asn Leu Leu His Gln Ile Cys Leu Cys Gly Tyr Tyr Glu Asn Leu
        50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

-continued

```
Leu Val Asp Trp Met Met Gln Gln Thr Pro Cys Val His Ser Arg Thr
            245                 250                 255
Gln Ala Val Gly Met Trp Gln Val Leu Leu Glu Asp Gly Val Leu Asn
        260                 265                 270
His Val Asp Gln Glu His His Phe Gln Asp Lys Tyr Leu Phe Tyr Arg
    275                 280                 285
Phe Leu Asp Asp Glu His Glu Asp Ala Pro Leu Pro Thr Glu Glu Glu
290                 295                 300
Lys Lys Glu Cys Asp Glu Leu Gln Asp Thr Met Leu Leu Leu Leu Ser
305                 310                 315                 320
Gln Met Gly Pro Asp Ala His Met Arg Met Ile Leu Arg Lys Pro Pro
                325                 330                 335
Gly Gln Arg Thr Val Asp Asp Leu Glu Ile Ile Tyr Glu Glu Leu Leu
            340                 345                 350
His Ile Lys Ala Leu Ser His Leu Ser Thr Thr Val Lys Arg Glu Leu
        355                 360                 365
Ala Gly Val Leu Ile Phe Glu Ser His Ala Lys Gly Gly Thr Val Leu
    370                 375                 380
Phe Asn Gln Gly Glu Glu Gly Thr Ser Trp Tyr Ile Ile Leu Lys Gly
385                 390                 395                 400
Ser Val Asn Val Val Ile Tyr Gly Lys Gly Val Val Cys Thr Leu His
                405                 410                 415
Glu Gly Asp Asp Phe Gly Lys Leu Ala Leu Val Asn Asp Ala Pro Arg
            420                 425                 430
Ala Ala Ser Ile Val Leu Arg Glu Asp Asn Cys His Phe Leu Arg Val
        435                 440                 445
Asp Lys Glu Asp Phe Asn Arg Ile Leu Arg Arg Ala Asn Val Tyr Ile
    450                 455                 460
Lys Ala Asp Lys Gln Lys Asn Gly Ile Lys Ala Asn Phe Lys Ile Arg
465                 470                 475                 480
His Asn Ile Glu Asp Gly Gly Val Gln Leu Ala Tyr His Tyr Gln Gln
                485                 490                 495
Asn Thr Pro Ile Gly Asp Gly Pro Val Leu Leu Pro Asp Asn His Tyr
            500                 505                 510
Leu Ser Val Gln Ser Ile Leu Ser Lys Asp Pro Asn Glu Lys Arg Asp
        515                 520                 525
His Met Val Leu Leu Glu Phe Val Thr Ala Ala Gly Ile Thr Leu Gly
    530                 535                 540
Met Asp Glu Leu Tyr Lys Gly Gly Thr Gly Gly Ser Met Val Ser Lys
545                 550                 555                 560
Gly Glu Glu Leu Phe Thr Gly Val Val Pro Ile Gln Val Glu Leu Asp
                565                 570                 575
Gly Asp Val Asn Gly His Lys Phe Ser Val Ser Gly Glu Gly Glu Gly
            580                 585                 590
Asp Ala Thr Tyr Gly Lys Leu Thr Leu Lys Phe Ile Cys Thr Thr Gly
        595                 600                 605
Lys Leu Pro Val Pro Trp Pro Thr Leu Val Thr Thr Leu Thr Tyr Gly
    610                 615                 620
Val Gln Cys Phe Ser Arg Tyr Pro Asp His Met Lys Gln His Asp Phe
625                 630                 635                 640
Phe Lys Ser Ala Met Pro Glu Gly Tyr Ile Gln Glu Arg Thr Ile Phe
                645                 650                 655
Phe Lys Asp Asp Gly Asn Tyr Lys Thr Arg Ala Glu Val Lys Phe Glu
```

```
              660                 665                 670
Gly Asp Thr Leu Val Asn Arg Ile Glu Leu Lys Gly Ile Asp Phe Lys
            675                 680                 685

Glu Asp Gly Asn Ile Leu Gly His Lys Leu Glu Tyr
            690                 695                 700

<210> SEQ ID NO 17
<211> LENGTH: 1256
<212> TYPE: PRT
<213> ORGANISM: Artificial Sequence
<220> FEATURE:
<223> OTHER INFORMATION: Synthetic

<400> SEQUENCE: 17

Met Val Ala Ala His Ala His Ser Ser Ser Ala Glu Trp Ile
1               5                   10                  15

Ala Cys Leu Asp Lys Arg Pro Leu Glu Arg Ser Ser Glu Asp Val Asp
                20                  25                  30

Ile Ile Phe Thr Arg Leu Lys Glu Val Lys Ala Phe Glu Lys Phe His
            35                  40                  45

Pro Asn Leu Leu His Gln Ile Cys Leu Cys Gly Tyr Tyr Glu Asn Leu
50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
```

```
                        325                 330                 335
Gly Gln Arg Thr Val Asp Asp Leu Glu Ile Ile Tyr Glu Glu Leu Leu
                340                 345                 350
His Ile Lys Ala Leu Ser His Leu Ser Thr Thr Val Lys Arg Glu Leu
                355                 360                 365
Ala Gly Val Leu Ile Phe Glu Ser His Ala Lys Gly Gly Thr Val Leu
                370                 375                 380
Phe Asn Gln Gly Glu Glu Gly Thr Ser Trp Tyr Ile Ile Leu Lys Gly
385                 390                 395                 400
Ser Val Asn Val Val Ile Tyr Gly Lys Gly Val Val Cys Thr Leu His
                405                 410                 415
Glu Gly Asp Asp Phe Gly Lys Leu Ala Leu Val Asn Asp Ala Pro Arg
                420                 425                 430
Ala Ala Ser Ile Val Leu Arg Glu Asp Asn Cys His Phe Leu Arg Val
                435                 440                 445
Asp Lys Glu Asp Phe Asn Arg Ile Leu Arg Asp Val Glu Ala Asn Leu
                450                 455                 460
Glu Asn Val Tyr Ile Lys Ala Asp Lys Gln Lys Asn Gly Ile Lys Ala
465                 470                 475                 480
Asn Phe Lys Ile Arg His Asn Ile Glu Asp Gly Gly Val Gln Leu Ala
                485                 490                 495
Tyr His Tyr Gln Gln Asn Thr Pro Ile Gly Asp Gly Pro Val Leu Leu
                500                 505                 510
Pro Asp Asn His Tyr Leu Ser Val Gln Ser Ile Leu Ser Lys Asp Pro
                515                 520                 525
Asn Glu Lys Arg Asp His Met Val Leu Leu Glu Phe Val Thr Ala Ala
                530                 535                 540
Gly Ile Thr Leu Gly Met Asp Glu Leu Tyr Lys Gly Gly Thr Gly Gly
545                 550                 555                 560
Ser Met Val Ser Lys Gly Glu Glu Leu Phe Thr Gly Val Val Pro Ile
                565                 570                 575
Gln Val Glu Leu Asp Gly Asp Val Asn Gly His Lys Phe Ser Val Ser
                580                 585                 590
Gly Glu Gly Glu Gly Asp Ala Thr Tyr Gly Lys Leu Thr Leu Lys Phe
                595                 600                 605
Ile Cys Thr Thr Gly Lys Leu Pro Val Pro Trp Pro Thr Leu Val Thr
                610                 615                 620
Thr Leu Thr Tyr Gly Val Gln Cys Phe Ser Arg Tyr Pro Asp His Met
625                 630                 635                 640
Lys Gln His Asp Phe Phe Lys Ser Ala Met Pro Glu Gly Tyr Ile Gln
                645                 650                 655
Glu Arg Thr Ile Phe Phe Lys Asp Asp Gly Asn Tyr Lys Thr Arg Ala
                660                 665                 670
Glu Val Lys Phe Glu Gly Asp Thr Leu Val Asn Arg Ile Glu Leu Lys
                675                 680                 685
Gly Ile Asp Phe Lys Glu Asp Gly Asn Ile Leu Gly His Lys Leu Glu
                690                 695                 700
Tyr Asn Thr Arg Thr Val Arg Leu Lys Glu His Asp Gln Asp Val Leu
705                 710                 715                 720
Val Leu Glu Lys Val Pro Ala Gly Asn Arg Ala Ser Asn Gln Gly Asn
                725                 730                 735
Ser Gln Pro Gln Gln Lys Tyr Thr Val Met Ser Gly Thr Pro Glu Lys
                740                 745                 750
```

```
Ile Leu Glu His Phe Leu Glu Thr Ile Arg Leu Glu Ala Thr Leu Asn
            755                 760                 765
Glu Ala Thr Asp Ser Val Leu Asn Asp Phe Ile Met Met His Cys Val
770                 775                 780
Phe Met Pro Asn Thr Gln Leu Cys Pro Ala Leu Val Ala His Tyr His
785                 790                 795                 800
Ala Gln Pro Ser Gln Gly Thr Glu Gln Glu Lys Met Asp Tyr Ala Leu
                805                 810                 815
Asn Asn Lys Arg Arg Val Ile Arg Leu Val Leu Gln Trp Ala Ala Met
                820                 825                 830
Tyr Gly Asp Leu Leu Gln Glu Asp Val Ser Met Ala Phe Leu Glu
            835                 840                 845
Glu Phe Tyr Val Ser Val Ser Asp Asp Ala Arg Met Ile Ala Ala Leu
            850                 855                 860
Lys Glu Gln Leu Pro Glu Leu Glu Lys Ile Val Lys Gln Ile Ser Glu
865                 870                 875                 880
Asp Ala Lys Ala Pro Gln Lys Lys His Lys Val Leu Leu Gln Gln Phe
                885                 890                 895
Asn Thr Gly Asp Glu Arg Ala Gln Lys Arg Gln Pro Ile Arg Gly Ser
            900                 905                 910
Asp Glu Val Leu Phe Lys Val Tyr Cys Met Asp Pro Thr Tyr Thr Thr
            915                 920                 925
Ile Arg Val Pro Val Ala Thr Ser Val Lys Glu Val Ile Ser Ala Val
            930                 935                 940
Ala Asp Lys Leu Gly Ser Gly Glu Gly Leu Ile Ile Val Lys Met Ser
945                 950                 955                 960
Ser Gly Gly Glu Lys Val Val Leu Lys Pro Asn Asp Val Ser Val Phe
                965                 970                 975
Met Thr Leu Thr Ile Asn Gly Arg Leu Phe Ala Cys Pro Arg Glu Gln
            980                 985                 990
Phe Asp Ser Leu Thr Pro Leu Pro  Glu Gln Glu Gly Pro  Thr Val Gly
            995                 1000                1005
Thr Val  Gly Thr Phe Glu Leu  Met Ser Ser Lys Asp  Leu Ala Tyr
    1010                 1015                1020
Gln Met  Thr Ile Tyr Asp Trp  Glu Leu Phe Asn Cys  Val His Glu
    1025                 1030                1035
Leu Glu  Leu Ile Tyr His Thr  Phe Gly Arg His Asn  Phe Lys Lys
    1040                 1045                1050
Thr Thr  Ala Asn Leu Asp Leu  Phe Leu Arg Arg Phe  Asn Glu Ile
    1055                 1060                1065
Gln Phe  Trp Val Val Thr Glu  Ile Cys Leu Cys Ser  Gln Leu Ser
    1070                 1075                1080
Lys Arg  Val Gln Leu Leu Lys  Lys Phe Ile Lys Ile  Ala Ala His
    1085                 1090                1095
Cys Lys  Glu Tyr Lys Asn Leu  Asn Ser Phe Phe Ala  Ile Val Met
    1100                 1105                1110
Gly Leu  Ser Asn Val Ala Val  Ser Arg Leu Ala Leu  Thr Trp Glu
    1115                 1120                1125
Lys Leu  Pro Ser Lys Phe Lys  Lys Phe Tyr Ala Glu  Phe Glu Ser
    1130                 1135                1140
Leu Met  Asp Pro Ser Arg Asn  His Arg Ala Tyr Arg  Leu Thr Val
    1145                 1150                1155
```

Ala Lys Leu Glu Pro Pro Leu Ile Pro Phe Met Pro Leu Leu Ile
    1160                1165                1170

Lys Asp Met Thr Phe Thr His Glu Gly Asn Lys Thr Phe Ile Asp
    1175                1180                1185

Asn Leu Val Asn Phe Glu Lys Met Arg Met Ile Ala Asn Thr Ala
    1190                1195                1200

Arg Thr Val Arg Tyr Tyr Arg Ser Gln Pro Phe Asn Pro Asp Ala
    1205                1210                1215

Ala Gln Ala Asn Lys Asn His Gln Asp Val Arg Ser Tyr Val Arg
    1220                1225                1230

Gln Leu Asn Val Ile Asp Asn Gln Arg Thr Leu Ser Gln Met Ser
    1235                1240                1245

His Arg Leu Glu Pro Arg Arg Pro
    1250                1255

<210> SEQ ID NO 18
<211> LENGTH: 1255
<212> TYPE: PRT
<213> ORGANISM: Artificial Sequence
<220> FEATURE:
<223> OTHER INFORMATION: Synthetic

<400> SEQUENCE: 18

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
                20                  25                  30

Ile Ile Phe Thr Arg Leu Lys Glu Val Lys Ala Phe Glu Lys Phe His
            35                  40                  45

Pro Asn Leu Leu His Gln Ile Cys Leu Cys Gly Tyr Tyr Glu Asn Leu
        50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
                100                 105                 110

Phe Gly Glu Ser Ile Leu Asp Asn Thr Pro Arg His Ala Thr Ile Val
            115                 120                 125

Thr Arg Glu Ser Ser Glu Leu Leu Arg Ile Glu Gln Lys Asp Phe Lys
130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
                180                 185                 190

Asn Thr Ile Thr Lys Val Pro Ser Glu Lys Ile Leu Arg Ala Gly Lys
            195                 200                 205

Ile Leu Arg Asn Ala Ile Leu Ser Arg Ala Pro His Met Ile Arg Asp
        210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

-continued

Gln Ala Val Gly Met Trp Gln Val Leu Leu Glu Asp Gly Val Leu Asn
                260                 265                 270

His Val Asp Gln Glu His His Phe Gln Asp Lys Tyr Leu Phe Tyr Arg
            275                 280                 285

Phe Leu Asp Asp Glu His Glu Asp Ala Pro Leu Pro Thr Glu Glu Glu
        290                 295                 300

Lys Lys Glu Cys Asp Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
    370                 375                 380

Phe Asn Gln Gly Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Leu Glu Asn Val Tyr Ile
    450                 455                 460

Lys Ala Asp Lys Gln Lys Asn Gly Ile Lys Ala Asn Phe Lys Ile Arg
465                 470                 475                 480

His Asn Ile Glu Asp Gly Gly Val Gln Leu Ala Tyr His Tyr Gln Gln
                485                 490                 495

Asn Thr Pro Ile Gly Asp Gly Pro Val Leu Leu Pro Asp Asn His Tyr
            500                 505                 510

Leu Ser Val Gln Ser Ile Leu Ser Lys Asp Pro Asn Glu Lys Arg Asp
        515                 520                 525

His Met Val Leu Leu Glu Phe Val Thr Ala Ala Gly Ile Thr Leu Gly
    530                 535                 540

Met Asp Glu Leu Tyr Lys Gly Gly Thr Gly Gly Ser Met Val Ser Lys
545                 550                 555                 560

Gly Glu Glu Leu Phe Thr Gly Val Val Pro Ile Gln Val Glu Leu Asp
                565                 570                 575

Gly Asp Val Asn Gly His Lys Phe Ser Val Ser Gly Glu Gly Glu Gly
            580                 585                 590

Asp Ala Thr Tyr Gly Lys Leu Thr Leu Lys Phe Ile Cys Thr Thr Gly
        595                 600                 605

Lys Leu Pro Val Pro Trp Pro Thr Leu Val Thr Thr Leu Thr Tyr Gly
    610                 615                 620

Val Gln Cys Phe Ser Arg Tyr Pro Asp His Met Lys Gln His Asp Phe
625                 630                 635                 640

Phe Lys Ser Ala Met Pro Glu Gly Tyr Ile Gln Glu Arg Thr Ile Phe
                645                 650                 655

Phe Lys Asp Asp Gly Asn Tyr Lys Thr Arg Ala Glu Val Lys Phe Glu
            660                 665                 670

Gly Asp Thr Leu Val Asn Arg Ile Glu Leu Lys Gly Ile Asp Phe Lys

```
                675                 680                 685
Glu Asp Gly Asn Ile Leu Gly His Lys Leu Glu Tyr Asn Thr Arg Val
690                 695                 700
Glu Ala Asn Thr Val Arg Leu Lys Glu His Asp Gln Asp Val Leu Val
705                 710                 715                 720
Leu Glu Lys Val Pro Ala Gly Asn Arg Ala Ser Asn Gln Gly Asn Ser
                725                 730                 735
Gln Pro Gln Gln Lys Tyr Thr Val Met Ser Gly Thr Pro Glu Lys Ile
                740                 745                 750
Leu Glu His Phe Leu Glu Thr Ile Arg Leu Glu Ala Thr Leu Asn Glu
                755                 760                 765
Ala Thr Asp Ser Val Leu Asn Asp Phe Ile Met Met His Cys Val Phe
770                 775                 780
Met Pro Asn Thr Gln Leu Cys Pro Ala Leu Val Ala His Tyr His Ala
785                 790                 795                 800
Gln Pro Ser Gln Gly Thr Glu Gln Glu Lys Met Asp Tyr Ala Leu Asn
                805                 810                 815
Asn Lys Arg Arg Val Ile Arg Leu Val Leu Gln Trp Ala Ala Met Tyr
                820                 825                 830
Gly Asp Leu Leu Gln Glu Asp Val Ser Met Ala Phe Leu Glu Glu
                835                 840                 845
Phe Tyr Val Ser Val Ser Asp Asp Ala Arg Met Ile Ala Ala Leu Lys
                850                 855                 860
Glu Gln Leu Pro Glu Leu Glu Lys Ile Val Lys Gln Ile Ser Glu Asp
865                 870                 875                 880
Ala Lys Ala Pro Gln Lys Lys His Lys Val Leu Leu Gln Gln Phe Asn
                885                 890                 895
Thr Gly Asp Glu Arg Ala Gln Lys Arg Gln Pro Ile Arg Gly Ser Asp
                900                 905                 910
Glu Val Leu Phe Lys Val Tyr Cys Met Asp Pro Thr Tyr Thr Thr Ile
                915                 920                 925
Arg Val Pro Val Ala Thr Ser Val Lys Glu Val Ile Ser Ala Val Ala
930                 935                 940
Asp Lys Leu Gly Ser Gly Glu Gly Leu Ile Ile Val Lys Met Ser Ser
945                 950                 955                 960
Gly Gly Glu Lys Val Val Leu Lys Pro Asn Asp Val Ser Val Phe Met
                965                 970                 975
Thr Leu Thr Ile Asn Gly Arg Leu Phe Ala Cys Pro Arg Glu Gln Phe
                980                 985                 990
Asp Ser Leu Thr Pro Leu Pro Glu Gln Glu Gly Pro Thr Val Gly Thr
                995                 1000                1005
Val Gly Thr Phe Glu Leu Met Ser Ser Lys Asp Leu Ala Tyr Gln
                1010                1015                1020
Met Thr Ile Tyr Asp Trp Glu Leu Phe Asn Cys Val His Glu Leu
                1025                1030                1035
Glu Leu Ile Tyr His Thr Phe Gly Arg His Asn Phe Lys Lys Thr
                1040                1045                1050
Thr Ala Asn Leu Asp Leu Phe Leu Arg Arg Phe Asn Glu Ile Gln
                1055                1060                1065
Phe Trp Val Val Thr Glu Ile Cys Leu Cys Ser Gln Leu Ser Lys
                1070                1075                1080
Arg Val Gln Leu Leu Lys Lys Phe Ile Lys Ile Ala Ala His Cys
                1085                1090                1095
```

```
Lys Glu Tyr Lys Asn Leu Asn Ser Phe Phe Ala Ile Val Met Gly
    1100                1105                1110

Leu Ser Asn Val Ala Val Ser Arg Leu Ala Leu Thr Trp Glu Lys
    1115                1120                1125

Leu Pro Ser Lys Phe Lys Lys Phe Tyr Ala Glu Phe Glu Ser Leu
    1130                1135                1140

Met Asp Pro Ser Arg Asn His Arg Ala Tyr Arg Leu Thr Val Ala
    1145                1150                1155

Lys Leu Glu Pro Pro Leu Ile Pro Phe Met Pro Leu Leu Ile Lys
    1160                1165                1170

Asp Met Thr Phe Thr His Glu Gly Asn Lys Thr Phe Ile Asp Asn
    1175                1180                1185

Leu Val Asn Phe Glu Lys Met Arg Met Ile Ala Asn Thr Ala Arg
    1190                1195                1200

Thr Val Arg Tyr Tyr Arg Ser Gln Pro Phe Asn Pro Asp Ala Ala
    1205                1210                1215

Gln Ala Asn Lys Asn His Gln Asp Val Arg Ser Tyr Val Arg Gln
    1220                1225                1230

Leu Asn Val Ile Asp Asn Gln Arg Thr Leu Ser Gln Met Ser His
    1235                1240                1245

Arg Leu Glu Pro Arg Arg Pro
    1250                1255

<210> SEQ ID NO 19
<211> LENGTH: 1258
<212> TYPE: PRT
<213> ORGANISM: Artificial Sequence
<220> FEATURE:
<223> OTHER INFORMATION: Synthetic

<400> SEQUENCE: 19

Met Val Ala Ala His Ala Ala His Ser Ser Ser Ala Glu Trp Ile
1               5                   10                  15

Ala Cys Leu Asp Lys Arg Pro Leu Glu Arg Ser Ser Glu Asp Val Asp
                20                  25                  30

Ile Ile Phe Thr Arg Leu Lys Glu Val Lys Ala Phe Glu Lys Phe His
            35                  40                  45

Pro Asn Leu Leu His Gln Ile Cys Leu Cys Gly Tyr Tyr Glu Asn Leu
        50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
                100                 105                 110

Phe Gly Glu Ser Ile Leu Asp Asn Thr Pro Arg His Ala Thr Ile Val
            115                 120                 125

Thr Arg Glu Ser Ser Glu Leu Leu Arg Ile Glu Gln Lys Asp Phe Lys
        130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190
```

-continued

```
Asn Thr Ile Thr Lys Val Pro Ser Glu Lys Ile Leu Arg Ala Gly Lys
        195                 200                 205
Ile Leu Arg Asn Ala Ile Leu Ser Arg Ala Pro His Met Ile Arg Asp
210                 215                 220
Arg Lys Tyr His Leu Lys Thr Tyr Arg Gln Cys Cys Val Gly Thr Glu
225                 230                 235                 240
Leu Val Asp Trp Met Met Gln Gln Thr Pro Cys Val His Ser Arg Thr
                245                 250                 255
Gln Ala Val Gly Met Trp Gln Val Leu Leu Glu Asp Gly Val Leu Asn
                260                 265                 270
His Val Asp Gln Glu His His Phe Gln Asp Lys Tyr Leu Phe Tyr Arg
        275                 280                 285
Phe Leu Asp Asp Glu His Glu Asp Ala Pro Leu Pro Thr Glu Glu Glu
        290                 295                 300
Lys Lys Glu Cys Asp Glu Leu Gln Asp Thr Met Leu Leu Leu Ser
305                 310                 315                 320
Gln Met Gly Pro Asp Ala His Met Arg Met Ile Leu Arg Lys Pro Pro
                325                 330                 335
Gly Gln Arg Thr Val Asp Asp Leu Glu Ile Ile Tyr Glu Glu Leu Leu
        340                 345                 350
His Ile Lys Ala Leu Ser His Leu Ser Thr Thr Val Lys Arg Glu Leu
        355                 360                 365
Ala Gly Val Leu Ile Phe Glu Ser His Ala Lys Gly Thr Val Leu
        370                 375                 380
Phe Asn Gln Gly Glu Gly Thr Ser Trp Tyr Ile Ile Leu Lys Gly
385                 390                 395                 400
Ser Val Asn Val Val Ile Tyr Gly Lys Gly Val Val Cys Thr Leu His
                405                 410                 415
Glu Gly Asp Asp Phe Gly Lys Leu Ala Leu Val Asn Asp Ala Pro Arg
                420                 425                 430
Ala Ala Ser Ile Val Leu Arg Glu Asp Asn Cys His Phe Leu Arg Val
        435                 440                 445
Asp Lys Glu Asp Phe Asn Arg Ile Leu Arg Leu Glu Asn Val Tyr Ile
        450                 455                 460
Lys Ala Asp Lys Gln Lys Asn Gly Ile Lys Ala Asn Phe Lys Ile Arg
465                 470                 475                 480
His Asn Ile Glu Asp Gly Gly Val Gln Leu Ala Tyr His Tyr Gln Gln
                485                 490                 495
Asn Thr Pro Ile Gly Asp Gly Pro Val Leu Leu Pro Asp Asn His Tyr
                500                 505                 510
Leu Ser Val Gln Ser Ile Leu Ser Lys Asp Pro Asn Glu Lys Arg Asp
        515                 520                 525
His Met Val Leu Leu Glu Phe Val Thr Ala Ala Gly Ile Thr Leu Gly
        530                 535                 540
Met Asp Glu Leu Tyr Lys Gly Gly Thr Gly Gly Ser Met Val Ser Lys
545                 550                 555                 560
Gly Glu Glu Leu Phe Thr Gly Val Val Pro Ile Gln Val Glu Leu Asp
                565                 570                 575
Gly Asp Val Asn Gly His Lys Phe Ser Val Ser Gly Glu Gly Glu Gly
                580                 585                 590
Asp Ala Thr Tyr Gly Lys Leu Thr Leu Lys Phe Ile Cys Thr Thr Gly
        595                 600                 605
```

-continued

| | | | | | | | | | | | | |
|---|---|---|---|---|---|---|---|---|---|---|---|---|
|Lys|Leu|Pro|Val|Pro|Trp|Pro|Thr|Leu|Val|Thr|Thr|Leu|Thr|Tyr|Gly|
|610| | | | |615| | | |620| | | | | | |

Val Gln Cys Phe Ser Arg Tyr Pro Asp His Met Lys Gln His Asp Phe
625            630            635            640

Phe Lys Ser Ala Met Pro Glu Gly Tyr Ile Gln Glu Arg Thr Ile Phe
            645            650            655

Phe Lys Asp Asp Gly Asn Tyr Lys Thr Arg Ala Glu Val Lys Phe Glu
            660            665            670

Gly Asp Thr Leu Val Asn Arg Ile Glu Leu Lys Gly Ile Asp Phe Lys
            675            680            685

Glu Asp Gly Asn Ile Leu Gly His Lys Leu Glu Tyr Asn Thr Arg Ile
690            695            700

Leu Arg Asp Val Glu Ala Asn Thr Val Arg Leu Lys Glu His Asp Gln
705            710            715            720

Asp Val Leu Val Leu Glu Lys Val Pro Ala Gly Asn Arg Ala Ser Asn
            725            730            735

Gln Gly Asn Ser Gln Pro Gln Lys Tyr Thr Val Met Ser Gly Thr
            740            745            750

Pro Glu Lys Ile Leu Glu His Phe Leu Glu Thr Ile Arg Leu Glu Ala
            755            760            765

Thr Leu Asn Glu Ala Thr Asp Ser Val Leu Asn Asp Phe Ile Met Met
770            775            780

His Cys Val Phe Met Pro Asn Thr Gln Leu Cys Pro Ala Leu Val Ala
785            790            795            800

His Tyr His Ala Gln Pro Ser Gln Gly Thr Glu Gln Glu Lys Met Asp
            805            810            815

Tyr Ala Leu Asn Asn Lys Arg Arg Val Ile Arg Leu Val Leu Gln Trp
            820            825            830

Ala Ala Met Tyr Gly Asp Leu Leu Gln Glu Asp Asp Val Ser Met Ala
            835            840            845

Phe Leu Glu Glu Phe Tyr Val Ser Val Ser Asp Ala Arg Met Ile
850            855            860

Ala Ala Leu Lys Glu Gln Leu Pro Glu Leu Glu Lys Ile Val Lys Gln
865            870            875            880

Ile Ser Glu Asp Ala Lys Ala Pro Gln Lys Lys His Lys Val Leu Leu
            885            890            895

Gln Gln Phe Asn Thr Gly Asp Glu Arg Ala Gln Lys Arg Gln Pro Ile
            900            905            910

Arg Gly Ser Asp Glu Val Leu Phe Lys Val Tyr Cys Met Asp Pro Thr
            915            920            925

Tyr Thr Thr Ile Arg Val Pro Val Ala Thr Ser Val Lys Glu Val Ile
930            935            940

Ser Ala Val Ala Asp Lys Leu Gly Ser Gly Glu Gly Leu Ile Ile Val
945            950            955            960

Lys Met Ser Ser Gly Gly Glu Lys Val Val Leu Lys Pro Asn Asp Val
            965            970            975

Ser Val Phe Met Thr Leu Thr Ile Asn Gly Arg Leu Phe Ala Cys Pro
            980            985            990

Arg Glu Gln Phe Asp Ser Leu Thr Pro Leu Pro Glu Gln Glu Gly Pro
            995            1000            1005

Thr Val Gly Thr Val Gly Thr Phe Glu Leu Met Ser Ser Lys Asp
            1010            1015            1020

Leu Ala Tyr Gln Met Thr Ile Tyr Asp Trp Glu Leu Phe Asn Cys

```
            1025                1030                1035

Val His Glu Leu Glu Leu Ile Tyr His Thr Phe Gly Arg His Asn
    1040                1045                1050

Phe Lys Lys Thr Thr Ala Asn Leu Asp Leu Phe Leu Arg Arg Phe
    1055                1060                1065

Asn Glu Ile Gln Phe Trp Val Val Thr Glu Ile Cys Leu Cys Ser
    1070                1075                1080

Gln Leu Ser Lys Arg Val Gln Leu Leu Lys Lys Phe Ile Lys Ile
    1085                1090                1095

Ala Ala His Cys Lys Glu Tyr Lys Asn Leu Asn Ser Phe Phe Ala
    1100                1105                1110

Ile Val Met Gly Leu Ser Asn Val Ala Val Ser Arg Leu Ala Leu
    1115                1120                1125

Thr Trp Glu Lys Leu Pro Ser Lys Phe Lys Phe Tyr Ala Glu
    1130                1135                1140

Phe Glu Ser Leu Met Asp Pro Ser Arg Asn His Arg Ala Tyr Arg
    1145                1150                1155

Leu Thr Val Ala Lys Leu Glu Pro Pro Leu Ile Pro Phe Met Pro
    1160                1165                1170

Leu Leu Ile Lys Asp Met Thr Phe Thr His Glu Gly Asn Lys Thr
    1175                1180                1185

Phe Ile Asp Asn Leu Val Asn Phe Glu Lys Met Arg Met Ile Ala
    1190                1195                1200

Asn Thr Ala Arg Thr Val Arg Tyr Tyr Arg Ser Gln Pro Phe Asn
    1205                1210                1215

Pro Asp Ala Ala Gln Ala Asn Lys Asn His Gln Asp Val Arg Ser
    1220                1225                1230

Tyr Val Arg Gln Leu Asn Val Ile Asp Asn Gln Arg Thr Leu Ser
    1235                1240                1245

Gln Met Ser His Arg Leu Glu Pro Arg Arg
    1250                1255

<210> SEQ ID NO 20
<211> LENGTH: 1252
<212> TYPE: PRT
<213> ORGANISM: Artificial Sequence
<220> FEATURE:
<223> OTHER INFORMATION: Synthetic

<400> SEQUENCE: 20

Met Val Ala Ala His Ala Ala His Ser Ser Ser Ala Glu Trp Ile
1               5                   10                  15

Ala Cys Leu Asp Lys Arg Pro Leu Glu Arg Ser Ser Glu Asp Val Asp
                20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
```

-continued

```
            115                 120                 125
Thr Arg Glu Ser Ser Glu Leu Leu Arg Ile Glu Gln Lys Asp Phe Lys
    130                 135                 140
Ala Leu Trp Glu Lys Tyr Arg Gln Tyr Met Ala Gly Leu Leu Ala Pro
145                 150                 155                 160
Pro Tyr Gly Val Met Glu Thr Gly Ser Asn Asn Asp Arg Ile Pro Asp
                165                 170                 175
Lys Glu Asn Thr Pro Leu Ile Glu Pro His Val Pro Leu Arg Pro Ala
            180                 185                 190
Asn Thr Ile Thr Lys Val Pro Ser Glu Lys Ile Leu Arg Ala Gly Lys
            195                 200                 205
Ile Leu Arg Asn Ala Ile Leu Ser Arg Ala Pro His Met Ile Arg Asp
    210                 215                 220
Arg Lys Tyr His Leu Lys Thr Tyr Arg Gln Cys Cys Val Gly Thr Glu
225                 230                 235                 240
Leu Val Asp Trp Met Met Gln Gln Thr Pro Cys Val His Ser Arg Thr
                245                 250                 255
Gln Ala Val Gly Met Trp Gln Val Leu Leu Glu Asp Gly Val Leu Asn
            260                 265                 270
His Val Asp Gln Glu His His Phe Gln Asp Lys Tyr Leu Phe Tyr Arg
    275                 280                 285
Phe Leu Asp Asp Glu His Glu Asp Ala Pro Leu Pro Thr Glu Glu Glu
290                 295                 300
Lys Lys Glu Cys Asp Glu Glu Leu Gln Asp Thr Met Leu Leu Leu Ser
305                 310                 315                 320
Gln Met Gly Pro Asp Ala His Met Arg Met Ile Leu Arg Lys Pro Pro
                325                 330                 335
Gly Gln Arg Thr Val Asp Asp Leu Glu Ile Ile Tyr Glu Glu Leu Leu
            340                 345                 350
His Ile Lys Ala Leu Ser His Leu Ser Thr Thr Val Lys Arg Glu Leu
            355                 360                 365
Ala Gly Val Leu Ile Phe Glu Ser His Ala Lys Gly Gly Thr Val Leu
    370                 375                 380
Phe Asn Gln Gly Glu Glu Gly Thr Ser Trp Tyr Ile Ile Leu Lys Gly
385                 390                 395                 400
Ser Val Asn Val Val Ile Tyr Gly Lys Gly Val Val Cys Thr Leu His
                405                 410                 415
Glu Gly Asp Asp Phe Gly Lys Leu Ala Leu Val Asn Asp Ala Pro Arg
            420                 425                 430
Ala Ala Ser Ile Val Leu Arg Glu Asp Asn Cys His Phe Leu Arg Val
            435                 440                 445
Asp Lys Glu Asp Phe Asn Arg Ile Leu Arg Leu Glu Asn Val Tyr Ile
    450                 455                 460
Lys Ala Asp Lys Gln Lys Asn Gly Ile Lys Ala Asn Phe Lys Ile Arg
465                 470                 475                 480
His Asn Ile Glu Asp Gly Gly Val Gln Leu Ala Tyr His Tyr Gln Gln
                485                 490                 495
Asn Thr Pro Ile Gly Asp Gly Pro Val Leu Leu Pro Asn His Tyr
            500                 505                 510
Leu Ser Val Gln Ser Ile Leu Ser Lys Asp Pro Asn Glu Lys Arg Asp
            515                 520                 525
His Met Val Leu Leu Glu Phe Val Thr Ala Ala Gly Ile Thr Leu Gly
            530                 535                 540
```

```
Met Asp Glu Leu Tyr Lys Gly Gly Thr Gly Gly Ser Met Val Ser Lys
545                 550                 555                 560
Gly Glu Glu Leu Phe Thr Gly Val Val Pro Ile Gln Val Glu Leu Asp
                565                 570                 575
Gly Asp Val Asn Gly His Lys Phe Ser Val Ser Gly Glu Gly Glu Gly
            580                 585                 590
Asp Ala Thr Tyr Gly Lys Leu Thr Leu Lys Phe Ile Cys Thr Thr Gly
        595                 600                 605
Lys Leu Pro Val Pro Trp Pro Thr Leu Val Thr Thr Leu Thr Tyr Gly
610                 615                 620
Val Gln Cys Phe Ser Arg Tyr Pro Asp His Met Lys Gln His Asp Phe
625                 630                 635                 640
Phe Lys Ser Ala Met Pro Glu Gly Tyr Ile Gln Glu Arg Thr Ile Phe
                645                 650                 655
Phe Lys Asp Asp Gly Asn Tyr Lys Thr Arg Ala Glu Val Lys Phe Glu
            660                 665                 670
Gly Asp Thr Leu Val Asn Arg Ile Glu Leu Lys Gly Ile Asp Phe Lys
        675                 680                 685
Glu Asp Gly Asn Ile Leu Gly His Lys Leu Glu Tyr Asn Thr Arg Asn
690                 695                 700
Thr Val Arg Leu Lys Glu His Asp Gln Asp Val Leu Val Leu Glu Lys
705                 710                 715                 720
Val Pro Ala Gly Asn Arg Ala Ser Asn Gln Gly Asn Ser Gln Pro Gln
                725                 730                 735
Gln Lys Tyr Thr Val Met Ser Gly Thr Pro Glu Lys Ile Leu Glu His
            740                 745                 750
Phe Leu Glu Thr Ile Arg Leu Glu Ala Thr Leu Asn Glu Ala Thr Asp
        755                 760                 765
Ser Val Leu Asn Asp Phe Ile Met Met His Cys Val Phe Met Pro Asn
770                 775                 780
Thr Gln Leu Cys Pro Ala Leu Val Ala His Tyr His Ala Gln Pro Ser
785                 790                 795                 800
Gln Gly Thr Glu Gln Glu Lys Met Asp Tyr Ala Leu Asn Asn Lys Arg
                805                 810                 815
Arg Val Ile Arg Leu Val Leu Gln Trp Ala Ala Met Tyr Gly Asp Leu
            820                 825                 830
Leu Gln Glu Asp Asp Val Ser Met Ala Phe Leu Glu Glu Phe Tyr Val
        835                 840                 845
Ser Val Ser Asp Asp Ala Arg Met Ile Ala Ala Leu Lys Glu Gln Leu
850                 855                 860
Pro Glu Leu Glu Lys Ile Val Lys Gln Ile Ser Glu Asp Ala Lys Ala
865                 870                 875                 880
Pro Gln Lys Lys His Lys Val Leu Leu Gln Gln Phe Asn Thr Gly Asp
                885                 890                 895
Glu Arg Ala Gln Lys Arg Gln Pro Ile Arg Gly Ser Asp Glu Val Leu
            900                 905                 910
Phe Lys Val Tyr Cys Met Asp Pro Thr Tyr Thr Thr Ile Arg Val Pro
        915                 920                 925
Val Ala Thr Ser Val Lys Glu Val Ile Ser Ala Val Ala Asp Lys Leu
930                 935                 940
Gly Ser Gly Glu Gly Leu Ile Ile Val Lys Met Ser Ser Gly Gly Glu
945                 950                 955                 960
```

-continued

Lys Val Val Leu Lys Pro Asn Asp Val Ser Val Phe Met Thr Leu Thr
            965             970                 975

Ile Asn Gly Arg Leu Phe Ala Cys Pro Arg Glu Gln Phe Asp Ser Leu
            980             985                 990

Thr Pro Leu Pro Glu Gln Glu Gly Pro Thr Val Gly Thr Val Gly Thr
            995             1000                1005

Phe Glu Leu Met Ser Ser Lys Asp Leu Ala Tyr Gln Met Thr Ile
    1010            1015                1020

Tyr Asp Trp Glu Leu Phe Asn Cys Val His Glu Leu Glu Leu Ile
    1025            1030                1035

Tyr His Thr Phe Gly Arg His Asn Phe Lys Lys Thr Thr Ala Asn
    1040            1045                1050

Leu Asp Leu Phe Leu Arg Arg Phe Asn Glu Ile Gln Phe Trp Val
    1055            1060                1065

Val Thr Glu Ile Cys Leu Cys Ser Gln Leu Ser Lys Arg Val Gln
    1070            1075                1080

Leu Leu Lys Lys Phe Ile Lys Ile Ala Ala His Cys Lys Glu Tyr
    1085            1090                1095

Lys Asn Leu Asn Ser Phe Phe Ala Ile Val Met Gly Leu Ser Asn
    1100            1105                1110

Val Ala Val Ser Arg Leu Ala Leu Thr Trp Glu Lys Leu Pro Ser
    1115            1120                1125

Lys Phe Lys Lys Phe Tyr Ala Glu Phe Glu Ser Leu Met Asp Pro
    1130            1135                1140

Ser Arg Asn His Arg Ala Tyr Arg Leu Thr Val Ala Lys Leu Glu
    1145            1150                1155

Pro Pro Leu Ile Pro Phe Met Pro Leu Leu Ile Lys Asp Met Thr
    1160            1165                1170

Phe Thr His Glu Gly Asn Lys Thr Phe Ile Asp Asn Leu Val Asn
    1175            1180                1185

Phe Glu Lys Met Arg Met Ile Ala Asn Thr Ala Arg Thr Val Arg
    1190            1195                1200

Tyr Tyr Arg Ser Gln Pro Phe Asn Pro Asp Ala Ala Gln Ala Asn
    1205            1210                1215

Lys Asn His Gln Asp Val Arg Ser Tyr Val Arg Gln Leu Asn Val
    1220            1225                1230

Ile Asp Asn Gln Arg Thr Leu Ser Gln Met Ser His Arg Leu Glu
    1235            1240                1245

Pro Arg Arg Pro
    1250

<210> SEQ ID NO 21
<211> LENGTH: 1260
<212> TYPE: PRT
<213> ORGANISM: Artificial Sequence
<220> FEATURE:
<223> OTHER INFORMATION: Synthetic

<400> SEQUENCE: 21

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

-continued

```
Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Leu Glu Asn Val Tyr Ile
450                 455                 460

Lys Ala Asp Lys Gln Lys Asn Gly Ile Lys Ala Asn Phe Lys Ile Arg
```

-continued

```
465                 470                 475                 480
His Asn Ile Glu Asp Gly Gly Val Gln Leu Ala Tyr His Tyr Gln Gln
                    485                 490                 495

Asn Thr Pro Ile Gly Asp Gly Pro Val Leu Pro Asp Asn His Tyr
                500                 505                 510

Leu Ser Val Gln Ser Ile Leu Ser Lys Asp Pro Asn Glu Lys Arg Asp
                    515                 520                 525

His Met Val Leu Leu Glu Phe Val Thr Ala Ala Gly Ile Thr Leu Gly
            530                 535                 540

Met Asp Glu Leu Tyr Lys Gly Gly Thr Gly Gly Ser Met Val Ser Lys
545                 550                 555                 560

Gly Glu Glu Leu Phe Thr Gly Val Val Pro Ile Gln Val Glu Leu Asp
                        565                 570                 575

Gly Asp Val Asn Gly His Lys Phe Ser Val Ser Gly Glu Gly Glu Gly
                580                 585                 590

Asp Ala Thr Tyr Gly Lys Leu Thr Leu Lys Phe Ile Cys Thr Thr Gly
            595                 600                 605

Lys Leu Pro Val Pro Trp Pro Thr Leu Val Thr Thr Leu Thr Tyr Gly
610                 615                 620

Val Gln Cys Phe Ser Arg Tyr Pro Asp His Met Lys Gln His Asp Phe
625                 630                 635                 640

Phe Lys Ser Ala Met Pro Glu Gly Tyr Ile Gln Glu Arg Thr Ile Phe
                645                 650                 655

Phe Lys Asp Asp Gly Asn Tyr Lys Thr Arg Ala Glu Val Lys Phe Glu
                660                 665                 670

Gly Asp Thr Leu Val Asn Arg Ile Glu Leu Lys Gly Ile Asp Phe Lys
            675                 680                 685

Glu Asp Gly Asn Ile Leu Gly His Lys Leu Glu Tyr Asn Thr Arg Asn
            690                 695                 700

Arg Ile Leu Arg Asp Val Glu Ala Asn Thr Val Arg Leu Lys Glu His
705                 710                 715                 720

Asp Gln Asp Val Leu Val Leu Glu Lys Val Pro Ala Gly Asn Arg Ala
                    725                 730                 735

Ser Asn Gln Gly Asn Ser Gln Pro Gln Lys Tyr Thr Val Met Ser
                740                 745                 750

Gly Thr Pro Glu Lys Ile Leu Glu His Phe Leu Glu Thr Ile Arg Leu
            755                 760                 765

Glu Ala Thr Leu Asn Glu Ala Thr Asp Ser Val Leu Asn Asp Phe Ile
770                 775                 780

Met Met His Cys Val Phe Met Pro Asn Thr Gln Leu Cys Pro Ala Leu
785                 790                 795                 800

Val Ala His Tyr His Ala Gln Pro Ser Gln Gly Thr Glu Gln Glu Lys
                    805                 810                 815

Met Asp Tyr Ala Leu Asn Asn Lys Arg Arg Val Ile Arg Leu Val Leu
                820                 825                 830

Gln Trp Ala Ala Met Tyr Gly Asp Leu Leu Gln Glu Asp Asp Val Ser
                835                 840                 845

Met Ala Phe Leu Glu Glu Phe Tyr Val Ser Val Ser Asp Asp Ala Arg
            850                 855                 860

Met Ile Ala Ala Leu Lys Glu Gln Leu Pro Glu Leu Glu Lys Ile Val
865                 870                 875                 880

Lys Gln Ile Ser Glu Asp Ala Lys Ala Pro Gln Lys Lys His Lys Val
                    885                 890                 895
```

Leu Leu Gln Gln Phe Asn Thr Gly Asp Glu Arg Ala Gln Lys Arg Gln
            900                 905                 910

Pro Ile Arg Gly Ser Asp Glu Val Leu Phe Lys Val Tyr Cys Met Asp
            915                 920                 925

Pro Thr Tyr Thr Thr Ile Arg Val Pro Val Ala Thr Ser Val Lys Glu
    930                 935                 940

Val Ile Ser Ala Val Ala Asp Lys Leu Gly Ser Gly Glu Gly Leu Ile
945                 950                 955                 960

Ile Val Lys Met Ser Ser Gly Gly Glu Lys Val Val Leu Lys Pro Asn
                965                 970                 975

Asp Val Ser Val Phe Met Thr Leu Thr Ile Asn Gly Arg Leu Phe Ala
            980                 985                 990

Cys Pro Arg Glu Gln Phe Asp Ser Leu Thr Pro Leu Pro Glu Gln Glu
            995                 1000                1005

Gly Pro Thr Val Gly Thr Val Gly Thr Phe Glu Leu Met Ser Ser
    1010                1015                1020

Lys Asp Leu Ala Tyr Gln Met Thr Ile Tyr Asp Trp Glu Leu Phe
    1025                1030                1035

Asn Cys Val His Glu Leu Glu Leu Ile Tyr His Thr Phe Gly Arg
    1040                1045                1050

His Asn Phe Lys Lys Thr Thr Ala Asn Leu Asp Leu Phe Leu Arg
    1055                1060                1065

Arg Phe Asn Glu Ile Gln Phe Trp Val Val Thr Glu Ile Cys Leu
    1070                1075                1080

Cys Ser Gln Leu Ser Lys Arg Val Gln Leu Leu Lys Lys Phe Ile
    1085                1090                1095

Lys Ile Ala Ala His Cys Lys Glu Tyr Lys Asn Leu Asn Ser Phe
    1100                1105                1110

Phe Ala Ile Val Met Gly Leu Ser Asn Val Ala Val Ser Arg Leu
    1115                1120                1125

Ala Leu Thr Trp Glu Lys Leu Pro Ser Lys Phe Lys Lys Phe Tyr
    1130                1135                1140

Ala Glu Phe Glu Ser Leu Met Asp Pro Ser Arg Asn His Arg Ala
    1145                1150                1155

Tyr Arg Leu Thr Val Ala Lys Leu Glu Pro Pro Leu Ile Pro Phe
    1160                1165                1170

Met Pro Leu Leu Ile Lys Asp Met Thr Phe Thr His Glu Gly Asn
    1175                1180                1185

Lys Thr Phe Ile Asp Asn Leu Val Asn Phe Glu Lys Met Arg Met
    1190                1195                1200

Ile Ala Asn Thr Ala Arg Thr Val Arg Tyr Tyr Arg Ser Gln Pro
    1205                1210                1215

Phe Asn Pro Asp Ala Ala Gln Ala Asn Lys Asn His Gln Asp Val
    1220                1225                1230

Arg Ser Tyr Val Arg Gln Leu Asn Val Ile Asp Asn Gln Arg Thr
    1235                1240                1245

Leu Ser Gln Met Ser His Arg Leu Glu Pro Arg Arg
    1250                1255                1260

<210> SEQ ID NO 22
<211> LENGTH: 1270
<212> TYPE: PRT
<213> ORGANISM: Artificial Sequence
<220> FEATURE:

<223> OTHER INFORMATION: Synthetic

<400> SEQUENCE: 22

```
Met Val Ala Ala His Ala Ala His Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
            35                  40                  45

Pro Asn Leu Leu His Gln Ile Cys Leu Cys Gly Tyr Tyr Glu Asn Leu
50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
            115                 120                 125

Thr Arg Glu Ser Ser Glu Leu Leu Arg Ile Glu Gln Lys Asp Phe Lys
130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
            195                 200                 205

Ile Leu Arg Asn Ala Ile Leu Ser Arg Ala Pro His Met Ile Arg Asp
210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
            275                 280                 285

Phe Leu Asp Asp Glu His Glu Asp Ala Pro Leu Pro Thr Glu Glu Glu
290                 295                 300

Lys Lys Glu Cys Asp Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
            355                 360                 365

Ala Gly Val Leu Ile Phe Glu Ser His Ala Lys Gly Thr Val Leu
370                 375                 380

Phe Asn Gln Gly Glu Glu Gly Thr Ser Trp Tyr Ile Ile Leu Lys Gly
385                 390                 395                 400
```

```
Ser Val Asn Val Val Ile Tyr Gly Lys Gly Val Cys Thr Leu His
                    405             410             415

Glu Gly Asp Asp Phe Gly Lys Leu Ala Leu Val Asn Asp Ala Pro Arg
            420             425             430

Ala Ala Ser Ile Val Leu Arg Glu Asp Asn Cys His Phe Leu Arg Val
            435             440             445

Asp Lys Glu Asp Phe Asn Arg Ile Leu Arg Asp Val Glu Ala Asn Leu
        450             455             460

Glu Asn Val Tyr Ile Lys Ala Asp Lys Gln Lys Asn Gly Ile Lys Ala
465             470             475             480

Asn Phe Lys Ile Arg His Asn Ile Glu Asp Gly Gly Val Gln Leu Ala
                485             490             495

Tyr His Tyr Gln Gln Asn Thr Pro Ile Gly Asp Gly Pro Val Leu Leu
            500             505             510

Pro Asp Asn His Tyr Leu Ser Val Gln Ser Ile Leu Ser Lys Asp Pro
            515             520             525

Asn Glu Lys Arg Asp His Met Val Leu Leu Glu Phe Val Thr Ala Ala
        530             535             540

Gly Ile Thr Leu Gly Met Asp Glu Leu Tyr Lys Gly Gly Thr Gly Gly
545             550             555             560

Ser Met Val Ser Lys Gly Glu Glu Leu Phe Thr Gly Val Val Pro Ile
                565             570             575

Gln Val Glu Leu Asp Gly Asp Val Asn Gly His Lys Phe Ser Val Ser
            580             585             590

Gly Glu Gly Glu Gly Asp Ala Thr Tyr Gly Lys Leu Thr Leu Lys Phe
            595             600             605

Ile Cys Thr Thr Gly Lys Leu Pro Val Pro Trp Pro Thr Leu Val Thr
            610             615             620

Thr Leu Thr Tyr Gly Val Gln Cys Phe Ser Arg Tyr Pro Asp His Met
625             630             635             640

Lys Gln His Asp Phe Phe Lys Ser Ala Met Pro Glu Gly Tyr Ile Gln
                645             650             655

Glu Arg Thr Ile Phe Phe Lys Asp Asp Gly Asn Tyr Lys Thr Arg Ala
            660             665             670

Glu Val Lys Phe Glu Gly Asp Thr Leu Val Asn Arg Ile Glu Leu Lys
        675             680             685

Gly Ile Asp Phe Lys Glu Asp Gly Asn Ile Leu Gly His Lys Leu Glu
        690             695             700

Tyr Asn Thr Arg Lys Glu Asp Phe Asn Arg Ile Leu Arg Asp Val Glu
705             710             715             720

Ala Asn Thr Val Arg Leu Lys Glu His Asp Gln Asp Val Leu Val Leu
                725             730             735

Glu Lys Val Pro Ala Gly Asn Arg Ala Ser Asn Gln Gly Asn Ser Gln
            740             745             750

Pro Gln Gln Lys Tyr Thr Val Met Ser Gly Thr Pro Glu Lys Ile Leu
            755             760             765

Glu His Phe Leu Glu Thr Ile Arg Leu Glu Ala Thr Leu Asn Glu Ala
        770             775             780

Thr Asp Ser Val Leu Asn Asp Phe Ile Met Met His Cys Val Phe Met
785             790             795             800

Pro Asn Thr Gln Leu Cys Pro Ala Leu Val Ala His Tyr His Ala Gln
                805             810             815

Pro Ser Gln Gly Thr Glu Gln Glu Lys Met Asp Tyr Ala Leu Asn Asn
```

```
                820                 825                 830
Lys Arg Arg Val Ile Arg Leu Val Leu Gln Trp Ala Ala Met Tyr Gly
            835                 840                 845

Asp Leu Leu Gln Glu Asp Asp Val Ser Met Ala Phe Leu Glu Glu Phe
850                 855                 860

Tyr Val Ser Val Ser Asp Asp Ala Arg Met Ile Ala Ala Leu Lys Glu
865                 870                 875                 880

Gln Leu Pro Glu Leu Glu Lys Ile Val Lys Gln Ile Ser Glu Asp Ala
                885                 890                 895

Lys Ala Pro Gln Lys Lys His Lys Val Leu Leu Gln Gln Phe Asn Thr
            900                 905                 910

Gly Asp Glu Arg Ala Gln Lys Arg Gln Pro Ile Arg Gly Ser Asp Glu
            915                 920                 925

Val Leu Phe Lys Val Tyr Cys Met Asp Pro Thr Tyr Thr Thr Ile Arg
            930                 935                 940

Val Pro Val Ala Thr Ser Val Lys Glu Val Ile Ser Ala Val Ala Asp
945                 950                 955                 960

Lys Leu Gly Ser Gly Glu Gly Leu Ile Ile Val Lys Met Ser Ser Gly
                965                 970                 975

Gly Glu Lys Val Val Leu Lys Pro Asn Asp Val Ser Val Phe Met Thr
            980                 985                 990

Leu Thr Ile Asn Gly Arg Leu Phe  Ala Cys Pro Arg Glu  Gln Phe Asp
            995                 1000                1005

Ser Leu  Thr Pro Leu Pro Glu  Gln Glu Gly Pro Thr  Val Gly Thr
    1010                1015                1020

Val Gly  Thr Phe Glu Leu Met  Ser Ser Lys Asp Leu  Ala Tyr Gln
    1025                1030                1035

Met Thr  Ile Tyr Asp Trp Glu  Leu Phe Asn Cys Val  His Glu Leu
    1040                1045                1050

Glu Leu  Ile Tyr His Thr Phe  Gly Arg His Asn Phe  Lys Lys Thr
    1055                1060                1065

Thr Ala  Asn Leu Asp Leu Phe  Leu Arg Arg Phe Asn  Glu Ile Gln
    1070                1075                1080

Phe Trp  Val Val Thr Glu Ile  Cys Leu Cys Ser Gln  Leu Ser Lys
    1085                1090                1095

Arg Val  Gln Leu Leu Lys Lys  Phe Ile Lys Ile Ala  Ala His Cys
    1100                1105                1110

Lys Glu  Tyr Lys Asn Leu Asn  Ser Phe Phe Ala Ile  Val Met Gly
    1115                1120                1125

Leu Ser  Asn Val Ala Val Ser  Arg Leu Ala Leu Thr  Trp Glu Lys
    1130                1135                1140

Leu Pro  Ser Lys Phe Lys Lys  Phe Tyr Ala Glu Phe  Glu Ser Leu
    1145                1150                1155

Met Asp  Pro Ser Arg Asn His  Arg Ala Tyr Arg Leu  Thr Val Ala
    1160                1165                1170

Lys Leu  Glu Pro Pro Leu Ile  Pro Phe Met Pro Leu  Leu Ile Lys
    1175                1180                1185

Asp Met  Thr Phe Thr His Glu  Gly Asn Lys Thr Phe  Ile Asp Asn
    1190                1195                1200

Leu Val  Asn Phe Glu Lys Met  Arg Met Ile Ala Asn  Thr Ala Arg
    1205                1210                1215

Thr Val  Arg Tyr Tyr Arg Ser  Gln Pro Phe Asn Pro  Asp Ala Ala
    1220                1225                1230
```

```
Gln Ala Asn Lys Asn His Gln Asp Val Arg Ser Tyr Val Arg Gln
    1235                1240                1245

Leu Asn Val Ile Asp Asn Gln Arg Thr Leu Ser Gln Met Ser His
1250                1255                1260

Arg Leu Glu Pro Arg Arg Pro
    1265                1270

<210> SEQ ID NO 23
<211> LENGTH: 1253
<212> TYPE: PRT
<213> ORGANISM: Artificial Sequence
<220> FEATURE:
<223> OTHER INFORMATION: Synthetic

<400> SEQUENCE: 23

Met Val Ala Ala His Ala Ala His Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
                35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Leu Gln Asp Thr Met Leu Leu Leu Ser
305                 310                 315                 320
```

```
Gln Met Gly Pro Asp Ala His Met Arg Met Ile Leu Arg Lys Pro Pro
                325                 330                 335
Gly Gln Arg Thr Val Asp Asp Leu Glu Ile Ile Tyr Glu Glu Leu Leu
                340                 345                 350
His Ile Lys Ala Leu Ser His Leu Ser Thr Thr Val Lys Arg Glu Leu
                355                 360                 365
Ala Gly Val Leu Ile Phe Glu Ser His Ala Lys Gly Gly Thr Val Leu
        370                 375                 380
Phe Asn Gln Gly Glu Glu Gly Thr Ser Trp Tyr Ile Ile Leu Lys Gly
385                 390                 395                 400
Ser Val Asn Val Val Ile Tyr Gly Lys Gly Val Val Cys Thr Leu His
                405                 410                 415
Glu Gly Asp Asp Phe Gly Lys Leu Ala Leu Val Asn Asp Ala Pro Arg
                420                 425                 430
Ala Ala Ser Ile Val Leu Arg Glu Asp Asn Cys His Phe Leu Arg Val
        435                 440                 445
Asp Lys Glu Asp Phe Asn Arg Ile Leu Arg Asp Val Leu Glu Asn Val
        450                 455                 460
Tyr Ile Lys Ala Asp Lys Gln Lys Asn Gly Ile Lys Ala Asn Phe Lys
465                 470                 475                 480
Ile Arg His Asn Ile Glu Asp Gly Gly Val Gln Leu Ala Tyr His Tyr
                485                 490                 495
Gln Gln Asn Thr Pro Ile Gly Asp Gly Pro Val Leu Leu Pro Asp Asn
                500                 505                 510
His Tyr Leu Ser Val Gln Ser Ile Leu Ser Lys Asp Pro Asn Glu Lys
        515                 520                 525
Arg Asp His Met Val Leu Leu Glu Phe Val Thr Ala Ala Gly Ile Thr
        530                 535                 540
Leu Gly Met Asp Glu Leu Tyr Lys Gly Gly Thr Gly Gly Ser Met Val
545                 550                 555                 560
Ser Lys Gly Glu Glu Leu Phe Thr Gly Val Val Pro Ile Gln Val Glu
                565                 570                 575
Leu Asp Gly Asp Val Asn Gly His Lys Phe Ser Val Ser Gly Glu Gly
                580                 585                 590
Glu Gly Asp Ala Thr Tyr Gly Lys Leu Thr Leu Lys Phe Ile Cys Thr
        595                 600                 605
Thr Gly Lys Leu Pro Val Pro Trp Pro Thr Leu Val Thr Thr Leu Thr
        610                 615                 620
Tyr Gly Val Gln Cys Phe Ser Arg Tyr Pro Asp His Met Lys Gln His
625                 630                 635                 640
Asp Phe Phe Lys Ser Ala Met Pro Glu Gly Tyr Ile Gln Glu Arg Thr
                645                 650                 655
Ile Phe Phe Lys Asp Asp Gly Asn Tyr Lys Thr Arg Ala Glu Val Lys
                660                 665                 670
Phe Glu Gly Asp Thr Leu Val Asn Arg Ile Glu Leu Lys Gly Ile Asp
        675                 680                 685
Phe Lys Glu Asp Gly Asn Ile Leu Gly His Lys Leu Glu Tyr Asn Thr
        690                 695                 700
Arg Thr Val Arg Leu Lys Glu His Asp Gln Asp Val Leu Val Leu Glu
705                 710                 715                 720
Lys Val Pro Ala Gly Asn Arg Ala Ser Asn Gln Gly Asn Ser Gln Pro
                725                 730                 735
```

-continued

Gln Gln Lys Tyr Thr Val Met Ser Gly Thr Pro Glu Lys Ile Leu Glu
        740                 745                 750

His Phe Leu Glu Thr Ile Arg Leu Glu Ala Thr Leu Asn Glu Ala Thr
            755                 760                 765

Asp Ser Val Leu Asn Asp Phe Ile Met Met His Cys Val Phe Met Pro
    770                 775                 780

Asn Thr Gln Leu Cys Pro Ala Leu Val Ala His Tyr His Ala Gln Pro
785                 790                 795                 800

Ser Gln Gly Thr Glu Gln Glu Lys Met Asp Tyr Ala Leu Asn Asn Lys
                805                 810                 815

Arg Arg Val Ile Arg Leu Val Leu Gln Trp Ala Ala Met Tyr Gly Asp
            820                 825                 830

Leu Leu Gln Glu Asp Val Ser Met Ala Phe Leu Glu Glu Phe Tyr
                835                 840                 845

Val Ser Val Ser Asp Asp Ala Arg Met Ile Ala Ala Leu Lys Glu Gln
    850                 855                 860

Leu Pro Glu Leu Glu Lys Ile Val Lys Gln Ile Ser Glu Asp Ala Lys
865                 870                 875                 880

Ala Pro Gln Lys Lys His Lys Val Leu Leu Gln Gln Phe Asn Thr Gly
                885                 890                 895

Asp Glu Arg Ala Gln Lys Arg Gln Pro Ile Arg Gly Ser Asp Glu Val
            900                 905                 910

Leu Phe Lys Val Tyr Cys Met Asp Pro Thr Tyr Thr Thr Ile Arg Val
            915                 920                 925

Pro Val Ala Thr Ser Val Lys Glu Val Ile Ser Ala Val Ala Asp Lys
    930                 935                 940

Leu Gly Ser Gly Glu Gly Leu Ile Ile Val Lys Met Ser Ser Gly Gly
945                 950                 955                 960

Glu Lys Val Val Leu Lys Pro Asn Asp Val Ser Val Phe Met Thr Leu
                965                 970                 975

Thr Ile Asn Gly Arg Leu Phe Ala Cys Pro Arg Glu Gln Phe Asp Ser
            980                 985                 990

Leu Thr Pro Leu Pro Glu Gln Glu Gly Pro Thr Val Gly Thr Val Gly
    995                 1000                1005

Thr Phe Glu Leu Met Ser Ser Lys Asp Leu Ala Tyr Gln Met Thr
    1010                1015                1020

Ile Tyr Asp Trp Glu Leu Phe Asn Cys Val His Glu Leu Glu Leu
    1025                1030                1035

Ile Tyr His Thr Phe Gly Arg His Asn Phe Lys Lys Thr Thr Ala
    1040                1045                1050

Asn Leu Asp Leu Phe Leu Arg Arg Phe Asn Glu Ile Gln Phe Trp
    1055                1060                1065

Val Val Thr Glu Ile Cys Leu Cys Ser Gln Leu Ser Lys Arg Val
    1070                1075                1080

Gln Leu Leu Lys Lys Phe Ile Lys Ile Ala Ala His Cys Lys Glu
    1085                1090                1095

Tyr Lys Asn Leu Asn Ser Phe Phe Ala Ile Val Met Gly Leu Ser
    1100                1105                1110

Asn Val Ala Val Ser Arg Leu Ala Leu Thr Trp Glu Lys Leu Pro
    1115                1120                1125

Ser Lys Phe Lys Lys Phe Tyr Ala Glu Phe Glu Ser Leu Met Asp
    1130                1135                1140

Pro Ser Arg Asn His Arg Ala Tyr Arg Leu Thr Val Ala Lys Leu 1145                1150                1155

Glu Pro  Pro Leu Ile Pro Phe  Met Pro Leu Leu Ile  Lys Asp Met
         1160                1165                 1170

Thr Phe  Thr His Glu Gly Asn  Lys Thr Phe Ile Asp  Asn Leu Val
         1175                1180                 1185

Asn Phe  Glu Lys Met Arg Met  Ile Ala Asn Thr Ala  Arg Thr Val
         1190                1195                 1200

Arg Tyr  Tyr Arg Ser Gln Pro  Phe Asn Pro Asp Ala  Ala Gln Ala
         1205                1210                 1215

Asn Lys  Asn His Gln Asp Val  Arg Ser Tyr Val Arg  Gln Leu Asn
         1220                1225                 1230

Val Ile  Asp Asn Gln Arg Thr  Leu Ser Gln Met Ser  His Arg Leu
         1235                1240                 1245

Glu Pro  Arg Arg Pro
         1250

<210> SEQ ID NO 24
<211> LENGTH: 1256
<212> TYPE: PRT
<213> ORGANISM: Artificial Sequence
<220> FEATURE:
<223> OTHER INFORMATION: Synthetic

<400> SEQUENCE: 24

Met Val Ala Ala His Ala Ala His Ser Ser Ser Ala Glu Trp Ile
1               5                   10                  15

Ala Cys Leu Asp Lys Arg Pro Leu Glu Arg Ser Ser Glu Asp Val Asp
                20                  25                  30

Ile Ile Phe Thr Arg Leu Lys Glu Val Lys Ala Phe Glu Lys Phe His
            35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr

-continued

```
                245                 250                 255
Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Leu Gln Asp Thr Met Leu Leu Leu Ser
305                 310                 315                 320

Gln Met Gly Pro Asp Ala His Met Arg Met Ile Leu Arg Lys Pro Pro
            325                 330                 335

Gly Gln Arg Thr Val Asp Asp Leu Glu Ile Ile Tyr Glu Glu Leu Leu
        340                 345                 350

His Ile Lys Ala Leu Ser His Leu Ser Thr Thr Val Lys Arg Glu Leu
    355                 360                 365

Ala Gly Val Leu Ile Phe Glu Ser His Ala Lys Gly Gly Thr Val Leu
370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
            405                 410                 415

Glu Gly Asp Asp Phe Gly Lys Leu Ala Leu Val Asn Asp Ala Pro Arg
        420                 425                 430

Ala Ala Ser Ile Val Leu Arg Glu Asp Asn Cys His Phe Leu Arg Val
    435                 440                 445

Asp Lys Glu Asp Phe Asn Arg Ile Leu Arg Met Ser Asn Val Tyr Ile
    450                 455                 460

Lys Ala Asp Lys Gln Lys Asn Gly Ile Lys Ala Asn Phe Lys Ile Arg
465                 470                 475                 480

His Asn Ile Glu Asp Gly Gly Val Gln Leu Ala Tyr His Tyr Gln Gln
            485                 490                 495

Asn Thr Pro Ile Gly Asp Gly Pro Val Leu Leu Pro Asp Asn His Tyr
        500                 505                 510

Leu Ser Val Gln Ser Ile Leu Ser Lys Asp Pro Asn Glu Lys Arg Asp
    515                 520                 525

His Met Val Leu Leu Glu Phe Val Thr Ala Ala Gly Ile Thr Leu Gly
    530                 535                 540

Met Asp Glu Leu Tyr Lys Gly Gly Thr Gly Gly Ser Met Val Ser Lys
545                 550                 555                 560

Gly Glu Glu Leu Phe Thr Gly Val Val Pro Ile Gln Val Glu Leu Asp
            565                 570                 575

Gly Asp Val Asn Gly His Lys Phe Ser Val Ser Gly Glu Gly Glu Gly
        580                 585                 590

Asp Ala Thr Tyr Gly Lys Leu Thr Leu Lys Phe Ile Cys Thr Thr Gly
    595                 600                 605

Lys Leu Pro Val Pro Trp Pro Thr Leu Val Thr Thr Leu Thr Tyr Gly
    610                 615                 620

Val Gln Cys Phe Ser Arg Tyr Pro Asp His Met Lys Gln His Asp Phe
625                 630                 635                 640

Phe Lys Ser Ala Met Pro Glu Gly Tyr Ile Gln Glu Arg Thr Ile Phe
            645                 650                 655

Phe Lys Asp Asp Gly Asn Tyr Lys Thr Arg Ala Glu Val Lys Phe Glu
        660                 665                 670
```

```
Gly Asp Thr Leu Val Asn Arg Ile Glu Leu Lys Gly Ile Asp Phe Lys
            675                 680                 685

Glu Asp Gly Asn Ile Leu Gly His Lys Leu Glu Tyr Asn Val Ser Asp
    690                 695                 700

Val Glu Ala Asn Thr Val Arg Leu Lys Glu His Asp Gln Asp Val Leu
705                 710                 715                 720

Val Leu Glu Lys Val Pro Ala Gly Asn Arg Ala Ser Asn Gln Gly Asn
                725                 730                 735

Ser Gln Pro Gln Gln Lys Tyr Thr Val Met Ser Gly Thr Pro Glu Lys
            740                 745                 750

Ile Leu Glu His Phe Leu Glu Thr Ile Arg Leu Glu Ala Thr Leu Asn
            755                 760                 765

Glu Ala Thr Asp Ser Val Leu Asn Asp Phe Ile Met Met His Cys Val
770                 775                 780

Phe Met Pro Asn Thr Gln Leu Cys Pro Ala Leu Val Ala His Tyr His
785                 790                 795                 800

Ala Gln Pro Ser Gln Gly Thr Glu Gln Glu Lys Met Asp Tyr Ala Leu
                805                 810                 815

Asn Asn Lys Arg Arg Val Ile Arg Leu Val Leu Gln Trp Ala Ala Met
            820                 825                 830

Tyr Gly Asp Leu Leu Gln Glu Asp Val Ser Met Ala Phe Leu Glu
            835                 840                 845

Glu Phe Tyr Val Ser Val Ser Asp Asp Ala Arg Met Ile Ala Ala Leu
850                 855                 860

Lys Glu Gln Leu Pro Glu Leu Glu Lys Ile Val Lys Gln Ile Ser Glu
865                 870                 875                 880

Asp Ala Lys Ala Pro Gln Lys Lys His Lys Val Leu Leu Gln Gln Phe
                885                 890                 895

Asn Thr Gly Asp Glu Arg Ala Gln Lys Arg Gln Pro Ile Arg Gly Ser
            900                 905                 910

Asp Glu Val Leu Phe Lys Val Tyr Cys Met Asp Pro Thr Tyr Thr Thr
            915                 920                 925

Ile Arg Val Pro Val Ala Thr Ser Val Lys Glu Val Ile Ser Ala Val
            930                 935                 940

Ala Asp Lys Leu Gly Ser Gly Glu Gly Leu Ile Ile Val Lys Met Ser
945                 950                 955                 960

Ser Gly Gly Glu Lys Val Val Leu Lys Pro Asn Asp Val Ser Val Phe
                965                 970                 975

Met Thr Leu Thr Ile Asn Gly Arg Leu Phe Ala Cys Pro Arg Glu Gln
            980                 985                 990

Phe Asp Ser Leu Thr Pro Leu Pro  Glu Gln Glu Gly Pro  Thr Val Gly
            995                 1000                1005

Thr Val  Gly Thr Phe Glu Leu  Met Ser Ser Lys Asp  Leu Ala Tyr
1010                1015                1020

Gln Met  Thr Ile Tyr Asp Trp  Glu Leu Phe Asn Cys  Val His Glu
    1025                1030                1035

Leu Glu  Leu Ile Tyr His Thr  Phe Gly Arg His Asn  Phe Lys Lys
    1040                1045                1050

Thr Thr  Ala Asn Leu Asp Leu  Phe Leu Arg Arg Phe  Asn Glu Ile
    1055                1060                1065

Gln Phe  Trp Val Val Thr Glu  Ile Cys Leu Cys Ser  Gln Leu Ser
    1070                1075                1080
```

-continued

```
Lys Arg Val Gln Leu Leu Lys Lys Phe Ile Lys Ile Ala Ala His
1085                1090                1095

Cys Lys Glu Tyr Lys Asn Leu Asn Ser Phe Phe Ala Ile Val Met
1100                1105                1110

Gly Leu Ser Asn Val Ala Val Ser Arg Leu Ala Leu Thr Trp Glu
1115                1120                1125

Lys Leu Pro Ser Lys Phe Lys Phe Tyr Ala Glu Phe Glu Ser
1130                1135                1140

Leu Met Asp Pro Ser Arg Asn His Arg Ala Tyr Arg Leu Thr Val
1145                1150                1155

Ala Lys Leu Glu Pro Pro Leu Ile Pro Phe Met Pro Leu Leu Ile
1160                1165                1170

Lys Asp Met Thr Phe Thr His Glu Gly Asn Lys Thr Phe Ile Asp
1175                1180                1185

Asn Leu Val Asn Phe Glu Lys Met Arg Met Ile Ala Asn Thr Ala
1190                1195                1200

Arg Thr Val Arg Tyr Tyr Arg Ser Gln Pro Phe Asn Pro Asp Ala
1205                1210                1215

Ala Gln Ala Asn Lys Asn His Gln Asp Val Arg Ser Tyr Val Arg
1220                1225                1230

Gln Leu Asn Val Ile Asp Asn Gln Arg Thr Leu Ser Gln Met Ser
1235                1240                1245

His Arg Leu Glu Pro Arg Arg Pro
1250                1255
```

<210> SEQ ID NO 25
<211> LENGTH: 1256
<212> TYPE: PRT
<213> ORGANISM: Artificial Sequence
<220> FEATURE:
<223> OTHER INFORMATION: Synthetic

<400> SEQUENCE: 25

```
Met Val Ala Ala His Ala Ala His Ser Ser Ser Ser Ala Glu Trp Ile
1                5                10                15

Ala Cys Leu Asp Lys Arg Pro Leu Glu Arg Ser Ser Glu Asp Val Asp
                20                25                30

Ile Ile Phe Thr Arg Leu Lys Glu Val Lys Ala Phe Glu Lys Phe His
            35                40                45

Pro Asn Leu Leu His Gln Ile Cys Leu Cys Gly Tyr Tyr Glu Asn Leu
        50                55                60

Glu Lys Gly Ile Thr Leu Phe Arg Gln Gly Asp Ile Gly Thr Asn Trp
65                70                75                80

Tyr Ala Val Leu Ala Gly Ser Leu Asp Val Lys Val Ser Glu Thr Ser
                85                90                95

Ser His Gln Asp Ala Val Thr Ile Cys Thr Leu Gly Ile Gly Thr Ala
            100                105                110

Phe Gly Glu Ser Ile Leu Asp Asn Thr Pro Arg His Ala Thr Ile Val
        115                120                125

Thr Arg Glu Ser Ser Glu Leu Leu Arg Ile Glu Gln Lys Asp Phe Lys
    130                135                140

Ala Leu Trp Glu Lys Tyr Arg Gln Tyr Met Ala Gly Leu Leu Ala Pro
145                150                155                160

Pro Tyr Gly Val Met Glu Thr Gly Ser Asn Asn Asp Arg Ile Pro Asp
                165                170                175
```

```
Lys Glu Asn Thr Pro Leu Ile Glu Pro His Val Pro Leu Arg Pro Ala
                180                 185                 190

Asn Thr Ile Thr Lys Val Pro Ser Glu Lys Ile Leu Arg Ala Gly Lys
            195                 200                 205

Ile Leu Arg Asn Ala Ile Leu Ser Arg Ala Pro His Met Ile Arg Asp
        210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
290                 295                 300

Lys Lys Glu Cys Asp Glu Leu Gln Asp Thr Met Leu Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
        435                 440                 445

Asp Lys Glu Asp Phe Asn Arg Ile Leu Arg Leu Glu Asn Val Tyr Ile
450                 455                 460

Lys Ala Asp Lys Gln Lys Asn Gly Ile Lys Ala Asn Phe Lys Ile Arg
465                 470                 475                 480

His Asn Ile Glu Asp Gly Gly Val Gln Leu Ala Tyr His Tyr Gln Gln
                485                 490                 495

Asn Thr Pro Ile Gly Asp Gly Pro Val Leu Leu Pro Asp Asn His Tyr
            500                 505                 510

Leu Ser Val Gln Ser Ile Leu Ser Lys Asp Pro Asn Glu Lys Arg Asp
        515                 520                 525

His Met Val Leu Leu Glu Phe Val Thr Ala Ala Gly Ile Thr Leu Gly
530                 535                 540

Met Asp Glu Leu Tyr Lys Gly Gly Thr Gly Gly Ser Met Val Ser Lys
545                 550                 555                 560

Gly Glu Glu Leu Phe Thr Gly Val Val Pro Ile Gln Val Glu Leu Asp
                565                 570                 575

Gly Asp Val Asn Gly His Lys Phe Ser Val Ser Gly Glu Gly Glu Gly
            580                 585                 590

Asp Ala Thr Tyr Gly Lys Leu Thr Leu Lys Phe Ile Cys Thr Thr Gly
```

```
              595                 600                 605
Lys Leu Pro Val Pro Trp Pro Thr Leu Val Thr Thr Leu Thr Tyr Gly
        610                 615                 620

Val Gln Cys Phe Ser Arg Tyr Pro Asp His Met Lys Gln His Asp Phe
625                 630                 635                 640

Phe Lys Ser Ala Met Pro Glu Gly Tyr Ile Gln Glu Arg Thr Ile Phe
                645                 650                 655

Phe Lys Asp Asp Gly Asn Tyr Lys Thr Arg Ala Glu Val Lys Phe Glu
            660                 665                 670

Gly Asp Thr Leu Val Asn Arg Ile Glu Leu Lys Gly Ile Asp Phe Lys
        675                 680                 685

Glu Asp Gly Asn Ile Leu Gly His Lys Leu Glu Tyr Asn Thr Arg Asp
    690                 695                 700

Val Glu Ala Asn Thr Val Arg Leu Lys Glu His Asp Gln Asp Val Leu
705                 710                 715                 720

Val Leu Glu Lys Val Pro Ala Gly Asn Arg Ala Ser Asn Gln Gly Asn
                725                 730                 735

Ser Gln Pro Gln Gln Lys Tyr Thr Val Met Ser Gly Thr Pro Glu Lys
            740                 745                 750

Ile Leu Glu His Phe Leu Glu Thr Ile Arg Leu Glu Ala Thr Leu Asn
        755                 760                 765

Glu Ala Thr Asp Ser Val Leu Asn Asp Phe Ile Met Met His Cys Val
    770                 775                 780

Phe Met Pro Asn Thr Gln Leu Cys Pro Ala Leu Val Ala His Tyr His
785                 790                 795                 800

Ala Gln Pro Ser Gln Gly Thr Glu Gln Glu Lys Met Asp Tyr Ala Leu
                805                 810                 815

Asn Asn Lys Arg Arg Val Ile Arg Leu Val Leu Gln Trp Ala Ala Met
            820                 825                 830

Tyr Gly Asp Leu Leu Gln Glu Asp Asp Val Ser Met Ala Phe Leu Glu
        835                 840                 845

Glu Phe Tyr Val Ser Val Ser Asp Asp Ala Arg Met Ile Ala Ala Leu
    850                 855                 860

Lys Glu Gln Leu Pro Glu Leu Glu Lys Ile Val Lys Gln Ile Ser Glu
865                 870                 875                 880

Asp Ala Lys Ala Pro Gln Lys Lys His Lys Val Leu Leu Gln Gln Phe
                885                 890                 895

Asn Thr Gly Asp Glu Arg Ala Gln Lys Arg Gln Pro Ile Arg Gly Ser
            900                 905                 910

Asp Glu Val Leu Phe Lys Val Tyr Cys Met Asp Pro Thr Tyr Thr Thr
        915                 920                 925

Ile Arg Val Pro Val Ala Thr Ser Val Lys Glu Val Ile Ser Ala Val
    930                 935                 940

Ala Asp Lys Leu Gly Ser Gly Glu Gly Leu Ile Ile Val Lys Met Ser
945                 950                 955                 960

Ser Gly Gly Glu Lys Val Val Leu Lys Pro Asn Asp Val Ser Val Phe
                965                 970                 975

Met Thr Leu Thr Ile Asn Gly Arg Leu Phe Ala Cys Pro Arg Glu Gln
            980                 985                 990

Phe Asp Ser Leu Thr Pro Leu  Pro Glu Gln Glu Gly Pro  Thr Val Gly
        995                 1000                1005

Thr Val  Gly Thr Phe Glu Leu  Met Ser Ser Lys Asp  Leu Ala Tyr
        1010                1015                1020
```

-continued

```
Gln Met Thr Ile Tyr Asp Trp Glu Leu Phe Asn Cys Val His Glu
    1025                1030                1035

Leu Glu Leu Ile Tyr His Thr Phe Gly Arg His Asn Phe Lys Lys
    1040                1045                1050

Thr Thr Ala Asn Leu Asp Leu Phe Leu Arg Arg Phe Asn Glu Ile
    1055                1060                1065

Gln Phe Trp Val Val Thr Glu Ile Cys Leu Cys Ser Gln Leu Ser
    1070                1075                1080

Lys Arg Val Gln Leu Leu Lys Lys Phe Ile Lys Ile Ala Ala His
    1085                1090                1095

Cys Lys Glu Tyr Lys Asn Leu Asn Ser Phe Phe Ala Ile Val Met
    1100                1105                1110

Gly Leu Ser Asn Val Ala Val Ser Arg Leu Ala Leu Thr Trp Glu
    1115                1120                1125

Lys Leu Pro Ser Lys Phe Lys Lys Phe Tyr Ala Glu Phe Glu Ser
    1130                1135                1140

Leu Met Asp Pro Ser Arg Asn His Arg Ala Tyr Arg Leu Thr Val
    1145                1150                1155

Ala Lys Leu Glu Pro Pro Leu Ile Pro Phe Met Pro Leu Leu Ile
    1160                1165                1170

Lys Asp Met Thr Phe Thr His Glu Gly Asn Lys Thr Phe Ile Asp
    1175                1180                1185

Asn Leu Val Asn Phe Glu Lys Met Arg Met Ile Ala Asn Thr Ala
    1190                1195                1200

Arg Thr Val Arg Tyr Tyr Arg Ser Gln Pro Phe Asn Pro Asp Ala
    1205                1210                1215

Ala Gln Ala Asn Lys Asn His Gln Asp Val Arg Ser Tyr Val Arg
    1220                1225                1230

Gln Leu Asn Val Ile Asp Asn Gln Arg Thr Leu Ser Gln Met Ser
    1235                1240                1245

His Arg Leu Glu Pro Arg Arg Pro
    1250                1255
```

<210> SEQ ID NO 26
<211> LENGTH: 1258
<212> TYPE: PRT
<213> ORGANISM: Artificial Sequence
<220> FEATURE:
<223> OTHER INFORMATION: Synthetic

<400> SEQUENCE: 26

```
Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
                20                  25                  30

Ile Ile Phe Thr Arg Leu Lys Glu Val Lys Ala Phe Glu Lys Phe His
            35                  40                  45

Pro Asn Leu Leu His Gln Ile Cys Leu Cys Gly Tyr Tyr Glu Asn Leu
        50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
                100                 105                 110
```

Phe Gly Glu Ser Ile Leu Asp Asn Thr Pro Arg His Ala Thr Ile Val
            115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
                180                 185                 190

Asn Thr Ile Thr Lys Val Pro Ser Glu Lys Ile Leu Arg Ala Gly Lys
                195                 200                 205

Ile Leu Arg Asn Ala Ile Leu Ser Arg Ala Pro His Met Ile Arg Asp
210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
                260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
        290                 295                 300

Lys Lys Glu Cys Asp Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
                340                 345                 350

His Ile Lys Ala Leu Ser His Leu Ser Thr Thr Val Lys Arg Glu Leu
        355                 360                 365

Ala Gly Val Leu Ile Phe Glu Ser His Ala Lys Gly Gly Thr Val Leu
        370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
                420                 425                 430

Ala Ala Ser Ile Val Leu Arg Glu Asp Asn Cys His Phe Leu Arg Val
                435                 440                 445

Asp Lys Glu Asp Phe Asn Arg Ile Leu Arg Leu Val Ser His Asn Val
        450                 455                 460

Tyr Ile Lys Ala Asp Lys Gln Lys Asn Gly Ile Lys Ala Asn Phe Lys
465                 470                 475                 480

Ile Arg His Asn Ile Glu Asp Gly Gly Val Gln Leu Ala Tyr His Tyr
                485                 490                 495

Gln Gln Asn Thr Pro Ile Gly Asp Gly Pro Val Leu Leu Pro Asp Asn
                500                 505                 510

His Tyr Leu Ser Val Gln Ser Ile Leu Ser Lys Asp Pro Asn Glu Lys
        515                 520                 525

```
Arg Asp His Met Val Leu Leu Glu Phe Val Thr Ala Ala Gly Ile Thr
    530                 535                 540

Leu Gly Met Asp Glu Leu Tyr Lys Gly Thr Gly Gly Ser Met Val
545                 550                 555                 560

Ser Lys Gly Glu Glu Leu Phe Thr Gly Val Val Pro Ile Gln Val Glu
                565                 570                 575

Leu Asp Gly Asp Val Asn Gly His Lys Phe Ser Val Ser Gly Glu Gly
                580                 585                 590

Glu Gly Asp Ala Thr Tyr Gly Lys Leu Thr Leu Lys Phe Ile Cys Thr
            595                 600                 605

Thr Gly Lys Leu Pro Val Pro Trp Pro Thr Leu Val Thr Thr Leu Thr
610                 615                 620

Tyr Gly Val Gln Cys Phe Ser Arg Tyr Pro Asp His Met Lys Gln His
625                 630                 635                 640

Asp Phe Phe Lys Ser Ala Met Pro Glu Gly Tyr Ile Gln Glu Arg Thr
                645                 650                 655

Ile Phe Phe Lys Asp Asp Gly Asn Tyr Lys Thr Arg Ala Glu Val Lys
                660                 665                 670

Phe Glu Gly Asp Thr Leu Val Asn Arg Ile Glu Leu Lys Gly Ile Asp
            675                 680                 685

Phe Lys Glu Asp Gly Asn Ile Leu Gly His Lys Leu Glu Tyr Asn Phe
690                 695                 700

Asn Asp Val Glu Ala Asn Thr Val Arg Leu Lys Glu His Asp Gln Asp
705                 710                 715                 720

Val Leu Val Leu Glu Lys Val Pro Ala Gly Asn Arg Ala Ser Asn Gln
                725                 730                 735

Gly Asn Ser Gln Pro Gln Gln Lys Tyr Thr Val Met Ser Gly Thr Pro
            740                 745                 750

Glu Lys Ile Leu Glu His Phe Leu Glu Thr Ile Arg Leu Glu Ala Thr
            755                 760                 765

Leu Asn Glu Ala Thr Asp Ser Val Leu Asn Asp Phe Ile Met Met His
    770                 775                 780

Cys Val Phe Met Pro Asn Thr Gln Leu Cys Pro Ala Leu Val Ala His
785                 790                 795                 800

Tyr His Ala Gln Pro Ser Gln Gly Thr Glu Gln Lys Met Asp Tyr
                805                 810                 815

Ala Leu Asn Asn Lys Arg Arg Val Ile Arg Leu Val Leu Gln Trp Ala
                820                 825                 830

Ala Met Tyr Gly Asp Leu Leu Gln Glu Asp Val Ser Met Ala Phe
            835                 840                 845

Leu Glu Glu Phe Tyr Val Ser Val Ser Asp Ala Arg Met Ile Ala
850                 855                 860

Ala Leu Lys Glu Gln Leu Pro Glu Leu Glu Lys Ile Val Lys Gln Ile
865                 870                 875                 880

Ser Glu Asp Ala Lys Ala Pro Gln Lys Lys His Lys Val Leu Leu Gln
                885                 890                 895

Gln Phe Asn Thr Gly Asp Glu Arg Ala Gln Lys Arg Gln Pro Ile Arg
            900                 905                 910

Gly Ser Asp Glu Val Leu Phe Lys Val Tyr Cys Met Asp Pro Thr Tyr
            915                 920                 925

Thr Thr Ile Arg Val Pro Val Ala Thr Ser Val Lys Glu Val Ile Ser
    930                 935                 940

Ala Val Ala Asp Lys Leu Gly Ser Gly Glu Gly Leu Ile Ile Val Lys
```

Met Ser Ser Gly Gly Glu Lys Val Val Leu Lys Pro Asn Asp Val Ser
945                 950                 955                 960

Val Phe Met Thr Leu Thr Ile Asn Gly Arg Leu Phe Ala Cys Pro Arg
        965                 970                 975

Glu Gln Phe Asp Ser Leu Thr Pro Leu Pro Glu Gln Glu Gly Pro Thr
            980                 985                 990

Val Gly Thr Val Gly Thr Phe Glu Leu Met Ser Ser Lys Asp Leu
        995                 1000                1005

Ala Tyr Gln Met Thr Ile Tyr Asp Trp Glu Leu Phe Asn Cys Val
    1010                1015                1020

His Glu Leu Glu Leu Ile Tyr His Thr Phe Gly Arg His Asn Phe
    1025                1030                1035

Lys Lys Thr Thr Ala Asn Leu Asp Leu Phe Leu Arg Arg Phe Asn
    1040                1045                1050

Glu Ile Gln Phe Trp Val Val Thr Glu Ile Cys Leu Cys Ser Gln
    1055                1060                1065

Leu Ser Lys Arg Val Gln Leu Leu Lys Lys Phe Ile Lys Ile Ala
    1070                1075                1080

Ala His Cys Lys Glu Tyr Lys Asn Leu Asn Ser Phe Phe Ala Ile
    1085                1090                1095

Val Met Gly Leu Ser Asn Val Ala Val Ser Arg Leu Ala Leu Thr
    1100                1105                1110

Trp Glu Lys Leu Pro Ser Lys Phe Lys Lys Phe Tyr Ala Glu Phe
    1115                1120                1125

Glu Ser Leu Met Asp Pro Ser Arg Asn His Arg Ala Tyr Arg Leu
    1130                1135                1140

Thr Val Ala Lys Leu Glu Pro Pro Leu Ile Pro Phe Met Pro Leu
    1145                1150                1155

Leu Ile Lys Asp Met Thr Phe Thr His Glu Gly Asn Lys Thr Phe
    1160                1165                1170

Ile Asp Asn Leu Val Asn Phe Glu Lys Met Arg Met Ile Ala Asn
    1175                1180                1185

Thr Ala Arg Thr Val Arg Tyr Tyr Arg Ser Gln Pro Phe Asn Pro
    1190                1195                1200

Asp Ala Ala Gln Ala Asn Lys Asn His Gln Asp Val Arg Ser Tyr
    1205                1210                1215

Val Arg Gln Leu Asn Val Ile Asp Asn Gln Arg Thr Leu Ser Gln
    1220                1225                1230

Met Ser His Arg Leu Glu Pro Arg Arg Pro
    1235                1240

<210> SEQ ID NO 27
<211> LENGTH: 1439
<212> TYPE: PRT
<213> ORGANISM: Artificial Sequence
<220> FEATURE:
<223> OTHER INFORMATION: Synthetic

<400> SEQUENCE: 27

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
                20                  25                  30

Ile Ile Phe Thr Arg Leu Lys Glu Val Lys Ala Phe Glu Lys Phe His

```
                35                  40                  45
    Pro Asn Leu Leu His Gln Ile Cys Leu Cys Gly Tyr Tyr Glu Asn Leu
                        50                  55                  60
    Glu Lys Gly Ile Thr Leu Phe Arg Gln Gly Asp Ile Gly Thr Asn Trp
    65                  70                  75                  80
    Tyr Ala Val Leu Ala Gly Ser Leu Asp Val Lys Val Ser Glu Thr Ser
                    85                  90                  95
    Ser His Gln Asp Ala Val Thr Ile Cys Thr Leu Gly Ile Gly Thr Ala
                    100                 105                 110
    Phe Gly Glu Ser Ile Leu Asp Asn Thr Pro Arg His Ala Thr Ile Val
                115                 120                 125
    Thr Arg Glu Ser Ser Glu Leu Leu Arg Ile Glu Gln Lys Asp Phe Lys
            130                 135                 140
    Ala Leu Trp Glu Lys Tyr Arg Gln Tyr Met Ala Gly Leu Leu Ala Pro
    145                 150                 155                 160
    Pro Tyr Gly Val Met Glu Thr Gly Ser Asn Asn Asp Arg Ile Pro Asp
                    165                 170                 175
    Lys Glu Asn Thr Pro Leu Ile Glu Pro His Val Pro Leu Arg Pro Ala
                180                 185                 190
    Asn Thr Ile Thr Lys Val Pro Ser Glu Lys Ile Leu Arg Ala Gly Lys
                195                 200                 205
    Ile Leu Arg Asn Ala Ile Leu Ser Arg Ala Pro His Met Ile Arg Asp
        210                 215                 220
    Arg Lys Tyr His Leu Lys Thr Tyr Arg Gln Cys Cys Val Gly Thr Glu
    225                 230                 235                 240
    Leu Val Asp Trp Met Met Gln Gln Thr Pro Cys Val His Ser Arg Thr
                    245                 250                 255
    Gln Ala Val Gly Met Trp Gln Val Leu Leu Glu Asp Gly Val Leu Asn
                260                 265                 270
    His Val Asp Gln Glu His His Phe Gln Asp Lys Tyr Leu Phe Tyr Arg
                275                 280                 285
    Phe Leu Asp Asp Glu His Glu Asp Ala Pro Leu Pro Thr Glu Glu Glu
            290                 295                 300
    Lys Lys Glu Cys Asp Glu Glu Leu Gln Asp Thr Met Leu Leu Leu Ser
    305                 310                 315                 320
    Gln Met Gly Pro Asp Ala His Met Arg Met Ile Leu Arg Lys Pro Pro
                    325                 330                 335
    Gly Gln Arg Thr Val Asp Asp Leu Glu Ile Ile Tyr Glu Glu Leu Leu
                340                 345                 350
    His Ile Lys Ala Leu Ser His Leu Ser Thr Thr Val Lys Arg Glu Leu
            355                 360                 365
    Ala Gly Val Leu Ile Phe Glu Ser His Ala Lys Gly Thr Val Leu
        370                 375                 380
    Phe Asn Gln Gly Glu Glu Gly Thr Ser Trp Tyr Ile Ile Leu Lys Gly
    385                 390                 395                 400
    Ser Val Asn Val Val Ile Tyr Gly Lys Gly Val Val Cys Thr Leu His
                    405                 410                 415
    Glu Gly Asp Asp Phe Gly Lys Leu Ala Leu Val Asn Asp Ala Pro Arg
                420                 425                 430
    Ala Ala Ser Ile Val Leu Arg Glu Asp Asn Cys His Phe Leu Arg Val
            435                 440                 445
    Asp Lys Glu Asp Phe Asn Arg Ile Leu Arg Asp Val Glu Ala Asn Thr
    450                 455                 460
```

```
Val Arg Leu Lys Glu His Asp Gln Asp Val Leu Val Leu Glu Lys Val
465                 470                 475                 480

Pro Ala Gly Asn Arg Ala Ser Asn Gln Gly Asn Ser Gln Pro Gln Gln
                485                 490                 495

Lys Tyr Thr Val Met Ser Gly Thr Pro Glu Lys Ile Leu Glu His Phe
            500                 505                 510

Leu Glu Thr Ile Arg Leu Glu Ala Thr Leu Asn Glu Ala Thr Asp Ser
        515                 520                 525

Val Leu Asn Asp Phe Ile Met Met His Cys Val Phe Met Pro Asn Thr
530                 535                 540

Gln Leu Cys Pro Ala Leu Val Ala His Tyr His Ala Gln Pro Ser Gln
545                 550                 555                 560

Gly Thr Glu Gln Glu Lys Met Asp Tyr Ala Leu Asn Asn Lys Arg Arg
            565                 570                 575

Val Ile Arg Leu Val Leu Gln Trp Ala Ala Met Tyr Gly Asp Leu Leu
            580                 585                 590

Gln Glu Asp Asp Val Ser Met Ala Phe Leu Glu Glu Phe Tyr Val Ser
        595                 600                 605

Val Ser Asp Asp Ala Arg Met Ile Ala Ala Leu Lys Glu Gln Leu Pro
610                 615                 620

Glu Leu Glu Lys Ile Val Lys Gln Ile Ser Glu Asp Ala Lys Ala Pro
625                 630                 635                 640

Gln Lys Lys His Lys Val Leu Leu Gln Gln Phe Asn Thr Gly Asp Glu
                645                 650                 655

Arg Ala Gln Lys Arg Gln Pro Ile Arg Gly Ser Asp Glu Val Leu Phe
            660                 665                 670

Lys Val Tyr Cys Met Asp Pro Thr Tyr Thr Thr Ile Arg Val Pro Val
            675                 680                 685

Ala Thr Ser Val Lys Glu Val Ile Ser Ala Val Ala Asp Lys Leu Gly
        690                 695                 700

Ser Gly Glu Gly Leu Ile Ile Val Lys Met Ser Ser Gly Gly Glu Lys
705                 710                 715                 720

Val Val Leu Lys Pro Asn Asp Val Ser Val Phe Met Thr Leu Thr Ile
            725                 730                 735

Asn Gly Arg Leu Phe Ala Cys Pro Arg Glu Gln Phe Asp Ser Leu Thr
            740                 745                 750

Pro Leu Pro Glu Gln Glu Gly Pro Thr Val Gly Thr Val Gly Thr Phe
        755                 760                 765

Glu Leu Met Ser Ser Lys Asp Leu Ala Tyr Gln Met Thr Ile Tyr Asp
770                 775                 780

Trp Glu Leu Phe Asn Cys Val His Glu Leu Glu Leu Ile Tyr His Thr
785                 790                 795                 800

Phe Gly Arg His Asn Phe Lys Lys Thr Thr Ala Asn Leu Asp Leu Phe
                805                 810                 815

Leu Arg Arg Phe Asn Glu Ile Gln Phe Trp Val Val Thr Glu Ile Cys
            820                 825                 830

Leu Cys Ser Gln Leu Ser Lys Arg Val Gln Leu Leu Lys Lys Phe Ile
            835                 840                 845

Lys Ile Ala Ala His Cys Lys Glu Tyr Lys Asn Leu Asn Ser Phe Phe
        850                 855                 860

Ala Ile Val Met Gly Leu Ser Asn Val Ala Val Ser Arg Leu Ala Leu
865                 870                 875                 880
```

-continued

```
Thr Trp Glu Lys Leu Pro Ser Lys Phe Lys Phe Tyr Ala Glu Phe
            885                 890                 895

Glu Ser Leu Met Asp Pro Ser Arg Asn His Arg Ala Tyr Arg Leu Thr
            900                 905                 910

Val Ala Lys Leu Glu Pro Pro Leu Ile Pro Phe Met Pro Leu Leu Ile
            915                 920                 925

Lys Asp Met Thr Phe Thr His Glu Gly Asn Lys Thr Phe Ile Asp Asn
            930                 935                 940

Leu Val Asn Phe Glu Lys Met Arg Met Ile Ala Asn Thr Ala Arg Thr
945                 950                 955                 960

Val Arg Tyr Tyr Arg Ser Gln Pro Phe Asn Pro Asp Ala Ala Gln Ala
            965                 970                 975

Asn Lys Asn His Gln Asp Val Arg Ser Tyr Val Arg Gln Leu Asn Val
            980                 985                 990

Ile Asp Asn Gln Arg Thr Leu Ser  Gln Met Ser His Arg  Leu Glu Pro
            995                 1000                1005

Arg Arg  Pro Leu Glu Asn Val  Tyr Ile Lys Ala Asp  Lys Gln Lys
    1010                1015                1020

Asn Gly  Ile Lys Ala Asn Phe  Lys Ile Arg His Asn  Ile Glu Asp
    1025                1030                1035

Gly Gly  Val Gln Leu Ala Tyr  His Tyr Gln Gln Asn  Thr Pro Ile
    1040                1045                1050

Gly Asp  Gly Pro Val Leu Leu  Pro Asp Asn His Tyr  Leu Ser Val
    1055                1060                1065

Gln Ser  Ile Leu Ser Lys Asp  Pro Asn Glu Lys Arg  Asp His Met
    1070                1075                1080

Val Leu  Leu Glu Phe Val Thr  Ala Ala Gly Ile Thr  Leu Gly Met
    1085                1090                1095

Asp Glu  Leu Tyr Lys Gly Gly  Thr Gly Gly Ser Met  Val Ser Lys
    1100                1105                1110

Gly Glu  Glu Leu Phe Thr Gly  Val Val Pro Ile Gln  Val Glu Leu
    1115                1120                1125

Asp Gly  Asp Val Asn Gly His  Lys Phe Ser Val Ser  Gly Glu Gly
    1130                1135                1140

Glu Gly  Asp Ala Thr Tyr Gly  Lys Leu Thr Leu Lys  Phe Ile Cys
    1145                1150                1155

Thr Thr  Gly Lys Leu Pro Val  Pro Trp Pro Thr Leu  Val Thr Thr
    1160                1165                1170

Leu Thr  Tyr Gly Val Gln Cys  Phe Ser Arg Tyr Pro  Asp His Met
    1175                1180                1185

Lys Gln  His Asp Phe Phe Lys  Ser Ala Met Pro Glu  Gly Tyr Ile
    1190                1195                1200

Gln Glu  Arg Thr Ile Phe Phe  Lys Asp Asp Gly Asn  Tyr Lys Thr
    1205                1210                1215

Arg Ala  Glu Val Lys Phe Glu  Gly Asp Thr Leu Val  Asn Arg Ile
    1220                1225                1230

Glu Leu  Lys Gly Ile Asp Phe  Lys Glu Asp Gly Asn  Ile Leu Gly
    1235                1240                1245

His Lys  Leu Glu Tyr Asn Thr  Arg Arg Glu Tyr Lys  Leu Val Val
    1250                1255                1260

Leu Gly  Ser Gly Gly Val Gly  Lys Ser Ala Leu Thr  Val Gln Phe
    1265                1270                1275

Val Gln  Gly Ile Phe Val Glu  Lys Tyr Asp Pro Thr  Ile Glu Asp
```

| | | | |
|---|---|---|---|
| 1280 | | 1285 | 1290 |

Ser Tyr Arg Lys Gln Val Glu Val Asp Ala Gln Gln Cys Met Leu
    1295                        1300                        1305

Glu Ile Leu Asp Thr Ala Gly Thr Glu Gln Phe Thr Ala Met Arg
    1310                        1315                        1320

Asp Leu Tyr Met Lys Asn Gly Gln Gly Phe Ala Leu Val Tyr Ser
    1325                        1330                        1335

Ile Thr Ala Gln Ser Thr Phe Asn Asp Leu Gln Asp Leu Arg Glu
    1340                        1345                        1350

Gln Ile Leu Arg Val Lys Asp Thr Asp Val Pro Met Ile Leu
    1355                        1360                        1365

Val Gly Asn Lys Cys Asp Leu Glu Asp Glu Arg Val Val Gly Lys
    1370                        1375                        1380

Glu Gln Gly Gln Asn Leu Ala Arg Gln Trp Asn Asn Cys Ala Phe
    1385                        1390                        1395

Leu Glu Ser Ser Ala Lys Ser Lys Ile Asn Val Asn Glu Ile Phe
    1400                        1405                        1410

Tyr Asp Leu Val Arg Gln Ile Asn Arg Lys Thr Pro Val Pro Gly
    1415                        1420                        1425

Lys Ala Arg Lys Lys Ser Ser Cys Gln Leu Leu
    1430                        1435

<210> SEQ ID NO 28
<211> LENGTH: 1256
<212> TYPE: PRT
<213> ORGANISM: Artificial Sequence
<220> FEATURE:
<223> OTHER INFORMATION: Synthetic

<400> SEQUENCE: 28

Met Val Ala Ala His Ala Ala His Ser Ser Ser Ala Glu Trp Ile
1             5                    10                  15

Ala Cys Leu Asp Lys Arg Pro Leu Glu Arg Ser Ser Glu Asp Val Asp
          20                    25                    30

Ile Ile Phe Thr Arg Leu Lys Glu Val Lys Ala Phe Glu Lys Phe His
          35                    40                    45

Pro Asn Leu Leu His Gln Ile Cys Leu Cys Gly Tyr Tyr Glu Asn Leu
    50                    55                    60

Glu Lys Gly Ile Thr Leu Phe Arg Gln Gly Asp Ile Gly Thr Asn Trp
65             70                    75                    80

Tyr Ala Val Leu Ala Gly Ser Leu Asp Val Lys Val Ser Glu Thr Ser
                 85                    90                    95

Ser His Gln Asp Ala Val Thr Ile Cys Thr Leu Gly Ile Gly Thr Ala
          100                    105                    110

Phe Gly Glu Ser Ile Leu Asp Asn Thr Pro Arg His Ala Thr Ile Val
               115                    120                    125

Thr Arg Glu Ser Ser Glu Leu Leu Arg Ile Glu Gln Lys Asp Phe Lys
          130                    135                    140

Ala Leu Trp Glu Lys Tyr Arg Gln Tyr Met Ala Gly Leu Leu Ala Pro
145             150                    155                    160

Pro Tyr Gly Val Met Glu Thr Gly Ser Asn Asn Asp Arg Ile Pro Asp
               165                    170                    175

Lys Glu Asn Thr Pro Leu Ile Glu Pro His Val Pro Leu Arg Pro Ala
          180                    185                    190

Asn Thr Ile Thr Lys Val Pro Ser Glu Lys Ile Leu Arg Ala Gly Lys

```
                195                 200                 205
Ile Leu Arg Asn Ala Ile Leu Ser Arg Ala Pro His Met Ile Arg Asp
210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
                260                 265                 270

His Val Asp Gln Glu His His Phe Gln Asp Lys Tyr Leu Phe Tyr Arg
                275                 280                 285

Phe Leu Asp Asp Glu His Glu Asp Ala Pro Leu Pro Thr Glu Glu Glu
290                 295                 300

Lys Lys Glu Cys Asp Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
                340                 345                 350

His Ile Lys Ala Leu Ser His Leu Ser Thr Thr Val Lys Arg Glu Leu
                355                 360                 365

Ala Gly Val Leu Ile Phe Glu Ser His Ala Lys Gly Gly Thr Val Leu
370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
                420                 425                 430

Ala Ala Ser Ile Val Leu Arg Glu Asp Asn Cys His Phe Leu Arg Val
                435                 440                 445

Asp Lys Glu Asp Phe Asn Arg Ile Leu Arg Asp Val Glu Leu Glu Asn
                450                 455                 460

Val Tyr Ile Lys Ala Asp Lys Gln Lys Asn Gly Ile Lys Ala Asn Phe
465                 470                 475                 480

Lys Ile Arg His Asn Ile Glu Asp Gly Gly Val Gln Leu Ala Tyr His
                485                 490                 495

Tyr Gln Gln Asn Thr Pro Ile Gly Asp Gly Pro Val Leu Leu Pro Asp
                500                 505                 510

Asn His Tyr Leu Ser Val Gln Ser Ile Leu Ser Lys Asp Pro Asn Glu
                515                 520                 525

Lys Arg Asp His Met Val Leu Leu Glu Phe Val Thr Ala Ala Gly Ile
                530                 535                 540

Thr Leu Gly Met Asp Glu Leu Tyr Lys Gly Gly Thr Gly Gly Ser Met
545                 550                 555                 560

Val Ser Lys Gly Glu Glu Leu Phe Thr Gly Val Val Pro Ile Gln Val
                565                 570                 575

Glu Leu Asp Gly Asp Val Asn Gly His Lys Phe Ser Val Ser Gly Glu
                580                 585                 590

Gly Glu Gly Asp Ala Thr Tyr Gly Lys Leu Thr Leu Lys Phe Ile Cys
                595                 600                 605

Thr Thr Gly Lys Leu Pro Val Pro Trp Pro Thr Leu Val Thr Thr Leu
610                 615                 620
```

```
Thr Tyr Gly Val Gln Cys Phe Ser Arg Tyr Pro Asp His Met Lys Gln
625                 630                 635                 640

His Asp Phe Phe Lys Ser Ala Met Pro Glu Gly Tyr Ile Gln Glu Arg
            645                 650                 655

Thr Ile Phe Phe Lys Asp Asp Gly Asn Tyr Lys Thr Arg Ala Glu Val
            660                 665                 670

Lys Phe Glu Gly Asp Thr Leu Val Asn Arg Ile Glu Leu Lys Gly Ile
        675                 680                 685

Asp Phe Lys Glu Asp Gly Asn Ile Leu Gly His Lys Leu Glu Tyr Asn
690                 695                 700

Thr Arg Ala Asn Thr Val Arg Leu Lys Glu His Asp Gln Asp Val Leu
705                 710                 715                 720

Val Leu Glu Lys Val Pro Ala Gly Asn Arg Ala Ser Asn Gln Gly Asn
                725                 730                 735

Ser Gln Pro Gln Gln Lys Tyr Thr Val Met Ser Gly Thr Pro Glu Lys
            740                 745                 750

Ile Leu Glu His Phe Leu Glu Thr Ile Arg Leu Glu Ala Thr Leu Asn
        755                 760                 765

Glu Ala Thr Asp Ser Val Leu Asn Asp Phe Ile Met Met His Cys Val
770                 775                 780

Phe Met Pro Asn Thr Gln Leu Cys Pro Ala Leu Val Ala His Tyr His
785                 790                 795                 800

Ala Gln Pro Ser Gln Gly Thr Glu Gln Glu Lys Met Asp Tyr Ala Leu
                805                 810                 815

Asn Asn Lys Arg Arg Val Ile Arg Leu Val Leu Gln Trp Ala Ala Met
            820                 825                 830

Tyr Gly Asp Leu Leu Gln Glu Asp Val Ser Met Ala Phe Leu Glu
        835                 840                 845

Glu Phe Tyr Val Ser Val Ser Asp Asp Ala Arg Met Ile Ala Ala Leu
850                 855                 860

Lys Glu Gln Leu Pro Glu Leu Glu Lys Ile Val Lys Gln Ile Ser Glu
865                 870                 875                 880

Asp Ala Lys Ala Pro Gln Lys Lys His Lys Val Leu Leu Gln Gln Phe
            885                 890                 895

Asn Thr Gly Asp Glu Arg Ala Gln Lys Arg Gln Pro Ile Arg Gly Ser
            900                 905                 910

Asp Glu Val Leu Phe Lys Val Tyr Cys Met Asp Pro Thr Tyr Thr Thr
            915                 920                 925

Ile Arg Val Pro Val Ala Thr Ser Val Lys Glu Val Ile Ser Ala Val
            930                 935                 940

Ala Asp Lys Leu Gly Ser Gly Glu Gly Leu Ile Ile Val Lys Met Ser
945                 950                 955                 960

Ser Gly Gly Glu Lys Val Val Leu Lys Pro Asn Asp Val Ser Val Phe
                965                 970                 975

Met Thr Leu Thr Ile Asn Gly Arg Leu Phe Ala Cys Pro Arg Glu Gln
            980                 985                 990

Phe Asp Ser Leu Thr Pro Leu Pro Glu Gln Glu Gly Pro Thr Val Gly
            995                 1000                1005

Thr Val Gly Thr Phe Glu Leu Met Ser Ser Lys Asp Leu Ala Tyr
        1010                1015                1020

Gln Met Thr Ile Tyr Asp Trp Glu Leu Phe Asn Cys Val His Glu
        1025                1030                1035
```

Leu Glu Leu Ile Tyr His Thr Phe Gly Arg His Asn Phe Lys Lys
1040                1045                1050

Thr Thr Ala Asn Leu Asp Leu Phe Leu Arg Arg Phe Asn Glu Ile
1055                1060                1065

Gln Phe Trp Val Val Thr Glu Ile Cys Leu Cys Ser Gln Leu Ser
1070                1075                1080

Lys Arg Val Gln Leu Leu Lys Lys Phe Ile Lys Ile Ala Ala His
1085                1090                1095

Cys Lys Glu Tyr Lys Asn Leu Asn Ser Phe Phe Ala Ile Val Met
1100                1105                1110

Gly Leu Ser Asn Val Ala Val Ser Arg Leu Ala Leu Thr Trp Glu
1115                1120                1125

Lys Leu Pro Ser Lys Phe Lys Lys Phe Tyr Ala Glu Phe Glu Ser
1130                1135                1140

Leu Met Asp Pro Ser Arg Asn His Arg Ala Tyr Arg Leu Thr Val
1145                1150                1155

Ala Lys Leu Glu Pro Pro Leu Ile Pro Phe Met Pro Leu Leu Ile
1160                1165                1170

Lys Asp Met Thr Phe Thr His Glu Gly Asn Lys Thr Phe Ile Asp
1175                1180                1185

Asn Leu Val Asn Phe Glu Lys Met Arg Met Ile Ala Asn Thr Ala
1190                1195                1200

Arg Thr Val Arg Tyr Tyr Arg Ser Gln Pro Phe Asn Pro Asp Ala
1205                1210                1215

Ala Gln Ala Asn Lys Asn His Gln Asp Val Arg Ser Tyr Val Arg
1220                1225                1230

Gln Leu Asn Val Ile Asp Asn Gln Arg Thr Leu Ser Gln Met Ser
1235                1240                1245

His Arg Leu Glu Pro Arg Arg Pro
1250                1255

<210> SEQ ID NO 29
<211> LENGTH: 1256
<212> TYPE: PRT
<213> ORGANISM: Artificial Sequence
<220> FEATURE:
<223> OTHER INFORMATION: Synthetic

<400> SEQUENCE: 29

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
                20                  25                  30

Ile Ile Phe Thr Arg Leu Lys Glu Val Lys Ala Phe Glu Lys Phe His
            35                  40                  45

Pro Asn Leu Leu His Gln Ile Cys Leu Cys Gly Tyr Tyr Glu Asn Leu
        50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

```
Thr Arg Glu Ser Ser Glu Leu Leu Arg Ile Glu Gln Lys Asp Phe Lys
    130                 135                 140
Ala Leu Trp Glu Lys Tyr Arg Gln Tyr Met Ala Gly Leu Leu Ala Pro
145                 150                 155                 160
Pro Tyr Gly Val Met Glu Thr Gly Ser Asn Asn Asp Arg Ile Pro Asp
                165                 170                 175
Lys Glu Asn Thr Pro Leu Ile Glu Pro His Val Pro Leu Arg Pro Ala
            180                 185                 190
Asn Thr Ile Thr Lys Val Pro Ser Glu Lys Ile Leu Arg Ala Gly Lys
        195                 200                 205
Ile Leu Arg Asn Ala Ile Leu Ser Arg Ala Pro His Met Ile Arg Asp
    210                 215                 220
Arg Lys Tyr His Leu Lys Thr Tyr Arg Gln Cys Cys Val Gly Thr Glu
225                 230                 235                 240
Leu Val Asp Trp Met Met Gln Gln Thr Pro Cys Val His Ser Arg Thr
                245                 250                 255
Gln Ala Val Gly Met Trp Gln Val Leu Leu Glu Asp Gly Val Leu Asn
            260                 265                 270
His Val Asp Gln Glu His His Phe Gln Asp Lys Tyr Leu Phe Tyr Arg
        275                 280                 285
Phe Leu Asp Asp Glu His Glu Asp Ala Pro Leu Pro Thr Glu Glu Glu
    290                 295                 300
Lys Lys Glu Cys Asp Glu Glu Leu Gln Asp Thr Met Leu Leu Leu Ser
305                 310                 315                 320
Gln Met Gly Pro Asp Ala His Met Arg Met Ile Leu Arg Lys Pro Pro
                325                 330                 335
Gly Gln Arg Thr Val Asp Asp Leu Glu Ile Ile Tyr Glu Glu Leu Leu
            340                 345                 350
His Ile Lys Ala Leu Ser His Leu Ser Thr Thr Val Lys Arg Glu Leu
        355                 360                 365
Ala Gly Val Leu Ile Phe Glu Ser His Ala Lys Gly Gly Thr Val Leu
    370                 375                 380
Phe Asn Gln Gly Glu Glu Gly Thr Ser Trp Tyr Ile Ile Leu Lys Gly
385                 390                 395                 400
Ser Val Asn Val Val Ile Tyr Gly Lys Gly Val Val Cys Thr Leu His
                405                 410                 415
Glu Gly Asp Asp Phe Gly Lys Leu Ala Leu Val Asn Asp Ala Pro Arg
            420                 425                 430
Ala Ala Ser Ile Val Leu Arg Glu Asp Asn Cys His Phe Leu Arg Val
        435                 440                 445
Asp Lys Glu Asp Phe Asn Arg Ile Leu Arg Asp Val Glu Ala Asn Thr
    450                 455                 460
Val Arg Leu Lys Glu His Asp Gln Asp Val Leu Val Leu Glu Lys Val
465                 470                 475                 480
Pro Ala Gly Asn Arg Ala Ser Asn Gln Gly Asn Ser Gln Pro Gln Gln
                485                 490                 495
Lys Tyr Thr Val Met Ser Gly Thr Pro Glu Lys Ile Leu Glu His Phe
            500                 505                 510
Leu Glu Thr Ile Arg Leu Leu Glu Asn Val Tyr Ile Lys Ala Asp Lys
        515                 520                 525
Gln Lys Asn Gly Ile Lys Ala Asn Phe Lys Ile Arg His Asn Ile Glu
    530                 535                 540
Asp Gly Gly Val Gln Leu Ala Tyr His Tyr Gln Gln Asn Thr Pro Ile
```

```
               545                 550                 555                 560
           Gly Asp Gly Pro Val Leu Leu Pro Asp Asn His Tyr Leu Ser Val Gln
                           565                 570                 575
           Ser Ile Leu Ser Lys Asp Pro Asn Glu Lys Arg Asp His Met Val Leu
                           580                 585                 590
           Leu Glu Phe Val Thr Ala Ala Gly Ile Thr Leu Gly Met Asp Glu Leu
                           595                 600                 605
           Tyr Lys Gly Gly Thr Gly Gly Ser Met Val Ser Lys Gly Glu Glu Leu
                           610                 615                 620
           Phe Thr Gly Val Val Pro Ile Gln Val Glu Leu Asp Gly Asp Val Asn
           625                 630                 635                 640
           Gly His Lys Phe Ser Val Ser Gly Glu Gly Glu Gly Asp Ala Thr Tyr
                           645                 650                 655
           Gly Lys Leu Thr Leu Lys Phe Ile Cys Thr Thr Gly Lys Leu Pro Val
                           660                 665                 670
           Pro Trp Pro Thr Leu Val Thr Thr Leu Thr Tyr Gly Val Gln Cys Phe
                           675                 680                 685
           Ser Arg Tyr Pro Asp His Met Lys Gln His Asp Phe Phe Lys Ser Ala
                           690                 695                 700
           Met Pro Glu Gly Tyr Ile Gln Glu Arg Thr Ile Phe Phe Lys Asp Asp
           705                 710                 715                 720
           Gly Asn Tyr Lys Thr Arg Ala Glu Val Lys Phe Glu Gly Asp Thr Leu
                           725                 730                 735
           Val Asn Arg Ile Glu Leu Lys Gly Ile Asp Phe Lys Glu Asp Gly Asn
                           740                 745                 750
           Ile Leu Gly His Lys Leu Glu Tyr Asn Thr Arg Glu Ala Thr Leu Asn
                           755                 760                 765
           Glu Ala Thr Asp Ser Val Leu Asn Asp Phe Ile Met Met His Cys Val
                           770                 775                 780
           Phe Met Pro Asn Thr Gln Leu Cys Pro Ala Leu Val Ala His Tyr His
           785                 790                 795                 800
           Ala Gln Pro Ser Gln Gly Thr Glu Gln Glu Lys Met Asp Tyr Ala Leu
                           805                 810                 815
           Asn Asn Lys Arg Arg Val Ile Arg Leu Val Leu Gln Trp Ala Ala Met
                           820                 825                 830
           Tyr Gly Asp Leu Leu Gln Glu Asp Asp Val Ser Met Ala Phe Leu Glu
                           835                 840                 845
           Glu Phe Tyr Val Ser Val Ser Asp Asp Ala Arg Met Ile Ala Ala Leu
                           850                 855                 860
           Lys Glu Gln Leu Pro Glu Leu Glu Lys Ile Val Lys Gln Ile Ser Glu
           865                 870                 875                 880
           Asp Ala Lys Ala Pro Gln Lys Lys His Lys Val Leu Leu Gln Gln Phe
                           885                 890                 895
           Asn Thr Gly Asp Glu Arg Ala Gln Lys Arg Gln Pro Ile Arg Gly Ser
                           900                 905                 910
           Asp Glu Val Leu Phe Lys Val Tyr Cys Met Asp Pro Thr Tyr Thr Thr
                           915                 920                 925
           Ile Arg Val Pro Val Ala Thr Ser Val Lys Glu Val Ile Ser Ala Val
                           930                 935                 940
           Ala Asp Lys Leu Gly Ser Gly Glu Gly Leu Ile Ile Val Lys Met Ser
           945                 950                 955                 960
           Ser Gly Gly Glu Lys Val Val Leu Lys Pro Asn Asp Val Ser Val Phe
                           965                 970                 975
```

Met Thr Leu Thr Ile Asn Gly Arg Leu Phe Ala Cys Pro Arg Glu Gln
                980                 985                 990

Phe Asp Ser Leu Thr Pro Leu Pro Glu Gln Glu Gly Pro Thr Val Gly
            995                 1000                1005

Thr Val Gly Thr Phe Glu Leu Met Ser Ser Lys Asp Leu Ala Tyr
    1010                1015                1020

Gln Met Thr Ile Tyr Asp Trp Glu Leu Phe Asn Cys Val His Glu
    1025                1030                1035

Leu Glu Leu Ile Tyr His Thr Phe Gly Arg His Asn Phe Lys Lys
    1040                1045                1050

Thr Thr Ala Asn Leu Asp Leu Phe Leu Arg Arg Phe Asn Glu Ile
    1055                1060                1065

Gln Phe Trp Val Val Thr Glu Ile Cys Leu Cys Ser Gln Leu Ser
    1070                1075                1080

Lys Arg Val Gln Leu Leu Lys Lys Phe Ile Lys Ile Ala Ala His
    1085                1090                1095

Cys Lys Glu Tyr Lys Asn Leu Asn Ser Phe Phe Ala Ile Val Met
    1100                1105                1110

Gly Leu Ser Asn Val Ala Val Ser Arg Leu Ala Leu Thr Trp Glu
    1115                1120                1125

Lys Leu Pro Ser Lys Phe Lys Lys Phe Tyr Ala Glu Phe Glu Ser
    1130                1135                1140

Leu Met Asp Pro Ser Arg Asn His Arg Ala Tyr Arg Leu Thr Val
    1145                1150                1155

Ala Lys Leu Glu Pro Pro Leu Ile Pro Phe Met Pro Leu Leu Ile
    1160                1165                1170

Lys Asp Met Thr Phe Thr His Glu Gly Asn Lys Thr Phe Ile Asp
    1175                1180                1185

Asn Leu Val Asn Phe Glu Lys Met Arg Met Ile Ala Asn Thr Ala
    1190                1195                1200

Arg Thr Val Arg Tyr Tyr Arg Ser Gln Pro Phe Asn Pro Asp Ala
    1205                1210                1215

Ala Gln Ala Asn Lys Asn His Gln Asp Val Arg Ser Tyr Val Arg
    1220                1225                1230

Gln Leu Asn Val Ile Asp Asn Gln Arg Thr Leu Ser Gln Met Ser
    1235                1240                1245

His Arg Leu Glu Pro Arg Arg Pro
    1250                1255

<210> SEQ ID NO 30
<211> LENGTH: 1256
<212> TYPE: PRT
<213> ORGANISM: Artificial Sequence
<220> FEATURE:
<223> OTHER INFORMATION: Synthetic

<400> SEQUENCE: 30

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
                20                  25                  30

Ile Ile Phe Thr Arg Leu Lys Glu Val Lys Ala Phe Glu Lys Phe His
            35                  40                  45

Pro Asn Leu Leu His Gln Ile Cys Leu Cys Gly Tyr Tyr Glu Asn Leu
        50                  55                  60

```
Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
            115                 120                 125

Thr Arg Glu Ser Ser Glu Leu Leu Arg Ile Glu Gln Lys Asp Phe Lys
            130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
            195                 200                 205

Ile Leu Arg Asn Ala Ile Leu Ser Arg Ala Pro His Met Ile Arg Asp
210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
                260                 265                 270

His Val Asp Gln Glu His His Phe Gln Asp Lys Tyr Leu Phe Tyr Arg
            275                 280                 285

Phe Leu Asp Asp Glu His Glu Asp Ala Pro Leu Pro Thr Glu Glu Glu
            290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu
            340                 345                 350

His Ile Lys Ala Leu Ser His Leu Ser Thr Thr Val Lys Arg Glu Leu
            355                 360                 365

Ala Gly Val Leu Ile Phe Glu Ser His Ala Lys Gly Gly Thr Val Leu
            370                 375                 380

Phe Asn Gln Gly Glu Glu Gly Thr Ser Trp Tyr Ile Ile Leu Lys Gly
385                 390                 395                 400

Ser Val Asn Val Val Ile Tyr Gly Lys Gly Val Val Cys Thr Leu His
                405                 410                 415

Glu Gly Asp Asp Phe Gly Lys Leu Ala Leu Val Asn Asp Ala Pro Arg
            420                 425                 430

Ala Ala Ser Ile Val Leu Arg Glu Asp Asn Cys His Phe Leu Arg Val
            435                 440                 445

Asp Lys Glu Asp Phe Asn Arg Ile Leu Leu Glu Asn Val Tyr Ile Lys
            450                 455                 460

Ala Asp Lys Gln Lys Asn Gly Ile Lys Ala Asn Phe Lys Ile Arg His
465                 470                 475                 480
```

-continued

Asn Ile Glu Asp Gly Gly Val Gln Leu Ala Tyr His Tyr Gln Gln Asn
                485                 490                 495

Thr Pro Ile Gly Asp Gly Pro Val Leu Leu Pro Asp Asn His Tyr Leu
            500                 505                 510

Ser Val Gln Ser Ile Leu Ser Lys Asp Pro Asn Glu Lys Arg Asp His
        515                 520                 525

Met Val Leu Leu Glu Phe Val Thr Ala Ala Gly Ile Thr Leu Gly Met
    530                 535                 540

Asp Glu Leu Tyr Lys Gly Gly Thr Gly Gly Ser Met Val Ser Lys Gly
545                 550                 555                 560

Glu Glu Leu Phe Thr Gly Val Val Pro Ile Gln Val Glu Leu Asp Gly
                565                 570                 575

Asp Val Asn Gly His Lys Phe Ser Val Ser Gly Glu Gly Glu Gly Asp
            580                 585                 590

Ala Thr Tyr Gly Lys Leu Thr Leu Lys Phe Ile Cys Thr Thr Gly Lys
        595                 600                 605

Leu Pro Val Pro Trp Pro Thr Leu Val Thr Thr Leu Thr Tyr Gly Val
    610                 615                 620

Gln Cys Phe Ser Arg Tyr Pro Asp His Met Lys Gln His Asp Phe Phe
625                 630                 635                 640

Lys Ser Ala Met Pro Glu Gly Tyr Ile Gln Glu Arg Thr Ile Phe Phe
                645                 650                 655

Lys Asp Asp Gly Asn Tyr Lys Thr Arg Ala Glu Val Lys Phe Glu Gly
            660                 665                 670

Asp Thr Leu Val Asn Arg Ile Glu Leu Lys Gly Ile Asp Phe Lys Glu
        675                 680                 685

Asp Gly Asn Ile Leu Gly His Lys Leu Glu Tyr Asn Thr Arg Arg Asp
    690                 695                 700

Val Glu Ala Asn Thr Val Arg Leu Lys Glu His Asp Gln Asp Val Leu
705                 710                 715                 720

Val Leu Glu Lys Val Pro Ala Gly Asn Arg Ala Ser Asn Gln Gly Asn
                725                 730                 735

Ser Gln Pro Gln Gln Lys Tyr Thr Val Met Ser Gly Thr Pro Glu Lys
            740                 745                 750

Ile Leu Glu His Phe Leu Glu Thr Ile Arg Leu Glu Ala Thr Leu Asn
        755                 760                 765

Glu Ala Thr Asp Ser Val Leu Asn Asp Phe Ile Met Met His Cys Val
    770                 775                 780

Phe Met Pro Asn Thr Gln Leu Cys Pro Ala Leu Val Ala His Tyr His
785                 790                 795                 800

Ala Gln Pro Ser Gln Gly Thr Glu Gln Glu Lys Met Asp Tyr Ala Leu
                805                 810                 815

Asn Asn Lys Arg Arg Val Ile Arg Leu Val Leu Gln Trp Ala Ala Met
            820                 825                 830

Tyr Gly Asp Leu Leu Gln Glu Asp Asp Val Ser Met Ala Phe Leu Glu
        835                 840                 845

Glu Phe Tyr Val Ser Val Ser Asp Asp Ala Arg Met Ile Ala Ala Leu
    850                 855                 860

Lys Glu Gln Leu Pro Glu Leu Glu Lys Ile Val Lys Gln Ile Ser Glu
865                 870                 875                 880

Asp Ala Lys Ala Pro Gln Lys Lys His Lys Val Leu Leu Gln Gln Phe
                885                 890                 895

Asn Thr Gly Asp Glu Arg Ala Gln Lys Arg Gln Pro Ile Arg Gly Ser

```
                    900                 905                 910
Asp Glu Val Leu Phe Lys Val Tyr Cys Met Asp Pro Thr Tyr Thr Thr
                915                 920                 925

Ile Arg Val Pro Val Ala Thr Ser Val Lys Glu Val Ile Ser Ala Val
                930                 935                 940

Ala Asp Lys Leu Gly Ser Gly Glu Gly Leu Ile Ile Val Lys Met Ser
945                 950                 955                 960

Ser Gly Gly Glu Lys Val Val Leu Lys Pro Asn Asp Val Ser Val Phe
                965                 970                 975

Met Thr Leu Thr Ile Asn Gly Arg Leu Phe Ala Cys Pro Arg Glu Gln
                980                 985                 990

Phe Asp Ser Leu Thr Pro Leu Pro Glu Gln Glu Gly Pro Thr Val Gly
                995                 1000                1005

Thr Val Gly Thr Phe Glu Leu Met Ser Ser Lys Asp Leu Ala Tyr
            1010                1015                1020

Gln Met Thr Ile Tyr Asp Trp Glu Leu Phe Asn Cys Val His Glu
            1025                1030                1035

Leu Glu Leu Ile Tyr His Thr Phe Gly Arg His Asn Phe Lys Lys
            1040                1045                1050

Thr Thr Ala Asn Leu Asp Leu Phe Leu Arg Arg Phe Asn Glu Ile
            1055                1060                1065

Gln Phe Trp Val Val Thr Glu Ile Cys Leu Cys Ser Gln Leu Ser
            1070                1075                1080

Lys Arg Val Gln Leu Leu Lys Lys Phe Ile Lys Ile Ala Ala His
            1085                1090                1095

Cys Lys Glu Tyr Lys Asn Leu Asn Ser Phe Phe Ala Ile Val Met
            1100                1105                1110

Gly Leu Ser Asn Val Ala Val Ser Arg Leu Ala Leu Thr Trp Glu
            1115                1120                1125

Lys Leu Pro Ser Lys Phe Lys Lys Phe Tyr Ala Glu Phe Glu Ser
            1130                1135                1140

Leu Met Asp Pro Ser Arg Asn His Arg Ala Tyr Arg Leu Thr Val
            1145                1150                1155

Ala Lys Leu Glu Pro Pro Leu Ile Pro Phe Met Pro Leu Leu Ile
            1160                1165                1170

Lys Asp Met Thr Phe Thr His Glu Gly Asn Lys Thr Phe Ile Asp
            1175                1180                1185

Asn Leu Val Asn Phe Glu Lys Met Arg Met Ile Ala Asn Thr Ala
            1190                1195                1200

Arg Thr Val Arg Tyr Tyr Arg Ser Gln Pro Phe Asn Pro Asp Ala
            1205                1210                1215

Ala Gln Ala Asn Lys Asn His Gln Asp Val Arg Ser Tyr Val Arg
            1220                1225                1230

Gln Leu Asn Val Ile Asp Asn Gln Arg Thr Leu Ser Gln Met Ser
            1235                1240                1245

His Arg Leu Glu Pro Arg Arg Pro
            1250                1255

<210> SEQ ID NO 31
<211> LENGTH: 1256
<212> TYPE: PRT
<213> ORGANISM: Artificial Sequence
<220> FEATURE:
<223> OTHER INFORMATION: Synthetic
```

```
<400> SEQUENCE: 31

Met Val Ala Ala His Ala Ala His Ser Ser Ser Ala Glu Trp Ile
1               5                   10                  15

Ala Cys Leu Asp Lys Arg Pro Leu Glu Arg Ser Ser Glu Asp Val Asp
                20                  25                  30

Ile Ile Phe Thr Arg Leu Lys Glu Val Lys Ala Phe Glu Lys Phe His
            35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
                100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
    290                 295                 300

Lys Lys Glu Cys Asp Glu Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Leu Glu Asn Val Tyr Ile Lys Ala Asp Lys Gln
            340                 345                 350

Lys Asn Gly Ile Lys Ala Asn Phe Lys Ile Arg His Asn Ile Glu Asp
        355                 360                 365

Gly Gly Val Gln Leu Ala Tyr His Tyr Gln Gln Asn Thr Pro Ile Gly
    370                 375                 380

Asp Gly Pro Val Leu Leu Pro Asp Asn His Tyr Leu Ser Val Gln Ser
385                 390                 395                 400

Ile Leu Ser Lys Asp Pro Asn Glu Lys Arg Asp His Met Val Leu Leu
                405                 410                 415
```

```
Glu Phe Val Thr Ala Ala Gly Ile Thr Leu Gly Met Asp Glu Leu Tyr
            420                 425                 430

Lys Gly Gly Thr Gly Gly Ser Met Val Ser Lys Gly Glu Glu Leu Phe
            435                 440                 445

Thr Gly Val Val Pro Ile Gln Val Glu Leu Asp Gly Asp Val Asn Gly
            450                 455                 460

His Lys Phe Ser Val Ser Gly Glu Gly Glu Gly Asp Ala Thr Tyr Gly
465                 470                 475                 480

Lys Leu Thr Leu Lys Phe Ile Cys Thr Thr Gly Lys Leu Pro Val Pro
                485                 490                 495

Trp Pro Thr Leu Val Thr Thr Leu Thr Tyr Gly Val Gln Cys Phe Ser
            500                 505                 510

Arg Tyr Pro Asp His Met Lys Gln His Asp Phe Phe Lys Ser Ala Met
            515                 520                 525

Pro Glu Gly Tyr Ile Gln Glu Arg Thr Ile Phe Phe Lys Asp Asp Gly
            530                 535                 540

Asn Tyr Lys Thr Arg Ala Glu Val Lys Phe Glu Gly Asp Thr Leu Val
545                 550                 555                 560

Asn Arg Ile Glu Leu Lys Gly Ile Asp Phe Lys Glu Asp Gly Asn Ile
                565                 570                 575

Leu Gly His Lys Leu Glu Tyr Asn Thr Arg Asp Asp Leu Glu Ile Ile
            580                 585                 590

Tyr Glu Glu Leu Leu His Ile Lys Ala Leu Ser His Leu Ser Thr Thr
            595                 600                 605

Val Lys Arg Glu Leu Ala Gly Val Leu Ile Phe Glu Ser His Ala Lys
            610                 615                 620

Gly Gly Thr Val Leu Phe Asn Gln Gly Glu Glu Gly Thr Ser Trp Tyr
625                 630                 635                 640

Ile Ile Leu Lys Gly Ser Val Asn Val Ile Tyr Gly Lys Gly Val
                645                 650                 655

Val Cys Thr Leu His Glu Gly Asp Asp Phe Gly Lys Leu Ala Leu Val
            660                 665                 670

Asn Asp Ala Pro Arg Ala Ala Ser Ile Val Leu Arg Glu Asp Asn Cys
            675                 680                 685

His Phe Leu Arg Val Asp Lys Glu Asp Phe Asn Arg Ile Leu Arg Asp
            690                 695                 700

Val Glu Ala Asn Thr Val Arg Leu Lys Glu His Asp Gln Asp Val Leu
705                 710                 715                 720

Val Leu Glu Lys Val Pro Ala Gly Asn Arg Ala Ser Asn Gln Gly Asn
                725                 730                 735

Ser Gln Pro Gln Gln Lys Tyr Thr Val Met Ser Gly Thr Pro Glu Lys
            740                 745                 750

Ile Leu Glu His Phe Leu Glu Thr Ile Arg Leu Glu Ala Thr Leu Asn
            755                 760                 765

Glu Ala Thr Asp Ser Val Leu Asn Asp Phe Ile Met Met His Cys Val
            770                 775                 780

Phe Met Pro Asn Thr Gln Leu Cys Pro Ala Leu Val Ala His Tyr His
785                 790                 795                 800

Ala Gln Pro Ser Gln Gly Thr Glu Gln Glu Lys Met Asp Tyr Ala Leu
                805                 810                 815

Asn Asn Lys Arg Arg Val Ile Arg Leu Val Leu Gln Trp Ala Ala Met
            820                 825                 830
```

```
Tyr Gly Asp Leu Leu Gln Glu Asp Val Ser Met Ala Phe Leu Glu
        835                 840                 845

Glu Phe Tyr Val Ser Val Ser Asp Asp Ala Arg Met Ile Ala Ala Leu
850                 855                 860

Lys Glu Gln Leu Pro Glu Leu Glu Lys Ile Val Lys Gln Ile Ser Glu
865                 870                 875                 880

Asp Ala Lys Ala Pro Gln Lys Lys His Lys Val Leu Leu Gln Gln Phe
                885                 890                 895

Asn Thr Gly Asp Glu Arg Ala Gln Lys Arg Gln Pro Ile Arg Gly Ser
                900                 905                 910

Asp Glu Val Leu Phe Lys Val Tyr Cys Met Asp Pro Thr Tyr Thr Thr
                915                 920                 925

Ile Arg Val Pro Val Ala Thr Ser Val Lys Glu Val Ile Ser Ala Val
        930                 935                 940

Ala Asp Lys Leu Gly Ser Gly Glu Gly Leu Ile Ile Val Lys Met Ser
945                 950                 955                 960

Ser Gly Gly Glu Lys Val Val Leu Lys Pro Asn Asp Val Ser Val Phe
                965                 970                 975

Met Thr Leu Thr Ile Asn Gly Arg Leu Phe Ala Cys Pro Arg Glu Gln
                980                 985                 990

Phe Asp Ser Leu Thr Pro Leu Pro Glu Gln Glu Gly Pro Thr Val Gly
                995                 1000                1005

Thr Val Gly Thr Phe Glu Leu Met Ser Ser Lys Asp Leu Ala Tyr
        1010                1015                1020

Gln Met Thr Ile Tyr Asp Trp Glu Leu Phe Asn Cys Val His Glu
        1025                1030                1035

Leu Glu Leu Ile Tyr His Thr Phe Gly Arg His Asn Phe Lys Lys
        1040                1045                1050

Thr Thr Ala Asn Leu Asp Leu Phe Leu Arg Arg Phe Asn Glu Ile
        1055                1060                1065

Gln Phe Trp Val Val Thr Glu Ile Cys Leu Cys Ser Gln Leu Ser
        1070                1075                1080

Lys Arg Val Gln Leu Leu Lys Lys Phe Ile Lys Ile Ala Ala His
        1085                1090                1095

Cys Lys Glu Tyr Lys Asn Leu Asn Ser Phe Phe Ala Ile Val Met
        1100                1105                1110

Gly Leu Ser Asn Val Ala Val Ser Arg Leu Ala Leu Thr Trp Glu
        1115                1120                1125

Lys Leu Pro Ser Lys Phe Lys Lys Phe Tyr Ala Glu Phe Glu Ser
        1130                1135                1140

Leu Met Asp Pro Ser Arg Asn His Arg Ala Tyr Arg Leu Thr Val
        1145                1150                1155

Ala Lys Leu Glu Pro Pro Leu Ile Pro Phe Met Pro Leu Leu Ile
        1160                1165                1170

Lys Asp Met Thr Phe Thr His Glu Gly Asn Lys Thr Phe Ile Asp
        1175                1180                1185

Asn Leu Val Asn Phe Glu Lys Met Arg Met Ile Ala Asn Thr Ala
        1190                1195                1200

Arg Thr Val Arg Tyr Arg Ser Gln Pro Phe Asn Pro Asp Ala
        1205                1210                1215

Ala Gln Ala Asn Lys Asn His Gln Asp Val Arg Ser Tyr Val Arg
        1220                1225                1230

Gln Leu Asn Val Ile Asp Asn Gln Arg Thr Leu Ser Gln Met Ser
```

His Arg Leu Glu Pro Arg Arg Pro
1250             1255

<210> SEQ ID NO 32
<211> LENGTH: 1256
<212> TYPE: PRT
<213> ORGANISM: Artificial Sequence
<220> FEATURE:
<223> OTHER INFORMATION: Synthetic

<400> SEQUENCE: 32

Met Val Ala Ala His Ala Ala His Ser Ser Ser Ala Glu Trp Ile
1               5                   10                  15

Ala Cys Leu Asp Lys Arg Pro Leu Glu Arg Ser Ser Glu Asp Val Asp
                20                  25                  30

Ile Ile Phe Thr Arg Leu Lys Glu Val Lys Ala Phe Glu Lys Phe His
            35                  40                  45

Pro Asn Leu Leu His Gln Ile Cys Leu Cys Gly Tyr Tyr Glu Asn Leu
        50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270

His Val Asp Gln Glu His His Phe Gln Asp Lys Tyr Leu Phe Tyr Arg
        275                 280                 285

Phe Leu Asp Asp Glu His Glu Asp Ala Pro Leu Pro Thr Glu Glu Glu
290                 295                 300

Lys Lys Glu Cys Asp Glu Leu Gln Asp Thr Met Leu Leu Leu Ser
305                 310                 315                 320

Gln Met Gly Pro Asp Ala His Met Arg Met Ile Leu Arg Lys Pro Pro
                325                 330                 335

Gly Gln Arg Thr Val Asp Asp Leu Glu Ile Ile Tyr Glu Glu Leu Leu

```
              340                 345                 350
His Ile Lys Ala Leu Ser His Leu Ser Thr Val Lys Arg Glu Leu
            355                 360                 365
Ala Gly Val Leu Ile Phe Glu Ser His Ala Lys Gly Thr Val Leu
        370                 375                 380
Phe Asn Gln Gly Glu Glu Gly Thr Ser Trp Tyr Ile Ile Leu Lys Gly
385                 390                 395                 400
Ser Val Asn Val Val Ile Tyr Gly Lys Gly Val Val Cys Thr Leu His
                405                 410                 415
Glu Gly Asp Asp Phe Gly Lys Leu Ala Leu Val Asn Asp Ala Pro Arg
            420                 425                 430
Ala Ala Ser Ile Val Leu Arg Glu Asp Asn Cys His Phe Leu Arg Val
        435                 440                 445
Asp Lys Glu Asp Phe Asn Arg Ile Leu Arg Asp Val Glu Ala Asn Thr
    450                 455                 460
Val Arg Leu Lys Glu His Asp Gln Asp Val Leu Val Leu Glu Lys Val
465                 470                 475                 480
Pro Ala Gly Asn Arg Ala Leu Glu Asn Val Tyr Ile Lys Ala Asp Lys
                485                 490                 495
Gln Lys Asn Gly Ile Lys Ala Asn Phe Lys Ile Arg His Asn Ile Glu
            500                 505                 510
Asp Gly Gly Val Gln Leu Ala Tyr His Tyr Gln Gln Asn Thr Pro Ile
        515                 520                 525
Gly Asp Gly Pro Val Leu Leu Pro Asp Asn His Tyr Leu Ser Val Gln
    530                 535                 540
Ser Ile Leu Ser Lys Asp Pro Asn Glu Lys Arg Asp His Met Val Leu
545                 550                 555                 560
Leu Glu Phe Val Thr Ala Ala Gly Ile Thr Leu Gly Met Asp Glu Leu
                565                 570                 575
Tyr Lys Gly Gly Thr Gly Gly Ser Met Val Ser Lys Gly Glu Glu Leu
            580                 585                 590
Phe Thr Gly Val Val Pro Ile Gln Val Glu Leu Asp Gly Asp Val Asn
        595                 600                 605
Gly His Lys Phe Ser Val Ser Gly Glu Gly Glu Gly Asp Ala Thr Tyr
    610                 615                 620
Gly Lys Leu Thr Leu Lys Phe Ile Cys Thr Thr Gly Lys Leu Pro Val
625                 630                 635                 640
Pro Trp Pro Thr Leu Val Thr Thr Leu Thr Tyr Gly Val Gln Cys Phe
                645                 650                 655
Ser Arg Tyr Pro Asp His Met Lys Gln His Asp Phe Phe Lys Ser Ala
            660                 665                 670
Met Pro Glu Gly Tyr Ile Gln Glu Arg Thr Ile Phe Phe Lys Asp Asp
        675                 680                 685
Gly Asn Tyr Lys Thr Arg Ala Glu Val Lys Phe Glu Gly Asp Thr Leu
    690                 695                 700
Val Asn Arg Ile Glu Leu Lys Gly Ile Asp Phe Lys Glu Asp Gly Asn
705                 710                 715                 720
Ile Leu Gly His Lys Leu Glu Tyr Asn Thr Arg Ser Asn Gln Gly Asn
                725                 730                 735
Ser Gln Pro Gln Gln Lys Tyr Thr Val Met Ser Gly Thr Pro Glu Lys
            740                 745                 750
Ile Leu Glu His Phe Leu Glu Thr Ile Arg Leu Glu Ala Thr Leu Asn
        755                 760                 765
```

Glu Ala Thr Asp Ser Val Leu Asn Asp Phe Ile Met Met His Cys Val
770                 775                 780

Phe Met Pro Asn Thr Gln Leu Cys Pro Ala Leu Val Ala His Tyr His
785                 790                 795                 800

Ala Gln Pro Ser Gln Gly Thr Glu Gln Glu Lys Met Asp Tyr Ala Leu
                805                 810                 815

Asn Asn Lys Arg Arg Val Ile Arg Leu Val Leu Gln Trp Ala Ala Met
                820                 825                 830

Tyr Gly Asp Leu Leu Gln Glu Asp Val Ser Met Ala Phe Leu Glu
            835                 840                 845

Glu Phe Tyr Val Ser Val Ser Asp Asp Ala Arg Met Ile Ala Ala Leu
850                 855                 860

Lys Glu Gln Leu Pro Glu Leu Glu Lys Ile Val Lys Gln Ile Ser Glu
865                 870                 875                 880

Asp Ala Lys Ala Pro Gln Lys Lys His Lys Val Leu Leu Gln Gln Phe
                885                 890                 895

Asn Thr Gly Asp Glu Arg Ala Gln Lys Arg Gln Pro Ile Arg Gly Ser
                900                 905                 910

Asp Glu Val Leu Phe Lys Val Tyr Cys Met Asp Pro Thr Tyr Thr Thr
            915                 920                 925

Ile Arg Val Pro Val Ala Thr Ser Val Lys Glu Val Ile Ser Ala Val
930                 935                 940

Ala Asp Lys Leu Gly Ser Gly Glu Gly Leu Ile Ile Val Lys Met Ser
945                 950                 955                 960

Ser Gly Gly Glu Lys Val Val Leu Lys Pro Asn Asp Val Ser Val Phe
                965                 970                 975

Met Thr Leu Thr Ile Asn Gly Arg Leu Phe Ala Cys Pro Arg Glu Gln
            980                 985                 990

Phe Asp Ser Leu Thr Pro Leu Pro Glu Gln Glu Gly Pro Thr Val Gly
            995                 1000                1005

Thr Val Gly Thr Phe Glu Leu Met Ser Ser Lys Asp Leu Ala Tyr
    1010                1015                1020

Gln Met Thr Ile Tyr Asp Trp Glu Leu Phe Asn Cys Val His Glu
    1025                1030                1035

Leu Glu Leu Ile Tyr His Thr Phe Gly Arg His Asn Phe Lys Lys
    1040                1045                1050

Thr Thr Ala Asn Leu Asp Leu Phe Leu Arg Arg Phe Asn Glu Ile
    1055                1060                1065

Gln Phe Trp Val Val Thr Glu Ile Cys Leu Cys Ser Gln Leu Ser
    1070                1075                1080

Lys Arg Val Gln Leu Leu Lys Lys Phe Ile Lys Ile Ala Ala His
    1085                1090                1095

Cys Lys Glu Tyr Lys Asn Leu Asn Ser Phe Phe Ala Ile Val Met
    1100                1105                1110

Gly Leu Ser Asn Val Ala Val Ser Arg Leu Ala Leu Thr Trp Glu
    1115                1120                1125

Lys Leu Pro Ser Lys Phe Lys Phe Tyr Ala Glu Phe Glu Ser
    1130                1135                1140

Leu Met Asp Pro Ser Arg Asn His Arg Ala Tyr Arg Leu Thr Val
    1145                1150                1155

Ala Lys Leu Glu Pro Pro Leu Ile Pro Phe Met Pro Leu Leu Ile
    1160                1165                1170

```
Lys Asp Met Thr Phe Thr His Glu Gly Asn Lys Thr Phe Ile Asp
    1175                1180                1185

Asn Leu Val Asn Phe Glu Lys Met Arg Met Ile Ala Asn Thr Ala
    1190                1195                1200

Arg Thr Val Arg Tyr Tyr Arg Ser Gln Pro Phe Asn Pro Asp Ala
    1205                1210                1215

Ala Gln Ala Asn Lys Asn His Gln Asp Val Arg Ser Tyr Val Arg
    1220                1225                1230

Gln Leu Asn Val Ile Asp Asn Gln Arg Thr Leu Ser Gln Met Ser
    1235                1240                1245

His Arg Leu Glu Pro Arg Arg Pro
    1250                1255

<210> SEQ ID NO 33
<211> LENGTH: 1256
<212> TYPE: PRT
<213> ORGANISM: Artificial Sequence
<220> FEATURE:
<223> OTHER INFORMATION: Synthetic

<400> SEQUENCE: 33

Met Val Ala Ala His Ala Ala His Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
        35                  40                  45

Pro Asn Leu Leu His Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Lys Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Thr Pro Leu Ile Glu Pro His Val Pro Leu Arg Pro Ala
            180                 185                 190

Asn Thr Ile Thr Lys Val Pro Ser Glu Lys Ile Leu Arg Ala Gly Lys
        195                 200                 205

Ile Leu Arg Asn Ala Ile Leu Ser Arg Ala Pro His Met Ile Arg Asp
    210                 215                 220

Arg Lys Tyr His Leu Lys Thr Tyr Arg Gln Cys Cys Val Gly Thr Glu
225                 230                 235                 240

Leu Val Asp Trp Met Met Gln Gln Thr Pro Cys Val His Ser Arg Thr
                245                 250                 255

Gln Ala Val Gly Met Trp Gln Val Leu Leu Glu Asp Gly Val Leu Asn
            260                 265                 270
```

```
His Val Asp Gln Glu His His Phe Gln Asp Lys Tyr Leu Phe Tyr Arg
            275                 280                 285
Phe Leu Asp Asp Glu His Glu Asp Ala Pro Leu Pro Thr Glu Glu
    290                 295                 300
Lys Lys Glu Cys Asp Glu Leu Gln Asp Thr Met Leu Leu Leu Ser
305                 310                 315                 320
Gln Met Gly Pro Asp Ala His Met Arg Met Ile Leu Arg Lys Pro Pro
                325                 330                 335
Gly Gln Arg Thr Val Asp Asp Leu Glu Ile Ile Tyr Glu Glu Leu Leu
            340                 345                 350
His Ile Lys Ala Leu Ser His Leu Ser Thr Thr Val Lys Arg Glu Leu
            355                 360                 365
Ala Gly Val Leu Ile Phe Glu Ser His Ala Lys Gly Thr Val Leu
    370                 375                 380
Phe Asn Gln Gly Glu Glu Gly Thr Ser Trp Tyr Ile Ile Leu Lys Gly
385                 390                 395                 400
Ser Val Asn Val Val Ile Tyr Gly Lys Gly Val Val Cys Thr Leu His
                405                 410                 415
Glu Gly Asp Asp Phe Gly Lys Leu Ala Leu Val Asn Asp Ala Pro Arg
            420                 425                 430
Ala Ala Ser Ile Val Leu Arg Glu Asp Asn Cys His Phe Leu Arg Val
        435                 440                 445
Asp Lys Glu Asp Phe Asn Arg Ile Leu Arg Asp Val Glu Ala Asn Thr
    450                 455                 460
Val Arg Leu Lys Glu His Asp Gln Asp Val Leu Val Leu Glu Lys Val
465                 470                 475                 480
Pro Ala Gly Asn Arg Ala Ser Asn Gln Gly Asn Ser Gln Pro Gln Gln
                485                 490                 495
Lys Tyr Thr Val Met Ser Gly Thr Pro Glu Lys Ile Leu Glu His Phe
            500                 505                 510
Leu Glu Thr Ile Arg Leu Glu Ala Leu Glu Asn Val Tyr Ile Lys Ala
            515                 520                 525
Asp Lys Gln Lys Asn Gly Ile Lys Ala Asn Phe Lys Ile Arg His Asn
    530                 535                 540
Ile Glu Asp Gly Gly Val Gln Leu Ala Tyr His Tyr Gln Gln Asn Thr
545                 550                 555                 560
Pro Ile Gly Asp Gly Pro Val Leu Leu Pro Asp Asn His Tyr Leu Ser
                565                 570                 575
Val Gln Ser Ile Leu Ser Lys Asp Pro Asn Glu Lys Arg Asp His Met
            580                 585                 590
Val Leu Leu Glu Phe Val Thr Ala Ala Gly Ile Thr Leu Gly Met Asp
            595                 600                 605
Glu Leu Tyr Lys Gly Gly Thr Gly Gly Ser Met Val Ser Lys Gly Glu
    610                 615                 620
Glu Leu Phe Thr Gly Val Val Pro Ile Gln Val Glu Leu Asp Gly Asp
625                 630                 635                 640
Val Asn Gly His Lys Phe Ser Val Ser Gly Glu Gly Glu Gly Asp Ala
                645                 650                 655
Thr Tyr Gly Lys Leu Thr Leu Lys Phe Ile Cys Thr Thr Gly Lys Leu
            660                 665                 670
Pro Val Pro Trp Pro Thr Leu Val Thr Thr Leu Thr Tyr Gly Val Gln
            675                 680                 685
Cys Phe Ser Arg Tyr Pro Asp His Met Lys Gln His Asp Phe Phe Lys
```

-continued

```
            690                 695                 700
Ser Ala Met Pro Glu Gly Tyr Ile Gln Glu Arg Thr Ile Phe Phe Lys
705                 710                 715                 720

Asp Asp Gly Asn Tyr Lys Thr Arg Ala Glu Val Lys Phe Glu Gly Asp
                725                 730                 735

Thr Leu Val Asn Arg Ile Glu Leu Lys Gly Ile Asp Phe Lys Glu Asp
                740                 745                 750

Gly Asn Ile Leu Gly His Lys Leu Glu Tyr Asn Thr Arg Thr Leu Asn
                755                 760                 765

Glu Ala Thr Asp Ser Val Leu Asn Asp Phe Ile Met Met His Cys Val
            770                 775                 780

Phe Met Pro Asn Thr Gln Leu Cys Pro Ala Leu Val Ala His Tyr His
785                 790                 795                 800

Ala Gln Pro Ser Gln Gly Thr Glu Gln Glu Lys Met Asp Tyr Ala Leu
                805                 810                 815

Asn Asn Lys Arg Arg Val Ile Arg Leu Val Leu Gln Trp Ala Ala Met
                820                 825                 830

Tyr Gly Asp Leu Leu Gln Glu Asp Val Ser Met Ala Phe Leu Glu
            835                 840                 845

Glu Phe Tyr Val Ser Val Ser Asp Ala Arg Met Ile Ala Ala Leu
850                 855                 860

Lys Glu Gln Leu Pro Glu Leu Glu Lys Ile Val Lys Gln Ile Ser Glu
865                 870                 875                 880

Asp Ala Lys Ala Pro Gln Lys Lys His Lys Val Leu Leu Gln Gln Phe
                885                 890                 895

Asn Thr Gly Asp Glu Arg Ala Gln Lys Arg Gln Pro Ile Arg Gly Ser
                900                 905                 910

Asp Glu Val Leu Phe Lys Val Tyr Cys Met Asp Pro Thr Tyr Thr Thr
            915                 920                 925

Ile Arg Val Pro Val Ala Thr Ser Val Lys Glu Val Ile Ser Ala Val
            930                 935                 940

Ala Asp Lys Leu Gly Ser Gly Glu Gly Leu Ile Ile Val Lys Met Ser
945                 950                 955                 960

Ser Gly Gly Glu Lys Val Val Leu Lys Pro Asn Asp Val Ser Val Phe
                965                 970                 975

Met Thr Leu Thr Ile Asn Gly Arg Leu Phe Ala Cys Pro Arg Glu Gln
                980                 985                 990

Phe Asp Ser Leu Thr Pro Leu Pro Glu Gln Glu Gly Pro Thr Val Gly
                995                 1000                1005

Thr Val Gly Thr Phe Glu Leu Met Ser Ser Lys Asp Leu Ala Tyr
            1010                1015                1020

Gln Met Thr Ile Tyr Asp Trp Glu Leu Phe Asn Cys Val His Glu
            1025                1030                1035

Leu Glu Leu Ile Tyr His Thr Phe Gly Arg His Asn Phe Lys Lys
            1040                1045                1050

Thr Thr Ala Asn Leu Asp Leu Phe Leu Arg Arg Phe Asn Glu Ile
            1055                1060                1065

Gln Phe Trp Val Val Thr Glu Ile Cys Leu Cys Ser Gln Leu Ser
            1070                1075                1080

Lys Arg Val Gln Leu Leu Lys Phe Ile Lys Ile Ala Ala His
            1085                1090                1095

Cys Lys Glu Tyr Lys Asn Leu Asn Ser Phe Phe Ala Ile Val Met
            1100                1105                1110
```

```
Gly Leu Ser Asn Val Ala Val Ser Arg Leu Ala Leu Thr Trp Glu
    1115                1120                1125

Lys Leu Pro Ser Lys Phe Lys Phe Tyr Ala Glu Phe Glu Ser
    1130                1135                1140

Leu Met Asp Pro Ser Arg Asn His Arg Ala Tyr Arg Leu Thr Val
    1145                1150                1155

Ala Lys Leu Glu Pro Pro Leu Ile Pro Phe Met Pro Leu Leu Ile
    1160                1165                1170

Lys Asp Met Thr Phe Thr His Glu Gly Asn Lys Thr Phe Ile Asp
    1175                1180                1185

Asn Leu Val Asn Phe Glu Lys Met Arg Met Ile Ala Asn Thr Ala
    1190                1195                1200

Arg Thr Val Arg Tyr Tyr Arg Ser Gln Pro Phe Asn Pro Asp Ala
    1205                1210                1215

Ala Gln Ala Asn Lys Asn His Gln Asp Val Arg Ser Tyr Val Arg
    1220                1225                1230

Gln Leu Asn Val Ile Asp Asn Gln Arg Thr Leu Ser Gln Met Ser
    1235                1240                1245

His Arg Leu Glu Pro Arg Arg Pro
    1250                1255

<210> SEQ ID NO 34
<211> LENGTH: 14
<212> TYPE: PRT
<213> ORGANISM: Homo sapiens

<400> SEQUENCE: 34

Lys Glu Asp Phe Asn Arg Ile Leu Arg Asp Val Glu Ala Asn
1               5                   10

<210> SEQ ID NO 35
<211> LENGTH: 1011
<212> TYPE: PRT
<213> ORGANISM: Homo sapiens

<400> SEQUENCE: 35

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
                20                  25                  30

Ile Ile Phe Thr Arg Leu Lys Glu Val Lys Ala Phe Glu Lys Phe His
            35                  40                  45

Pro Asn Leu Leu His Gln Ile Cys Leu Cys Gly Tyr Tyr Glu Asn Leu
        50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
                100                 105                 110

Phe Gly Glu Ser Ile Leu Asp Asn Thr Pro Arg His Ala Thr Ile Val
            115                 120                 125

Thr Arg Glu Ser Ser Glu Leu Leu Arg Ile Glu Gln Lys Asp Phe Lys
        130                 135                 140

Ala Leu Trp Glu Lys Tyr Arg Gln Tyr Met Ala Gly Leu Leu Ala Pro
145                 150                 155                 160
```

```
Pro Tyr Gly Val Met Glu Thr Gly Ser Asn Asn Asp Arg Ile Pro Asp
                165                 170                 175
Lys Glu Asn Thr Pro Leu Ile Glu Pro His Val Pro Leu Arg Pro Ala
            180                 185                 190
Asn Thr Ile Thr Lys Val Pro Ser Glu Lys Ile Leu Arg Ala Gly Lys
        195                 200                 205
Ile Leu Arg Asn Ala Ile Leu Ser Arg Ala Pro His Met Ile Arg Asp
    210                 215                 220
Arg Lys Tyr His Leu Lys Thr Tyr Arg Gln Cys Cys Val Gly Thr Glu
225                 230                 235                 240
Leu Val Asp Trp Met Met Gln Gln Thr Pro Cys Val His Ser Arg Thr
                245                 250                 255
Gln Ala Val Gly Met Trp Gln Val Leu Leu Glu Asp Gly Val Leu Asn
            260                 265                 270
His Val Asp Gln Glu His His Phe Gln Asp Lys Tyr Leu Phe Tyr Arg
        275                 280                 285
Phe Leu Asp Asp Glu His Glu Asp Ala Pro Leu Pro Thr Glu Glu Glu
    290                 295                 300
Lys Lys Glu Cys Asp Glu Leu Gln Asp Thr Met Leu Leu Leu Ser
305                 310                 315                 320
Gln Met Gly Pro Asp Ala His Met Arg Met Ile Leu Arg Lys Pro Pro
                325                 330                 335
Gly Gln Arg Thr Val Asp Asp Leu Glu Ile Ile Tyr Glu Glu Leu Leu
            340                 345                 350
His Ile Lys Ala Leu Ser His Leu Ser Thr Thr Val Lys Arg Glu Leu
        355                 360                 365
Ala Gly Val Leu Ile Phe Glu Ser His Ala Lys Gly Gly Thr Val Leu
    370                 375                 380
Phe Asn Gln Gly Glu Glu Gly Thr Ser Trp Tyr Ile Ile Leu Lys Gly
385                 390                 395                 400
Ser Val Asn Val Val Ile Tyr Gly Lys Gly Val Val Cys Thr Leu His
                405                 410                 415
Glu Gly Asp Asp Phe Gly Lys Leu Ala Leu Val Asn Asp Ala Pro Arg
            420                 425                 430
Ala Ala Ser Ile Val Leu Arg Glu Asp Asn Cys His Phe Leu Arg Val
        435                 440                 445
Asp Lys Glu Asp Phe Asn Arg Ile Leu Arg Asp Val Glu Ala Asn Thr
    450                 455                 460
Val Arg Leu Lys Glu His Asp Gln Asp Val Leu Val Leu Glu Lys Val
465                 470                 475                 480
Pro Ala Gly Asn Arg Ala Ser Asn Gln Gly Asn Ser Gln Pro Gln Gln
                485                 490                 495
Lys Tyr Thr Val Met Ser Gly Thr Pro Glu Lys Ile Leu Glu His Phe
            500                 505                 510
Leu Glu Thr Ile Arg Leu Glu Ala Thr Leu Asn Glu Ala Thr Asp Ser
        515                 520                 525
Val Leu Asn Asp Phe Ile Met Met His Cys Val Phe Met Pro Asn Thr
    530                 535                 540
Gln Leu Cys Pro Ala Leu Val Ala His Tyr His Ala Gln Pro Ser Gln
545                 550                 555                 560
Gly Thr Glu Gln Glu Lys Met Asp Tyr Ala Leu Asn Asn Lys Arg Arg
                565                 570                 575
```

```
Val Ile Arg Leu Val Leu Gln Trp Ala Ala Met Tyr Gly Asp Leu Leu
            580                 585                 590

Gln Glu Asp Asp Val Ser Met Ala Phe Leu Glu Glu Phe Tyr Val Ser
        595                 600                 605

Val Ser Asp Asp Ala Arg Met Ile Ala Ala Leu Lys Glu Gln Leu Pro
    610                 615                 620

Glu Leu Glu Lys Ile Val Lys Gln Ile Ser Glu Asp Ala Lys Ala Pro
625                 630                 635                 640

Gln Lys Lys His Lys Val Leu Leu Gln Gln Phe Asn Thr Gly Asp Glu
                645                 650                 655

Arg Ala Gln Lys Arg Gln Pro Ile Arg Gly Ser Asp Glu Val Leu Phe
            660                 665                 670

Lys Val Tyr Cys Met Asp Pro Thr Tyr Thr Thr Ile Arg Val Pro Val
        675                 680                 685

Ala Thr Ser Val Lys Glu Val Ile Ser Ala Val Ala Asp Lys Leu Gly
    690                 695                 700

Ser Gly Glu Gly Leu Ile Ile Val Lys Met Ser Ser Gly Gly Glu Lys
705                 710                 715                 720

Val Val Leu Lys Pro Asn Asp Val Ser Val Phe Met Thr Leu Thr Ile
                725                 730                 735

Asn Gly Arg Leu Phe Ala Cys Pro Arg Glu Gln Phe Asp Ser Leu Thr
            740                 745                 750

Pro Leu Pro Glu Gln Glu Gly Pro Thr Val Gly Thr Val Gly Thr Phe
        755                 760                 765

Glu Leu Met Ser Ser Lys Asp Leu Ala Tyr Gln Met Thr Ile Tyr Asp
770                 775                 780

Trp Glu Leu Phe Asn Cys Val His Glu Leu Glu Leu Ile Tyr His Thr
785                 790                 795                 800

Phe Gly Arg His Asn Phe Lys Lys Thr Thr Ala Asn Leu Asp Leu Phe
                805                 810                 815

Leu Arg Arg Phe Asn Glu Ile Gln Phe Trp Val Val Thr Glu Ile Cys
            820                 825                 830

Leu Cys Ser Gln Leu Ser Lys Arg Val Gln Leu Leu Lys Lys Phe Ile
        835                 840                 845

Lys Ile Ala Ala His Cys Lys Glu Tyr Lys Asn Leu Asn Ser Phe Phe
850                 855                 860

Ala Ile Val Met Gly Leu Ser Asn Val Ala Val Ser Arg Leu Ala Leu
865                 870                 875                 880

Thr Trp Glu Lys Leu Pro Ser Lys Phe Lys Lys Phe Tyr Ala Glu Phe
                885                 890                 895

Glu Ser Leu Met Asp Pro Ser Arg Asn His Arg Ala Tyr Arg Leu Thr
            900                 905                 910

Val Ala Lys Leu Glu Pro Pro Leu Ile Pro Phe Met Pro Leu Leu Ile
        915                 920                 925

Lys Asp Met Thr Phe Thr His Glu Gly Asn Lys Thr Phe Ile Asp Asn
930                 935                 940

Leu Val Asn Phe Glu Lys Met Arg Met Ile Ala Asn Thr Ala Arg Thr
945                 950                 955                 960

Val Arg Tyr Tyr Arg Ser Gln Pro Phe Asn Pro Asp Ala Ala Gln Ala
                965                 970                 975

Asn Lys Asn His Gln Asp Val Arg Ser Tyr Val Arg Gln Leu Asn Val
            980                 985                 990

Ile Asp Asn Gln Arg Thr Leu Ser  Gln Met Ser His Arg  Leu Glu Pro
```

Arg Arg Pro
    1010

<210> SEQ ID NO 36
<211> LENGTH: 124
<212> TYPE: PRT
<213> ORGANISM: Artificial Sequence
<220> FEATURE:
<223> OTHER INFORMATION: Synthetic

<400> SEQUENCE: 36

Ala Phe Glu Lys Phe His Pro Asn Leu Leu His Gln Ile Cys Leu Cys
1               5                   10                  15

Gly Tyr Tyr Glu Asn Leu Glu Lys Gly Ile Thr Leu Phe Arg Gln Gly
            20                  25                  30

Asp Ile Gly Thr Asn Trp Tyr Ala Val Leu Ala Gly Ser Leu Asp Val
        35                  40                  45

Lys Val Ser Glu Thr Ser Ser His Gln Asp Ala Val Thr Ile Cys Thr
50                  55                  60

Leu Gly Ile Gly Thr Ala Phe Gly Glu Ser Ile Leu Asp Asn Thr Pro
65                  70                  75                  80

Arg His Ala Thr Ile Val Thr Arg Glu Ser Ser Glu Leu Leu Arg Ile
                85                  90                  95

Glu Gln Lys Asp Phe Lys Ala Leu Trp Glu Lys Tyr Arg Gln Tyr Met
            100                 105                 110

Ala Gly Leu Leu Ala Pro Pro Tyr Gly Val Met Glu
        115                 120

<210> SEQ ID NO 37
<211> LENGTH: 121
<212> TYPE: PRT
<213> ORGANISM: Artificial Sequence
<220> FEATURE:
<223> OTHER INFORMATION: Synthetic

<400> SEQUENCE: 37

Ala Leu Ser His Leu Ser Thr Thr Val Lys Arg Glu Leu Ala Gly Val
1               5                   10                  15

Leu Ile Phe Glu Ser His Ala Lys Gly Gly Thr Val Leu Phe Asn Gln
            20                  25                  30

Gly Glu Glu Gly Thr Ser Trp Tyr Ile Ile Leu Lys Gly Ser Val Asn
        35                  40                  45

Val Val Ile Tyr Gly Lys Gly Val Val Cys Thr Leu His Glu Gly Asp
50                  55                  60

Asp Phe Gly Lys Leu Ala Leu Val Asn Asp Ala Pro Arg Ala Ala Ser
65                  70                  75                  80

Ile Val Leu Arg Glu Asp Asn Cys His Phe Leu Arg Val Asp Lys Glu
                85                  90                  95

Asp Phe Asn Arg Ile Leu Arg Asp Val Glu Ala Asn Thr Val Arg Leu
            100                 105                 110

Lys Glu His Asp Gln Asp Val Leu Val
        115                 120

<210> SEQ ID NO 38
<211> LENGTH: 241
<212> TYPE: PRT
<213> ORGANISM: Artificial Sequence
<220> FEATURE:

<223> OTHER INFORMATION: Synthetic

<400> SEQUENCE: 38

```
Asn Val Tyr Ile Lys Ala Asp Lys Gln Lys Asn Gly Ile Lys Ala Asn
1               5                   10                  15
Phe Lys Ile Arg His Asn Ile Glu Asp Gly Gly Val Gln Leu Ala Tyr
            20                  25                  30
His Tyr Gln Gln Asn Thr Pro Ile Gly Asp Gly Pro Val Leu Leu Pro
        35                  40                  45
Asp Asn His Tyr Leu Ser Val Gln Ser Ala Leu Ser Lys Asp Pro Asn
    50                  55                  60
Glu Lys Arg Asp His Met Val Leu Leu Glu Phe Val Thr Ala Ala Gly
65                  70                  75                  80
Ile Thr His Gly Met Asp Glu Leu Tyr Lys Gly Gly Thr Gly Gly Ser
                85                  90                  95
Met Val Ser Lys Gly Glu Glu Leu Phe Thr Gly Val Val Pro Ile Gln
            100                 105                 110
Val Glu Leu Asp Gly Asp Val Asn Gly His Lys Phe Ser Val Ser Gly
        115                 120                 125
Glu Gly Glu Gly Asp Ala Thr Tyr Gly Lys Leu Thr Leu Lys Phe Ile
    130                 135                 140
Cys Thr Thr Gly Lys Leu Pro Val Pro Trp Pro Thr Leu Val Thr Thr
145                 150                 155                 160
Leu Thr Tyr Gly Val Gln Cys Phe Ser Arg Tyr Pro Asp His Met Lys
                165                 170                 175
Gln His Asp Phe Phe Lys Ser Ala Met Pro Glu Gly Tyr Ile Gln Glu
            180                 185                 190
Arg Thr Ile Phe Phe Lys Asp Asp Gly Asn Tyr Lys Thr Arg Ala Glu
        195                 200                 205
Val Lys Phe Glu Gly Asp Thr Leu Val Asn Arg Ile Glu Leu Lys Gly
    210                 215                 220
Ile Asp Phe Lys Glu Asp Gly Asn Ile Leu Gly His Lys Leu Glu Tyr
225                 230                 235                 240
Asn
```

<210> SEQ ID NO 39
<211> LENGTH: 3033
<212> TYPE: DNA
<213> ORGANISM: Homo sapiens

<400> SEQUENCE: 39

```
atggtcgctg cgcacgctgc ccattcttcc tcctctgccg agtggatcgc ctgcctggat      60
aaaagaccac tggagcgatc cagcgaagat gtggatataa tcttcactcg actgaaagaa     120
gttaaagctt ttgagaaatt tcacccaaat ctccttcatc agatttgctt atgtggttat     180
tatgagaatc tggaaaaggg aataacatta tttcgccagg gtgatattgg aacaaactgg     240
tatgctgtcc tggcagggtc tttggatgtt aaagtatctg agaccagcag tcaccaggat     300
gctgtgacca tctgtaccct gggaattggg acggcctttg agagtccatc tctggacaac     360
acaccccgcc atgcaaccat cgttaccagg gagagcagtg aactgctccg catcgagcag     420
aaggacttca aggcactatg ggagaaatat cgacagtata tggcaggact tctggctcct     480
ccttatggtg ttatggaaac gggctctaac aatgacagga ttcctgacaa ggagaacaca     540
cctctcattg aacctcacgt tcctcttcgt cctgctaaca ccattaccaa ggtcccttca     600
```

-continued

```
gagaagatcc tcagagctgg aaaaatttta cgaaatgcca ttctctctcg agcacctcac    660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc ccctttgcct    900
actgaggaga agaagaagga gtgtgatgag agctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aagggacgtg   1380
gaggcgaata cagtcagact taaagaacat gaccaagatg tcttggtgct ggagaaggtc   1440
ccagcaggga acagagcttc taatcaagga aactcacagc tcagcaaaa gtatactgtg   1500 atgtcaggaa cacctgaaaa aatttttagag cattttctag aaacaatacg ccttgaggca   1560
actttaaatg aagcaacaga ttctgtttta aatgactttta ttatgatgca ctgtgttttt   1620
atgccaaata cccagctttg cccggcactg gtggcccact accacgcaca gccttcacaa   1680
ggtacagaac aggagaaaat ggattatgcc ctcaacaata agaggcgagt catccgcctg   1740
gttctacagt gggctgccat gtatggagac ctcctgcaag aggatgacgt gtctatggcc   1800
ttcctggagg agttttatgt atctgtatca gatgatgccc ggatgattgc tgccctcaag   1860
gagcaactgc cagagttgga gaagattgtc aagcaaatct cagaagatgc aaaggcacca   1920
caaaagaagc acaaggttct tttgcaacag ttcaatacgg gcgatgagag agcccagaag   1980
cgccagccta tccgcggctc tgatgaagtt ctgtttaagg tctattgcat ggaccccacc   2040
tacacaacca ttcgggtgcc agtggccact tcggtgaagg aagtcatcag tgcagttgcc   2100
gacaagctgg gctccgggga gggcctgatc atagtcaaga tgagttccgg aggagaaaag   2160
gtggtgctca aacctaatga tgtttcagta tttatgacgc tcaccattaa tggacgcctg   2220
tttgcttgcc cgcgagagca attcgattca ctgactccct taccagaaca ggaaggccca   2280
actgttggaa cagtgggaac ttttgaactg atgagctcca agatttagc ataccagatg   2340 acaatttatg attgggaact cttcaactgc gtgcatgagc tggagctaat ctatcacaca   2400
tttggaaggc ataattttaa aaagaccaca gcaaacttgg atttgttcct gaggagattt   2460
aatgaaattc agttttgggt cgtcactgag atctgccttt gttctcagct cagcaagcgt   2520
gttcagctat taaaaaaatt tattaagata gcagcccact gtaaggagta aaaaatctg    2580 aattccttttt ttgccatcgt catgggacta agtaacgttg ctgtgagccg cttggcacta   2640
acgtgggaga aactgccaag caagttcaag aagttctatg cggagtttga agtttaatg    2700 gacccttcaa ggaaccacag ggcctacagg ctgacagtag ctaagctgga acctcctctc   2760
atccccttca tgcctttgct cattaaagat atgacattta ctcatgaggg gaacaagacg   2820
ttcattgaca atctagtaaa ctttgaaaaa atgcgcatga ttgcaaatac ggccagaaca   2880
gtgagatact acaggagcca acccttcaat cctgatgcag ctcaagctaa taagaaccat   2940
caggatgtcc ggagttatgt acggcaatta aatgtgattg acaaccagag aactttatca   3000
```

| cagatgtcac acagattaga gcctcgtcga cca | 3033 |

<210> SEQ ID NO 40
<211> LENGTH: 42
<212> TYPE: DNA
<213> ORGANISM: Homo sapiens

<400> SEQUENCE: 40

| aaggaggatt tcaaccggat cctaagggac gtggaggcga at | 42 |

<210> SEQ ID NO 41
<211> LENGTH: 2217
<212> TYPE: DNA
<213> ORGANISM: Artificial Sequence
<220> FEATURE:
<223> OTHER INFORMATION: Synthetic

<400> SEQUENCE: 41

| atgggctcta acaatgacag gattcctgac aaggagaaca cacctctcat tgaacctcac | 60 |
| gttcctcttc gtcctgctaa caccattacc aaggtccctt cagagaagat cctcagagct | 120 |
| ggaaaaattt tacgaaatgc cattctctct cgagcacctc acatgataag agatagaaaa | 180 |
| taccacctaa agacatacag acaatgctgt gtgggaactg aactggtgga ctggatgatg | 240 |
| cagcagacac catgtgttca ctcccggact caagctgttg gcatgtggca agtcctgtta | 300 |
| gaagatggtg ttctcaacca cgtggaccag gagcaccatt tccaagacaa atatttattc | 360 |
| tatcgatttc tggatgatga gcacgaggat gcccctttgc ctactgagga ggagaagaag | 420 |
| gagtgtgatg aggagctcca ggacaccatg ctgctgctgt cacagatggg ccccgacgcc | 480 |
| cacatgagga tgatccttcg caaaccacct ggccagagga ctgtggatga cctagagatt | 540 |
| atctatgagg agcttcttca tattaaagcc ttatcccatc tttctaccac agtgaaacga | 600 |
| gagttagcag gtgttctcat ttttgagtct cacgccaaag agggactgt gttgtttaac | 660 |
| cagggggaag aaggtacctc ctggtacatt attctaaaag gatcagtgaa tgtagtcatt | 720 |
| tacggcaagg gtgtggtctg caccctgcat gaaggagatg acttcggcaa gttagcacta | 780 |
| gtgaatgatg ccccacgagc tgcctctatc gtcttacgag aagataactg ccatttctta | 840 |
| agagtagaca aggaggattt caaccggatc ctaaggctgg tgtcgcacaa cgtctatatc | 900 |
| aaggccgaca gcagaagaa cggcatcaag gcgaacttca gatccgcca caacatcgag | 960 |
| gacggcggcg tgcagctcgc ctaccactac cagcagaaca ccccatcgg cgacggcccc | 1020 |
| gtgctgctgc ccgacaacca ctacctgagc gtgcagtcca tactttcgaa agaccccaac | 1080 |
| gagaagcgcg atcacatggt cctgctggag ttcgtgaccg ccgcgggat cactctcggc | 1140 |
| atggacgagc tgtacaaggg cggtaccgga gggagcatgg tgagcaaggg cgaggagctg | 1200 |
| ttcaccgggg tggtgcccat ccaggtcgag ctggacggcg acgtaaacgg ccacaagttc | 1260 |
| agcgtgtccg gcgagggtga gggcgatgcc acctacggca gctgaccct gaagttcatc | 1320 |
| tgcaccaccg gcaagctgcc cgtgccctgg cccaccctcg tgaccaccct gacctacggc | 1380 |
| gtgcagtgct tcagccgcta ccccgaccac atgaagcagc acgacttctt caagtccgcc | 1440 |
| atgcccgaag gctacatcca ggagcgcacc atcttcttca aggacgacgg caactacaag | 1500 |
| acccgcgccg aggtgaagtt cgagggcgac accctggtga accgcatcga gctgaagggc | 1560 |
| atcgacttca aggaggacgg caacatcctg gggcacaagc tggagtacaa cttcaacaac | 1620 |
| cctgacgtgg aggcgaatac agtcagactt aaagaacatg accaagatgt cttggtgctg | 1680 |

| | |
|---|---|
| gagaaggtcc cagcagggaa cagagcttct aatcaaggaa actcacagcc tcagcaaaag | 1740 |
| tatactgtga tgtcaggaac acctgaaaaa attttagagc attttctaga acaatacgc | 1800 |
| cttgaggcaa ctttaaatga agcaacagat tctgttttaa atgactttat tatgatgcac | 1860 |
| tgtgttttta tgccaaatac ccagctttgc ccggcactgg tggcccacta ccacgcacag | 1920 |
| ccttcacaag gtacagaaca ggagaaaatg gattatgccc tcaacaataa gaggcgagtc | 1980 |
| atccgcctgg ttctacagtg ggctgccatg tatggagacc tcctgcaaga ggatgacgtg | 2040 |
| tctatggcct tcctggagga gttttatgta tctgtatcag atgatgcccg gatgattgct | 2100 |
| gccctcaagg agcaactgcc agagttggag aagattgtca agcaaatctc agaagatgca | 2160 |
| aaggcaccac aaaagaagca caaggttctt ttgcaacagt tcaatacggg cgatgag | 2217 |

<210> SEQ ID NO 42
<211> LENGTH: 3807
<212> TYPE: DNA
<213> ORGANISM: Artificial Sequence
<220> FEATURE:
<223> OTHER INFORMATION: Synthetic

<400> SEQUENCE: 42

| | |
|---|---|
| atggtcgctg cgcacgctgc ccattcttcc tcctctgccg agtggatcgc ctgcctggat | 60 |
| aaaagaccac tggagcgatc cagcgaagat gtggatataa tcttcactcg actgaaagaa | 120 |
| gttaaagctt tgagaaatt tcacccaaat ctccttcatc agatttgctt atgtggttat | 180 |
| tatgagaatc tggaaagggg aataacatta tttcgccagg gtgatattgg aacaaactgg | 240 |
| tatgctgtcc tggcagggtc tttggatgtt aaagtatctg agaccagcag tcaccaggat | 300 |
| gctgtgacca tctgtaccct gggaattggg acggcctttg gagagtccat tctggacaac | 360 |
| acacccgcc atgcaaccat cgttaccagg agagcagtg aactgctccg catcgagcag | 420 |
| aaggacttca aggcactatg ggagaaatat cgacagtata tggcaggact tctggctcct | 480 |
| ccttatggtg ttatggaaac gggctctaac aatgacagga ttcctgacaa ggagaacaca | 540 |
| cctctcattg aacctcacgt tcctcttcgt cctgctaaca ccattaccaa ggtcccttca | 600 |
| gagaagatcc tcagagctgg aaaaatttta cgaaatgcca ttctctctcg agcacctcac | 660 |
| atgataagag atagaaaata ccacctaaag acatacagac aatgctgtgt gggaactgaa | 720 |
| ctggtggact ggatgatgca gcagacacca tgtgttcact cccggactca agctgttggc | 780 |
| atgtggcaag tcctgttaga gatggtgtt ctcaaccacg tggaccagga gcaccatttc | 840 |
| caagacaaat atttattcta tcgatttctg gatgatgagc acgaggatgc ccctttgcct | 900 |
| actgaggagg agaagaagga gtgtgatgag agctccagg acaccatgct gctgctgtca | 960 |
| cagatgggcc ccgacgccca catgaggatg atccttcgca aaccacctgg ccagaggact | 1020 |
| gtggatgacc tagagattat ctatgaggag cttcttcata ttaaagcctt atcccatctt | 1080 |
| tctaccacag tgaaacgaga gttagcaggt gttctcattt ttgagtctca cgccaaagga | 1140 |
| gggactgtgt tgtttaacca gggggaagaa ggtacctcct ggtacattat tctaaaagga | 1200 |
| tcagtgaatg tagtcatttta cggcaagggt gtggtctgca ccctgcatga aggagatgac | 1260 |
| ttcggcaagt tagcactagt gaatgatgcc ccacgagctg cctctatcgt cttacgagaa | 1320 |
| gataactgcc atttcttaag agtagacaag gaggatttca accggatcct aagggacgtg | 1380 |
| gaggcgctcg agaacgtcta tatcaaggcc gacaagcaga agaacggcat caaggcgaac | 1440 |
| ttcaagatcc gccacaacat cgaggacggc ggcgtgcagc tcgcctacca ctaccagcag | 1500 |
| aacacccca tcggcgacgg ccccgtgctg ctgcccgaca accactacct gagcgtgcag | 1560 |

```
tccatactttt cgaaagaccc caacgagaag cgcgatcaca tggtcctgct ggagttcgtg    1620
accgccgccg ggatcactct cggcatggac gagctgtaca agggcggtac cggagggagc    1680
atggtgagca agggcgagga gctgttcacc ggggtggtgc ccatccaggt cgagctggac    1740
ggcgacgtaa acggccacaa gttcagcgtg tccggcgagg gtgagggcga tgccacctac    1800
ggcaagctga ccctgaagtt catctgcacc accggcaagc tgcccgtgcc ctggcccacc    1860
ctcgtgacca ccctgaccta cggcgtgcag tgcttcagcc gctaccccga ccacatgaag    1920
cagcacgact tcttcaagtc cgccatgccc gaaggctaca tccaggagcg caccatcttc    1980
ttcaaggacg acggcaacta caagacccgc gccgaggtga agttcgaggg cgacaccctg    2040
gtgaaccgca tcgagctgaa gggcatcgac ttcaaggagg acggcaacat cctggggcac    2100
aagctggagt acaacacgcg taaggaggat ttcaaccgga tcctaaggga cgtggaggcg    2160
aatacagtca gacttaaaga acatgaccaa gatgtcttgg tgctggagaa ggtcccagca    2220
gggaacagag cttctaatca aggaaactca cagcctcagc aaaagtatac tgtgatgtca    2280
ggaacacctg aaaaaatttt agagcatttt ctagaaacaa tacgccttga ggcaacttta    2340
aatgaagcaa cagattctgt tttaaatgac tttattatga tgcactgtgt ttttatgcca    2400
aatacccagc tttgcccggc actggtggcc cactaccacg cacagccttc acaaggtaca    2460
gaacaggaga aaatggatta tgccctcaac aataagaggc gagtcatccg cctggttcta    2520
cagtgggctg ccatgtatgg agacctcctg caagaggatg acgtgtctat ggccttcctg    2580
gaggagtttt atgtatctgt atcagatgat gcccggatga ttgctgccct caaggagcaa    2640
ctgccagagt tggagaagat tgtcaagcaa atctcagaag atgcaaaggc accacaaaag    2700
aagcacaagg ttcttttgca acagttcaat acgggcgatg agagagccca gaagcgccag    2760
cctatccgcg gctctgatga agttctgttt aaggtctatt gcatggaccc cacctacaca    2820
accattcggg tgccagtggc cacttcggtg aaggaagtca tcagtgcagt tgccgacaag    2880
ctgggctccg gggagggcct gatcatagtc aagatgagtt ccggaggaga aaggtggtg    2940 ctcaaaccta tgatgtttc agtatttatg acgctcacca ttaatggacg cctgtttgct    3000
tgcccgcgag agcaattcga ttcactgact cccttaccag aacaggaagg cccaactgtt    3060
ggaacagtgg gaactttga actgatgagc tccaaagatt tagcatacca gatgacaatt    3120
tatgattggg aactcttcaa ctgcgtgcat gagctggagc taatctatca cactttgga    3180 aggcataatt ttaaaagac cacagcaaac ttggatttgt tcctgaggag atttaatgaa    3240
attcagtttt gggtcgtcac tgagatctgc ctttgttctc agctcagcaa gcgtgttcag    3300
ctattaaaaa aatttattaa gatagcagcc cactgtaagg agtataaaaa tctgaattcc    3360
ttttttgcca tcgtcatggg actaagtaac gttgctgtga gccgcttggc actaacgtgg    3420
gagaaactgc caagcaagtt caagaagttc tatgcggagt ttgaaagttt aatggaccct    3480
tcaaggaacc acagggccta caggctgaca gtagctaagc tggaacctcc tctcatcccc    3540
ttcatgcctt tgctcattaa agatatgaca tttactcatg aggggaacaa gacgttcatt    3600
gacaatctag taaactttga aaaaatgcgc atgattgcaa atacggccag aacagtgaga    3660
tactacagga gccaaccctt caatcctgat gcagctcaag ctaataagaa ccatcaggat    3720
gtccggagtt atgtacggca attaaatgtg attgacaacc agagaacttt atcacagatg    3780
tcacacagat tagagcctcg tcgacca                                         3807

<210> SEQ ID NO 43
```

<211> LENGTH: 2244
<212> TYPE: DNA
<213> ORGANISM: Artificial Sequence
<220> FEATURE:
<223> OTHER INFORMATION: Synthetic

<400> SEQUENCE: 43

| | | | | | |
|---|---|---|---|---|---|
| atgggctcta | acaatgacag | gattcctgac | aaggagaaca | cacctctcat | tgaacctcac | 60 |
| gttcctcttc | gtcctgctaa | caccattacc | aaggtccctt | cagagaagat | cctcagagct | 120 |
| ggaaaatttt | tacgaaatgc | cattctctct | cgagcacctc | acatgataag | agatagaaaa | 180 |
| taccacctaa | agacatacag | acaatgctgt | gtgggaactg | aactggtgga | ctggatgatg | 240 |
| cagcagacac | catgtgttca | ctcccggact | caagctgttg | gcatgtggca | agtcctgtta | 300 |
| gaagatggtg | ttctcaacca | cgtggaccag | gagcaccatt | tccaagacaa | atatttattc | 360 |
| tatcgatttc | tggatgatga | gcacgaggat | gccccttttgc | ctactgagga | ggagaagaag | 420 |
| gagtgtgatg | aggagctcca | ggacaccatg | ctgctgctgt | cacagatggg | ccccgacgcc | 480 |
| cacatgagga | tgatccttcg | caaaccacct | ggccagagga | ctgtggatga | cctagagatt | 540 |
| atctatgagg | agcttcttca | tattaaagcc | ttatcccatc | tttctaccac | agtgaaacga | 600 |
| gagttagcag | gtgttctcat | ttttgagtct | cacgccaaag | gagggactgt | gttgtttaac | 660 |
| caggggggaag | aaggtacctc | ctggtacatt | attctaaaag | gatcagtgaa | tgtagtcatt | 720 |
| tacggcaagg | gtgtggtctg | caccctgcat | gaaggagatg | acttcggcaa | gttagcacta | 780 |
| gtgaatgatg | ccccacgagc | tgcctctatc | gtcttacgag | aagataactg | ccatttctta | 840 |
| agagtagaca | aggaggattt | caaccggatc | ctaaggggacg | tggaggcgct | cgagaacgtc | 900 |
| tatatcaagg | ccgacaagca | gaagaacggc | atcaaggcga | acttcaagat | ccgccacaac | 960 |
| atcgaggacg | gcgcgtgca | gctcgcctac | cactaccagc | agaacacccc | catcggcgac | 1020 |
| ggccccgtgc | tgctgcccga | caaccactac | ctgagcgtgc | agtccatact | ttcgaaagac | 1080 |
| cccaacgaga | agcgcgatca | catggtcctg | ctggagttcg | tgaccgccgc | cgggatcact | 1140 |
| ctcggcatgg | acgagctgta | caagggcggt | accggaggga | gcatggtgag | caagggcgag | 1200 |
| gagctgttca | ccggggtggt | gcccatccag | gtcgagctgg | acggcgacgt | aaacggccac | 1260 |
| aagttcagcg | tgtccggcga | gggtgagggc | gatgccacct | acggcaagct | gaccctgaag | 1320 |
| ttcatctgca | ccaccggcaa | gctgcccgtg | ccctggccca | ccctcgtgac | caccctgacc | 1380 |
| tacggcgtgc | agtgcttcag | ccgctacccc | gaccacatga | agcagcacga | cttcttcaag | 1440 |
| tccgccatgc | ccgaaggcta | catccaggag | cgcaccatct | tcttcaagga | cgacggcaac | 1500 |
| tacaagaccc | gcgccgaggt | gaagttcgag | ggcgacaccc | tggtgaaccg | catcgagctg | 1560 |
| aagggcatcg | acttcaagga | ggacggcaac | atcctgggc | acaagctgga | gtacaacacg | 1620 |
| cgtaaggagg | atttcaaccg | gatcctaagg | gacgtggagg | cgaatacagt | cagacttaaa | 1680 |
| gaacatgacc | aagatgtctt | ggtgctggag | aaggtcccag | cagggaacag | agcttctaat | 1740 |
| caaggaaact | cacagcctca | gcaaaagtat | actgtgatgt | caggaacacc | tgaaaaaatt | 1800 |
| ttagagcatt | ttctagaaac | aatacgcctt | gaggcaactt | taaatgaagc | aacagattct | 1860 |
| gttttaaatg | actttattat | gatgcactgt | gtttttatgc | caaatacccca | gctttgcccg | 1920 |
| gcactggtgg | cccactacca | cgcacagcct | tcacaaggta | cagaacagga | gaaaatggat | 1980 |
| tatgccctca | acaataagag | gcgagtcatc | cgcctggttc | tacagtgggc | tgccatgtat | 2040 |
| ggagacctcc | tgcaagagga | tgacgtgtct | atggccttcc | tggaggagtt | ttatgtatct | 2100 |
| gtatcagatg | atgcccggat | gattgctgcc | ctcaaggagc | aactgccaga | gttggagaag | 2160 |

```
attgtcaagc aaatctcaga agatgcaaag gcaccacaaa agaagcacaa ggttctttg      2220 caacagttca atacgggcga tgag                                             2244

<210> SEQ ID NO 44
<211> LENGTH: 3780
<212> TYPE: DNA
<213> ORGANISM: Artificial Sequence
<220> FEATURE:
<223> OTHER INFORMATION: Synthetic

<400> SEQUENCE: 44
atggtcgctg cgcacgctgc ccattcttcc tcctctgccg agtggatcgc ctgcctggat       60
aaaagaccac tggagcgatc cagcgaagat gtggatataa tcttcactcg actgaaagaa      120
gttaaagctt tgagaaaatt tcacccaaat ctccttcatc agatttgctt atgtggttat      180
tatgagaatc tggaaaaggg aataacatta tttcgccagg gtgatattgg aacaaactgg      240
tatgctgtcc tggcagggtc tttggatgtt aaagtatctg agaccagcag tcaccaggat      300
gctgtgacca tctgtaccct gggaattggg acggcctttg gagagtccat tctggacaac      360 acacccgcc atgcaaccat cgttaccagg gagagcagtg aactgctccg catcgagcag      420
aaggacttca aggcactatg ggagaaatat cgacagtata tggcaggact tctggctcct      480
ccttatggtg ttatggaaac gggctctaac aatgacagga ttcctgacaa ggagaacaca      540
cctctcattg aacctcacgt tcctcttcgt cctgctaaca ccattaccaa ggtcccttca      600
gagaagatcc tcagagctgg aaaaatttta cgaaatgcca ttctctctcg agcacctcac      660
atgataagag atagaaaata ccacctaaag acatacagac aatgctgtgt gggaactgaa      720
ctggtggact ggatgatgca gcagacacca tgtgttcact cccggactca agctgttggc      780
atgtggcaag tcctgttaga gatggtgtt ctcaaccacg tggaccagga gcaccatttc      840
caagacaaat atttattcta tcgatttctg gatgatgagc acgaggatgc ccctttgcct      900
actgaggagg agaagaagga gtgtgatgag agctccagg acaccatgct gctgctgtca      960
cagatgggcc ccgacgccca catgaggatg atccttcgca aaccacctgg ccagaggact     1020
gtggatgacc tagagattat ctatgaggag cttcttcata ttaaagcctt atcccatctt     1080
tctaccacag tgaaacgaga gttagcaggt gttctcattt ttgagtctca cgccaaagga     1140
gggactgtgt tgtttaacca gggggaagaa ggtacctcct ggtacattat tctaaaagga     1200
tcagtgaatg tagtcattta cggcaagggt gtggtctgca ccctgcatga aggagatgac     1260
ttcggcaagt tagcactagt gaatgatgcc ccacgagctg cctctatcgt cttacgagaa     1320
gataactgcc atttcttaag agtagacaag gaggatttca accggatcct aaggctggtg     1380
tcgcacaacg tctatatcaa ggccgacaag cagaagaacg gcatcaaggc gaacttcaag     1440
atccgccaca acatcgagga cggcggcgtg cagctcgcct accactacca gcagaacacc     1500
cccatcggcg acggccccgt gctgctgccc gacaaccact acctgagcgt gcagtccata     1560
ctttcgaaag accccaacga gaagcgcgat cacatggtcc tgctggagtt cgtgaccgcc     1620
gccgggatca ctctcggcat ggacgagctg tacaagggcg gtaccggagg gagcatggtg     1680
agcaagggcg aggagctgtt caccggggtg gtgcccatcc aggtcgagct ggacggcgac     1740
gtaaacggcc acaagttcag cgtgtccggc gagggtgagg gcgatgccac ctacggcaag     1800
ctgaccctga gttcatctg caccaccggc aagctgcccg tgccctggcc caccctcgtg     1860
accaccctga cctacggcgt gcagtgcttc agccgctacc ccgaccacat gaagcagcac     1920
```

| | |
|---|---|
| gacttcttca agtccgccat gcccgaaggc tacatccagg agcgcaccat cttcttcaag | 1980 |
| gacgacggca actacaagac ccgcgccgag gtgaagttcg agggcgacac cctggtgaac | 2040 |
| cgcatcgagc tgaagggcat cgacttcaag gaggacggca catcctgggg cacaagctg | 2100 |
| gagtacaact tcaacaaccc tgacgtggag gcgaatacag tcagacttaa gaacatgac | 2160 |
| caagatgtct tggtgctgga aaggtccca gcagggaaca gagcttctaa tcaaggaaac | 2220 |
| tcacagcctc agcaaaagta tactgtgatg tcaggaacac ctgaaaaaat tttagagcat | 2280 |
| tttctagaaa caatacgcct tgaggcaact ttaaatgaag caacagattc tgttttaaat | 2340 |
| gactttatta tgatgcactg tgttttatg ccaaatacccc agctttgccc ggcactggtg | 2400 |
| gcccactacc acgcacagcc ttcacaaggt acagaacagg agaaaatgga ttatgccctc | 2460 |
| aacaataaga ggcgagtcat ccgcctggtt ctacagtggg ctgccatgta tggagacctc | 2520 |
| ctgcaagagg atgacgtgtc tatggccttc ctggaggagt tttatgtatc tgtatcagat | 2580 |
| gatgcccgga tgattgctgc cctcaaggag caactgccag agttggagaa gattgtcaag | 2640 |
| caaatctcag aagatgcaaa ggcaccacaa agaagcaca aggttctttt gcaacagttc | 2700 |
| aatacgggcg atgagagagc ccagaagcgc cagcctatcc gcggctctga tgaagttctg | 2760 |
| tttaaggtct attgcatgga ccccacctac acaaccattc gggtgccagt ggccacttcg | 2820 |
| gtgaaggaag tcatcagtgc agttgccgac aagctgggct ccgggggggg cctgatcata | 2880 |
| gtcaagatga gttccggagg agaaaaggtg gtgctcaaac ctaatgatgt ttcagtattt | 2940 |
| atgacgctca ccattaatgg acgcctgttt gcttgcccgc gagagcaatt cgattcactg | 3000 |
| actcccttac cagaacagga aggcccaact gttggaacag tgggaacttt tgaactgatg | 3060 |
| agctccaaag atttagcata ccagatgaca atttatgatt gggaactctt caactgcgtg | 3120 |
| catgagctga agctaatcta tcacacattt ggaaggcata attttaaaaa gaccacagca | 3180 |
| aacttggatt tgttcctgag gagatttaat gaaattcagt tttgggtcgt cactgagatc | 3240 |
| tgcctttgtt ctcagctcag caagcgtgtt cagctattaa aaaaatttat taagatagca | 3300 |
| gcccactgta aggagtataa aaatctgaat tccttttttg ccatcgtcat gggactaagt | 3360 |
| aacgttgctg tgagccgctt ggcactaacg tgggagaaac tgccaagcaa gttcaagaag | 3420 |
| ttctatgcgg agttgaaag tttaatggac ccttcaagga ccacagggc ctacaggctg | 3480 |
| acagtagcta agctggaacc tcctctcatc cccttcatgc cttttgctcat taaagatatg | 3540 |
| acatttactc atgaggggaa caagacgttc attgacaatc tagtaaactt tgaaaaaatg | 3600 |
| cgcatgattg caaatacggc cagaacagtg agatactaca ggagccaacc cttcaatcct | 3660 |
| gatgcagctc aagctaataa gaaccatcag gatgtccgga gttatgtacg gcaattaaat | 3720 |
| gtgattgaca accagagaac tttatcacag atgtcacaca gattagagcc tcgtcgacca | 3780 |

<210> SEQ ID NO 45
<211> LENGTH: 3768
<212> TYPE: DNA
<213> ORGANISM: Artificial Sequence
<220> FEATURE:
<223> OTHER INFORMATION: Synthetic

<400> SEQUENCE: 45

| | |
|---|---|
| atggtcgctg cgcacgctgc ccattcttcc tcctctgccg agtggatcgc ctgcctggat | 60 |
| aaaagaccac tggagcgatc cagcgaagat gtggatataa tcttcactcg actgaaagaa | 120 |
| gttaaagctt tgagaaaatt tcacccaaat ctccttcatc agatttgctt atgtggttat | 180 |
| tatgagaatc tggaaaaggg aataacatta tttcgccagg gtgatattgg aacaaactgg | 240 |

-continued

| | |
|---|---|
| tatgctgtcc tggcagggtc tttggatgtt aaagtatctg agaccagcag tcaccaggat | 300 |
| gctgtgacca tctgtaccct gggaattggg acggcctttg agagtccat tctggacaac | 360 |
| acaccccgcc atgcaaccat cgttaccagg agagcagtg aactgctccg catcgagcag | 420 |
| aaggacttca aggcactatg ggagaaatat cgacagtata tggcaggact tctggctcct | 480 |
| ccttatggtg ttatggaaac gggctctaac aatgacagga ttcctgacaa ggagaacaca | 540 |
| cctctcattg aacctcacgt tcctcttcgt cctgctaaca ccattaccaa ggtcccttca | 600 |
| gagaagatcc tcagagctgg aaaaatttta cgaaatgcca ttctctctcg agcacctcac | 660 |
| atgataagag atagaaaata ccacctaaag acatacagac aatgctgtgt gggaactgaa | 720 |
| ctggtggact ggatgatgca gcagacacca tgtgttcact cccggactca agctgttggc | 780 |
| atgtggcaag tcctgttaga agatggtgtt ctcaaccacg tggaccagga gcaccatttc | 840 |
| caagacaaat atttattcta tcgatttctg gatgatgagc acgaggatgc ccctttgcct | 900 |
| actgaggagg agaagaagga gtgtgatgag gagctccagg acaccatgct gctgctgtca | 960 |
| cagatgggcc ccgacgccca catgaggatg atccttcgca aaccacctgg ccagaggact | 1020 |
| gtggatgacc tagagattat ctatgaggag cttcttcata ttaaagcctt atcccatctt | 1080 |
| tctaccacag tgaaacgaga gttagcaggt gttctcattt ttgagtctca cgccaaagga | 1140 |
| gggactgtgt tgtttaacca gggggaagaa ggtacctcct ggtacattat tctaaaagga | 1200 |
| tcagtgaatg tagtcatttta cggcaagggt gtggtctgca ccctgcatga aggagatgac | 1260 |
| ttcggcaagt tagcactagt gaatgatgcc ccacgagctg cctctatcgt cttacgagaa | 1320 |
| gataactgcc atttcttaag agtagacaag gaggatttca accggatcct aagggacgtg | 1380 |
| ctcgagaacg tctatatcaa ggccgacaag cagaagaacg gcatcaaggc gaacttcaag | 1440 |
| atccgccaca acatcgagga cggcggcgtg cagctcgcct accactacca gcagaacacc | 1500 |
| cccatcggcg acggccccgt gctgctgccc gacaaccact acctgagcgt gcagtccata | 1560 |
| cttttcgaaag accccaacga gaagcgcgat cacatggtcc tgctggagtt cgtgaccgcc | 1620 |
| gccgggatca ctctcggcat ggacgagctg tacaagggcg gtaccggagg gagcatggtg | 1680 |
| agcaagggcg aggagctgtt caccggggtg gtgcccatcc aggtcgagct ggacggcgac | 1740 |
| gtaaacggcc acaagttcag cgtgtccggc gagggtgagg gcgatgccac ctacggcaag | 1800 |
| ctgaccctga agttcatctg caccaccggc aagctgcccg tgccctggcc caccctcgtg | 1860 |
| accaccctga cctacggcgt gcagtgcttc agccgctacc ccgaccacat gaagcagcac | 1920 |
| gacttcttca gtccgccat gcccgaaggc tacatccagg agcgcaccat cttcttcaag | 1980 |
| gacgacggca actacaagac ccgcgccgag gtgaagttcg agggcgacac cctggtgaac | 2040 |
| cgcatcgagc tgaagggcat cgacttcaag gaggacggca acatcctggg gcacaagctg | 2100 |
| gagtacaaca cgcgtgaggc gaatacagtc agacttaaag aacatgacca agatgtcttg | 2160 |
| gtgctggaga aggtcccagc agggaacaga gcttctaatc aaggaaactc acagcctcag | 2220 |
| caaaagtata ctgtgatgtc aggaacacct gaaaaaattt tagagcattt tctagaaaca | 2280 |
| atacgccttg aggcaacttt aaatgaagca acagattctg ttttaaatga ctttattatg | 2340 |
| atgcactgtg ttttttatgcc aaatacccag cttttgcccgg cactggtggc ccactaccac | 2400 |
| gcacagcctt cacaaggtac agaacaggag aaaatggatt atgccctcaa caataagagg | 2460 |
| cgagtcatcc gcctggttct acagtgggct gccatgtatg agacctcct gcaagaggat | 2520 |
| gacgtgtcta tggccttcct ggaggagttt tatgtatctg tatcagatga tgcccggatg | 2580 |

| | |
|---|---|
| attgctgccc tcaaggagca actgccagag ttggagaaga ttgtcaagca aatctcagaa | 2640 |
| gatgcaaagg caccacaaaa gaagcacaag gttcttttgc aacagttcaa tacgggcgat | 2700 |
| gagagagccc agaagcgcca gcctatccgc ggctctgatg aagttctgtt taaggtctat | 2760 |
| tgcatggacc ccacctacac aaccattcgg gtgccagtgg ccacttcggt gaaggaagtc | 2820 |
| atcagtgcag ttgccgacaa gctgggctcc ggggagggcc tgatcatagt caagatgagt | 2880 |
| tccggaggag aaaaggtggt gctcaaacct aatgatgttt cagtatttat gacgctcacc | 2940 |
| attaatggac gcctgtttgc ttgcccgcga gagcaattcg attcactgac tcccttacca | 3000 |
| gaacaggaag gcccaactgt tggaacagtg ggaacttttg aactgatgag ctccaaagat | 3060 |
| ttagcatacc agatgacaat ttatgattgg gaactcttca actgcgtgca tgagctggag | 3120 |
| ctaatctatc acacatttgg aaggcataat tttaaaaaga ccacagcaaa cttggatttg | 3180 |
| ttcctgagga gatttaatga aattcagttt tgggtcgtca ctgagatctg cctttgttct | 3240 |
| cagctcagca agcgtgttca gctattaaaa aaatttatta agatagcagc ccactgtaag | 3300 |
| gagtataaaa atctgaattc cttttttgcc atcgtcatgg gactaagtaa cgttgctgtg | 3360 |
| agccgcttgg cactaacgtg ggagaaactg ccaagcaagt tcaagaagtt ctatgcggag | 3420 |
| tttgaaagtt taatggaccc ttcaaggaac cacagggcct acaggctgac agtagctaag | 3480 |
| ctggaacctc ctctcatccc cttcatgcct ttgctcatta agatatgac atttactcat | 3540 |
| gaggggaaca agacgttcat tgacaatcta gtaaactttg aaaaaatgcg catgattgca | 3600 |
| aatacggcca gaacagtgag atactacagg agccaaccct tcaatcctga tgcagctcaa | 3660 |
| gctaataaga accatcagga tgtccggagt tatgtacggc aattaaatgt gattgacaac | 3720 |
| cagagaactt tatcacagat gtcacacaga ttagagcctc gtcgacca | 3768 |

<210> SEQ ID NO 46
<211> LENGTH: 1605
<212> TYPE: DNA
<213> ORGANISM: Artificial Sequence
<220> FEATURE:
<223> OTHER INFORMATION: Synthetic

<400> SEQUENCE: 46

| | |
|---|---|
| atgggctcta caatgacag gattcctgac aaggagaaca cacctctcat tgaacctcac | 60 |
| gttcctcttc gtcctgctaa caccattacc aaggtcccctt cagagaagat cctcagagct | 120 |
| ggaaaaattt tacgaaatgc cattctctct cgagcacctc acatgataag agatagaaaa | 180 |
| taccacctaa agacatacag acaatgctgt gtgggaactg aactggtgga ctggatgatg | 240 |
| cagcagacac catgtgttca ctcccggact caagctgttg gcatgtggca agtcctgtta | 300 |
| gaagatggtg ttctcaacca cgtggaccag gagcaccatt tccaagacaa atatttattc | 360 |
| tatcgatttc tggatgatga gcacgaggat gccccttgc ctactgagga ggagaagaag | 420 |
| gagtgtgatg aggagctcca ggacaccatg ctgctgctgt cacagatggg ccccgacgcc | 480 |
| cacatgagga tgatccttcg caaaccacct ggccagagga ctgtggatga cctagagatt | 540 |
| atctatgagg agcttcttca tattaaagcc ttatcccatc tttctaccac agtgaaacga | 600 |
| gagttagcag gtgttctcat ttttgagtct cacgccaaag agggactgt gttgtttaac | 660 |
| caggggaag aaggtaccctc ctggtacatt attctaaaag gatcagtgaa tgtagtcatt | 720 |
| tacggcaagg gtgtggtctg caccctgcat gaaggagatg acttcggcaa gttagcacta | 780 |
| gtgaatgatg ccccacgagc tgcctctatc gtcttacgag aagataactg ccatttctta | 840 |
| agagtagaca aggaggattt caaccggatc ctaaggcgtg cgaacgtcta tatcaaggcc | 900 |

```
gacaagcaga agaacggcat caaggcgaac ttcaagatcc gccacaacat cgaggacggc      960
ggcgtgcagc tcgcctacca ctaccagcag aacaccccca tcggcgacgg ccccgtgctg     1020
ctgcccgaca accactacct gagcgtgcag tccatacttt cgaaagaccc aacgagaag     1080 cgcgatcaca tggtcctgct ggagttcgtg accgccgccg gatcactct cggcatggac     1140 gagctgtaca agggcggtac cggagggagc atggtgagca agggcgagga gctgttcacc     1200
ggggtggtgc ccatccaggt cgagctggac ggcgacgtaa acggccacaa gttcagcgtg     1260
tccggcgagg gtgagggcga tgccacctac ggcaagctga ccctgaagtt catctgcacc     1320
accggcaagc tgcccgtgcc ctggcccacc tcgtgacca ccctgaccta cggcgtgcag     1380
tgcttcagcc gctaccccga ccacatgaag cagcacgact tcttcaagtc cgccatgccc     1440
gaaggctaca tccaggagcg caccatcttc ttcaaggacg acggcaacta caagacccgc     1500
gccgaggtga agttcgaggg cgacaccctg gtgaaccgca tcgagctgaa gggcatcgac     1560
ttcaaggagg acggcaacat cctggggcac aagctggagt acaac                    1605

<210> SEQ ID NO 47
<211> LENGTH: 3795
<212> TYPE: DNA
<213> ORGANISM: Artificial Sequence
<220> FEATURE:
<223> OTHER INFORMATION: Synthetic

<400> SEQUENCE: 47
atggtcgctg cgcacgctgc ccattcttcc tcctctgccg agtggatcgc ctgcctggat       60
aaaagaccac tggagcgatc cagcgaagat gtggatataa tcttcactcg actgaaagaa      120
gttaaagctt ttgagaaatt tcacccaaat ctccttcatc agatttgctt atgtggttat      180
tatgagaatc tggaaaaggg aataacatta tttcgccagg gtgatattgg aacaaactgg      240
tatgctgtcc tggcagggtc tttggatgtt aaagtatctg agaccagcag tcaccaggat      300
gctgtgacca tctgtaccct gggaattggg acggcctttg gagagtccat tctggacaac      360
acaccccgcc atgcaaccat cgttaccagg gagagcagtg aactgctccg catcgagcag      420
aaggacttca aggcactatg ggagaaatat cgacagtata tggcaggact tctggctcct      480
ccttatggtg ttatggaaac gggctctaac aatgacagga ttcctgacaa ggagaacaca      540
cctctcattg aacctcacgt tcctcttcgt cctgctaaca ccattaccaa ggtcccttca      600
gagaagatcc tcagagctgg aaaaatttta cgaaatgcca ttctctctcg agcacctcac      660
atgataagag atagaaaata ccacctaaag acatacagac aatgctgtgt gggaactgaa      720
ctggtggact ggatgatgca gcagacacca tgtgttcact cccggactca agctgttggc      780
atgtggcaag tcctgttaga agatggtgtt ctcaaccacg tggaccagga gcaccatttc      840
caagacaaat atttattcta tcgatttctg gatgatgagc acgaggatgc ccctttgcct      900
actgaggagg agaagaagga gtgtgatgag agctccagg acaccatgct gctgctgtca      960
cagatgggcc ccgacgccca catgaggatg atccttcgca aaccacctgg ccagaggact     1020
gtggatgacc tagagattat ctatgaggag cttcttcata ttaaagcctt atcccatctt     1080
tctaccacag tgaaacgaga gttagcaggt gttctcattt ttgagtctca cgccaaagga     1140
gggactgtgt tgtttaacca ggggaagaa ggtacctcct ggtacattat tctaaaagga     1200
tcagtgaatg tagtcatttta cggcaagggt gtggtctgca ccctgcatga aggagatgac     1260
ttcggcaagt tagcactagt gaatgatgcc ccacgagctg cctctatcgt cttacgagaa     1320
```

```
gataactgcc atttcttaag agtagacaag gaggatttca accggatcct aaggctcgag    1380
aacgtctata tcaaggccga caagcagaag aacggcatca aggcgaactt caagatccgc    1440
cacaacatcg aggacggcgg cgtgcagctc gcctaccact accagcagaa cacccccatc    1500
ggcgacggcc ccgtgctgct gcccgacaac cactacctga gcgtgcagtc catactttcg    1560
aaagacccca acgagaagcg cgatcacatg gtcctgctgg agttcgtgac cgccgccggg    1620
atcactctcg gcatggacga gctgtacaag ggcggtaccg agggagcat ggtgagcaag     1680
ggcgaggagc tgttcaccgg ggtggtgccc atccaggtcg agctggacgg cgacgtaaac    1740
ggccacaagt tcagcgtgtc cggcgagggt gagggcgatg ccacctacgg caagctgacc    1800
ctgaagttca tctgcaccac cggcaagctg cccgtgccct ggcccaccct cgtgaccacc    1860
ctgacctacg gcgtgcagtg cttcagccgc taccccgacc acatgaagca gcacgacttc    1920
ttcaagtccg ccatgcccga aggctacatc caggagcgca ccatcttctt caaggacgac    1980
ggcaactaca agacccgcgc cgaggtgaag ttcgagggcg acaccctggt gaaccgcatc    2040
gagctgaagg gcatcgactt caaggaggac ggcaacatcc tggggcacaa gctggagtac    2100
aacacgcgta aggaggattt caaccggatc ctaagggacg tggaggcgaa tacagtcaga    2160
cttaaagaac atgaccaaga tgtcttggtg ctggagaagg tcccagcagg gaacagagct    2220
tctaatcaag gaaactcaca gcctcagcaa aagtatactg tgatgtcagg aacacctgaa    2280
aaaatttttag agcattttct agaaacaata cgccttgagg caactttaaa tgaagcaaca    2340
gattctgttt taaatgactt tattatgatg cactgtgttt ttatgccaaa tacccagctt    2400
tgcccggcac tggtggccca ctaccacgca cagccttcac aaggtacaga acaggagaaa    2460
atggattatg ccctcaacaa taagaggcga gtcatccgcc tggttctaca gtgggctgcc    2520
atgtatggag acctcctgca agaggatgac gtgtctatgg ccttcctgga ggagttttat    2580
gtatctgtat cagatgatgc ccggatgatt gctgccctca aggagcaact gccagagttg    2640
gagaagattg tcaagcaaat ctcagaagat gcaaaggcac acaaaagaa gcacaaggtt     2700
cttttgcaac agttcaatac gggcgatgag agagcccaga gcgccagcc tatccgcggc     2760
tctgatgaag ttctgtttaa ggtctattgc atggacccca cctacacaac cattcgggtg    2820
ccagtggcca cttcggtgaa ggaagtcatc agtgcagttg ccgacaagct gggctccggg    2880
gagggcctga tcatagtcaa gatgagttcc ggaggagaaa aggtggtgct caaacctaat    2940
gatgtttcag tatttatgac gctcaccatt aatggacgcc tgtttgcttg cccgcgagag    3000
caattcgatt cactgactcc cttaccagaa caggaaggcc caactgttgg aacagtggga    3060
acttttgaac tgatgagctc caaagattta gcataccaga tgacaattta tgattgggaa    3120
ctcttcaact gcgtgcatga gctggagcta atctatcaca catttggaag gcataatttt    3180
aaaaagacca cagcaaactt ggatttgttc ctgaggagat ttaatgaaat tcagttttgg    3240
gtcgtcactg agatctgcct tgttctcag ctcagcaagc gtgttcagct attaaaaaaa     3300
tttattaaga tagcagccca ctgtaaggag tataaaaatc tgaattcctt tttttgccatc   3360
gtcatgggac taagtaacgt tgctgtgagc cgcttggcac taacgtggga gaaactgcca    3420
agcaagttca agaagttcta tgcggagttt gaaagtttaa tggacccttc aaggaaccac    3480
agggcctaca ggctgacagt agctaagctg gaacctcctc tcatccccct catgcctttg    3540
ctcattaaag atatgacatt tactcatgag gggaacaaga cgttcattga caatctagta    3600
aactttgaaa aaatgcgcat gattgcaaat acgccagaa cagtgagata ctacaggagc    3660
caacccttca atcctgatgc agctcaagct aataagaacc atcaggatgt ccggagttat    3720
```

| | | |
|---|---|---|
| gtacggcaat taaatgtgat tgacaaccag agaactttat cacagatgtc acacagatta | 3780 |
| gagcctcgtc gacca | 3795 |

<210> SEQ ID NO 48
<211> LENGTH: 3771
<212> TYPE: DNA
<213> ORGANISM: Artificial Sequence
<220> FEATURE:
<223> OTHER INFORMATION: Synthetic

<400> SEQUENCE: 48

| | |
|---|---|
| atggtcgctg cgcacgctgc ccattcttcc tcctctgccg agtggatcgc ctgcctggat | 60 |
| aaaagaccac tggagcgatc cagcgaagat gtggatataa tcttcactcg actgaaagaa | 120 |
| gttaaagctt ttgagaaatt tcacccaaat ctccttcatc agatttgctt atgtggttat | 180 |
| tatgagaatc tggaaaaggg aataacatta tttcgccagg gtgatattgg aacaaactgg | 240 |
| tatgctgtcc tggcagggtc tttggatgtt aaagtatctg agaccagcag tcaccaggat | 300 |
| gctgtgacca tctgtaccct gggaattggg acggcctttg gagagtccat tctggacaac | 360 |
| acaccccgcc atgcaaccat cgttaccagg gagagcagtg aactgctccg catcgagcag | 420 |
| aaggacttca aggcactatg ggagaaatat cgacagtata tggcaggact tctggctcct | 480 |
| ccttatggtg ttatggaaac gggctctaac aatgacagga ttcctgacaa ggagaacaca | 540 |
| cctctcattg aacctcacgt tcctcttcgt cctgctaaca ccattaccaa ggtcccttca | 600 |
| gagaagatcc tcagagctgg aaaaatttta cgaaatgcca ttctctctcg agcacctcac | 660 |
| atgataagag atagaaaata ccacctaaag acatacagac aatgctgtgt gggaactgaa | 720 |
| ctggtggact ggatgatgca gcagacacca tgtgttcact cccggactca agctgttggc | 780 |
| atgtggcaag tcctgttaga agatggtgtt ctcaaccacg tggaccagga gcaccatttc | 840 |
| caagacaaat atttattcta tcgatttctg gatgatgagc acgaggatgc ccctttgcct | 900 |
| actgaggagg agaagaagga gtgtgatgag gagctccagg acaccatgct gctgctgtca | 960 |
| cagatgggcc ccgacgccca catgaggatg atccttcgca aaccacctgg ccagaggact | 1020 |
| gtggatgacc tagagattat ctatgaggag cttcttcata ttaaagcctt atcccatctt | 1080 |
| tctaccacag tgaaacgaga gttagcaggt gttctcatt ttgagtctca cgccaaagga | 1140 |
| gggactgtgt tgtttaacca gggggaagaa ggtacctcct ggtacattat tctaaaagga | 1200 |
| tcagtgaatg tagtcattta cggcaagggt gtggtctgca ccctgcatga aggagatgac | 1260 |
| ttcggcaagt tagcactagt gaatgatgcc ccacgagctg cctctatcgt cttacgagaa | 1320 |
| gataactgcc atttcttaag agtagacaag gaggatttca accggatcct aagggacgtg | 1380 |
| ctcgagaacg tctatatcaa ggccgacaag cagaagaacg gcatcaaggc gaacttcaag | 1440 |
| atccgccaca catcgaggac ggcggcgtg cagctcgcct accactacca gcagaacacc | 1500 |
| cccatcggcg acggccccgt gctgctgccc gacaaccact acctgagcgt gcagtccata | 1560 |
| ctttcgaaag accccaacga gaagcgcgat cacatggtcc tgctggagtt cgtgaccgcc | 1620 |
| gccgggatca ctctcggcat ggacgagctg tacaagggcg gtaccggagg gagcatggtg | 1680 |
| agcaagggcg aggaggtttc ctccgggggg gtgcccatcc aggtcgagct ggacggcgac | 1740 |
| gtaaacggcc acaagttcag cgtgtccggc gagggtgagg gcgatgccac ctacggcaag | 1800 |
| ctgacccctga agttcatctg caccaccggc aagctgcccg tgccctggcc cacccctgtg | 1860 |
| accaccctga cctacggcgt gcagtgcttc agccgctacc ccgaccacat gaagcagcac | 1920 |

| | |
|---|---|
| gacttcttca agtccgccat gcccgaaggc tacatccagg agcgcaccat cttcttcaag | 1980 |
| gacgacggca actacaagac ccgcgccgag gtgaagttcg agggcgacac cctggtgaac | 2040 |
| cgcatcgagc tgaagggcat cgacttcaag gaggacggca acatcctggg gcacaagctg | 2100 |
| gagtacaaca cgcgtgtgga ggcgaataca gtcagactta agaacatga ccaagatgtc | 2160 |
| ttggtgctgg agaaggtccc agcagggaac agagcttcta atcaaggaaa ctcacagcct | 2220 |
| cagcaaaagt atactgtgat gtcaggaaca cctgaaaaaa ttttagagca ttttctagaa | 2280 |
| acaatacgcc ttgaggcaac tttaaatgaa gcaacagatt ctgttttaaa tgactttatt | 2340 |
| atgatgcact gtgtttttat gccaaatacc cagctttgcc cggcactggt ggcccactac | 2400 |
| cacgcacagc cttcacaagg tacagaacag agaaaatggg attatgccct caacaataag | 2460 |
| aggcgagtca tccgcctggt tctacagtgg gctgccatgt atggagacct cctgcaagag | 2520 |
| gatgacgtgt ctatggcctt cctggaggag ttttatgtat ctgtatcaga tgatgcccgg | 2580 |
| atgattgctg ccctcaagga gcaactgcca gagttggaga agattgtcaa gcaaatctca | 2640 |
| gaagatgcaa aggcaccaca aaagaagcac aaggttctt tgcaacagtt caatacgggc | 2700 |
| gatgagagag cccagaagcg ccagcctatc cgcggctctg atgaagttct gtttaaggtc | 2760 |
| tattgcatgg accccaccta cacaaccatt cgggtgccag tggccacttc ggtgaaggaa | 2820 |
| gtcatcagtg cagttgccga caagctgggc tccggggagg gcctgatcat agtcaagatg | 2880 |
| agttccggag gagaaaaggt ggtgctcaaa cctaatgatg tttcagtatt tatgacgctc | 2940 |
| accattaatg gacgcctgtt tgcttgcccg cgagagcaat tcgattcact gactccctta | 3000 |
| ccagaacagg aaggcccaac tgttggaaca gtgggaactt tgaactgat gagctccaaa | 3060 |
| gatttagcat accagatgac aatttatgat tgggaactct tcaactgcgt gcatgagctg | 3120 |
| gagctaatct atcacacatt tggaaggcat aattttaaaa agaccacagc aaacttggat | 3180 |
| ttgttcctga ggagatttaa tgaaattcag ttttgggtcg tcactgagat ctgcctttgt | 3240 |
| tctcagctca gcaagcgtgt tcagctatta aaaaaattta ttaagatagc agcccactgt | 3300 |
| aaggagtata aaaatctgaa ttcctttttt gccatcgtca tgggactaag taacgttgct | 3360 |
| gtgagccgct tggcactaac gtgggagaaa ctgccaagca agttcaagaa gttctatgcg | 3420 |
| gagtttgaaa gtttaatgga cccttcaagg aaccacaggg cctacaggct gacagtagct | 3480 |
| aagctggaac ctcctctcat ccccttcatg cctttgctca ttaaagatat gacatttact | 3540 |
| catgagggga acaagacgtt cattgacaat ctagtaaact ttgaaaaaat gcgcatgatt | 3600 |
| gcaaatacgg ccagaacagt gagatactac aggagccaac ccttcaatcc tgatgcagct | 3660 |
| caagctaata agaaccatca ggatgtccgg agttatgtac ggcaattaaa tgtgattgac | 3720 |
| aaccagagaa ctttatcaca gatgtcacac agattagagc ctcgtcgacc a | 3771 |

<210> SEQ ID NO 49
<211> LENGTH: 3765
<212> TYPE: DNA
<213> ORGANISM: Artificial Sequence
<220> FEATURE:
<223> OTHER INFORMATION: Synthetic

<400> SEQUENCE: 49

| | |
|---|---|
| atggtcgctg cgcacgctgc ccattcttcc tcctctgccg agtggatcgc ctgcctggat | 60 |
| aaaagaccac tggagcgatc cagcgaagat gtggatataa tcttcactcg actgaaagaa | 120 |
| gttaaagctt tgagaaaatt tcacccaaat ctccttcatc agatttgctt atgtggttat | 180 |
| tatgagaatc tggaaaaggg aataacatta tttcgccagg gtgatattgg aacaaactgg | 240 |

-continued

| | |
|---|---|
| tatgctgtcc tggcagggtc tttggatgtt aaagtatctg agaccagcag tcaccaggat | 300 |
| gctgtgacca tctgtaccct gggaattggg acggcctttg agagtccat tctggacaac | 360 |
| acaccccgcc atgcaaccat cgttaccagg gagagcagtg aactgctccg catcgagcag | 420 |
| aaggacttca aggcactatg ggagaaatat cgacagtata tggcaggact tctggctcct | 480 |
| ccttatggtg ttatggaaac gggctctaac aatgacagga ttcctgacaa ggagaacaca | 540 |
| cctctcattg aacctcacgt tcctcttcgt cctgctaaca ccattaccaa ggtcccttca | 600 |
| gagaagatcc tcagagctgg aaaaatttta cgaaatgcca ttctctctcg agcacctcac | 660 |
| atgataagag atagaaaata ccacctaaag acatacagac aatgctgtgt gggaactgaa | 720 |
| ctggtggact ggatgatgca gcagacacca tgtgttcact cccggactca agctgttggc | 780 |
| atgtggcaag tcctgttaga agatggtgtt ctcaaccacg tggaccagga gcaccatttc | 840 |
| caagacaaat atttattcta tcgatttctg gatgatgagc acgaggatgc ccctttgcct | 900 |
| actgaggagg agaagaagga gtgtgatgag gagctccagg acaccatgct gctgctgtca | 960 |
| cagatgggcc ccgacgccca catgaggatg atccttcgca aaccacctgg ccagaggact | 1020 |
| gtggatgacc tagagattat ctatgaggag cttcttcata ttaaagcctt atcccatctt | 1080 |
| tctaccacag tgaaacgaga gttagcaggt gttctcattt ttgagtctca cgccaaagga | 1140 |
| gggactgtgt tgtttaacca gggggaagaa ggtacctcct ggtacattat tctaaaagga | 1200 |
| tcagtgaatg tagtcattta cggcaagggt gtggtctgca ccctgcatga aggagatgac | 1260 |
| ttcggcaagt tagcactagt gaatgatgcc ccacgagctg cctctatcgt cttacgagaa | 1320 |
| gataactgcc atttcttaag agtagacaag gaggatttca accggatcct aagggacgtg | 1380 |
| ctcgagaacg tctatatcaa ggccgacaag cagaagaacg gcatcaaggc gaacttcaag | 1440 |
| atccgccaca acatcgagga cggcggcgtg cagctcgcct accactacca gcagaacacc | 1500 |
| cccatcggcg acggccccgt gctgctgccc gacaaccact acctgagcgt gcagtccata | 1560 |
| ctttcgaaag accccaacga gaagcgcgat cacatggtcc tgctggagtt cgtgaccgcc | 1620 |
| gccgggatca ctctcggcat ggacgagctg tacaagggcg gtaccggagg gagcatggtg | 1680 |
| agcaagggcg aggagctgtt caccggggtg gtgcccatcc aggtcgagct ggacggcgac | 1740 |
| gtaaacggcc acaagttcag cgtgtccggc gagggtgagg gcgatgccac ctacggcaag | 1800 |
| ctgaccctga agttcatctg caccaccggc aagctgcccg tgccctggcc caccctcgtg | 1860 |
| accaccctga cctacggcgt gcagtgcttc agccgctacc ccgaccacat gaagcagcac | 1920 |
| gacttcttca gtccgccat gcccgaaggc tacatccagg agcgcaccat cttcttcaag | 1980 |
| gacgacggca actacaagac ccgcgccgag gtgaagttcg agggcgacac cctggtgaac | 2040 |
| cgcatcgagc tgaagggcat cgacttcaag gaggacggca acatcctggg cacaagctg | 2100 |
| gagtacaaca cgcgtgcgaa tacagtcaga cttaaagaac atgaccaaga tgtcttggtg | 2160 |
| ctggagaagg tccagcagg gaacagagct tctaatcaag gaaactcaca gcctcagcaa | 2220 |
| aagtatactg tgatgtcagg aacacctgaa aaaattttag agcattttct agaaacaata | 2280 |
| cgccttgagg caactttaaa tgaagcaaca gattctgttt taaatgactt tattatgatg | 2340 |
| cactgtgttt ttatgccaaa tacccagctt tgcccggcac tggtggccca ctaccacgca | 2400 |
| cagccttcac aaggtacaga acaggagaaa atggattatg ccctcaacaa taagaggcga | 2460 |
| gtcatccgcc tggttctaca gtgggctgcc atgtatggag acctcctgca agaggatgac | 2520 |
| gtgtctatgg ccttcctgga ggagtttta gtatctgtat cagatgatgc ccggatgatt | 2580 |

|  |  |
|---|---|
| gctgccctca aggagcaact gccagagttg agaagattg tcaagcaaat ctcagaagat | 2640 |
| gcaaaggcac cacaaaagaa gcacaaggtt cttttgcaac agttcaatac gggcgatgag | 2700 |
| agagcccaga agcgccagcc tatccgcggc tctgatgaag ttctgtttaa ggtctattgc | 2760 |
| atggacccca cctacacaac cattcgggtg ccagtggcca cttcggtgaa ggaagtcatc | 2820 |
| agtgcagttg ccgacaagct gggctccggg gagggcctga tcatagtcaa gatgagttcc | 2880 |
| ggaggagaaa aggtggtgct caaacctaat gatgtttcag tatttatgac gctcaccatt | 2940 |
| aatggacgcc tgtttgcttg cccgcgagag caattcgatt cactgactcc cttaccagaa | 3000 |
| caggaaggcc caactgttgg aacagtggga acttttgaac tgatgagctc caaagattta | 3060 |
| gcataccaga tgacaattta tgattgggaa ctcttcaact gcgtgcatga gctggagcta | 3120 |
| atctatcaca catttggaag gcataatttt aaaaagacca cagcaaactt ggatttgttc | 3180 |
| ctgaggagat ttaatgaaat tcagttttgg gtcgtcactg agatctgcct tgttctcag | 3240 |
| ctcagcaagc gtgttcagct attaaaaaaa tttattaaga tagcagccca ctgtaaggag | 3300 |
| tataaaaatc tgaattcctt ttttgccatc gtcatgggac taagtaacgt tgctgtgagc | 3360 |
| cgcttggcac taacgtggga gaaactgcca agcaagttca agaagttcta tgcggagttt | 3420 |
| gaaagtttaa tggacccttc aaggaaccac agggcctaca ggctgacagt agctaagctg | 3480 |
| gaacctcctc tcatcccctt catgcctttg ctcattaaag atatgacatt tactcatgag | 3540 |
| gggaacaaga cgttcattga caatctagta aactttgaaa aaatgcgcat gattgcaaat | 3600 |
| acggccagaa cagtgagata ctacaggagc caacccttca atcctgatgc agctcaagct | 3660 |
| aataagaacc atcaggatgt ccggagttat gtacggcaat aaatgtgat tgacaaccag | 3720 |
| agaactttat cacagatgtc acacagatta gagcctcgtc gacca | 3765 |

<210> SEQ ID NO 50
<211> LENGTH: 3780
<212> TYPE: DNA
<213> ORGANISM: Artificial Sequence
<220> FEATURE:
<223> OTHER INFORMATION: Synthetic

<400> SEQUENCE: 50

|  |  |
|---|---|
| atggtcgctg cgcacgctgc ccattcttcc tcctctgccg agtggatcgc ctgcctggat | 60 |
| aaaagaccac tggagcgatc cagcgaagat gtggatataa tcttcactcg actgaaagaa | 120 |
| gttaaagctt ttgagaaatt tcacccaaat ctccttcatc agatttgctt atgtggttat | 180 |
| tatgagaatc tggaaaaggg aataacatta tttcgccagg gtgatattgg aacaaactgg | 240 |
| tatgctgtcc tggcagggtc tttggatgtt aaagtatctg agaccagcag tcaccaggat | 300 |
| gctgtgacca tctgtaccct gggaattggg acggcctttg agagtccat tctgacaac | 360 |
| acaccccgcc atgcaaccat cgttaccagg agagcagtg aactgctccg catcgagcag | 420 |
| aaggacttca aggcactatg ggagaaatat cgacagtata tggcaggact tctggctcct | 480 |
| ccttatggtg ttatggaaac gggctctaac aatgacagga ttcctgacaa ggagaacaca | 540 |
| cctctcattg aacctcacgt tcctcttcgt cctgctaaca ccattaccaa ggtcccttca | 600 |
| gagaagatcc tcagagctgg aaaaatttta cgaaatgcca ttctctctcg agcacctcac | 660 |
| atgataagag atagaaaata ccacctaaag acatacagac aatgctgtgt gggaactgaa | 720 |
| ctggtggact ggatgatgca gcagacacca tgtgttcact cccggactca agctgttggc | 780 |
| atgtggcaag tcctgttaga agatggtgtt ctcaaccacg tggaccagga gcaccatttc | 840 |
| caagacaaat atttattcta tcgatttctg gatgatgagc acgaggatgc ccctttgcct | 900 |

```
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aaggctcgag   1380
aacgtctata tcaaggccga caagcagaag aacggcatca aggcgaactt caagatccgc   1440
cacaacatcg aggacggcgg cgtgcagctc gcctaccact accagcagaa cacccccatc   1500
ggcgacggcc ccgtgctgct gcccgacaac cactacctga gcgtgcagtc catactttcg   1560
aaagacccca cgagaagcg cgatcacatg gtcctgctgg agttcgtgac cgccgccggg   1620
atcactctcg gcatggacga gctgtacaag ggcggtaccg agggagcat ggtgagcaag   1680
ggcgaggagc tgttcaccgg ggtggtgccc atccaggtcg agctgacgg cgacgtaaac   1740
ggccacaagt tcagcgtgtc cggcgagggt gagggcgatg ccacctacgg caagctgacc   1800
ctgaagttca tctgcaccac cggcaagctg cccgtgccct ggcccaccct cgtgaccacc   1860
ctgacctacg gcgtgcagtg cttcagccgc taccccgacc acatgaagca gcacgacttc   1920
ttcaagtccg ccatgcccga aggctacatc caggagcgca ccatcttctt caaggacgac   1980
ggcaactaca agacccgcgc cgaggtgaag ttcgagggcg acaccctggt gaaccgcatc   2040
gagctgaagg gcatcgactt caaggaggac ggcaacatcc tggggcacaa gctggagtac   2100
aacacgcgtc ggatcctaag ggacgtggag gcgaatacag tcagacttaa agaacatgac   2160
caagatgtct tggtgctgga aaggtccca gcagggaaca gagcttctaa tcaaggaaac   2220
tcacagcctc agcaaaagta tactgtgatg tcaggaacac ctgaaaaaat tttagagcat   2280
tttctagaaa caatacgcct tgaggcaact ttaaatgaag caacagattc tgtttttaaat   2340
gactttatta tgatgcactg tgttttatg ccaaatacc agctttgccc ggcactggtg   2400
gcccactacc acgcacagcc ttcacaaggt acagaacagg agaaaatgga ttatgccctc   2460
aacaataaga ggcgagtcat ccgcctggtt ctacagtggg ctgccatgta tggagacctc   2520
ctgcaagagg atgacgtgtc tatggccttc ctggaggagt tttatgtatc tgtatcagat   2580
gatgcccgga tgattgctgc cctcaaggag caactgccag agttggagaa gattgtcaag   2640
caaatctcag aagatgcaaa ggcaccacaa aagaagcaca aggttctttt gcaacagttc   2700
aatacgggcg atgagagagc ccagaagcgc cagcctatcc gcggctctga tgaagttctg   2760
tttaaggtct attgcatgga ccccacctac acaaccattc gggtgccagt ggccacttcg   2820
gtgaaggaag tcatcagtgc agttgccgac aagctgggct ccggggaggg cctgatcata   2880
gtcaagatga gttccggagg agaaaaggtg gtgctcaaac ctaatgatgt ttcagtattt   2940
atgacgctca ccattaatgg acgcctgttt gcttgcccgc gagagcaatt cgattcactg   3000
actcccttac cagaacagga aggcccaact gttggaacag tgggaacttt tgaactgatg   3060
agctccaaag atttagcata ccagatgaca atttatgatt gggaactctt caactgcgtg   3120
catgagctgg agctaatcta tcacacattt ggaaggcata attttaaaaa gaccacagca   3180
aacttggatt tgttcctgag gagatttaat gaaattcagt tttgggtcgt cactgagatc   3240
```

| | |
|---|---|
| tgcctttgtt ctcagctcag caagcgtgtt cagctattaa aaaaatttat taagatagca | 3300 |
| gcccactgta aggagtataa aaatctgaat tccttttttg ccatcgtcat gggactaagt | 3360 |
| aacgttgctg tgagccgctt ggcactaacg tgggagaaac tgccaagcaa gttcaagaag | 3420 |
| ttctatgcgg agtttgaaag tttaatggac ccttcaagga accacagggc ctacaggctg | 3480 |
| acagtagcta agctggaacc tcctctcatc cccttcatgc ctttgctcat taagatatg | 3540 |
| acatttactc atgagggaa caagacgttc attgacaatc tagtaaactt tgaaaaaatg | 3600 |
| cgcatgattg caaatacggc cagaacagtg agatactaca ggagccaacc cttcaatcct | 3660 |
| gatgcagctc aagctaataa gaaccatcag gatgtccgga gttatgtacg gcaattaaat | 3720 |
| gtgattgaca accagagaac tttatcacag atgtcacaca gattagagcc tcgtcgacca | 3780 |

<210> SEQ ID NO 51
<211> LENGTH: 3768
<212> TYPE: DNA
<213> ORGANISM: Artificial Sequence
<220> FEATURE:
<223> OTHER INFORMATION: Synthetic

<400> SEQUENCE: 51

| | |
|---|---|
| atggtcgctg cgcacgctgc ccattcttcc tcctctgccg agtggatcgc ctgcctggat | 60 |
| aaaagaccac tggagcgatc cagcgaagat gtggatataa tcttcactcg actgaaagaa | 120 |
| gttaaagctt tgagaaatt tcacccaaat ctccttcatc agatttgctt atgtggttat | 180 |
| tatgagaatc tggaaaaggg aataacatta tttcgccagg gtgatattgg aacaaactgg | 240 |
| tatgctgtcc tggcagggtc tttggatgtt aaagtatctg agaccagcag tcaccaggat | 300 |
| gctgtgacca tctgtaccct gggaattggg acggcctttg gagagtccat tctggacaac | 360 |
| acaccccgcc atgcaaccat cgttaccagg agagcagtg aactgctccg catcgagcag | 420 |
| aaggacttca aggcactatg ggagaaatat cgacagtata tggcaggact tctggctcct | 480 |
| ccttatggtg ttatggaaac gggctctaac aatgacagga ttcctgacaa ggagaacaca | 540 |
| cctctcattg aacctcacgt tcctcttcgt cctgctaaca ccattaccaa ggtcccttca | 600 |
| gagaagatcc tcagagctgg aaaaatttta cgaaatgcca ttctctctcg agcacctcac | 660 |
| atgataagag atagaaaata ccacctaaag acatacagac aatgctgtgt gggaactgaa | 720 |
| ctggtggact ggatgatgca gcagacacca tgtgttcact cccggactca agctgttggc | 780 |
| atgtggcaag tcctgttaga agatggtgtt ctcaaccacg tggaccagga gcaccatttc | 840 |
| caagacaaat atttattcta tcgatttctg gatgatgagc acgaggatgc cccttttgcct | 900 |
| actgaggagg agaagaagga gtgtgatgag gagctccagg acaccatgct gctgctgtca | 960 |
| cagatgggcc ccgacgccca catgaggatg atccttcgca aaccacctgg ccagaggact | 1020 |
| gtggatgacc tagagattat ctatgaggag cttcttcata ttaaagcctt atcccatctt | 1080 |
| tctaccacag tgaaacgaga gttagcaggt gttctcattt ttgagtctca cgccaaagga | 1140 |
| gggactgtgt tgtttaacca gggggaagaa ggtacctcct ggtacattat tctaaaagga | 1200 |
| tcagtgaatg tagtcatttta cggcaagggt gtggtctgca ccctgcatga aggagatgac | 1260 |
| ttcggcaagt tagcactagt gaatgatgcc ccacgagctg cctctatcgt cttacgagaa | 1320 |
| gataactgcc atttcttaag agtagacaag gaggatttca accggatcct aagggacgtg | 1380 |
| ctcgagaacg tctatatcaa ggccgacaag cagaagaacg gcatcaaggc gaacttcaag | 1440 |
| atccgccaca catcgagga cggcggcgtg cagctcgcct accactacca gcagaacacc | 1500 |
| cccatcggcg acggccccgt gctgctgccc gacaaccact acctgagcgt gcagtccata | 1560 |

```
ctttcgaaag accccaacga gaagcgcgat cacatggtcc tgctggagtt cgtgaccgcc   1620
gccgggatca ctctcggcat ggacgagctg tacaagggcg gtaccggagg gagcatggtg   1680
agcaagggcg aggagctgtt caccggggtg gtgcccatcc aggtcgagct ggacggcgac   1740
gtaaacggcc acaagttcag cgtgtccggc gagggtgagg gcgatgccac ctacggcaag   1800
ctgaccctga agttcatctg caccaccggc aagctgcccg tgccctggcc caccctcgtg   1860
accaccctga cctacggcgt gcagtgcttc agccgctacc ccgaccacat gaagcagcac   1920
gacttcttca gtccgccat gcccgaaggc tacatccagg agcgcaccat cttcttcaag   1980
gacgacggca actacaagac ccgcgccgag gtgaagttcg agggcgacac cctggtgaac   2040
cgcatcgagc tgaagggcat cgacttcaag gaggacggca acatcctggg cacaagctg   2100
gagtacaaca cgcgtgaggc gaatacagtc agacttaaag aacatgacca agatgtcttg   2160
gtgctggaga aggtcccagc agggaacaga gcttctaatc aaggaaactc acagcctcag   2220
caaaagtata ctgtgatgtc aggaacacct gaaaaaattt tagagcattt tctagaaaca   2280
atacgccttg aggcaacttt aaatgaagca acagattctg ttttaaatga ctttattatg   2340
atgcactgtg tttttatgcc aaataccag ctttgcccgg cactggtggc ccactaccac   2400
gcacagcctt cacaaggtac agaacaggag aaaatggatt atgccctcaa caataagagg   2460
cgagtcatcc gcctggttct acagtgggct gccatgtatg gagacctcct gcaagaggat   2520
gacgtgtcta tggccttcct ggaggagttt tatgtatctg tatcagatga tgcccggatg   2580
attgctgccc tcaaggagca actgccagag ttggagaaga ttgtcaagca aatctcagaa   2640
gatgcaaagg caccacaaaa gaagcacaag gttcttttgc aacagttcaa tacgggcgat   2700
gagagagccc agaagcgcca gcctatccgc ggctctgatg aagttctgtt taaggtctat   2760
tgcatggacc ccacctacac aaccattcgg gtgccagtgg ccacttcggt gaaggaagtc   2820
atcagtgcag ttgccgacaa gctgggctcc ggggagggcc tgatcatagt caagatgagt   2880
tccggaggag aaaaggtggt gctcaaacct aatgatgttt cagtatttat gacgctcacc   2940
attaatggac gcctgtttgc ttgcccgcga gagcaattcg attcactgac tcccttacca   3000
gaacaggaag gcccaactgt tggaacagtg ggaactttg aactgatgag ctccaaagat   3060
ttagcatacc agatgacaat ttatgattgg gaactcttca actgcgtgca tgagctggag   3120
ctaatctatc acacatttgg aaggcataat tttaaaaaga ccacagcaaa cttggatttg   3180
ttcctgagga gatttaatga aattcagttt tgggtcgtca ctgagatctg cctttgttct   3240
cagctcagca agcgtgttca gctattaaaa aaatttatta agatagcagc ccactgtaag   3300
gagtataaaa atctgaattc cttttttgcc atcgtcatgg gactaagtaa cgttgctgtg   3360
agccgcttgg cactaacgtg ggagaaactg ccaagcaagt tcaagaagtt ctatgcggag   3420
tttgaaagtt taatggaccc ttcaaggaac cacagggcct acaggctgac agtagctaag   3480
ctggaacctc ctctcatccc cttcatgcct ttgctcatta agatatgac atttactcat   3540
gaggggaaca agacgttcat tgacaatcta gtaaactttg aaaaaatgcg catgattgca   3600
aatacggcca gaacagtgag atactacagg agccaaccct tcaatcctga tgcagctcaa   3660
gctaataaga accatcagga tgtccggagt tatgtacggg aattaaatgt gattgacaac   3720
cagagaactt tatcacagat gtcacacaga ttagagcctc gtcgacca                3768

<210> SEQ ID NO 52
<211> LENGTH: 3789
<212> TYPE: DNA
```

<213> ORGANISM: Artificial Sequence
<220> FEATURE:
<223> OTHER INFORMATION: Synthetic

<400> SEQUENCE: 52

```
atggtcgctg cgcacgctgc ccattcttcc tcctctgccg agtggatcgc ctgcctggat      60
aaaagaccac tggagcgatc cagcgaagat gtggatataa tcttcactcg actgaaagaa     120
gttaaagctt ttgagaaatt tcacccaaat ctccttcatc agatttgctt atgtggttat     180
tatgagaatc tggaaaaggg aataacatta tttcgccagg gtgatattgg aacaaactgg     240
tatgctgtcc tggcagggtc tttggatgtt aaagtatctg agaccagcag tcaccaggat     300
gctgtgacca tctgtaccct gggaattggg acggcctttg gagagtccat tctggacaac     360
acacccgcc atgcaaccat cgttaccagg gagagcagtg aactgctccg catcgagcag      420
aaggacttca aggcactatg ggagaaatat cgacagtata tggcaggact tctggctcct     480
ccttatggtg ttatggaaac gggctctaac aatgacagga ttcctgacaa ggagaacaca     540
cctctcattg aacctcacgt tcctcttcgt cctgctaaca ccattaccaa ggtcccttca     600
gagaagatcc tcagagctgg aaaaatttta cgaaatgcca ttctctctcg agcacctcac     660
atgataagag atagaaaata ccacctaaag acatacagac aatgctgtgt gggaactgaa     720
ctggtggact ggatgatgca gcagacacca tgtgttcact cccggactca agctgttggc     780
atgtggcaag tcctgttaga agatggtgtt ctcaaccacg tggaccagga gcaccatttc     840
caagacaaat atttattcta tcgatttctg gatgatgagc acgaggatgc ccctttgcct     900
actgaggagg agaagaagga gtgtgatgag agctccagg acaccatgct gctgctgtca      960
cagatgggcc ccgacgccca catgaggatg atccttcgca aaccacctgg ccagaggact    1020
gtggatgacc tagagattat ctatgaggag cttcttcata ttaaagcctt atcccatctt    1080
tctaccacag tgaaacgaga gttagcaggt gttctcattt ttgagtctca cgccaaagga    1140
gggactgtgt tgtttaacca gggggaagaa ggtacctcct ggtacattat tctaaaagga    1200
tcagtgaatg tagtcattta cggcaagggt gtggtctgca ccctgcatga aggagatgac    1260
ttcggcaagt tagcactagt gaatgatgcc ccacgagctg cctctatcgt cttacgagaa    1320
gataactgcc atttcttaag agtagacaag gaggatttca accggatcct aagggacctc    1380
gagaacgtct atatcaaggc cgacaagcag aagaacggca tcaaggcgaa cttcaagatc    1440
cgccacaaca tcgaggacgg cggcgtgcag ctcgcctacc actaccagca gaacaccccc    1500
atcggcgacg gccccgtgct gctgcccgac aaccactacc tgagcgtgca gtccatactt    1560
tcgaaagacc ccaacgagaa gcgcgatcac atggtcctgc tggagttcgt gaccgccgcc    1620
gggatcactc tcggcatgga cgagctgtac aagggcggta ccggagggag catggtgagc    1680
aagggcgagg agctgttcac cggggtggtg cccatccagg tcgagctgga cggcgacgta    1740
aacggccaca gttcagcgt gtccggcgag ggtgagggcg atgccaccta cggcaagctg      1800
accctgaagt tcatctgcac caccggcaag ctgcccgtgc cctggcccac cctcgtgacc    1860
accctgacct acggcgtgca gtgcttcagc cgctaccccg accacatgaa gcagcacgac    1920
ttcttcaagt ccgccatgcc cgaaggctac atccaggagc gcaccatctt cttcaaggac    1980
gacggcaact acaagacccg cgccgaggtg aagttcgagg gcgacaccct ggtgaaccgc    2040
atcgagctga agggcatcga cttcaaggag gacggcaaca tcctggggca caagctggag    2100
tacaacacgc gtttcaaccg gatcctaagg gacgtggagg cgaatacagt cagacttaaa    2160
gaacatgacc aagatgtctt ggtgctggag aaggtcccag cagggaacag agcttctaat    2220
```

```
caaggaaact cacagcctca gcaaaagtat actgtgatgt caggaacacc tgaaaaaatt    2280
ttagagcatt ttctagaaac aatacgcctt gaggcaactt taaatgaagc aacagattct    2340
gttttaaatg actttattat gatgcactgt gtttttatgc caaataccca gctttgcccg    2400
gcactggtgg cccactacca cgcacagcct tcacaaggta cagaacagga gaaaatggat    2460
tatgccctca acaataagag gcgagtcatc cgcctggttc tacagtgggc tgccatgtat    2520
ggagacctcc tgcaagagga tgacgtgtct atggccttcc tggaggagtt ttatgtatct    2580
gtatcagatg atgcccggat gattgctgcc ctcaaggagc aactgccaga gttggagaag    2640
attgtcaagc aaatctcaga agatgcaaag gcaccacaaa agaagcacaa ggttcttttg    2700
caacagttca atacgggcga tgagagagcc agaagcgcc agcctatccg cggctctgat    2760
gaagttctgt ttaaggtcta ttgcatggac cccacctaca caaccattcg ggtgccagtg    2820
gccacttcgg tgaaggaagt catcagtgca gttgccgaca agctgggctc cggggagggc    2880
ctgatcatag tcaagatgag ttccggagga gaaaaggtgg tgctcaaacc taatgatgtt    2940
tcagtattta tgacgctcac cattaatgga cgcctgtttg cttgcccgcg agagcaattc    3000
gattcactga ctcccttacc agaacaggaa ggcccaactg ttggaacagt gggaactttt    3060
gaactgatga gctccaaaga tttagcatac cagatgacaa tttatgattg ggaactcttc    3120
aactgcgtgc atgagctgga gctaatctat cacacatttg gaaggcataa ttttaaaaag    3180
accacagcaa acttggattt gttcctgagg agatttaatg aaattcagtt ttgggtcgtc    3240
actgagatct gcctttgttc tcagctcagc aagcgtgttc agctattaaa aaaatttatt    3300
aagatagcag cccactgtaa ggagtataaa atctgaatt cctttttgc catcgtcatg    3360 ggactaagta acgttgctgt gagccgcttg gcactaacgt gggagaaact gccaagcaag    3420
ttcaagaagt tctatgcgga gtttgaaagt ttaatggacc cttcaaggaa ccacagggcc    3480
tacaggctga cagtagctaa gctggaacct cctctcatcc ccttcatgcc tttgctcatt    3540
aaagatatga catttactca tgagggaac aagacgttca ttgacaatct agtaaacttt    3600
gaaaaaatgc gcatgattgc aaatacggcc agaacagtga gatactacag gagccaaccc    3660
ttcaatcctg atgcagctca agctaataag aaccatcagg atgtccggag ttatgtacgg    3720
caattaaatg tgattgacaa ccagagaact ttatcacaga tgtcacacag attagagcct    3780
cgtcgacca                                                          3789

<210> SEQ ID NO 53
<211> LENGTH: 3764
<212> TYPE: DNA
<213> ORGANISM: Artificial Sequence
<220> FEATURE:
<223> OTHER INFORMATION: Synthetic

<400> SEQUENCE: 53
atggtcgctg cgcacgctgc ccattcttcc tcctctgccg agtggatcgc ctgcctggat      60
aaaagaccac tggagcgatc cagcgaagat gtggatataa tcttcactcg actgaaagaa     120
gttaaagctt ttgagaaatt tcacccaaat ctccttcatc agatttgctt atgtggttat     180
tatgagaatc tggaaaaggg aataacatta tttcgccagg gtgatattgg aacaaactgg     240
tatgctgtcc tggcagggtc tttggatgtt aaagtatctg agaccagcag tcaccaggat     300
gctgtgacca tctgtaccct gggaattggg acggcctttg gagagtccat tctggacaac     360
acaccccgcc atgcaaccat cgttaccagg gagagcagtg aactgctccg catcgagcag     420
```

```
aaggacttca aggcactatg ggagaaatat cgacagtata tggcaggact tctggctcct    480
ccttatggtg ttatggaaac gggctctaac aatgacagga ttcctgacaa ggagaacaca    540
cctctcattg aacctcacgt tcctcttcgt cctgctaaca ccattaccaa ggtcccttca    600
gagaagatcc tcagagctgg aaaaatttta cgaaatgcca ttctctctcg agcacctcac    660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc ccctttgcct    900
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aagggacgtg   1380
ctcgagaacg tctatatcaa ggccgacaag cagaagaacg gcatcaaggc gaacttcaag   1440
atccgccaca acatcgagga cggcggcgtg cagctcgcct accactacca gcagaacacc   1500
cccatcggcg acggccccgt gctgctgccc gacaaccact acctgagcgt gcagtccata   1560
ctttcgaaag accccaacga gaagcgcgat cacatggtcc tgctggagtt cgtgaccgcc   1620
gccgggatca ctctcggcat ggacgagctg tacaagggcg gtaccggagg gagcatggtg   1680
agcaagggcg aggagctgtt cacccggggg gtggtgccca tccaggtcga gctggacggc   1740
gacgtaaacg gccacaagtt cagcgtgtcc ggcgagggtg agggcgatgc cacctacggc   1800
aagctgaccc tgaagttcat ctgcaccacc ggcaagctgc ccgtgccctg gcccaccctc   1860
gtgaccaccc tgacctacgg cgtgcagtgc ttcagccgct accccgacca catgaagcag   1920
cacgacttct tcaagtccgc catgcccgaa ggctacatcc aggagcgcac catcttcttc   1980
aaggacgacg gcaactacaa gacccgcgcc gaggtgaagt tcgagggcga caccctggtg   2040
aaccgcatcg agctgaaggg catcgacttc aaggaggacg gcaacatcct ggggcacaag   2100
ctggagtaca acacgcgtaa tacagtcaga cttaaagaac atgaccaaga tgtcttggtg   2160
ctggagaagg tcccagcagg gaacagagct tctaatcaag gaaactcaca gcctcagcaa   2220
aagtatactg tgatgtcagg aacacctgaa aaaattttag agcattttct agaaacaata   2280
cgccttgagg caactttaaa tgaagcaaca gattctgttt taaatgactt tattatgatg   2340
cactgtgttt ttatgccaaa tacccagctt tgcccggcac tggtggccca ctaccacgca   2400
cagccttcac aaggtacaga acaggagaaa atggattatg ccctcaacaa taagaggcga   2460
gtcatccgcc tggttctaca gtgggctgcc atgtatggag acctcctgca gaggatgac   2520 gtgtctatgg ccttcctgga ggagttttat gtatctgtat cagatgatgc ccggatgatt   2580
gctgccctca aggagcaact gccagagttg gagaagattg tcaagcaaat ctcagaagat   2640
gcaaaggcac cacaaaagaa gcacaaggtt cttttgcaac agttcaatac gggcgatgag   2700
agagcccaga agcgccagcc tatccgcggc tctgatgaag ttctgtttaa ggtctattgc   2760 atggaccccca cctacacaac cattcgggtg ccagtggcca cttcggtgaa ggaagtcatc   2820
```

```
agtgcagttg ccgacaagct gggctccggg gagggcctga tcatagtcaa gatgagttcc    2880
ggaggagaaa aggtggtgct caaacctaat gatgtttcag tatttatgac gctcaccatt    2940
aatggacgcc tgtttgcttg cccgcgagag caattcgatt cactgactcc cttaccagaa    3000
caggaaggcc caactgttgg aacagtggga acttttgaac tgatgagctc caaagattta    3060
gcataccaga tgacaattta tgattgggaa ctcttcaact gcgtgcatga gctggagcta    3120
atctatcaca catttggaag gcataatttt aaaaagacca cagcaaactt ggatttgttc    3180
ctgaggagat ttaatgaaat tcagttttgg gtcgtcactg agatctgcct ttgttctcag    3240
ctcagcaagc gtgttcagct attaaaaaaa tttattaaga tagcagccca ctgtaaggag    3300
tataaaaatc tgaattcctt ttttgccatc gtcatgggac taagtaacgt tgctgtgagc    3360
cgcttggcac taacgtggga gaaactgcca agcaagttca agaagttcta tgcggagttt    3420
gaaagtttaa tggacccttc aaggaaccac agggcctaca ggctgacagt agctaagctg    3480
gaacctcctc tcatcccctt catgcctttg ctcattaaag atatgacatt tactcatgag    3540
gggaacaaga cgttcattga caatctagta aactttgaaa aaatgcgcat gattgcaaat    3600
acggccagaa cagtgagata ctacaggagc caacccttca atcctgatgc agctcaagct    3660
aataagaacc atcaggatgt ccggagttat gtacggcaat taaatgtgat tgacaaccag    3720
agaactttat cacagatgtc acacagatta gagcctcgtc gacc              3764
```

<210> SEQ ID NO 54
<211> LENGTH: 3765
<212> TYPE: DNA
<213> ORGANISM: Artificial Sequence
<220> FEATURE:
<223> OTHER INFORMATION: Synthetic

<400> SEQUENCE: 54

```
atggtcgctg cgcacgctgc ccattcttcc tcctctgccg agtggatcgc ctgcctggat      60
aaaagaccac tggagcgatc cagcgaagat gtggatataa tcttcactcg actgaaagaa     120
gttaaagctt ttgagaaatt tcacccaaat ctccttcatc agatttgctt atgtggttat     180
tatgagaatc tggaaaaggg aataacatta tttcgccagg gtgatattgg aacaaactgg     240
tatgctgtcc tggcagggtc tttggatgtt aaagtatctg agaccagcag tcaccaggat     300
gctgtgacca tctgtaccct gggaattggg acggcctttg gagagtccat tctggacaac     360
acaccccgcc atgcaaccat cgttaccagg gagagcagtg aactgctccg catcgagcag     420
aaggacttca aggcactatg ggagaaatat cgacagtata tggcaggact tctggctcct     480
ccttatggtg ttatggaaac gggctctaac aatgacagga ttcctgacaa ggagaacaca     540
cctctcattg aacctcacgt tcctcttcgt cctgctaaca ccattaccaa ggtcccttca     600
gagaagatcc tcagagctgg aaaaatttta cgaaatgcca ttctctctcg agcacctcac     660
atgataagag ataaaaaata ccacctaaag acatacagac aatgctgtgt gggaactgaa     720
ctggtggact ggatgatgca gcagacacca tgtgttcact cccggactca agctgttggc     780
atgtggcaag tcctgttaga agatggtgtt ctcaaccacg tggaccagga gcaccatttc     840
caagacaaat atttattcta tcgatttctg gatgatgagc acgaggatgc ccctttgcct     900
actgaggagg agaagaagga gtgtgatgag gagctccagg acaccatgct gctgctgtca     960
cagatgggcc ccgacgccca catgaggatg atccttcgca aaccacctgg ccagaggact    1020
gtggatgacc tagagattat ctatgaggag cttcttcata ttaaagcctt atcccatctt    1080
```

```
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aaggctcgag   1380
aacgtctata tcaaggccga caagcagaag aacggcatca aggcgaactt caagatccgc   1440
cacaacatcg aggacggcgg cgtgcagctc gcctaccact accagcagaa cacccccatc   1500
ggcgacggcc ccgtgctgct gcccgacaac cactacctga gcgtgcagtc catactttcg   1560
aaagacccca acgagaagcg cgatcacatg gtcctgctgg agttcgtgac cgccgccggg   1620
atcactctcg gcatggacga gctgttcaag ggcggtaccg agggagcat ggtgagcaag   1680
ggcgaggagc tgttcaccgg ggtggtgccc atccaggtcg agctggacgg cgacgtaaac   1740
ggccacaagt tcagcgtgtc cggcgagggt gagggcgatg ccacctacgg caagctgacc   1800
ctgaagttca tctgcaccac cggcaagctg cccgtgccct ggcccaccct cgtgaccacc   1860
ctgacctacg gcgtgcagtg cttcagccgc taccccgacc acatgaagca gcacgacttc   1920
ttcaagtccg ccatgcccga aggctacatc caggagcgca ccatcttctt caaggacgac   1980
ggcaactaca agacccgcgc cgaggtgaag ttcgagggcg acaccctggt gaaccgcatc   2040
gagctgaagg gcatcgactt caaggaggac ggcaacatcc tggggcacaa gctggagtac   2100
aacacgcgtg tggaggcgaa tacagtcaga cttaaagaac atgaccaaga tgtcttggtg   2160
ctggagaagg tccagcagg gaacagagct tctaatcaag gaaactcaca gcctcagcaa   2220
aagtatactg tgatgtcagg aacacctgaa aaatttttag agcattttct agaaacaata   2280
cgccttgagg caactttaaa tgaagcaaca gattctgttt taaatgactt tattatgatg   2340
cactgtgttt ttatgccaaa tacccagctt tgcccggcac tggtggccca ctaccacgca   2400
cagccttcac aagtacaga acaggagaaa atggattatg ccctcaacaa taagaggcga   2460
gtcatccgcc tggttctaca gtgggctgcc atgtatggag acctcctgca agaggatgac   2520
gtgtctatgg ccttcctgga ggagttttat gtatctgtat cagatgatgc ccggatgatt   2580
gctgccctca aggagcaact gccagagttg gagaagattg tcaagcaaat ctcagaagat   2640
gcaaaggcac cacaaaagaa gcacaaggtt cttttgcaac agttcaatac gggcgatgag   2700
agagcccaga agcgccagcc tatccgcggc tctgatgaag ttctgtttaa ggtctattgc   2760
atggacccca cctacacaac cattcgggtg ccagtggcca cttcggtgaa ggaagtcatc   2820
agtgcagttg ccgacaagct gggctccggg gagggcctga tcatagtcaa gatgagttcc   2880
ggaggagaaa aggtggtgct caaacctaat gatgtttcag tatttatgac gctcaccatt   2940
aatggacgcc tgtttgcttg cccgcgagag caattcgatt cactgactcc cttaccagaa   3000
caggaaggcc caactgttgg aacagtggga acttttgaac tgatgagctc aaagattta   3060
gcataccaga tgacaattta tgattgggaa ctcttcaact cgtgcatga gctggagcta   3120
atctatcaca catttggaag gcataatttt aaaaagacca cagcaaactt ggatttgttc   3180
ctgaggagat ttaatgaaat tcagttttgg gtcgtcactg agatctgcct ttgttctcag   3240
ctcagcaagc gtgttcagct attaaaaaaa tttattaaga tagcagccca ctgtaaggag   3300
tataaaaatc tgaattcctt ttttgccatc gtcatgggac taagtaacgt tgctgtgagc   3360
cgcttggcac taacgtggga gaaactgcca agcaagttca agaagttcta tgcggagttt   3420
gaaagtttaa tggaccccttc aaggaaccac agggcctaca ggctgacagt agctaagctg   3480
```

| | |
|---|---|
| gaacctcctc tcatcccctt catgcctttg ctcattaaag atatgacatt tactcatgag | 3540 |
| gggaacaaga cgttcattga caatctagta aactttgaaa aaatgcgcat gattgcaaat | 3600 |
| acggccagaa cagtgagata ctacaggagc caacccttca atcctgatgc agctcaagct | 3660 |
| aataagaacc atcaggatgt ccggagttat gtacggcaat taaatgtgat tgacaaccag | 3720 |
| agaactttat cacagatgtc acacagatta gagcctcgtc gacca | 3765 |

<210> SEQ ID NO 55
<211> LENGTH: 3783
<212> TYPE: DNA
<213> ORGANISM: Artificial Sequence
<220> FEATURE:
<223> OTHER INFORMATION: Synthetic

<400> SEQUENCE: 55

| | |
|---|---|
| atggtcgctg cgcacgctgc ccattcttcc tcctctgccg agtggatcgc ctgcctggat | 60 |
| aaaagaccac tggagcgatc cagcgaagat gtggatataa tcttcactcg actgaaagaa | 120 |
| gttaaagctt ttgagaaatt tcacccaaat ctccttcatc agatttgctt atgtggttat | 180 |
| tatgagaatc tggaaaaggg aataacatta tttcgccagg gtgatattgg aacaaactgg | 240 |
| tatgctgtcc tggcagggtc tttggatgtt aaagtatctg agaccagcag tcaccaggat | 300 |
| gctgtgacca tctgtaccct gggaattggg acggcctttg agagtccat tctggacaac | 360 |
| acaccccgcc atgcaaccat cgttaccagg agagcagtg aactgctccg catcgagcag | 420 |
| aaggacttca aggcactatg ggagaaatat cgacagtata tggcaggact tctggctcct | 480 |
| ccttatggtg ttatggaaac gggctctaac aatgacagga ttcctgacaa ggagaacaca | 540 |
| cctctcattg aacctcacgt tcctcttcgt cctgctaaca ccattaccaa ggtcccttca | 600 |
| gagaagatcc tcagagctgg aaaaatttta cgaaatgcca ttctctctcg agcacctcac | 660 |
| atgataagag atagaaaata ccacctaaag acatacagac aatgctgtgt gggaactgaa | 720 |
| ctggtggact ggatgatgca gcagacacca tgtgttcact cccggactca agctgttggc | 780 |
| atgtggcaag tcctgttaga agatggtgtt ctcaaccacg tggaccagga gcaccatttc | 840 |
| caagacaaat atttattcta tcgatttctg gatgatgagc acgaggatgc ccctttgcct | 900 |
| actgaggagg agaagaagga gtgtgatgag gagctccagg acaccatgct gctgctgtca | 960 |
| cagatgggcc ccgacgccca catgaggatg atccttcgca aaccacctgg ccagaggact | 1020 |
| gtggatgacc tagagattat ctatgaggag cttcttcata ttaaagcctt atcccatctt | 1080 |
| tctaccacag tgaaacgaga gttagcaggt gttctcattt ttgagtctca cgccaaagga | 1140 |
| gggactgtgt tgtttaacca gggggaagaa ggtacctcct ggtacattat tctaaaagga | 1200 |
| tcagtgaatg tagtcattta cggcaagggt gtggtctgca ccctgcatga aggagatgac | 1260 |
| ttcggcaagt tagcactagt gaatgatgcc ccacgagctg cctctatcgt cttacgagaa | 1320 |
| gataactgcc atttcttaag agtagacaag gaggatttca accggatcct aagggacgtg | 1380 |
| ctcgagaacg tctatatcaa ggccgacaag cagaagaacg catcaaggc gaacttcaag | 1440 |
| atccgccaca acatcgagga cggcggcgt cagctcgcct accactacca gcagaacacc | 1500 |
| cccatcggcg acggccccgt gctgctgccc gacaaccact acctgagcgt gcagtccata | 1560 |
| ctttcgaaag accccaacga gaagcgcgat cacatggtcc tgctggagtt cgtaaccgcc | 1620 |
| cccgggatca ctctcggcat ggacgagctg tacaagggcg gtaccggagg gagcatggtg | 1680 |
| agcaagggcg aggagctgtt caccggggtg gtgcccatcc aggtcgagct ggacggcgac | 1740 |

```
gtaaacggcc acaagttcag cgtgtccggc gagggtgagg gcgatgccac ctacggcaag    1800
ctgaccctga agttcatctg caccaccggc aagctgcccg tgccctggcc caccctcgtg    1860
accaccctga cctacggcgt gcagtgcttc agccgctacc ccgaccacat gaagcagcac    1920
gacttcttca gtccgccat gcccgaaggc tacatccagg agcgcaccat cttcttcaag    1980
gacgacggca actacaagac ccgcgccgag gtgaagttcg agggcgacac cctggtgaac    2040
cgcatcgagc tgaagggcat cgacttcaag gaggacggca acatcctggg gcacaagctg    2100
gagtacaaca cgcgtatcct aagggacgtg gaggcgaata cagtcagact taaagaacat    2160
gaccaagatg tcttggtgct ggagaaggtc ccagcaggga acagagcttc taatcaagga    2220
aactcacagc ctcagcaaaa gtatactgtg atgtcaggaa cacctgaaaa aattttagag    2280
cattttctag aaacaatacg ccttgaggca actttaaatg aagcaacaga ttctgtttta    2340
aatgacttta ttatgatgca ctgtgttttt atgccaaata cccagctttg cccggcactg    2400
gtggcccact accacgcaca gccttcacaa ggtacagaac aggagaaaat ggattatgcc    2460
ctcaacaata gaggcgagt catccgcctg gttctacagt gggctgccat gtatggagac    2520
ctcctgcaag aggatgacgt gtctatggcc ttcctggagg agttttatgt atctgtatca    2580
gatgatgccc ggatgattgc tgccctcaag gagcaactgc cagagttgga gaagattgtc    2640
aagcaaatct cagaagatgc aaaggcacca caaagaagc acaaggttct tttgcaacag    2700
ttcaatacgg gcgatgagag agcccagaag cgccagccta ccgcggctc tgatgaagtt    2760
ctgtttaagg tctattgcat ggaccccacc tacacaacca ttcgggtgcc agtggccact    2820
tcggtgaagg aagtcatcag tgcagttgcc gacaagctgg gctccgggga gggcctgatc    2880
atagtcaaga tgagttccgg aggagaaaag gtggtgctca aacctaatga tgtttcagta    2940
tttatgacgc tcaccattaa tggacgcctg tttgcttgcc cgcgagagca attcgattca    3000
ctgactccct taccagaaca ggaaggccca actgttggaa cagtgggaac ttttgaactg    3060
atgagctcca agatttagc ataccagatg acaatttatg attgggaact cttcaactgc    3120
gtgcatgagc tggagctaat ctatcacaca tttggaaggc ataattttaa aaagaccaca    3180
gcaaacttgg atttgttcct gaggagattt aatgaaattc agttttgggt cgtcactgag    3240
atctgccttt gttctcagct cagcaagcgt gttcagctat taaaaaatt tattaagata    3300
gcagcccact gtaaggagta taaaaatctg aattccttt ttgccatcgt catgggacta    3360
agtaacgttg ctgtgagccg cttggcacta acgtgggaga actgccaag caagttcaag    3420
aagttctatg cggagtttga agtttaatg gacccttcaa ggaaccacag ggcctacagg    3480
ctgacagtag ctaagctgga acctcctctc atcccccttca tgcctttgct cattaaagat    3540
atgacattta ctcatgaggg gaacaagacg ttcattgaca atctagtaaa cttttgaaaaa    3600
atgcgcatga ttgcaaatac ggccagaaca gtgagatact acaggagcca acccttcaat    3660
cctgatgcag ctcaagctaa taagaaccat caggatgtcc ggagttatgt acggcaatta    3720
aatgtgattg acaaccagag aactttatca cagatgtcac acagattaga gcctcgtcga    3780
cca                                                                  3783
```

<210> SEQ ID NO 56
<211> LENGTH: 2103
<212> TYPE: DNA
<213> ORGANISM: Artificial Sequence
<220> FEATURE:
<223> OTHER INFORMATION: Synthetic

<400> SEQUENCE: 56

```
atggtcgctg cgcacgctgc ccattcttcc tcctctgccg agtggatcgc ctgcctggat    60
aaaagaccac tggagcgatc cagcgaagat gtggatataa tcttcactcg actgaaagaa   120
gttaaagctt tgagaaatt tcacccaaat ctccttcatc agatttgctt atgtggttat   180
tatgagaatc tggaaaaggg aataacatta tttcgccagg gtgatattgg aacaaactgg   240
tatgctgtcc tggcagggtc tttggatgtt aaagtatctg agaccagcag tcaccaggat   300
gctgtgacca tctgtaccct gggaattggg acggcctttg gagagtccat tctgacaac   360
acaccccgcc atgcaaccat cgttaccagg gagagcagtg aactgctccg catcgagcag   420
aaggacttca aggcactatg ggagaaatat cgacagtata tggcaggact tctggctcct   480
ccttatggtg ttatggaaac gggctctaac aatgacagga ttcctgacaa ggagaacaca   540
cctctcattg aacctcacgt tcctcttcgt cctgctaaca ccattaccaa ggtcccttca   600
gagaagatcc tcagagctgg aaaaatttta cgaaatgcca ttctctctcg agcacctcac   660
atgataagag atagaaaata ccacctaaag acatacagac aatgctgtgt gggaactgaa   720
ctggtggact ggatgatgca gcagacacca tgtgttcact cccggactca agctgttggc   780
atgtggcaag tcctgttaga agatggtgtt ctcaaccacg tggaccagga gcaccatttc   840
caagacaaat atttattcta tcgatttctg gatgatgagc acgaggatgc ccctttgcct   900
actgaggagg agaagaagga gtgtgatgag gagctccagg acaccatgct gctgctgtca   960
cagatgggcc ccgacgccca catgaggatg atccttcgca aaccacctgg ccagaggact  1020
gtggatgacc tagagattat ctatgaggag cttcttcata ttaaagcctt atcccatctt  1080
tctaccacag tgaaacgaga gttagcaggt gttctcattt ttgagtctca cgccaaagga  1140
gggactgtgt tgtttaacca gggggaagaa ggtacctcct ggtacattat tctaaaagga  1200
tcagtgaatg tagtcattta cggcaagggt gtggtctgca ccctgcatga aggagatgac  1260
ttcggcaagt tagcactagt gaatgatgcc ccacgagctg cctctatcgt cttacgagaa  1320
gataactgcc atttcttaag agtagacaag gaggatttca accggatcct aaggcgtgcg  1380
aacgtctata tcaaggccga caagcagaag aacggcatca aggcgaactt caagatccgc  1440
cacaacatcg aggacggcgg cgtgcagctc gcctaccact accagcagaa cacccccatc  1500
ggcgacggcc ccgtgctgct gcccgacaac cactacctga gcgtgcagtc catactttcg  1560
aaagacccca acgagaagcg cgatcacatg gtcctgctgg agttcgtgac cgccgccggg  1620
atcactctcg gcatggacga gctgtacaag ggcggtaccg agggagcat ggtgagcaag  1680
ggcgaggagc tgttcaccgg ggtggtgccc atccaggtcg agctggacgg cgacgtaaac  1740
ggccacaagt tcagcgtgtc cggcgagggt gagggcgatg ccacctacgg caagctgacc  1800
ctgaagttca tctgcaccac cggcaagctg cccgtgccct ggcccaccct cgtgaccacc  1860
ctgacctacg gcgtgcagtg cttcagccgc taccccgacc acatgaagca gcacgacttc  1920
ttcaagtccg ccatgcccga aggctacatc caggagcgca ccatcttctt caaggacgac  1980
ggcaactaca agacccgcgc cgaggtgaag ttcgagggcg acaccctggt gaaccgcatc  2040
gagctgaagg gcatcgactt caaggaggac ggcaacatcc tggggcacaa gctggagtac  2100
aac                                                                2103
```

<210> SEQ ID NO 57
<211> LENGTH: 3768
<212> TYPE: DNA
<213> ORGANISM: Artificial Sequence
<220> FEATURE:

<223> OTHER INFORMATION: Synthetic

<400> SEQUENCE: 57

| | |
|---|---|
| atggtcgctg cgcacgctgc ccattcttcc tcctctgccg agtggatcgc ctgcctggat | 60 |
| aaaagaccac tggagcgatc cagcgaagat gtggatataa tcttcactcg actgaaagaa | 120 |
| gttaaagctt ttgagaaatt tcacccaaat ctccttcatc agatttgctt atgtggttat | 180 |
| tatgagaatc tggaaaaggg aataacatta tttcgccagg gtgatattgg aacaaactgg | 240 |
| tatgctgtcc tggcagggtc tttggatgtt aaagtatctg agaccagcag tcaccaggat | 300 |
| gctgtgacca tctgtaccct gggaattggg acggcctttg agagtccat tctggacaac | 360 |
| acaccccgcc atgcaaccat cgttaccagg gagagcagtg aactgctccg catcgagcag | 420 |
| aaggacttca aggcactatg ggagaaatat cgacagtata tggcaggact tctggctcct | 480 |
| ccttatggtg ttatggaaac gggctctaac aatgacagga ttcctgacaa ggagaacaca | 540 |
| cctctcattg aacctcacgt tcctcttcgt cctgctaaca ccattaccaa ggtcccttca | 600 |
| gagaagatcc tcagagctgg aaaaatttta cgaaatgcca ttctctctcg agcacctcac | 660 |
| atgataagag atagaaaata ccacctaaag acatacagac aatgctgtgt gggaactgaa | 720 |
| ctggtggact ggatgatgca gcagacacca tgtgttcact cccggactca agctgttggc | 780 |
| atgtggcaag tcctgttaga agatggtgtt ctcaaccacg tggaccagga gcaccatttc | 840 |
| caagacaaat atttattcta tcgatttctg gatgatgagc acgaggatgc ccctttgcct | 900 |
| actgaggagg agaagaagga gtgtgatgag gagctccagg acaccatgct gctgctgtca | 960 |
| cagatgggcc ccgacgccca catgaggatg atccttcgca aaccacctgg ccagaggact | 1020 |
| gtggatgacc tagagattat ctatgaggag cttcttcata ttaaagcctt atcccatctt | 1080 |
| tctaccacag tgaaacgaga gttagcaggt gttctcattt ttgagtctca cgccaaagga | 1140 |
| gggactgtgt tgtttaacca gggggaagaa ggtacctcct ggtacattat tctaaaagga | 1200 |
| tcagtgaata tagtcattta cggcaagggt gtggtctgca ccctgcatga aggagatgac | 1260 |
| ttcggcaagt tagcactagt gaatgatgcc ccacgagctg cctctatcgt cttacgagaa | 1320 |
| gataactgcc atttcttaag agtagacaag gaggatttca accggatcct aagggacgtg | 1380 |
| gaggcgaatc tcgagaacgt ctatatcaag gccgacaagc agaagaacgg catcaaggcg | 1440 |
| aacttcaaga tccgccacaa catcgaggac ggcggcgtgc agctcgccta ccactaccag | 1500 |
| cagaacaccc ccatcggcga cggccccgtg ctgctgcccg acaaccacta cctgagcgtg | 1560 |
| cagtccatac tttcgaaaga ccccaacgag aagcgcgatc acatggtcct gctggagttc | 1620 |
| gtgaccgccg ccgggatcac tctcggcatg gacgagctgt acaagggcgg taccggaggg | 1680 |
| agcatggtga gcaagggcga ggagctgttc accggggtgg tgcccatcca ggtcgagctg | 1740 |
| gacggcgacg taaacggcca aagttcagc gtgtccggcg agggtgaggg cgatgccacc | 1800 |
| tacggcaagc tgaccctgaa gttcatctgc accaccggca agctgcccgt gccctggccc | 1860 |
| accctcgtga ccaccctgac ctacggcgtg cagtgcttca gccgctaccc cgaccacatg | 1920 |
| aagcagcacg acttcttcaa gtccgccatg cccgaaggct acatccagga gcgcaccatc | 1980 |
| ttcttcaagg acgacggcaa ctacaagacc cgcgccgagg tgaagttcga gggcgacacc | 2040 |
| ctggtgaacc gcatcgagct gaagggcatc gacttcaagg aggacggcaa catcctgggg | 2100 |
| cacaagctgg agtacaacac gcgtacagtc agacttaaag aacatgacca agatgtcttg | 2160 |
| gtgctggaga aggtcccagc agggaacaga gcttctaatc aaggaaactc acagcctcag | 2220 |
| caaaagtata ctgtgatgtc aggaacacct gaaaaaattt tagagcattt tctagaaaca | 2280 |

```
atacgccttg aggcaacttt aaatgaagca acagattctg ttttaaatga ctttattatg    2340
atgcactgtg tttttatgcc aaatacccag ctttgcccgg cactggtggc ccactaccac    2400
gcacagcctt cacaaggtac agaacaggag aaaatggatt atgccctcaa caataagagg    2460
cgagtcatcc gcctggttct acagtgggct gccatgtatg agacctcct gcaagaggat     2520 gacgtgtcta tggccttcct ggaggagttt tatgtatctg tatcagatga tgcccggatg    2580
attgctgccc tcaaggagca actgccagag ttggagaaga ttgtcaagca aatctcagaa    2640
gatgcaaagg caccacaaaa gaagcacaag gttcttttgc aacagttcaa tacgggcgat    2700
gagagagccc agaagcgcca gcctatccgc ggctctgatg aagttctgtt taaggtctat    2760
tgcatggacc ccacctacac aaccattcgg gtgccagtgg ccacttcggt gaaggaagtc    2820
atcagtgcag ttgccgacaa gctgggctcc ggggagggcc tgatcatagt caagatgagt    2880
tccggaggag aaaaggtggt gctcaaacct aatgatgttt cagtatttat gacgctcacc    2940
attaatggac gcctgtttgc ttgcccgcga gagcaattcg attcactgac tcccttacca    3000
gaacaggaag gcccaactgt tggaacagtg ggaacttttg aactgatgag ctccaaagat    3060
ttagcatacc agatgacaat ttatgattgg gaactcttca actgcgtgca tgagctggag    3120
ctaatctatc acacatttgg aaggcataat tttaaaaaga ccacagcaaa cttggatttg    3180
ttcctgagga gatttaatga aattcagttt gggtcgtca ctgagatctg cctttgttct     3240
cagctcagca agcgtgttca gctattaaaa aaatttatta agatagcagc ccactgtaag    3300
gagtataaaa atctgaattc cttttttgcc atcgtcatgg gactaagtaa cgttgctgtg    3360
agccgcttgg cactaacgtg ggagaaactg ccaagcaagt tcaagaagtt ctatgcggag    3420
tttgaaagtt taatggaccc ttcaaggaac cacagggcct acaggctgac agtagctaag    3480
ctggaacctc ctctcatccc cttcatgcct ttgctcatta agatatgac atttactcat     3540 gaggggaaca agacgttcat tgacaatcta gtaaactttg aaaaaatgcg catgattgca    3600
aatacggcca gaacagtgag atactacagg agccaaccct tcaatcctga tgcagctcaa    3660
gctaataaga accatcagga tgtccggagt tatgtacggc aattaaatgt gattgacaac    3720
cagagaactt tatcacagat gtcacacaga ttagagcctc gtcgacca               3768
```

<210> SEQ ID NO 58
<211> LENGTH: 3765
<212> TYPE: DNA
<213> ORGANISM: Artificial Sequence
<220> FEATURE:
<223> OTHER INFORMATION: Synthetic

<400> SEQUENCE: 58

```
atggtcgctg cgcacgctgc ccattcttcc tcctctgccg agtggatcgc ctgcctggat      60
aaaagaccac tggagcgatc cagcgaagat gtggatataa tcttcactcg actgaaagaa    120
gttaaagctt tgagaaatt tcacccaaat ctccttcatc agatttgctt atgtggttat     180
tatgagaatc tggaaaaggg aataacatta tttcgccagg gtgatattgg aacaaactgg    240
tatgctgtcc tggcagggtc tttggatgtt aaagtatctg agaccagcag tcaccaggat    300
gctgtgacca tctgtaccct gggaattggg acggcctttg agagtccat ctggacaac     360 acaccccgcc atgcaaccat cgttaccagg agagcagtg aactgctccg catcgagcag    420
aaggacttca aggcactatg ggagaaatat cgacagtata tggcaggact tctggctcct    480
ccttatggtg ttatggaaac gggctctaac aatgacagga ttcctgacaa ggagaacaca    540
```

```
cctctcattg aacctcacgt tcctcttcgt cctgctaaca ccattaccaa ggtcccttca    600
gagaagatcc tcagagctgg aaaaatttta cgaaatgcca ttctctctcg agcacctcac    660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc ccctttgcct    900
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aaggctcgag   1380
aacgtctata tcaaggccga caagcagaag aacggcatca aggcgaactt caagatccgc   1440
cacaacatcg aggacggcgg cgtgcagctc gcctaccact accagcagaa cacccccatc   1500
ggcgacggcc ccgtgctgct gcccgacaac cactacctga gcgtgcagtc catactttcg   1560
aaagacccca acgagaagcg cgatcacatg gtcctgctgg agttcgtgac cgccgccggg   1620
atcactctcg gcatggacga gctgtacaag gcggtaccga gggagcat ggtgagcaag   1680 ggcgaggagc tgttcaccgg ggtggtgccc atccaggtcg agctggacgg cgacgtaaac   1740
ggccacaagt tcagcgtgtc cggcgagggt gagggcgatg ccacctacgg caagctgacc   1800
ctgaagttca tctgcaccac cggcaagctg cccgtgccct ggcccaccct cgtgaccacc   1860
ctgacctacg gcgtgcagtg cttcagccgc taccccgacc acatgaagca gcacgacttc   1920
ttcaagtccg ccatgcccga aggctacatc caggagcgca ccatcttctt caaggacgac   1980
ggcaactaca agacccgcgc cgaggtgaag ttcgagggcg acaccctggt gaaccgcatc   2040
gagctgaagg gcatcgactt caaggaggac ggcaacatcc tggggcacaa gctggagtac   2100
aacacgcgtg tggaggcgaa tacagtcaga cttaaagaac atgaccaaga tgtcttggtg   2160
ctggagaagg tcccagcagg gaacagagct tctaatcaag gaaactcaca gcctcagcaa   2220
aagtatactg tgatgtcagg aacacctgaa aaaattttag agcatttct  agaaacaata   2280 cgccttgagg caactttaaa tgaagcaaca gattctgttt taaatgactt tattatgatg   2340
cactgtgttt ttatgccaaa tacccagctt gccccggcac tggtgggcca ctaccacgca   2400
cagccttcac aaggtacaga acaggagaaa atggattatg ccctcaacaa taagaggcga   2460
gtcatccgcc tggttctaca gtgggctgcc atgtatggag acctcctgca agaggatgac   2520
gtgtctatgg ccttcctgga ggagttttat gtatctgtat cagatgatgc ccggatgatt   2580
gctgccctca aggagcaact gccagagttg gagaagattg tcaagcaaat ctcagaagat   2640
gcaaaggcac cacaaaagaa gcacaaggtt cttttgcaac agttcaatac gggcgatgag   2700
agagcccaga agcgccagcc tatccgcggc tctgatgaag ttctgtttaa ggtctattgc   2760
atggacccca cctacacaac cattcgggtg ccagtggcca cttcggtgaa ggaagtcatc   2820
agtgcagttg ccgacaagct gggctccggg gagggcctga tcatagtcaa gatgagttcc   2880
ggaggagaaa aggtggtgct caaacctaat gatgtttcag tatttatgac gctcaccatt   2940
```

| | |
|---|---|
| aatggacgcc tgtttgcttg cccgcgagag caattcgatt cactgactcc cttaccagaa | 3000 |
| caggaaggcc caactgttgg aacagtggga acttttgaac tgatgagctc caaagattta | 3060 |
| gcataccaga tgacaattta tgattgggaa ctcttcaact gcgtgcatga gctggagcta | 3120 |
| atctatcaca catttggaag gcataatttt aaaaagacca cagcaaactt ggatttgttc | 3180 |
| ctgaggagat ttaatgaaat tcagttttgg gtcgtcactg agatctgcct ttgttctcag | 3240 |
| ctcagcaagc gtgttcagct attaaaaaaa tttattaaga tagcagccca ctgtaaggag | 3300 |
| tataaaaatc tgaattcctt ttttgccatc gtcatgggac taagtaacgt tgctgtgagc | 3360 |
| cgcttggcac taacgtggga gaaactgcca agcaagttca agaagttcta tgcggagttt | 3420 |
| gaaagtttaa tggacccttc aaggaaccac agggcctaca ggctgacagt agctaagctg | 3480 |
| gaacctcctc tcatcccctt catgcctttg ctcattaaag atatgacatt tactcatgag | 3540 |
| gggaacaaga cgttcattga caatctagta aactttgaaa aaatgcgcat gattgcaaat | 3600 |
| acggccagaa cagtgagata ctacaggagc caacccttca atcctgatgc agctcaagct | 3660 |
| aataagaacc atcaggatgt ccggagttat gtacggcaat taaatgtgat tgacaaccag | 3720 |
| agaactttat cacagatgtc acacagatta gagcctcgtc gacca | 3765 |

<210> SEQ ID NO 59
<211> LENGTH: 3776
<212> TYPE: DNA
<213> ORGANISM: Artificial Sequence
<220> FEATURE:
<223> OTHER INFORMATION: Synthetic

<400> SEQUENCE: 59

| | |
|---|---|
| atggtcgctg cgcacgctgc ccattcttcc tcctctgccg agtggatcgc ctgcctggat | 60 |
| aaaagaccac tggagcgatc cagcgaagat gtggatataa tcttcactcg actgaaagaa | 120 |
| gttaaagctt ttgagaaatt tcacccaaat ctccttcatc agatttgctt atgtggttat | 180 |
| tatgagaatc tggaaaaggg aataacatta tttcgccagg gtgatattgg aacaaactgg | 240 |
| tatgctgtcc tggcagggtc tttggatgtt aaagtatctg agaccagcag tcaccaggat | 300 |
| gctgtgacca tctgtaccct gggaattggg acggcctttg gagtccat tctggacaac | 360 |
| acacccgcc atgcaaccat cgttaccagg gagagcagtg aactgctccg catcgagcag | 420 |
| aaggacttca aggcactatg ggagaaatat cgacagtata tggcaggact tctggctcct | 480 |
| ccttatggtg ttatggaaac gggctctaac aatgacagga ttcctgacaa ggagaacaca | 540 |
| cctctcattg aacctcacgt tcctcttcgt cctgctaaca ccattaccaa ggtcccttca | 600 |
| gagaagatcc tcagagctgg aaaaatttta cgaaatgcca ttctctctcg agcacctcac | 660 |
| atgataagag atagaaaata ccacctaaag acatacagac aatgctgtgt gggaactgaa | 720 |
| ctggtggact ggatgatgca gcagacacca tgtgttcact cccggactca agctgttggc | 780 |
| atgtggcaag tcctgttaga agatggtgtt ctcaaccacg tggaccagga gcaccatttc | 840 |
| caagacaaat atttattcta tcgatttctg gatgatgagc acgaggatgc ccctttgcct | 900 |
| actgaggagg agaagaagga gtgtgatgag gagctccagg acaccatgct gctgctgtca | 960 |
| cagatgggcc ccgacgccca catgaggatg atccttcgca aaccacctgg ccagaggact | 1020 |
| gtggatgacc tagagattat ctatgaggag cttcttcata ttaaagcctt atcccatctt | 1080 |
| tctaccacag tgaaacgaga gttagcaggt gttctcattt ttgagtctca cgccaaagga | 1140 |
| gggactgtgt tgtttaacca gggggaagaa ggtacctcct ggtacattat tctaaaagga | 1200 |

```
tcagtgaatg tagtcattta cggcaagggt gtggtctgca ccctgcatga aggagatgac    1260
ttcggcaagt tagcactagt gaatgatgcc ccacgagctg cctctatcgt cttacgagaa    1320
gataactgcc atttcttaag agtagacaag gaggatttca accggatcct aaggctcgag    1380
aacgtctata tcaaggccga caagcagaag aacggcatca aggcgaactt caagatccgc    1440
cacaacatcg aggacggcgg cgtgcagctc gcctaccact accagcagaa cacccccatc    1500
ggcgacggcc ccgtgctgct gcccgacaac cactacctga gcgtgcagtc catactttcg    1560
aaagacccca acgagaagcg cgatcacatg gtcctgctgg agttcgtgac cgccgccggg    1620
atcactctcg gcatggacga gctgtacaag gcggtaccg agggagcat ggtgagcaag    1680 ggcgaggagc tgttcaccgg ggtggtgccc atccaggtcg agctggacgg cgacgtaaac    1740
ggccacaagt tcagcgtgtc cggcgagggt gagggcgatg ccacctacgg caagctgacc    1800
ctgaagttca tctgcaccac cggcaagctg cccgtgccct ggcccaccct cgtgaccacc    1860
ctgacctacg gcgtgcagtg cttcagccgc taccccgacc acatgaagca gcacgacttc    1920
ttcaagtccg ccatgcccga aggctacatc caggagcgca ccatcttctt caaggacgac    1980
ggcaactaca agacccgcgc cgaggtgaag ttcgagggcg acaccctggt gaaccgcatc    2040
gagctgaagg gcatcgactt caaggaggac ggcaacatcc tggggcacaa gctggagtac    2100
aacacgcgta tcctaaggga cgtggaggcg aatacagtca gacttaaaga acatgaccaa    2160
gatgtcttgg tgctggagaa ggtcccagca gggaacagag cttctaatca aggaaactca    2220
cagcctcagc aaaagtatac tgtgatgtca ggaacacctg aaaaaatttt agagcatttt    2280
ctagaaacaa tacgccttga ggcaacttta aatgaagcaa cagattctgt tttaaatgac    2340
tttattatga tgcactgtgt ttttatgcca aatacccagc tttgcccggc actggtggcc    2400
cactaccacg cacagccttc acaaggtaca gaacaggaga aaatggatta tgccctcaac    2460
aataagaggc gagtcatccg cctggttcta cagtgggctg ccatgtatgg agacctcctg    2520
caagaggatg acgtgtctat ggccttcctg gaggagtttt atgtatctgt atcagatgat    2580
gcccggatga ttgctgccct caaggagcaa ctgccagagt tggagaagat tgtcaagcaa    2640
atctcagaag atgcaaaggc accacaaaag aagcacaagg ttcttttgca acagttcaat    2700
acgggcgatg agagagccca gaagcgccag cctatccgcg gctctgatga agttctgttt    2760
aaggtctatt gcatggaccc cacctacaca accattcggg tgccagtggc cacttcggtg    2820
aaggaagtca tcagtgcagt tgccgacaag ctgggctccg gggagggcct gatcatagtc    2880
aagatgagtt ccggaggaga aaaggtggtg ctcaaaccta atgatgtttc agtatttatg    2940
acgctcacca ttaatggacg cctgtttgct tgcccgcgag agcaattcga ttcactgact    3000
cccttaccag aacaggaagg cccaactgtt ggaacagtgg gaacttttga actgatgagc    3060
tccaaagatt tagcatacca gatgacaatt tatgattggg aactcttcaa ctgcgtgcat    3120
gagctggagc taatctatca cacatttgga aggcataatt ttaaaaagac cacagcaaac    3180
ttggatttgt tcctgaggag atttaatgaa attcagtttt gggtcgtcac tgagatctgc    3240
ctttgttctc agctcagcaa gcgtgttcag ctattaaaaa aatttattaa gatagcagcc    3300
cactgtaagg agtataaaaa tctgaattcc tttttttgcca tcgtcatggg actaagtaac    3360
gttgctgtga gccgcttggc actaacgtgg gagaaactgc caagcaagtt caagaagttc    3420
tatgcggagt ttgaaagttt aatggaccct tcaaggaacc acagggccta caggctgaca    3480
gtagctaagc tggaacctcc tctcatcccc ttcatgcctt tgctcattaa agatatgaca    3540
tttactcatg aggggaacaa gacgttcatt gacaatctag taaactttga aaaaatgcgc    3600
```

| | |
|---|---|
| atgattgcaa atacggccag aacagtgaga tactacagga gccaaccctt caatcctgat | 3660 |
| gcagctcaag ctaataagaa ccatcaggat gtccggagtt atgtacggca attaaatgtg | 3720 |
| attgacaacc agagaacttt atcacagatg tcacacagat tagagcctcg tcgacc | 3776 |

<210> SEQ ID NO 60
<211> LENGTH: 3756
<212> TYPE: DNA
<213> ORGANISM: Artificial Sequence
<220> FEATURE:
<223> OTHER INFORMATION: Synthetic

<400> SEQUENCE: 60

| | |
|---|---|
| atggtcgctg cgcacgctgc ccattcttcc tcctctgccg agtggatcgc ctgcctggat | 60 |
| aaaagaccac tggagcgatc cagcgaagat gtggatataa tcttcactcg actgaaagaa | 120 |
| gttaaagctt ttgagaaatt tcacccaaat ctccttcatc agatttgctt atgtggttat | 180 |
| tatgagaatc tggaaaaggg aataacatta tttcgccagg gtgatattgg aacaaactgg | 240 |
| tatgctgtcc tggcagggtc tttggatgtt aaagtatctg agaccagcag tcaccaggat | 300 |
| gctgtgacca tctgtaccct gggaattggg acggcctttg agagtccatc tctgacaac | 360 |
| acaccccgcc atgcaaccat cgttaccagg agagcagtg aactgctccg catcgagcag | 420 |
| aaggacttca aggcactatg ggagaaatat cgacagtata tggcaggact tctggctcct | 480 |
| ccttatggtg ttatggaaac gggctctaac aatgacagga ttcctgacaa ggagaacaca | 540 |
| cctctcattg aacctcacgt tcctcttcgt cctgctaaca ccattaccaa ggtcccttca | 600 |
| gagaagatcc tcagagctgg aaaaatttta cgaaatgcca ttctctctcg agcacctcac | 660 |
| atgataagag atagaaaata ccacctaaag acatacagac aatgctgtgt gggaactgaa | 720 |
| ctggtggact ggatgatgca gcagacacca tgtgttcact cccggactca agctgttggc | 780 |
| atgtggcaag tcctgttaga agatggtgtt ctcaaccacg tggaccagga gcaccatttc | 840 |
| caagacaaat atttattcta tcgatttctg gatgatgagc acgaggatgc ccctttgcct | 900 |
| actgaggagg agaagaagga gtgtgatgag gagctccagg acaccatgct gctgctgtca | 960 |
| cagatgggcc ccgacgccca catgaggatg atccttcgca aaccacctgg ccagaggact | 1020 |
| gtggatgacc tagagattat ctatgaggag cttcttcata ttaaagcctt atcccatctt | 1080 |
| tctaccacag tgaaacgaga gttagcaggt gttctcattt ttgagtctca cgccaaagga | 1140 |
| gggactgtgt tgtttaacca gggggaagaa ggtacctcct ggtacattat tctaaaagga | 1200 |
| tcagtgaatg tagtcattta cggcaagggt gtggtctgca ccctgcatga aggagatgac | 1260 |
| ttcggcaagt tagcactagt gaatgatgcc ccacgagctg cctctatcgt cttacgagaa | 1320 |
| gataactgcc atttcttaag agtagacaag gaggatttca accggatcct aaggctcgag | 1380 |
| aacgtctata tcaaggccga caagcagaag aacggcatca aggcgaactt caagatccgc | 1440 |
| cacaacatcg aggacggcgg cgtgcagctc gcctaccact accagcagaa cacccccatc | 1500 |
| ggcgacggcc ccgtgctgct gcccgacaac cactacctga gcgtgcagtc catactttcg | 1560 |
| aaagacccca acgagaagcg cgatcacatg gtcctgctgg agttcgtgac cgccgccggg | 1620 |
| atcactctcg gcatggacga gctgtacaag gcggtaccg agggagcat ggtgagcaag | 1680 |
| ggcgaggagc tgttcaccgg ggtggtgccc atccaggtcg agctggacgg cgacgtaaac | 1740 |
| ggccacaagt tcagcgtgtc cggcgagggt gagggcgatg ccacctacgg caagctgacc | 1800 |
| ctgaagttca tctgcaccac cggcaagctg cccgtgccct ggcccaccct cgtgaccacc | 1860 |

```
ctgacctacg gcgtgcagtg cttcagccgc taccccgacc acatgaagca gcacgacttc    1920
ttcaagtccg ccatgcccga aggctacatc caggagcgca ccatcttctt caaggacgac    1980
ggcaactaca agacccgcgc cgaggtgaag ttcgagggcg acaccctggt gaaccgcatc    2040
gagctgaagg gcatcgactt caaggaggac ggcaacatcc tggggcacaa gctggagtac    2100
aacacgcgta atacagtcag acttaaagaa catgaccaag atgtcttggt gctggagaag    2160
gtcccagcag ggaacagagc ttctaatcaa ggaaactcac agcctcagca aaagtatact    2220
gtgatgtcag gaacacctga aaaaatttta gagcattttc tagaaacaat acgccttgag    2280 gcaacttta atgaagcaac agattctgtt ttaaatgact ttattatgat gcactgtgtt    2340
tttatgccaa atacccagct ttgcccggca ctggtggccc actaccacgc acagccttca    2400
caaggtacag aacaggagaa aatggattat gccctcaaca ataagaggcg agtcatccgc    2460
ctggttctac agtgggctgc catgtatgga gacctcctgc aagaggatga cgtgtctatg    2520
gccttcctgg aggagtttta tgtatctgta tcagatgatg cccggatgat tgctgccctc    2580
aaggagcaac tgccagagtt ggagaagatt gtcaagcaaa tctcagaaga tgcaaaggca    2640
ccacaaaaga agcacaaggt tcttttgcaa cagttcaata cgggcgatga gagagcccag    2700
aagcgccagc ctatccgcgg ctctgatgaa gttctgtttt aaggtctattg catggacccc    2760 acctacacaa ccattcgggt gccagtggcc acttcggtga aggaagtcat cagtgcagtt    2820
gccgacaagc tgggctccgg ggagggcctg atcatagtca agatgagttc cggaggagaa    2880
aaggtggtgc tcaaacctaa tgatgtttca gtatttatga cgctcaccat taatggacgc    2940
ctgtttgctt gcccgcgaga gcaattcgat tcactgactc ccttaccaga acaggaaggc    3000
ccaactgttg gaacagtggg aacttttgaa ctgatgagct ccaaagattt agcataccag    3060
atgacaattt atgattggga actcttcaac tgcgtgcatg agctggagct aatctatcac    3120
acatttggaa ggcataattt taaaaagacc acagcaaact tggatttgtt cctgaggaga    3180
tttaatgaaa ttcagttttg ggtcgtcact gagatctgcc tttgttctca gctcagcaag    3240
cgtgttcagc tattaaaaaa atttattaag atagcagccc actgtaagga gtataaaaat    3300
ctgaattcct tttttgccat cgtcatggga ctaagtaacg ttgctgtgag ccgcttggca    3360
ctaacgtggg agaaactgcc aagcaagttc aagaagttct atgcggagtt tgaaagttta    3420 atggacccctt caaggaacca cagggcctac aggctgacag tagctaagct ggaacctcct    3480
ctcatcccct tcatgccttt gctcattaaa gatatgacat ttactcatga ggggaacaag    3540
acgttcattg acaatctagt aaactttgaa aaaatgcgca tgattgcaaa tacgccaga    3600 acagtgagat actacaggag ccaacccttc aatcctgatg cagctcaagc taataagaac    3660
catcaggatg tccggagtta tgtacggcaa ttaaatgtga ttgacaacca gagaactta    3720 tcacagatgt cacacagatt agagcctcgt cgacca                              3756

<210> SEQ ID NO 61
<211> LENGTH: 3783
<212> TYPE: DNA
<213> ORGANISM: Artificial Sequence
<220> FEATURE:
<223> OTHER INFORMATION: Synthetic

<400> SEQUENCE: 61
atggtcgctg cgcacgctgc ccattcttcc tcctctgccg agtggatcgc ctgcctggat      60
aaaagaccac tggagcgatc cagcgaagat gtggatataa tcttcactcg actgaaagaa     120
gttaaagctt ttgagaaatt tcacccaaat ctccttcatc agatttgctt atgtggttat     180
```

```
tatgagaatc tggaaaaggg aataacatta tttcgccagg gtgatattgg aacaaactgg    240
tatgctgtcc tggcagggtc tttggatgtt aaagtatctg agaccagcag tcaccaggat    300
gctgtgacca tctgtaccct gggaattggg acggcctttg agagtccat  tctggacaac    360 acaccccgcc atgcaaccat cgttaccagg gagagcagtg aactgctccg catcgagcag    420
aaggacttca aggcactatg ggagaaatat cgacagtata tggcaggact tctggctcct    480
ccttatggtg ttatggaaac gggctctaac aatgacagga ttcctgacaa ggagaacaca    540
cctctcattg aacctcacgt tcctcttcgt cctgctaaca ccattaccaa ggtcccttca    600
gagaagatcc tcagagctgg aaaaatttta cgaaatgcca ttctctctcg agcacctcac    660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc ccctttgcct    900
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcatttta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aaggctcgag   1380
aacgtctata tcaaggccga caagcagaag aacggcatca aggcgaactt caagatccgc   1440
cacaacatcg aggacggcgg cgtgcagctc gcctaccact accagcagaa cacccccatc   1500
ggcgacggcc ccgtgctgct gcccgacaac cactacctga gcgtgcagtc catactttcg   1560
aaagacccca cgagaagcg  cgatcacatg gtcctgctgg agttcgtgac cgccgccggg   1620
atcactctcg gcatggacga gctgtacaag ggcggtaccg gagggagcat ggtgagcaag   1680
ggcgaggagc tgttcaccgg ggtggtgccc atccaggtcg agctggacgg cgacgtaaac   1740
ggccacaagt tcagcgtgtc cggcgagggt gagggcgatg ccacctacgg caagctgacc   1800
ctgaagttca tctgcaccac cggcaagctg cccgtgccct ggcccaccct cgtgaccacc   1860
ctgacctacg gcgtgcagtg cttcagccgc taccccgacc acatgaagca gcacgacttc   1920
ttcaagtccg ccatgcccga aggctacatc caggagcgca ccatcttctt caaggacgac   1980
ggcaactaca agacccgcgc cgaggtgaag ttcgagggcg acaccctggt gaaccgcatc   2040
gagctgaagg gcatcgactt caaggaggac ggcaacatcc tggggcacaa gctggagtac   2100
aacacgcgta accggatcct aagggacgtg gaggcgaata cagtcagact taagaaacat   2160
gaccaagatg tcttggtgct ggagaaggtc ccagcaggga acagagcttc taatcaagga   2220
aactcacagc ctcagcaaaa gtatactgtg atgtcaggaa cacctgaaaa aatttttagag   2280 cattttctag aaacaatacg ccttgaggca actttaaatg aagcaacaga ttctgttta    2340 aatgacttta ttatgatgca ctgtgttttt atgccaaata cccagctttg cccggcactg   2400
gtggcccact accacgcaca gccttcacaa ggtacagaac aggagaaaat ggattatgcc   2460
ctcaacaata gaggcgagt  catccgcctg gttctacagt gggctgccat gtatggagac   2520
```

| | |
|---|---|
| ctcctgcaag aggatgacgt gtctatggcc ttcctggagg agttttatgt atctgtatca | 2580 |
| gatgatgccc ggatgattgc tgccctcaag gagcaactgc cagagttgga gaagattgtc | 2640 |
| aagcaaatct cagaagatgc aaaggcacca caaaagaagc acaaggttct tttgcaacag | 2700 |
| ttcaatacgg gcgatgagag agcccagaag cgccagccta ccgcggctc tgatgaagtt | 2760 |
| ctgtttaagg tctattgcat ggaccccacc tacacaacca ttcgggtgcc agtggccact | 2820 |
| tcggtgaagg aagtcatcag tgcagttgcc gacaagctgg gctccgggga gggcctgatc | 2880 |
| atagtcaaga tgagttccgg aggagaaaag gtggtgctca aacctaatga tgtttcagta | 2940 |
| tttatgacgc tcaccattaa tggacgcctg tttgcttgcc cgcgagca attcgattca | 3000 |
| ctgactccct taccagaaca ggaaggccca actgttggaa cagtgggaac ttttgaactg | 3060 |
| atgagctcca aagatttagc ataccagatg acaatttatg attgggaact cttcaactgc | 3120 |
| gtgcatgagc tggagctaat ctatcacaca tttggaaggc ataattttaa aaagaccaca | 3180 |
| gcaaacttgg atttgttcct gaggagattt aatgaaattc agttttgggt cgtcactgag | 3240 |
| atctgccttt gttctcagct cagcaagcgt gttcagctat taaaaaaatt tattaagata | 3300 |
| gcagcccact gtaaggagta taaaaatctg aattccttt ttgccatcgt catgggacta | 3360 |
| agtaacgttg ctgtgagccg cttggcacta acgtgggaga aactgccaag caagttcaag | 3420 |
| aagttctatg cggagtttga aagttttaatg daccccttcaa ggaaccacag ggcctacagg | 3480 |
| ctgacagtag ctaagctgga acctcctctc atccccttca tgccttgct cattaaagat | 3540 |
| atgacattta ctcatgaggg gaacaagacg ttcattgaca atctagtaaa ctttgaaaaa | 3600 |
| atgcgcatga ttgcaaatac ggccagaaca gtgagatact acaggagcca acccttcaat | 3660 |
| cctgatgcag ctcaagctaa taagaaccat caggatgtcc ggagttatgt acggcaatta | 3720 |
| aatgtgattg acaaccagag aactttatca cagatgtcac acagattaga gcctcgtcga | 3780 |
| cca | 3783 |

<210> SEQ ID NO 62
<211> LENGTH: 3810
<212> TYPE: DNA
<213> ORGANISM: Artificial Sequence
<220> FEATURE:
<223> OTHER INFORMATION: Synthetic

<400> SEQUENCE: 62

| | |
|---|---|
| atggtcgctg cgcacgctgc ccattcttcc tcctctgccg agtggatcgc ctgcctggat | 60 |
| aaaagaccac tggagcgatc cagcgaagat gtggatataa tcttcactcg actgaaagaa | 120 |
| gttaaagctt ttgagaaatt tcacccaaat ctccttcatc agatttgctt atgtggttat | 180 |
| tatgagaatc tggaaaaggg aataacatta tttcgccagg gtgatattgg aacaaactgg | 240 |
| tatgctgtcc tggcagggtc tttggatgtt aaagtatctg agaccagcag tcaccaggat | 300 |
| gctgtgacca tctgtaccct gggaattggg acggcctttg agagtccat tctgacaac | 360 |
| acaccccgcc atgcaaccat cgttaccagg gagagcagta actgctccg catcgagcag | 420 |
| aaggacttca aggcactatg ggagaaatat cgacagtata tggcaggact tctggctcct | 480 |
| ccttatggtg ttatggaaac gggctctaac aatgacagga ttcctgacaa ggagaacaca | 540 |
| cctctcattg aacctcacgt tcctcttcgt cctgctaaca ccattaccaa ggtcccttca | 600 |
| gagaagatcc tcagctggg aaaaattta cgaaatgcca ttctctctcg agcacctcac | 660 |
| atgataagag ataaaaata ccactaaag acatacagac aatgctgtgt gggaactgaa | 720 |
| ctggtggact ggatgatgca gcagacacca tgtgttcact cccggactca agctgttggc | 780 |

```
atgtggcaag tcctgttaga agatggtgtt ctcaaccacg tggaccagga gcaccatttc      840
caagacaaat atttattcta tcgatttctg gatgatgagc acgaggatgc ccctttgcct      900
actgaggagg agaagaagga gtgtgatgag gagctccagg acaccatgct gctgctgtca      960
cagatgggcc ccgacgccca catgaggatg atccttcgca aaccacctgg ccagaggact     1020
gtggatgacc tagagattat ctatgaggag cttcttcata ttaaagcctt atcccatctt     1080
tctaccacag tgaaacgaga gttagcaggt gttctcattt ttgagtctca cgccaaagga     1140
gggactgtgt tgtttaacca gggggaagaa ggtacctcct ggtacattat tctaaaagga     1200
tcagtgaatg tagtcattta cggcaagggt gtggtctgca ccctgcatga aggagatgac     1260
ttcggcaagt tagcactagt gaatgatgcc ccacgagctg cctctatcgt cttacgagaa     1320
gataactgcc atttcttaag agtagacaag gaggatttca accggatcct aagggacgtg     1380
gaggcgaatc tcgagaacgt ctatatcaag gccgacaagc agaagaacgg catcaaggcg     1440
aacttcaaga tccgccacaa catcgaggac ggcggcgtgc agctcgccta ccactaccag     1500
cagaacaccc ccatcggcga cggccccgtg ctgctgcccg acaaccacta cctgagcgtg     1560
cagtccatac tttcgaaaga ccccaacgag aagcgcgatc acatggtcct gctggagttc     1620
gtgaccgccg ccgggatcac tctcggcatg gacgagctgt acaagggcgg taccggaggg     1680
agcatggtga gcaagggcga ggagctgttc accggggtgg tgcccatcca ggtcgagctg     1740
gacggcgacg taaacggcca aagttcagc gtgtccggcg agggtgaggg cgatgccacc     1800
tacggcaagc tgaccctgaa gttcatctgc accaccggca agctgcccgt gccctggccc     1860
accctcgtga ccaccctgac ctacggcgtg cagtgcttca gccgctaccc cgaccacatg     1920
aagcagcacg acttcttcaa gtccgccatg cccgaaggct acatccagga gcgcaccatc     1980
ttcttcaagg acgacggcaa ctacaagacc cgcgccgagg tgaagttcga gggcgacacc     2040
ctggtgaacc gcatcgagct gaagggcatc gacttcaagg aggacggcaa catcctgggg     2100
cacaagctgg agtacaacac gcgtaaggag gatttcaacc ggatcctaag ggacgtggag     2160
gcgaatacag tcagacttaa agaacatgac caagatgtct tggtgctgga aaggtcccca     2220
gcagggaaca gagcttctaa tcaaggaaac tcacagcctc agcaaaagta tactgtgatg     2280
tcaggaacac ctgaaaaaat tttagagcat tttctagaaa caatacgcct tgaggcaact     2340
ttaaatgaag caacagattc tgttttaaat gactttatta tgatgcactg tgttttatg      2400 ccaaataccc agctttgccc ggcactggtg gcccactacc acgcacagcc ttcacaaggt     2460
acagaacagg agaaaatgga ttatgccctc aacaataaga ggcgagtcat ccgcctggtt     2520
ctacagtggg ctgccatgta tggagacctc ctgcaagagg atgacgtgtc tatggccttc     2580
ctggaggagt tttatgtatc tgtatcagat gatgcccgga tgattgctgc cctcaaggag     2640
caactgccag agttggagaa gattgtcaag caaatctcag aagatgcaaa ggcaccacaa     2700
aagaagcaca aggttctttt gcaacagttc aatacgggcg atgagagagc ccagaagcgc     2760
cagcctatcc gcggctctga tgaagttctg tttaaggtct attgcatgga ccccacctac     2820
acaaccattc gggtgccagt ggccacttcg gtgaaggaag tcatcagtgc agttgccgac     2880
aagctgggct ccggggaggg cctgatcata gtcaagatga gttccggagg agaaaaggtg     2940
gtgctcaaac ctaatgatgt ttcagtattt atgacgctca ccattaatgg acgcctgttt     3000
gcttgcccgc gagagcaatt cgattcactg actcccttac cagaacagga aggcccaact     3060
gttggaacag tgggaacttt tgaactgatg agctccaaag atttagcata ccagatgaca     3120
```

| | |
|---|---|
| atttatgatt gggaactctt caactgcgtg catgagctgg agctaatcta tcacacattt | 3180 |
| ggaaggcata attttaaaaa gaccacagca aacttggatt tgttcctgag gagatttaat | 3240 |
| gaaattcagt tttgggtcgt cactgagatc tgcctttgtt ctcagctcag caagcgtgtt | 3300 |
| cagctattaa aaaaatttat taagatagca gcccactgta aggagtataa aaatctgaat | 3360 |
| tcctttttg ccatcgtcat gggactaagt aacgttgctg tgagccgctt ggcactaacg | 3420 |
| tgggagaaac tgccaagcaa gttcaagaag ttctatgcgg agtttgaaag tttaatggac | 3480 |
| ccttcaagga accacagggc ctacaggctg acagtagcta agctggaacc tcctctcatc | 3540 |
| cccttcatgc ctttgctcat taaagatatg acatttactc atgaggggaa caagacgttc | 3600 |
| attgacaatc tagtaaactt tgaaaaaatg cgcatgattg caaatacggc cagaacagtg | 3660 |
| agatactaca ggagccaacc cttcaatcct gatgcagctc aagctaataa gaaccatcag | 3720 |
| gatgtccgga gttatgtacg gcaattaaat gtgattgaca accagagaac tttatcacag | 3780 |
| atgtcacaca gattagagcc tcgtcgacca | 3810 |

<210> SEQ ID NO 63
<211> LENGTH: 3759
<212> TYPE: DNA
<213> ORGANISM: Artificial Sequence
<220> FEATURE:
<223> OTHER INFORMATION: Synthetic

<400> SEQUENCE: 63

| | |
|---|---|
| atggtcgctg cgcacgctgc ccattcttcc tcctctgccg agtggatcgc ctgcctggat | 60 |
| aaaagaccac tggagcgatc cagcgaagat gtggatataa tcttcactcg actgaaagaa | 120 |
| gttaaagctt ttgagaaatt tcacccaaat ctccttcatc agatttgctt atgtggttat | 180 |
| tatgagaatc tggaaaaggg aataacatta tttcgccagg gtgatattgg aacaaactgg | 240 |
| tatgctgtcc tggcagggtc tttggatgtt aaagtatctg agaccagcag tcaccaggat | 300 |
| gctgtgacca tctgtaccct gggaattggg acggcctttg gagagtccat tctggacaac | 360 |
| acaccccgcc atgcaaccat cgttaccagg gagagcagtg aactgctccg catcgagcag | 420 |
| aaggacttca aggcactatg ggagaaatat cgacagtata tggcaggact tctggctcct | 480 |
| ccttatggtg ttatggaaac gggctctaac aatgacagga ttcctgacaa ggagaacaca | 540 |
| cctctcattg aacctcacgt tcctcttcgt cctgctaaca ccattaccaa ggtcccttca | 600 |
| gagaagatcc tcagagctgg aaaaatttta cgaaatgcca ttctctctcg agcacctcac | 660 |
| atgataagag atagaaaata ccacctaaag acatacagac aatgctgtgt gggaactgaa | 720 |
| ctggtggact ggatgatgca gcagacacca tgtgttcact cccggactca agctgttggc | 780 |
| atgtggcaag tcctgttaga agatggtgtt ctcaaccacg tggaccagga gcaccatttc | 840 |
| caagacaaat atttattcta tcgatttctg gatgatgagc acgaggatgc cccttttgcct | 900 |
| actgaggaga gaagaagga gtgtgatgag gagctccagg acaccatgct gctgctgtca | 960 |
| cagatgggcc ccgacgccca catgaggatg atccttcgca aaccacctgg ccagaggact | 1020 |
| gtggatgacc tagagattat ctatgaggag cttcttcata ttaaagcctt atcccatctt | 1080 |
| tctaccacag tgaaacgaga gttagcaggt gttctcattt ttgagtctca cgccaaagga | 1140 |
| gggactgtgt tgtttaacca gggggaagaa ggtacctcct ggtacattat tctaaaagga | 1200 |
| tcagtgaatg tagtcatttta cggcaagggt gtggtctgca ccctgcatga aggagatgac | 1260 |
| ttcggcaagt tagcactagt gaatgatgcc ccacgagctg cctctatcgt cttacgagaa | 1320 |
| gataactgcc atttcttaag agtagacaag gaggatttca accggatcct aagggacgtg | 1380 |

```
ctcgagaacg tctatatcaa ggccgacaag cagaagaacg gcatcaaggc gaacttcaag    1440
atccgccaca acatcgagga cggcggcgtg cagctcgcct accactacca gcagaacacc    1500
cccatcggcg acggccccgt gctgctgccc gacaaccact acctgagcgt gcagtccata    1560
cttccgaaag accccaacga gaagcgcgat cacatggtcc tgctggagtt cgtgaccgcc    1620
gccgggatca ctctcggcat ggacgagctg tacaagggcg gtaccggagg gagcatggtg    1680
agcaagggcg aggagctgtt caccggggtg gtgcccatcc aggtcgagct ggacggcgac    1740
gtaaacggcc acaagttcag cgtgtccggc gagggtgagg gcgatgccac ctacggcaag    1800
ctgaccctga agttcatctg caccaccggc aagctgcccg tgccctggcc caccctcgtg    1860
accaccctga cctacggcgt gcagtgcttc agccgctacc ccgaccacat gaagcagcac    1920
gacttcttca gtccgccat gcccgaaggc tacatccagg agcgcaccat cttcttcaag    1980
gacgacggca actacaagac ccgcgccgag gtgaagttcg agggcgacac cctggtgaac    2040
cgcatcgagc tgaagggcat cgacttcaag gaggacggca acatcctggg cacaagctg    2100 gagtacaaca cgcgtacagt cagacttaaa gaacatgacc aagatgtctt ggtgctggag    2160
aaggtcccag cagggaacag agcttctaat caaggaaact cacagcctca gcaaaagtat    2220
actgtgatgt caggaacacc tgaaaaaatt ttagagcatt ttctagaaac aatacgcctt    2280
gaggcaactt taaatgaagc aacagattct gttttaaatg actttattat gatgcactgt    2340 gttttttatgc caaatacccca gctttgcccg gcactggtgg cccactacca cgcacagcct    2400
tcacaaggta cagaacagga gaaaatggat tatgccctca acaataagag gcgagtcatc    2460
cgcctggttc tacagtgggc tgccatgtat ggagacctcc tgcaagagga tgacgtgtct    2520
atggccttcc tggaggagtt ttatgtatct gtatcagatg atgcccggat gattgctgcc    2580
ctcaaggagc aactgccaga gttggagaag attgtcaagc aaatctcaga agatgcaaag    2640
gcaccacaaa agaagcacaa ggttcttttg caacagttca atacgggcga tgagagagcc    2700
cagaagcgcc agcctatccg cggctctgat gaagttctgt taaggtcta ttgcatggac    2760 cccacctaca caaccattcg ggtgccagtg gccacttcgg tgaaggaagt catcagtgca    2820
gttgccgaca agctgggctc cggggagggc ctgatcatag tcaagatgag ttccggagga    2880
gaaaaggtgg tgctcaaacc taatgatgtt tcagtatta tgacgctcac cattaatgga    2940
cgcctgtttg cttgccgcg agagcaattc gattcactga ctcccttacc agaacaggaa    3000
ggcccaactg ttggaacagt gggaactttt gaactgatga gctccaaaga tttagcatac    3060
cagatgacaa tttatgattg ggaactcttc aactgcgtgc atgagctgga gctaatctat    3120
cacacatttg aaggcataa ttttaaaaag accacagcaa acttggattt gttcctgagg    3180
agatttaatg aaattcagtt tgggtcgtc actgagatct gcctttgttc tcagctcagc    3240
aagcgtgttc agctattaaa aaaatttatt aagatagcag cccactgtaa ggagtataaa    3300
aatctgaatt ccttttttgc catcgtcatg ggactaagta acgttgctgt gagccgcttg    3360
gcactaacgt gggagaaact gccaagcaag ttcaagaagt tctatgcgga gtttgaaagt    3420
ttaatggacc cttcaaggaa ccacagggcc tacaggctga cagtagctaa gctggaacct    3480
cctctcatcc ccttcatgcc tttgctcatt aaagatatga catttactca tgaggggaac    3540
aagacgttca ttgacaatct agtaaacttt gaaaaaatgc gcatgattgc aaatacggcc    3600
agaacagtga gatactacag gagccaaccc ttcaatcctg atgcagctca agctaataag    3660
aaccatcagg atgtccggag ttatgtacgg caattaaatg tgattgacaa ccagagaact    3720
```

| | |
|---|---|
| ttatcacaga tgtcacacag attagagcct cgtcgacca | 3759 |

<210> SEQ ID NO 64
<211> LENGTH: 3768
<212> TYPE: DNA
<213> ORGANISM: Artificial Sequence
<220> FEATURE:
<223> OTHER INFORMATION: Synthetic

<400> SEQUENCE: 64

| | |
|---|---|
| atggtcgctg cgcacgctgc ccattcttcc tcctctgccg agtggatcgc ctgcctggat | 60 |
| aaaagaccac tggagcgatc cagcgaagat gtggatataa tcttcactcg actgaaagaa | 120 |
| gttaaagctt ttgagaaatt tcacccaaat ctccttcatc agatttgctt atgtggttat | 180 |
| tatgagaatc tggaaaaggg aataacatta tttcgccagg gtgatattgg aacaaactgg | 240 |
| tatgctgtcc tggcagggtc tttggatgtt aaagtatctg agaccagcag tcaccaggat | 300 |
| gctgtgacca tctgtaccct gggaattggg acggcctttg agagtccat tctggacaac | 360 |
| acacccgcc atgcaaccat cgttaccagg agagcagtga actgctccg catcgagcag | 420 |
| aaggacttca aggcactatg ggagaaatat cgacagtata tggcaggact tctggctcct | 480 |
| ccttatggtg ttatggaaac gggctctaac aatgacagga ttcctgacaa ggagaacaca | 540 |
| cctctcattg aacctcacgt tcctcttcgt cctgctaaca ccattaccaa ggtcccttca | 600 |
| gagaagatcc tcagagctgg aaaaatttta cgaaatgcca ttctctctcg agcacctcac | 660 |
| atgataagag atagaaaata ccacctaaag acatacagac aatgctgtgt gggaactgaa | 720 |
| ctggtggact ggatgatgca gcagacacca tgtgttcact cccggactca agctgttggc | 780 |
| atgtggcaag tcctgttaga gatggtgtt ctcaaccacg tggaccagga gcaccatttc | 840 |
| caagacaaat atttattcta tcgatttctg gatgatgagc acgaggatgc ccctttgcct | 900 |
| actgaggagg agaagaagga gtgtgatgag gagctccagg acaccatgct gctgctgtca | 960 |
| cagatgggcc ccgacgccca catgaggatg atccttcgca aaccacctgg ccagaggact | 1020 |
| gtggatgacc tagagattat ctatgaggag cttcttcata ttaaagcctt atcccatctt | 1080 |
| tctaccacag tgaaacgaga gttagcaggt gttctcattt ttgagtctca cgccaaagga | 1140 |
| gggactgtgt tgtttaacca gggggaagaa ggtacctcct ggtacattat tctaaaagga | 1200 |
| tcagtgaatg tagtcatttta cggcaagggt gtggtctgca ccctgcatga aggagatgac | 1260 |
| ttcggcaagt tagcactagt gaatgatgcc ccacgagctg cctctatcgt cttacgagaa | 1320 |
| gataactgcc atttcttaag agtagacaag gaggatttca accggatcct aaggatgtcg | 1380 |
| aacgtctata tcaaggccga caagcagaag aacggcatca aggcgaactt caagatccgc | 1440 |
| cacaacatcg aggacggcgg cgtgcagctc gcctaccact accagcagaa cacccccatc | 1500 |
| ggcgacggcc ccgtgctgct gcccgacaac cactacctga gcgtgcagtc catactttcg | 1560 |
| aaagacccca cgagaagcg cgatcacatg gtcctgctgg agttcgtgac cgccgccggg | 1620 |
| atcactctcg gcatggacga gctgtacaag ggcggtaccg agggagcat ggtgagcaag | 1680 |
| ggcgaggagc tgttcaccgg ggtggtgccc atccaggtcg agctggacgg cgacgtaaac | 1740 |
| ggccacaagt tcagcgtgtc cggcgagggt gagggcgatg ccacctacgg caagctgacc | 1800 |
| ctgaagttca tctgcaccac cggcaagctg cccgtgccct ggcccaccct cgtgaccacc | 1860 |
| ctgacctacg gcgtgcagtg cttcagccgc taccccgacc acatgaagca gcacgacttc | 1920 |
| ttcaagtccg ccatgcccga aggctacatc caggagcgca ccatcttctt caaggacgac | 1980 |
| ggcaactaca agacccgcgc cgaggtgaag ttcgagggcg acacccctggt gaaccgcatc | 2040 |

```
gagctgaagg gcatcgactt caaggaggac ggcaacatcc tggggcacaa gctggagtac    2100
aacgtatcag acgtggaggc gaatacagtc agacttaaag aacatgacca agatgtcttg    2160
gtgctggaga aggtcccagc agggaacaga gcttctaatc aaggaaactc acagcctcag    2220
caaaagtata ctgtgatgtc aggaacacct gaaaaattt tagagcattt tctagaaaca     2280
atacgccttg aggcaacttt aaatgaagca acagattctg ttttaaatga ctttattatg    2340
atgcactgtg tttttatgcc aaatacccag ctttgcccgg cactggtggc ccactaccac    2400
gcacagcctt cacaaggtac agaacaggag aaaatggatt atgccctcaa caataagagg    2460
cgagtcatcc gcctggttct acagtgggct gccatgtatg agacctcct gcaagaggat     2520 gacgtgtcta tggccttcct ggaggagttt tatgtatctg tatcagatga tgcccggatg    2580
attgctgccc tcaaggagca actgccagag ttggagaaga ttgtcaagca aatctcagaa    2640
gatgcaaagg caccacaaaa gaagcacaag gttcttttgc aacagttcaa tacgggcgat    2700
gagagagccc agaagcgcca gcctatccgc ggctctgatg aagttctgtt taaggtctat    2760
tgcatggacc ccacctacac aaccattcgg gtgccagtgg ccacttcggt gaaggaagtc    2820
atcagtgcag ttgccgacaa gctgggctcc ggggagggcc tgatcatagt caagatgagt    2880
tccggaggag aaaaggtggt gctcaaacct aatgatgttt cagtatttat gacgctcacc    2940
attaatggac gcctgtttgc ttgcccgcga gagcaattcg attcactgac tcccttacca    3000
gaacaggaag gcccaactgt tggaacagtg ggaactttg aactgatgag ctccaaagat     3060
ttagcatacc agatgacaat ttatgattgg gaactcttca actgcgtgca tgagctggag    3120
ctaatctatc acacatttgg aaggcataat tttaaaaaga ccacagcaaa cttggatttg    3180
ttcctgagga gatttaatga aattcagttt tgggtcgtca ctgagatctg cctttgttct    3240
cagctcagca agcgtgttca gctattaaaa aaatttatta agatagcagc ccactgtaag    3300
gagtataaaa atctgaattc cttttttgcc atcgtcatgg gactaagtaa cgttgctgtg    3360
agccgcttgg cactaacgtg ggagaaactg ccaagcaagt tcaagaagtt ctatgcggag    3420
tttgaaagtt taatggaccc ttcaaggaac cacagggcct acaggctgac agtagctaag    3480
ctggaacctc ctctcatccc cttcatgcct ttgctcatta agatatgac atttactcat      3540 gaggggaaca agacgttcat tgacaatcta gtaaactttg aaaaaatgcg catgattgca    3600
aatacggcca gaacagtgag atactacagg agccaaccct tcaatcctga tgcagctcaa    3660
gctaataaga accatcagga tgtccggagt tatgtacggc aattaaatgt gattgacaac    3720
cagagaactt tatcacagat gtcacacaga ttagagcctc gtcgacca                 3768
```

<210> SEQ ID NO 65
<211> LENGTH: 3768
<212> TYPE: DNA
<213> ORGANISM: Artificial Sequence
<220> FEATURE:
<223> OTHER INFORMATION: Synthetic

<400> SEQUENCE: 65

```
atggtcgctg cgcacgctgc ccattcttcc tcctctgccg agtggatcgc ctgcctggat      60
aaaagaccac tggagcgatc cagcgaagat gtggatataa tcttcactcg actgaaagaa    120
gttaaagctt ttgagaaatt tcacccaaat ctccttcatc agatttgctt atgtggttat    180
tatgagaatc tggaaaaggg aataacatta tttcgccagg gtgatattgg aacaaactgg    240
tatgctgtcc tggcagggtc tttggatgtt aaagtatctg agaccagcag tcaccaggat    300
```

```
gctgtgacca tctgtaccct gggaattggg acggcctttg gagagtccat tctggacaac    360
acacccccgcc atgcaaccat cgttaccagg gagagcagtg aactgctccg catcgagcag    420
aaggacttca aggcactatg ggagaaatat cgacagtata tggcaggact tctggctcct    480
ccttatggtg ttatggaaac gggctctaac aatgacagga ttcctgacaa ggagaacaca    540
cctctcattg aacctcacgt tcctcttcgt cctgctaaca ccattaccaa ggtcccttca    600
gagaagatcc tcagagctgg aaaaatttta cgaaatgcca ttctctctcg agcacctcac    660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc ccctttgcct    900
actgaggagg agaagaagga gtgtgatgag agctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aaggctcgag   1380
aacgtctata tcaaggccga caagcagaag aacggcatca aggcgaactt caagatccgc   1440
cacaacatcg aggacggcgg cgtgcagctc gcctaccact accagcagaa cacccccatc   1500
ggcgacggcc ccgtgctgct gcccgacaac cactacctga gcgtgcagtc catactttcg   1560
aaagacccca acgagaagcg cgatcacatg gtcctgctgg agttcgtgac cgccgccggg   1620
atcactctcg gcatggacga gctgtacaag ggcggtaccg gagggagcat ggtgagcaag   1680
ggcgaggagc tgttcaccgg ggtggtgccc atccaggtcg agctggacgg cgacgtaaac   1740
ggccacaagt tcagcgtgtc cggcgagggt gagggcgatg ccacctacgg caagctgacc   1800
ctgaagttca tctgcaccac cggcaagctg cccgtgccct ggcccaccct cgtgaccacc   1860
ctgacctacg gcgtgcagtg cttcagccgc taccccgacc acatgaagca gcacgacttc   1920
ttcaagtccg ccatgcccga aggctacatc caggagcgca ccatcttctt caaggacgac   1980
ggcaactaca agacccgcgc cgaggtgaag ttcgagggcg acaccctggt gaaccgcatc   2040
gagctgaagg gcatcgactt caaggaggac ggcaacatcc tggggcacaa gctggagtac   2100
aacacgcgtg acgtggaggc gaatacagtc agacttaaag aacatgacca agatgtcttg   2160
gtgctggaga aggtcccagc agggaacaga gcttctaatc aaggaaactc acagcctcag   2220
caaaagtata ctgtgatgtc aggaacacct gaaaaatttt tagagcattt tctagaaaca   2280
atacgccttg aggcaacttt aaatgaagca acagattctg ttttaaatga ctttattatg   2340
atgcactgtg tttttatgcc aaataccccag ctttgcccgg cactggtggc ccactaccac   2400
gcacagcctt cacaaggtac agaacaggag aaaatggatt atgccctcaa caataagagg   2460
cgagtcatcc gcctggttct acagtgggct gccatgtatg agacctcct gcaagaggat   2520
gacgtgtcta tggccttcct ggaggagttt tatgtatctg tatcagatga tgcccggatg   2580
attgctgccc tcaaggagca actgccagag ttggagaaga ttgtcaagca aatctcagaa   2640
gatgcaaagg caccacaaaa gaagcacaag gttctttttgc aacagttcaa tacgggcgat   2700
```

```
gagagagccc agaagcgcca gcctatccgc ggctctgatg aagttctgtt taaggtctat    2760
tgcatggacc ccacctacac aaccattcgg gtgccagtgg ccacttcggt gaaggaagtc    2820
atcagtgcag ttgccgacaa gctgggctcc ggggagggcc tgatcatagt caagatgagt    2880
tccggaggag aaaaggtggt gctcaaacct aatgatgttt cagtatttat gacgctcacc    2940
attaatggac gcctgtttgc ttgcccgcga gagcaattcg attcactgac tcccttacca    3000
gaacaggaag gcccaactgt tggaacagtg gaacttttg aactgatgag ctccaaagat     3060
ttagcatacc agatgacaat ttatgattgg gaactcttca actgcgtgca tgagctggag    3120
ctaatctatc acacatttgg aaggcataat tttaaaaaga ccacagcaaa cttggatttg    3180
ttcctgagga gatttaatga aattcagttt tgggtcgtca ctgagatctg cctttgttct    3240
cagctcagca gcgtgttca gctattaaaa aaatttatta agatagcagc ccactgtaag     3300
gagtataaaa atctgaattc cttttttgcc atcgtcatgg gactaagtaa cgttgctgtg    3360
agccgcttgg cactaacgtg ggagaaactg ccaagcaagt tcaagaagtt ctatgcggag    3420
tttgaaagtt taatggaccc ttcaaggaac cacagggcct acaggctgac agtagctaag    3480
ctggaacctc ctctcatccc cttcatgcct ttgctcatta agatatgac atttactcat     3540 gaggggaaca agacgttcat tgacaatcta gtaaactttg aaaaaatgcg catgattgca    3600
aatacggcca gaacagtgag atactacagg agccaaccct tcaatcctga tgcagctcaa    3660
gctaataaga accatcagga tgtccggagt tatgtacggc aattaaatgt gattgacaac    3720
cagagaactt tatcacagat gtcacacaga ttagagcctc gtcgacca                3768

<210> SEQ ID NO 66
<211> LENGTH: 3774
<212> TYPE: DNA
<213> ORGANISM: Artificial Sequence
<220> FEATURE:
<223> OTHER INFORMATION: Synthetic

<400> SEQUENCE: 66
atggtcgctg cgcacgctgc ccattcttcc tcctctgccg agtggatcgc ctgcctggat      60
aaaagaccac tggagcgatc cagcgaagat gtggatataa tcttcactcg actgaaagaa     120
gttaaagctt ttgagaaatt tcacccaaat ctccttcatc agatttgctt atgtggttat     180
tatgagaatc tggaaaaggg aataacatta tttcgccagg gtgatattgg aacaaactgg     240
tatgctgtcc tggcagggtc tttggatgtt aaagtatctg agaccagcag tcaccaggat     300
gctgtgacca tctgtaccct gggaattggg acggcctttg gagagtccat tctggacaac     360
acaccccgcc atgcaaccat cgttaccagg gagagcagtg aactgctccg catcgagcag     420
aaggacttca aggcactatg ggagaaatat cgacagtata tggcaggact tctggctcct     480
ccttatggtg ttatggaaac gggctctaac aatgacagga ttcctgacaa ggagaacaca    540
cctctcattg aacctcacgt tcctcttcgt cctgctaaca ccattaccaa ggtcccttca     600
gagaagatcc tcagagctgg aaaaattta cgaaatgcca ttctctctcg agcacctcac     660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc cccttttgcct   900 actgaggagg agaagaagga gtgtgatgag gagctccagg acaccatgct gctgctgtca     960
```

```
cagatgggcc ccgacgccca catgaggatg atccttcgca aaccacctgg ccagaggact    1020
gtggatgacc tagagattat ctatgaggag cttcttcata ttaaagcctt atcccatctt    1080
tctaccacag tgaaacgaga gttagcaggt gttctcattt ttgagtctca cgccaaagga    1140
gggactgtgt tgtttaacca gggggaagaa ggtacctcct ggtacattat tctaaaagga    1200
tcagtgaatg tagtcattta cggcaagggt gtggtctgca ccctgcatga aggagatgac    1260
ttcggcaagt tagcactagt gaatgatgcc ccacgagctg cctctatcgt cttacgagaa    1320
gataactgcc atttcttaag agtagacaag gaggatttca accggatcct aaggctggtg    1380
tcgcacaact tctatatcaa ggccgacaag cagaagaacg gcatcaaggc gaacttcaag    1440
atccgccaca acatcgagga cggcggcgtg cagctcgcct accactacca gcagaacacc    1500
cccatcggcg acggccccgt gctgctgccc gacaaccact acctgagcgt gcagtccata    1560
ctttcgaaag accccaacga gaagcgcgat cacatggtcc tgctggagtt cgtgaccgcc    1620
gccgggatca ctctcggcat ggacgagctg tacaagggcg gtaccggagg gagcatggtg    1680
agcaagggcg aggagctgtt caccggggtg gtgcccatcc tggtcgagct ggacggcgac    1740
gtaaacggcc acaagttcag cgtgtccggc gagggtgagg gcgatgccac ctacggcaag    1800
ctgaccctga agttcatctg caccaccggc aagctgcccg tgccctggcc caccctcgtg    1860
accaccctga cctacggcgt gcagtgcttc agccgctacc ccgaccacat gaagcagcac    1920
gacttcttca gtccgccat gcccgaaggc tacatccagg agcgcaccat cttcttcaag    1980
gacgacggca actacaagac ccgcgccgag gtgaagttcg agggcgacac cctggtgaac    2040
cgcatcgagc tgaagggcat cgacttcaag gaggacggca acatcctggg gcacaagctg    2100
gagtacaact tcaacgacgt ggaggcgaat acagtcagac ttaaagaaca tgaccaagat    2160
gtcttggtgc tggagaaggt cccagcaggg aacagagctt ctaatcaagg aaactcacag    2220
cctcagcaaa agtatactgt gatgtcagga acacctgaaa aaattttaga gcattttcta    2280
gaaacaatac gccttgaggc aactttaaat gaagcaacag attctgtttt aaatgacttt    2340
attatgatgc actgtgtttt tatgccaaat acccagcttt gcccggcact ggtggcccac    2400
taccacgcac agccttcaca aggtacagaa caggagaaaa tggattatgc cctcaacaat    2460
aagaggcgag tcatccgcct ggttctacag tgggctgcca tgtatggaga cctcctgcaa    2520
gaggatgacg tgtctatggc cttcctggag agttttatg tatctgtatc agatgatgcc    2580
cggatgattg ctgccctcaa ggagcaactg ccagagttgg agaagattgt caagcaaatc    2640
tcagaagatg caaaggcacc acaaaagaag cacaaggttc ttttgcaaca gttcaatacg    2700
ggcgatgaga gagcccagaa gcgccagcct atccgcggct ctgatgaagt tctgtttaag    2760
gtctattgca tggaccccac ctacacaacc attcgggtgc cagtggccac ttcggtgaag    2820
gaagtcatca gtgcagttgc cgacaagctg ggctccgggg agggcctgat catagtcaag    2880
atgagttccg gaggagaaaa ggtggtgctc aaacctaatg atgtttcagt atttatgacg    2940
ctcaccatta tggacgcct gtttgcttgc ccgcgagagc aattcgattc actgactccc    3000
ttaccagaac aggaaggccc aactgttgga acagtgggaa cttttgaact gatgagctcc    3060
aaagatttag cataccagat gacaatttat gattgggaac tcttcaactg cgtgcatgag    3120
ctggagctaa tctatcacac atttggaagg cataatttta aaaagaccac agcaaacttg    3180
gatttgttcc tgaggagatt taatgaaatt cagttttggg tcgtcactga gatctgcctt    3240
tgttctcagc tcagcaagcg tgttcagcta ttaaaaaaat ttattaagat agcagcccac    3300
tgtaaggagt ataaaaatct gaattccttt tttgccatcg tcatgggact aagtaacgtt    3360
```

```
gctgtgagcc gcttggcact aacgtgggag aaactgccaa gcaagttcaa gaagttctat    3420
gcggagtttg aaagtttaat ggacccttca aggaaccaca gggcctacag gctgacagta    3480
gctaagctgg aacctcctct catccccttc atgcctttgc tcattaaaga tatgacattt    3540
actcatgagg ggaacaagac gttcattgac aatctagtaa actttgaaaa aatgcgcatg    3600
attgcaaata cggccagaac agtgagatac acaggagcc aacccttcaa tcctgatgca     3660
gctcaagcta ataagaacca tcaggatgtc cggagttatg tacggcaatt aaatgtgatt    3720
gacaaccaga gaactttatc acagatgtca cacagattag agcctcgtcg acca          3774
```

<210> SEQ ID NO 67
<211> LENGTH: 4317
<212> TYPE: DNA
<213> ORGANISM: Artificial Sequence
<220> FEATURE:
<223> OTHER INFORMATION: Synthetic

<400> SEQUENCE: 67

```
atggtcgctg cgcacgctgc ccattcttcc tcctctgccg agtggatcgc ctgcctggat      60
aaaagaccac tggagcgatc cagcgaagat gtggatataa tcttcactcg actgaaagaa    120
gttaaagctt ttgagaaatt tcacccaaat ctccttcatc agatttgctt atgtggttat    180
tatgagaatc tggaaaaggg aataacatta tttcgccagg gtgatattgg aacaaactgg    240
tatgctgtcc tggcagggtc tttggatgtt aaagtatctg agaccagcag tcaccaggat    300
gctgtgacca tctgtaccct gggaattggg acggcctttg gagagtccat tctggacaac    360
acaccccgcc atgcaaccat cgttaccagg gagagcagtg aactgctccg catcgagcag    420
aaggacttca aggcactatg ggagaaatat cgacagtata tggcaggact tctggctcct    480
ccttatggtg ttatggaaac gggctctaac aatgacagga ttcctgacaa ggagaacaca    540
cctctcattg aacctcacgt tcctcttcgt cctgctaaca ccattaccaa ggtcccttca    600
gagaagatcc tcagagctgg aaaaatttta cgaaatgcca ttctctctcg agcacctcac    660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg atgatgagc acgaggatgc ccctttgcct    900
actgaggagg agaagaagga gtgtgatgag gagctccagg acaccatgct gctgctgtca    960
cagatgggcc ccgacgccca catgaggatg atccttcgca aaccacctgg ccagaggact    1020
gtggatgacc tagagattat ctatgaggag cttcttcata ttaaagcctt atcccatctt    1080
tctaccacag tgaaacgaga gttagcaggt gttctcattt tgagtctca cgccaaagga    1140 gggactgtgt tgtttaacca gggggaagaa ggtacctcct ggtacattat tctaaaagga    1200
tcagtgaatg tagtcattta cggcaagggt gtggtctgca ccctgcatga aggagatgac    1260
ttcggcaagt tagcactagt gaatgatgcc ccacgagctg cctctatcgt cttacgagaa    1320
gataactgcc atttcttaag agtagacaag gaggatttca accggatcct aagggacgtg    1380
gaggcgaata cagtcagact taagaacat gaccaagatg tcttggtgct ggagaaggtc    1440
ccagcaggga acagagcttc taatcaagga aactcacagc ctcagcaaaa gtatactgtg    1500
atgtcaggaa cacctgaaaa aatttttagag cattttctag aaacaatacg ccttgaggca    1560
actttaaatg aagcaacaga ttctgtttta aatgacttta ttatgatgca ctgtgttttt    1620
```

-continued

| | | | | |
|---|---|---|---|---|
| atgccaaata | cccagctttg | cccggcactg | gtggcccact | accacgcaca gccttcacaa | 1680 |
| ggtacagaac | aggagaaaat | ggattatgcc | ctcaacaata | agaggcgagt catccgcctg | 1740 |
| gttctacagt | gggctgccat | gtatggagac | ctcctgcaag | aggatgacgt gtctatggcc | 1800 |
| ttcctggagg | agttttatgt | atctgtatca | gatgatgccc | ggatgattgc tgccctcaag | 1860 |
| gagcaactgc | cagagttgga | gaagattgtc | aagcaaatct | cagaagatgc aaaggcacca | 1920 |
| caaaagaagc | acaaggttct | tttgcaacag | ttcaatacgg | gcgatgagag agcccagaag | 1980 |
| cgccagccta | tccgcggctc | tgatgaagtt | ctgtttaagg | tctattgcat ggaccccacc | 2040 |
| tacacaacca | ttcgggtgcc | agtggccact | tcggtgaagg | aagtcatcag tgcagttgcc | 2100 |
| gacaagctgg | gctccgggga | gggcctgatc | atagtcaaga | tgagttccgg aggagaaaag | 2160 |
| gtggtgctca | aacctaatga | tgtttcagta | tttatgacgc | tcaccattaa tggacgcctg | 2220 |
| tttgcttgcc | cgcgagagca | attcgattca | ctgactccct | taccagaaca ggaaggccca | 2280 |
| actgttggaa | cagtgggaac | ttttgaactg | atgagctcca | agatttagc ataccagatg | 2340 |
| acaatttatg | attgggaact | cttcaactgc | gtgcatgagc | tggagctaat ctatcacaca | 2400 |
| tttggaaggc | ataattttaa | aaagaccaca | gcaaacttgg | atttgttcct gaggagattt | 2460 |
| aatgaaattc | agttttgggt | cgtcactgag | atctgccttt | gttctcagct cagcaagcgt | 2520 |
| gttcagctat | taaaaaaatt | tattaagata | gcagcccact | gtaaggagta taaaaatctg | 2580 |
| aattcctttt | ttgccatcgt | catgggacta | agtaacgttg | ctgtgagccg cttggcacta | 2640 |
| acgtgggaga | aactgccaag | caagttcaag | aagttctatg | cggagtttga agtttaatg | 2700 |
| gacccttcaa | ggaaccacag | ggcctacagg | ctgacagtag | ctaagctgga acctcctctc | 2760 |
| atccccttca | tgcctttgct | cattaaagat | atgacattta | ctcatgaggg gaacaagacg | 2820 |
| ttcattgaca | atctagtaaa | ctttgaaaaa | atgcgcatga | ttgcaaatac ggccagaaca | 2880 |
| gtgagatact | acaggagcca | acccttcaat | cctgatgcag | ctcaagctaa taagaaccat | 2940 |
| caggatgtcc | ggagttatgt | acggcaatta | aatgtgattg | acaaccagag aactttatca | 3000 |
| cagatgtcac | acagattaga | gcctcgtcga | ccactcgaga | acgtctatat caaggccgac | 3060 |
| aagcagaaga | acggcatcaa | ggcgaacttc | aagatccgcc | acaacatcga ggacggcggc | 3120 |
| gtgcagctcg | cctaccacta | ccagcagaac | acccccatcg | gcgacggccc cgtgctgctg | 3180 |
| cccgacaacc | actacctgag | cgtgcagtcc | atactttcga | aagacccaaa cgagaagcgc | 3240 |
| gatcacatgg | tcctgctgga | gttcgtgacc | gccgccggga | tcactctcgg catggacgag | 3300 |
| ctgtacaagg | gcggtaccgg | agggagcatg | gtgagcaagg | gcgaggagct gttcaccggg | 3360 |
| gtggtgccca | tccaggtcga | gctggacggc | gacgtaaacg | gccacaagtt cagcgtgtcc | 3420 |
| ggcgagggtg | agggcgatgc | cacctacggc | aagctgaccc | tgaagttcat ctgcaccacc | 3480 |
| ggcaagctgc | ccgtgccctg | gcccaccctc | gtgaccaccc | tgacctacgg cgtgcagtgc | 3540 |
| ttcagccgct | accccgacca | catgaagcag | cacgacttct | tcaagtccgc catgcccgaa | 3600 |
| ggctacatcc | aggagcgcac | catcttcttc | aaggacgacg | gcaactacaa gacccgcgcc | 3660 |
| gaggtgaagt | tcgagggcga | caccctggtg | aaccgcatcg | agctgaaggg catcgacttc | 3720 |
| aaggaggacg | gcaacatcct | ggggcacaag | ctggagtaca | acacgcgtcg tgagtataag | 3780 |
| ctagtcgttc | ttggctcagg | aggcgttgga | aagtctgctt | tgactgtaca atttgttcaa | 3840 |
| ggaattttg | tagaaaaata | cgatcctacg | atagaagatt | cttatagaaa gcaagttgaa | 3900 |
| gtagatgcac | aacagtgtat | gcttgaaatc | ttggatactg | caggaacgga gcaatttaca | 3960 |
| gcaatgaggg | atttatacat | gaaaaatgga | caaggatttg | cattagtttta ttccatcaca | 4020 |

| | |
|---|---|
| gcacagtcca catttaacga tttacaagac ctgagagaac agattcttcg agttaaagac | 4080 |
| actgatgatg ttccaatgat tcttgttggt aataagtgtg acttggaaga tgaaagagtt | 4140 |
| gtagggaagg aacaaggtca aaatctagca agacaatgga acaactgtgc attcttagaa | 4200 |
| tcttctgcaa aatcaaaaat aaatgttaat gagatctttt atgacctagt gcggcaaatt | 4260 |
| aacagaaaaa ctccagtgcc tgggaaggct cgcaaaaagt catcatgtca gctgctt | 4317 |

<210> SEQ ID NO 68
<211> LENGTH: 3768
<212> TYPE: DNA
<213> ORGANISM: Artificial Sequence
<220> FEATURE:
<223> OTHER INFORMATION: Synthetic

<400> SEQUENCE: 68

| | |
|---|---|
| atggtcgctg cgcacgctgc ccattcttcc tcctctgccg agtggatcgc ctgcctggat | 60 |
| aaaagaccac tggagcgatc cagcgaagat gtggatataa tcttcactcg actgaaagaa | 120 |
| gttaaagctt ttgagaaatt tcacccaaat ctccttcatc agatttgctt atgtggttat | 180 |
| tatgagaatc tggaaaaggg aataacatta tttcgccagg gtgatattgg aacaaactgg | 240 |
| tatgctgtcc tggcagggtc tttggatgtt aaagtatctg agaccagcag tcaccaggat | 300 |
| gctgtgacca tctgtaccct gggaattggg acggcctttg gagagtccat tctggacaac | 360 |
| acaccccgcc atgcaaccat cgttaccagg gagagcagtg aactgctccg catcgagcag | 420 |
| aaggacttca aggcactatg ggagaaatat cgacagtata tggcaggact tctggctcct | 480 |
| ccttatggtg ttatggaaac gggctctaac aatgacagga ttcctgacaa ggagaacaca | 540 |
| cctctcattg aacctcacgt tcctcttcgt cctgctaaca ccattaccaa ggtcccttca | 600 |
| gagaagatcc tcagagctgg aaaaatttta cgaaatgcca ttctctctcg agcacctcac | 660 |
| atgataagag atagaaaata ccacctaaag acatacagac aatgctgtgt gggaactgaa | 720 |
| ctggtggact ggatgatgca gcagacacca tgtgttcact cccggactca agctgttggc | 780 |
| atgtggcaag tcctgttaga agatggtgtt ctcaaccacg tggaccagga gcaccatttc | 840 |
| caagacaaat atttattcta tcgatttctg gatgatgagc acgaggatgc ccctttgcct | 900 |
| actgaggagg agaagaagga gtgtgatgag gagctccagg acaccatgct gctgctgtca | 960 |
| cagatgggcc ccgacgccca catgaggatg atccttcgca aaccacctgg ccagaggact | 1020 |
| gtggatgacc tagagattat ctatgaggag cttcttcata ttaaagcctt atcccatctt | 1080 |
| tctaccacag tgaaacgaga gttagcaggt gttctcattt ttgagtctca cgccaaagga | 1140 |
| gggactgtgt tgtttaacca gggggaagaa ggtacctcct ggtacattat tctaaaagga | 1200 |
| tcagtgaata tagtcattta cggcaagggt gtggtctgca ccctgcatga aggagatgac | 1260 |
| ttcggcaagt tagcactagt gaatgatgcc ccacgagctg cctctatcgt cttacgagaa | 1320 |
| gataactgcc atttcttaag agtagacaag gaggatttca accggatcct aagggacgtg | 1380 |
| gagctcgaga acgtctatat caaggccgac aagcagaaga acggcatcaa ggcgaacttc | 1440 |
| aagatccgcc acaacatcga ggacggcggc gtgcagctcg cctaccacta ccagcagaac | 1500 |
| accccccatcg gcgacggccc cgtgctgctg cccgacaacc actacctgag cgtgcagtcc | 1560 |
| atactttcga aagaccccaa cgagaagcgc gatcacatgg tcctgctgga gttcgtgacc | 1620 |
| gccgccggga tcactctcgg catggacgag ctgtacaagg cggtaccggg agggagcatg | 1680 |
| gtgagcaagg gcgaggagct gttcaccggg gtggtgccca tccaggtcga gctggacggc | 1740 |

```
gacgtaaacg gccacaagtt cagcgtgtcc ggcgagggtg agggcgatgc cacctacggc    1800
aagctgaccc tgaagttcat ctgcaccacc ggcaagctgc ccgtgccctg cccacccctc    1860
gtgaccaccc tgacctacgg cgtgcagtgc ttcagccgct accccgacca catgaagcag    1920
cacgacttct tcaagtccgc catgcccgaa ggctacatcc aggagcgcac catcttcttc    1980
aaggacgacg gcaactacaa gacccgcgcc gaggtgaagt tcgagggcga cacactggtg    2040
aaccgcatcg agctgaaggg catcgacttc aaggaggacg gcaacatcct ggggcacaag    2100
ctggagtaca acacgcgtgc gaatacagtc agacttaaag aacatgacca agatgtcttg    2160
gtgctggaga aggtcccagc agggaacaga gcttctaatc aaggaaactc acagcctcag    2220
caaaagtata ctgtgatgtc aggaacacct gaaaaattt tagagcattt tctagaaaca    2280
atacgccttg aggcaacttt aaatgaagca acagattctg ttttaaatga ctttattatg    2340
atgcactgtg tttttatgcc aaatacccag ctttgcccgg cactggtggc ccactaccac    2400
gcacagcctt cacaaggtac agaacaggag aaaatggatt atgccctcaa caataagagg    2460
cgagtcatcc gcctggttct acagtgggct gccatgtatg agacctcct gcaagaggat    2520
gacgtgtcta tggccttcct ggaggagttt tatgtatctg tatcagatga tgcccggatg    2580
attgctgccc tcaaggagca actgccagag ttggagaaga ttgtcaagca aatctcagaa    2640
gatgcaaagg caccacaaaa gaagcacaag gttcttttgc aacagttcaa tacgggcgat    2700
gagagagccc agaagcgcca gcctatccgc ggctctgatg aagttctgtt taaggtctat    2760
tgcatggacc ccacctacac aaccattcgg gtgccagtgg ccacttcggt gaaggaagtc    2820
atcagtgcag ttgccgacaa gctgggctcc ggggagggcc tgatcatagt caagatgagt    2880
tccggaggag aaaaggtggt gctcaaacct aatgatgttt cagtatttat gacgctcacc    2940
attaatggac gcctgtttgc ttgcccgcga gagcaattcg attcactgac tcccttacca    3000
gaacaggaag gcccaactgt tggaacagtg gaactttgg aactgatgag ctccaaagat    3060
ttagcatacc agatgacaat ttatgattgg gaactcttca actgcgtgca tgagctggag    3120
ctaatctatc acacatttgg aaggcataat tttaaaaaga ccacagcaaa cttggatttg    3180
ttcctgagga gatttaatga aattcagttt tgggtcgtca ctgagatctg cctttgttct    3240
cagctcagca agcgtgttca gctattaaaa aaatttatta agatagcagc ccactgtaag    3300
gagtataaaa atctgaattc cttttttgcc atcgtcatgg gactaagtaa cgttgctgtg    3360
agccgcttgg cactaacgtg ggagaaactg ccaagcaagt tcaagaagtt ctatgcggag    3420
tttgaaagtt taatggaccc ttcaaggaac cacagggcct acaggctgac agtagctaag    3480
ctggaacctc ctctcatccc cttcatgcct ttgctcatta agatatgac atttactcat    3540
gaggggaaca agacgttcat tgacaatcta gtaaactttg aaaaaatgcg catgattgca    3600
aatacggcca gaacagtgag atactacagg agccaaccct tcaatcctga tgcagctcaa    3660
gctaataaga accatcagga tgtccggagt tatgtacggc aattaaatgt gattgacaac    3720
cagagaactt tatcacagat gtcacacaga ttagagcctc gtcgacca                3768
```

<210> SEQ ID NO 69
<211> LENGTH: 3768
<212> TYPE: DNA
<213> ORGANISM: Artificial Sequence
<220> FEATURE:
<223> OTHER INFORMATION: Synthetic

<400> SEQUENCE: 69

```
atggtcgctg cgcacgctgc ccattcttcc tcctctgccg agtggatcgc ctgcctggat      60
```

```
aaaagaccac tggagcgatc cagcgaagat gtggatataa tcttcactcg actgaaagaa      120
gttaaagctt ttgagaaatt tcacccaaat ctccttcatc agatttgctt atgtggttat      180
tatgagaatc tggaaaaggg aataacatta tttcgccagg gtgatattgg aacaaactgg      240
tatgctgtcc tggcagggtc tttggatgtt aaagtatctg agaccagcag tcaccaggat      300
gctgtgacca tctgtaccct gggaattggg acggcctttg agagtccat tctggacaac      360 acaccccgcc atgcaaccat cgttaccagg gagagcagtg aactgctccg catcgagcag      420
aaggacttca aggcactatg ggagaaatat cgacagtata tggcaggact tctggctcct      480
ccttatggtg ttatggaaac gggctctaac aatgacagga ttcctgacaa ggagaacaca      540
cctctcattg aacctcacgt tcctcttcgt cctgctaaca ccattaccaa ggtcccttca      600
gagaagatcc tcagagctgg aaaaatttta cgaaatgcca ttctctctcg agcacctcac      660
atgataagag atagaaaata ccacctaaag acatacagac aatgctgtgt gggaactgaa      720
ctggtggact ggatgatgca gcagacacca tgtgttcact cccggactca agctgttggc      780
atgtggcaag tcctgttaga agatggtgtt ctcaaccacg tggaccagga gcaccatttc      840
caagacaaat atttattcta tcgatttctg gatgatgagc acgaggatgc ccctttgcct      900
actgaggagg agaagaagga gtgtgatgag gagctccagg acaccatgct gctgctgtca      960
cagatgggcc ccgacgccca catgaggatg atccttcgca aaccacctgg ccagaggact     1020
gtggatgacc tagagattat ctatgaggag cttcttcata ttaaagcctt atcccatctt     1080
tctaccacag tgaaacgaga gttagcaggt gttctcattt ttgagtctca cgccaaagga     1140
gggactgtgt tgtttaacca gggggaagaa ggtacctcct ggtacattat tctaaaagga     1200
tcagtgaatg tagtcattta cggcaagggg gtggtctgca ccctgcatga aggagatgac     1260
ttcggcaagt tagcactagt gaatgatgcc ccacgagctg cctctatcgt cttacgagaa     1320
gataactgcc atttcttaag agtagacaag gaggatttca accggatcct aagggacgtg     1380
gaggcgaata cagtcagact taagaacat gaccaagatg tcttggtgct ggagaaggtc     1440
ccagcaggga acagagcttc taatcaagga aactcacagc ctcagcaaaa gtatactgtg     1500
atgtcaggaa cacctgaaaa aattttagag cattttctag aaacaatacg ccttctcgag     1560
aacgtctata tcaaggccga caagcagaag aacggcatca aggcgaactt caagatccgc     1620
cacaacatcg aggacggcgg cgtgcagctc gcctaccact accagcagaa cacccccatc     1680
ggcgacggcc ccgtgctgct gcccgacaac cactacctga gcgtgcagtc catactttcg     1740
aaagacccca acgagaagcg cgatcacatg gtcctgctgg agttcgtgac cgccgccggg     1800
atcactctcg gcatggacga gctgtacaag ggcggtaccg agggagcat ggtgagcaag     1860 ggcgaggagc tgttcaccgg ggtggtgccc atccaggtcg agctggacgg cgacgtaaac     1920
ggccacaagt tcagcgtgtc cggcgagggt gagggcgatg ccacctacgg caagctgacc     1980
ctgaagttca tctgcaccac cggcaagctg cccgtgccct ggcccaccct cgtgaccacc     2040
ctgacctacg gcgtgcagtg cttcagccgc taccccgacc acatgaagca gcacgacttc     2100
ttcaagtccg ccatgcccga aggctacatc caggagcgca ccatcttctt caaggacgac     2160
ggcaactaca agacccgcgc cgaggtgaag ttcgagggcg acaccctggt gaaccgcatc     2220
gagctgaagg gcatcgactt caaggaggac ggcaacatcc tggggcacaa gctggagtac     2280
aacacgcgtg aggcaacttt aaatgaagca acagattctg ttttaaatga ctttattatg     2340
atgcactgtg ttttttatgcc aaatacccag ctttgcccgg cactggtggc ccactaccac     2400
```

-continued

| | |
|---|---|
| gcacagcctt cacaaggtac agaacaggag aaaatggatt atgccctcaa caataagagg | 2460 |
| cgagtcatcc gcctggttct acagtgggct gccatgtatg agacctcct gcaagaggat | 2520 |
| gacgtgtcta tggccttcct ggaggagttt tatgtatctg tatcagatga tgcccggatg | 2580 |
| attgctgccc tcaaggagca actgccagag ttggagaaga ttgtcaagca aatctcagaa | 2640 |
| gatgcaaagg caccacaaaa gaagcacaag gttcttttgc aacagttcaa tacgggcgat | 2700 |
| gagagagccc agaagcgcca gcctatccgc ggctctgatg aagttctgtt taaggtctat | 2760 |
| tgcatggacc ccacctacac aaccattcgg gtgccagtgg ccacttcggt gaaggaagtc | 2820 |
| atcagtgcag ttgccgacaa gctgggctcc ggggagggcc tgatcatagt caagatgagt | 2880 |
| tccggaggag aaaaggtggt gctcaaacct aatgatgttt cagtatttat gacgctcacc | 2940 |
| attaatggac gcctgtttgc ttgcccgcga gagcaattcg attcactgac tcccttacca | 3000 |
| gaacaggaag gcccaactgt tggaacagtg ggaacttttg aactgatgag ctccaaagat | 3060 |
| ttagcatacc agatgacaat ttatgattgg gaactcttca actgcgtgca tgagctggag | 3120 |
| ctaatctatc acacatttgg aaggcataat tttaaaaaga ccacagcaaa cttggatttg | 3180 |
| ttcctgagga gatttaatga aattcagttt tgggtcgtca ctgagatctg cctttgttct | 3240 |
| cagctcagca agcgtgttca gctattaaaa aaatttatta agatagcagc ccactgtaag | 3300 |
| gagtataaaa atctgaattc cttttttgcc atcgtcatgg gactaagtaa cgttgctgtg | 3360 |
| agccgcttgg cactaacgtg ggagaaactg ccaagcaagt tcaagaagtt ctatgcggag | 3420 |
| tttgaaagtt taatggaccc ttcaaggaac cacagggcct acaggctgac agtagctaag | 3480 |
| ctggaacctc ctctcatccc cttcatgcct tgctcatta agatatgac atttactcat | 3540 |
| gaggggaaca agacgttcat tgacaatcta gtaaactttg aaaaaatgcg catgattgca | 3600 |
| aatacggcca aacagtgag atactacagg agccaaccct tcaatcctga tgcagctcaa | 3660 |
| gctaataaga accatcagga tgtccggagt tatgtacggc aattaaatgt gattgacaac | 3720 |
| cagagaactt tatcacagat gtcacacaga ttagagcctc gtcgacca | 3768 |

<210> SEQ ID NO 70
<211> LENGTH: 3768
<212> TYPE: DNA
<213> ORGANISM: Artificial Sequence
<220> FEATURE:
<223> OTHER INFORMATION: Synthetic

<400> SEQUENCE: 70

| | |
|---|---|
| atggtcgctg cgcacgctgc ccattcttcc tcctctgccg agtggatcgc ctgcctggat | 60 |
| aaaagaccac tggagcgatc cagcgaagat gtggatataa tcttcactcg actgaaagaa | 120 |
| gttaaagctt ttgagaaatt tcacccaaat ctccttcatc agatttgctt atgtggttat | 180 |
| tatgagaatc tggaaaaggg aataacatta tttcgccagg gtgatattgg aacaaactgg | 240 |
| tatgctgtcc tggcagggtc tttggatgtt aaagtatctg agaccagcag tcaccaggat | 300 |
| gctgtgacca tctgtaccct gggaattggg acggcctttg agagtccat tctggacaac | 360 |
| acaccccgcc atgcaaccat cgttaccagg gagagcagtg aactgctccg catcgagcag | 420 |
| aaggacttca aggcactatg ggagaaatat cgacagtata tggcaggact tctggctcct | 480 |
| ccttatggtg ttatggaaac gggctctaac aatgacagga ttcctgacaa ggagaacaca | 540 |
| cctctcattg aacctcacgt tcctcttcgt cctgctaaca ccattaccaa ggtcccttca | 600 |
| gagaagatcc tcagagctgg aaaaatttta cgaaatgcca ttctctctcg agcacctcac | 660 |
| atgataagag atagaaaata ccacctaaag acatacagac aatgctgtgt gggaactgaa | 720 |

```
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc ccctttgcct    900
actgaggagg agaagaagga gtgtgatgag agctccagg acaccatgct gctgctgtca     960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct actcgagaac   1380
gtctatatca aggccgacaa gcagaagaac ggcatcaagg cgaacttcaa gatccgccac   1440
aacatcgagg acggcggcgt gcagctcgcc taccactacc agcagaacac ccccatcggc   1500
gacggccccg tgctgctgcc cgacaaccac tacctgagcg tgcagtccat actttcgaaa   1560
gaccccaacg agaagcgcga tcacatggtc ctgctggagt tcgtgaccgc cgccgggatc   1620
actctcggca tggacgagct gtacaagggc ggtaccggag ggagcatggt gagcaagggc   1680
gaggagctgt tcaccggggt ggtgcccatc caggtcgagc tggacggcga cgtaaacggc   1740
cacaagttca gcgtgtccgg cgagggtgag ggcgatgcca cctacggcaa gctgaccctg   1800
aagttcatct gcaccaccgg caagctgccc gtgccctggc ccaccctcgt gaccaccctg   1860
acctacggcg tgcagtgctt cagccgctac cccgaccaca tgaagcagca cgacttcttc   1920
aagtccgcca tgcccgaagg ctacatccag gagcgcacca tcttcttcaa ggacgacggc   1980
aactacaaga cccgcgccga ggtgaagttc gagggcgaca ccctggtgaa ccgcatcgag   2040
ctgaagggca tcgacttcaa ggaggacggc aacatcctgg ggcacaagct ggagtacaac   2100
acgcgtaggg acgtggaggc gaatacagtc agacttaaag aacatgacca agatgtcttg   2160
gtgctggaga aggtcccagc agggaacaga gcttctaatc aaggaaactc acagcctcag   2220
caaaagtata ctgtgatgtc aggaacacct gaaaaattt tagagcattt tctagaaaca   2280
atacgccttg aggcaacttt aaatgaagca acagattctg ttttaaatga ctttattatg   2340
atgcactgtg ttttatgcc aaatacccag cttttgcccgg cactggtggc ccactaccac   2400
gcacagcctt cacaaggtac agaacaggag aaaatggatt atgccctcaa caataagagg   2460
cgagtcatcc gcctggttct acagtgggct gccatgtatg agacctcct gcaagaggat   2520 gacgtgtcta tggccttcct ggaggagttt tatgtatctg tatcagatga tgcccggatg   2580
attgctgccc tcaaggagca actgccagag ttggagaaga ttgtcaagca aatctcagaa   2640
gatgcaaagg caccacaaaa gaagcacaag gttcttttgc aacagttcaa tacgggcgat   2700
gagagagccc agaagcgcca gcctatccgc ggctctgatg aagttctgtt taaggtctat   2760
tgcatggacc ccacctacac aaccattcgg gtgccagtgg ccacttcggt gaaggaagtc   2820
atcagtgcag ttgccgacaa gctgggctcc ggggagggcc tgatcatagt caagatgagt   2880
tccggaggag aaaaggtggt gctcaaacct aatgatgttt cagtatttat gacgctcacc   2940
attaatggac gcctgtttgc ttgcccgcga gagcaattcg attcactgac tcccttacca   3000
gaacaggaag gcccaactgt tggaacagtg ggaactttg aactgatgag ctccaaagat   3060
```

```
ttagcatacc agatgacaat ttatgattgg gaactcttca actgcgtgca tgagctggag    3120
ctaatctatc acacatttgg aaggcataat tttaaaaaga ccacagcaaa cttggatttg    3180
ttcctgagga gatttaatga aattcagttt tgggtcgtca ctgagatctg cctttgttct    3240
cagctcagca agcgtgttca gctattaaaa aaatttatta agatagcagc ccactgtaag    3300
gagtataaaa atctgaattc cttttttgcc atcgtcatgg gactaagtaa cgttgctgtg    3360
agccgcttgg cactaacgtg ggagaaactg ccaagcaagt tcaagaagtt ctatgcggag    3420
tttgaaagtt taatggaccc ttcaaggaac cacagggcct acaggctgac agtagctaag    3480
ctggaacctc ctctcatccc cttcatgcct ttgctcatta agatatgac atttactcat    3540 gaggggaaca agacgttcat tgacaatcta gtaaactttg aaaaaatgcg catgattgca    3600
aatacggcca aacagtgag atactacagg agccaaccct tcaatcctga tgcagctcaa    3660
gctaataaga accatcagga tgtccggagt tatgtacggc aattaaatgt gattgacaac    3720
cagagaactt tatcacagat gtcacacaga ttagagcctc gtcgacca                3768

<210> SEQ ID NO 71
<211> LENGTH: 3768
<212> TYPE: DNA
<213> ORGANISM: Artificial Sequence
<220> FEATURE:
<223> OTHER INFORMATION: Synthetic

<400> SEQUENCE: 71
atggtcgctg cgcacgctgc ccattcttcc tcctctgccg agtggatcgc ctgcctggat      60
aaaagaccac tggagcgatc cagcgaagat gtggatataa tcttcactcg actgaaagaa     120
gttaaagctt ttgagaaatt tcacccaaat ctccttcatc agatttgctt atgtggttat     180
tatgagaatc tggaaaaggg aataacatta tttcgccagg gtgatattgg aacaaactgg     240
tatgctgtcc tggcagggtc tttggatgtt aaagtatctg agaccagcag tcaccaggat     300
gctgtgacca tctgtaccct gggaattggg acggcctttg gagagtccat tctggacaac     360
acaccccgcc atgcaaccat cgttaccagg agagcagtg aactgctccg catcgagcag     420
aaggacttca aggcactatg ggagaaatat cgacagtata tggcaggact tctggctcct     480
ccttatggtg ttatggaaac gggctctaac aatgacagga ttcctgacaa ggagaacaca     540
cctctcattg aacctcacgt tcctcttcgt cctgctaaca ccattaccaa ggtcccttca     600
gagaagatcc tcagagctgg aaaaatttta cgaaatgcca ttctctctcg agcacctcac     660
atgataagag ataaaaata ccacctaaag acatacagac aatgctgtgt gggaactgaa     720
ctggtggact ggatgatgca gcagacacca tgtgttcact cccggactca agctgttggc     780
atgtggcaag tcctgttaga agatggtgtt ctcaaccacg tggaccagga gcaccatttc     840
caagacaaat atttattcta tcgatttctg gatgatgagc acgaggatgc ccctttgcct     900
actgaggagg agaagaagga gtgtgatgag gagctccagg acaccatgct gctgctgtca     960
cagatgggcc ccgacgccca catgaggatg atccttcgca aaccacctgg ccagaggact    1020
gtgctcgaga acgtctatat caaggccgac aagcagaaga acggcatcaa ggcgaacttc    1080
aagatccgcc acaacatcga ggacggcggc gtgcagctcg cctaccacta ccagcagaac    1140
acccccatcg gcgacggccc cgtgctgctg cccgacaacc actacctgag cgtgcagtcc    1200
atactttcga aagaccccaa cgagaagcgc gatcacatgg tcctgctgga gttcgtgacc    1260
gccgccggga tcactctcgg catggacgag ctgtacaagg cggtaccgg agggagcatg    1320 gtgagcaagg gcgaggagct gttcaccggg gtggtgccca tccaggtcga gctggacggc    1380
```

```
gacgtaaacg gccacaagtt cagcgtgtcc ggcgagggtg agggcgatgc cacctacggc   1440
aagctgaccc tgaagttcat ctgcaccacc ggcaagctgc ccgtgccctg cccacccctc   1500
gtgaccaccc tgacctacgg cgtgcagtgc ttcagccgct accccgacca catgaagcag   1560
cacgacttct tcaagtccgc catgcccgaa ggctacatcc aggagcgcac catcttcttc   1620
aaggacgacg gcaactacaa gacccgcgcc gaggtgaagt tcgagggcga caccctggtg   1680
aaccgcatcg agctgaaggg catcgacttc aaggaggacg gcaacatcct ggggcacaag   1740
ctggagtaca acacgcgtga tgacctagag attatctatg aggagcttct tcatattaaa   1800
gccttatccc atcttctac cacagtgaaa cgagagttag caggtgttct cattttgag    1860 tctcacgcca aggagggac tgtgttgttt aaccaggggg aagaaggtac ctcctggtac    1920
attattctaa aaggatcagt gaatgtagtc atttacggca agggtgtggt ctgcaccctg   1980
catgaaggag atgacttcgg caagttagca ctagtgaatg atgccccacg agctgcctct   2040
atcgtcttac gagaagataa ctgccatttc ttaagagtag acaaggagga tttcaaccgg   2100
atcctaaggg acgtggaggc gaatacagtc agacttaaag aacatgacca agatgtcttg   2160
gtgctggaga aggtcccagc agggaacaga gcttctaatc aaggaaactc acagcctcag   2220
caaaagtata ctgtgatgtc aggaacacct gaaaaattt tagagcattt tctagaaaca    2280
atacgccttg aggcaacttt aaatgaagca acagattctg ttttaaatga ctttattatg   2340
atgcactgtg tttttatgcc aaatacccag cttttgcccgg cactggtggc ccactaccac   2400
gcacagcctt cacaaggtac agaacaggag aaaatggatt atgccctcaa caataagagg   2460
cgagtcatcc gcctggttct acagtgggct gccatgtatg gagacctcct gcaagaggat   2520
gacgtgtcta tggccttcct ggaggagttt tatgtatctg tatcagatga tgcccggatg   2580
attgctgccc tcaaggagca actgccagag ttggagaaga ttgtcaagca atctcagaa    2640 gatgcaaagg caccacaaaa gaagcacaag gttctttttgc aacagttcaa tacgggcgat   2700
gagagagccc agaagcgcca gcctatccgc ggctctgatg aagttctgtt taaggtctat   2760
tgcatggacc ccacctacac aaccattcgg gtgccagtgg ccacttcggt gaaggaagtc   2820
atcagtgcag ttgccgacaa gctgggctcc ggggagggcc tgatcatagt caagatgagt   2880
tccggaggag aaaaggtggt gctcaaacct aatgatgttt cagtatttat gacgctcacc   2940
attaatggac gcctgtttgc ttgcccgcga gagcaattcg attcactgac tcccttacca   3000
gaacaggaag gcccaactgt tggaacagtg ggaacttttg aactgatgag ctccaaagat   3060
ttagcatacc agatgacaat ttatgattgg gaactcttca actgcgtgca tgagctggag   3120
ctaatctatc acacatttgg aaggcataat tttaaaaaga ccacagcaaa cttggatttg   3180
ttcctgagga gatttaatga aattcagttt tgggtcgtca ctgagatctg cctttgttct   3240
cagctcagca agcgtgttca gctattaaaa aaatttatta agatagcagc ccactgtaag   3300
gagtataaaa atctgaattc cttttttgcc atcgtcatgg gactaagtaa cgttgctgtg   3360
agccgcttgg cactaacgtg ggagaaactg ccaagcaagt tcaagaagtt ctatgcggag   3420
tttgaaagtt taatggaccc ttcaaggaac cacagggcct acaggctgac agtagctaag   3480
ctggaacctc ctctcatccc cttcatgcct ttgctcatta agatatgac atttactcat    3540 gaggggaaca agacgttcat tgacaatcta gtaaactttg aaaaaatgcg catgattgca   3600
aatacggcca gaacagtgag atactacagg agccaaccct tcaatcctga tgcagctcaa   3660
gctaataaga accatcagga tgtccggagt tatgtacggc aattaaatgt gattgacaac   3720
```
cagagaactt tatcacagat gtcacacaga ttagagcctc gtcgacca      3768

<210> SEQ ID NO 72
<211> LENGTH: 3768
<212> TYPE: DNA
<213> ORGANISM: Artificial Sequence
<220> FEATURE:
<223> OTHER INFORMATION: Synthetic

<400> SEQUENCE: 72

| | |
|---|---|
| atggtcgctg cgcacgctgc ccattcttcc tcctctgccg agtggatcgc ctgcctggat | 60 |
| aaaagaccac tggagcgatc cagcgaagat gtggatataa tcttcactcg actgaaagaa | 120 |
| gttaaagctt ttgagaaatt tcacccaaat ctccttcatc agatttgctt atgtggttat | 180 |
| tatgagaatc tggaaaaggg aataacatta tttcgccagg gtgatattgg aacaaactgg | 240 |
| tatgctgtcc tggcagggtc tttggatgtt aaagtatctg agaccagcag tcaccaggat | 300 |
| gctgtgacca tctgtaccct gggaattggg acggcctttg agagtccat tctggacaac | 360 |
| acacccgcc atgcaaccat cgttaccagg agagcagtg aactgctccg catcgagcag | 420 |
| aaggacttca aggcactatg ggagaaatat cgacagtata tggcaggact tctggctcct | 480 |
| ccttatggtg ttatggaaac gggctctaac aatgacagga ttcctgacaa ggagaacaca | 540 |
| cctctcattg aacctcacgt tcctcttcgt cctgctaaca ccattaccaa ggtcccttca | 600 |
| gagaagatcc tcagagctgg aaaaatttta cgaaatgcca ttctctctcg agcacctcac | 660 |
| atgataagag atagaaaata ccacctaaag acatacagac aatgctgtgt gggaactgaa | 720 |
| ctggtggact ggatgatgca gcagacacca tgtgttcact cccggactca agctgttggc | 780 |
| atgtggcaag tcctgttaga gatggtgtt ctcaaccacg tggaccagga gcaccatttc | 840 |
| caagacaaat atttattcta tcgatttctg gatgatgagc acgaggatgc ccctttgcct | 900 |
| actgaggagg agaagaagga gtgtgatgag gagctccagg acaccatgct gctgctgtca | 960 |
| cagatgggcc ccgacgccca catgaggatg atccttcgca aaccacctgg ccagaggact | 1020 |
| gtggatgacc tagagattat ctatgaggag cttcttcata ttaaagcctt atcccatctt | 1080 |
| tctaccacag tgaaacgaga gttagcaggt gttctcattt ttgagtctca cgccaaagga | 1140 |
| gggactgtgt tgtttaacca gggggaagaa ggtacctcct ggtacattat tctaaaagga | 1200 |
| tcagtgaatg tagtcatttta cggcaagggt gtggtctgca ccctgcatga aggagatgac | 1260 |
| ttcggcaagt tagcactagt gaatgatgcc ccacgagctg cctctatcgt cttacgagaa | 1320 |
| gataactgcc atttcttaag agtagacaag gaggatttca accggatcct aagggacgtg | 1380 |
| gaggcgaata cagtcagact taagaacat gaccaagatg tcttggtgct ggagaaggtc | 1440 |
| ccagcaggga acagagctct cgagaacgtc tatatcaagg ccgacaagca gaagaacggc | 1500 |
| atcaaggcga acttcaagat ccgccacaac atcgaggacg gcggcgtgca gctcgcctac | 1560 |
| cactaccagc agaacacccc catcggcgac ggccccgtgc tgctgcccga caaccactac | 1620 |
| ctgagcgtgc agtccatact ttcgaaagac cccaacgaga agcgcgatca catggtcctg | 1680 |
| ctggagttcg tgaccgccgc cgggatcact ctcggcatgg acgagctgta caagggcggt | 1740 |
| accgagggga gcatggtgag caagggcgag gagctgttca ccggggtggt gcccatccag | 1800 |
| gtcgagctgg acggcgacgt aaacggccac aagttcagcg tgtccggcga gggtgagggc | 1860 |
| gatgccacct acggcaagct gaccctgaag ttcatctgca ccaccggcaa gctgcccgtg | 1920 |
| ccctggccca cctcgtgac cacccctgacc tacggcgtgc agtgcttcag ccgctacccc | 1980 |
| gaccacatga agcagcacga cttcttcaag tccgccatgc ccgaaggcta catccaggag | 2040 |

```
cgcaccatct tcttcaagga cgacggcaac tacaagaccc gcgccgaggt gaagttcgag    2100
ggcgacaccc tggtgaaccg catcgagctg aagggcatcg acttcaagga ggacggcaac    2160
atcctggggc acaagctgga gtacaacacg cgttctaatc aaggaaactc acagcctcag    2220
caaaagtata ctgtgatgtc aggaacacct gaaaaaattt tagagcattt tctagaaaca    2280
atacgccttg aggcaacttt aaatgaagca acagattctg ttttaaatga ctttattatg    2340
atgcactgtg tttttatgcc aaatacccag ctttgcccgg cactggtggc ccactaccac    2400
gcacagcctt cacaaggtac agaacaggag aaaatggatt atgccctcaa caataagagg    2460
cgagtcatcc gcctggttct acagtgggct gccatgtatg agacctcct gcaagaggat     2520 gacgtgtcta tggccttcct ggaggagttt atgtatctg tatcagatga tgcccggatg     2580
attgctgccc tcaaggagca actgccagag ttggagaaga ttgtcaagca aatctcagaa    2640
gatgcaaagg caccacaaaa gaagcacaag gttcttttgc aacagttcaa tacgggcgat    2700
gagagagccc agaagcgcca gcctatccgc ggctctgatg aagttctgtt taaggtctat    2760
tgcatggacc ccacctacac aaccattcgg gtgccagtgg ccacttcggt gaaggaagtc    2820
atcagtgcag ttgccgacaa gctgggctcc ggggagggcc tgatcatagt caagatgagt    2880
tccggaggag aaaaggtggt gctcaaacct aatgatgttt cagtatttat gacgctcacc    2940
attaatggac gcctgtttgc ttgcccgcga gagcaattcg attcactgac tcccttacca    3000
gaacaggaag gcccaactgt tggaacagtg ggaacttttg aactgatgag ctccaaagat    3060
ttagcatacc agatgacaat ttatgattgg gaactcttca actgcgtgca tgagctggag    3120
ctaatctatc acacatttgg aaggcataat tttaaaaaga ccacagcaaa cttggatttg    3180
ttcctgagga gatttaatga aattcagttt tgggtcgtca ctgagatctg cctttgttct    3240
cagctcagca agcgtgttca gctattaaaa aaatttatta agatagcagc ccactgtaag    3300
gagtataaaa atctgaattc ctttttttgcc atcgtcatgg gactaagtaa cgttgctgtg    3360
agccgcttgg cactaacgtg ggagaaactg ccaagcaagt tcaagaagtt ctatgcggag    3420
tttgaaagtt taatggaccc ttcaaggaac cacagggcct acaggctgac agtagctaag    3480
ctggaacctc ctctcatccc cttcatgcct tgctcatta aagatatgac atttactcat     3540
gaggggaaca agacgttcat tgacaatcta gtaaactttg aaaaaatgcg catgattgca    3600
aatacggcca gaacagtgag atactacagg agccaaccct tcaatcctga tgcagctcaa    3660
gctaataaga accatcagga tgtccggagt tatgtacggc aattaaatgt gattgacaac    3720
cagagaactt tatcacagat gtcacacaga ttagagcctc gtcgacca                 3768
```

<210> SEQ ID NO 73
<211> LENGTH: 3768
<212> TYPE: DNA
<213> ORGANISM: Artificial Sequence
<220> FEATURE:
<223> OTHER INFORMATION: Synthetic

<400> SEQUENCE: 73

```
atggtcgctg cgcacgctgc ccattcttcc tcctctgccg agtggatcgc ctgcctggat      60
aaaagaccac tggagcgatc cagcgaagat gtggatataa tcttcactcg actgaaagaa     120
gttaaagctt ttgagaaatt tcacccaaat ctccttcatc agatttgctt atgtggttat     180
tatgagaatc tggaaaaggg aataacatta tttcgccagg gtgatattgg aacaaactgg    240
tatgctgtcc tggcagggtc tttggatgtt aaagtatctg agaccagcag tcaccaggat    300
```

```
gctgtgacca tctgtaccct gggaattggg acggcctttg gagagtccat tctggacaac    360 acacccgcc atgcaaccat cgttaccagg gagagcagtg aactgctccg catcgagcag    420
aaggacttca aggcactatg ggagaaatat cgacagtata tggcaggact tctggctcct    480
ccttatggtg ttatggaaac gggctctaac aatgacagga ttcctgacaa ggagaacaca    540
cctctcattg aacctcacgt tcctcttcgt cctgctaaca ccattaccaa ggtcccttca    600
gagaagatcc tcagagctgg aaaaatttta cgaaatgcca ttctctctcg agcacctcac    660
atgataagag atagaaaata ccacctaaag acatacagac aatgctgtgt gggaactgaa    720
ctggtggact ggatgatgca gcagacacca tgtgttcact cccggactca agctgttggc    780
atgtggcaag tcctgttaga agatggtgtt ctcaaccacg tggaccagga gcaccatttc    840
caagacaaat atttattcta tcgatttctg gatgatgagc acgaggatgc ccctttgcct    900
actgaggagg agaagaagga gtgtgatgag gagctccagg acaccatgct gctgctgtca    960
cagatgggcc ccgacgccca catgaggatg atccttcgca aaccacctgg ccagaggact   1020
gtggatgacc tagagattat ctatgaggag cttcttcata ttaaagcctt atcccatctt   1080
tctaccacag tgaaacgaga gttagcaggt gttctcattt ttgagtctca cgccaaagga   1140
gggactgtgt tgtttaacca gggggaagaa ggtacctcct ggtacattat tctaaaagga   1200
tcagtgaatg tagtcattta cggcaagggt gtggtctgca ccctgcatga aggagatgac   1260
ttcggcaagt tagcactagt gaatgatgcc ccacgagctg cctctatcgt cttacgagaa   1320
gataactgcc atttcttaag agtagacaag gaggatttca accggatcct aagggacgtg   1380
gaggcgaata cagtcagact taagaacat gaccaagatg tcttggtgct ggagaaggtc   1440
ccagcaggga acagagcttc taatcaagga aactcacagc ctcagcaaaa gtatactgtg   1500
atgtcaggaa cacctgaaaa aatttttagag cattttctag aaacaatacg ccttgaggca   1560
ctcgagaacg tctatatcaa ggccgacaag cagaagaacg gcatcaaggc gaacttcaag   1620
atccgccaca catcgagga cggcggcgtg cagctcgcct accactacca gcagaacacc   1680
cccatcggcg acggccccgt gctgctgccc gacaaccact acctgagcgt gcagtccata   1740 cttttcgaaag accccaacga gaagcgcgat cacatggtcc tgctggagtt cgtgaccgcc   1800
gccgggatca ctctcggcat ggacgagctg tacaagggcg gtaccggagg gagcatggtg   1860
agcaagggcg aggagctgtt caccggggtg gtgcccatcc aggtcgagct ggacggcgac   1920
gtaaacggcc acaagttcag cgtgtccggc gagggtgagg gcgatgccac ctacggcaag   1980
ctgaccctga gttcatctg caccaccggc aagctgcccg tgccctggcc cacccctgtg   2040
accaccctga cctacggcgt gcagtgcttc agccgctacc ccgaccacat gaagcagcac   2100
gacttcttca gtccgccat gcccgaaggc tacatccagg agcgcaccat cttcttcaag   2160
gacgacggca actacaagac ccgcgccgag gtgaagttcg agggcgacac cctggtgaac   2220
cgcatcgagc tgaagggcat cgacttcaag gaggacggca acatcctggg cacaagctg   2280 gagtacaaca cgcgtacttt aaatgaagca acagattctg ttttaaatga ctttattatg   2340
atgcactgtg ttttatgcc aaataccag cttttgcccgg cactggtggc ccactaccac   2400
gcacagcctt cacaaggtac agaacaggag aaaatggatt atgccctcaa caataagagg   2460
cgagtcatcc gcctggttct acagtgggct gccatgtatg agacctcct gcaagaggat   2520 gacgtgtcta tggccttcct ggaggagttt tatgtatctg tatcagatga tgcccggatg   2580
attgctgccc tcaaggagca actgccagag ttggagaaga ttgtcaagca aatctcagaa   2640
gatgcaaagg caccacaaaa gaagcacaag gttcttttgc aacagttcaa tacgggcgat   2700
```

-continued

```
gagagagccc agaagcgcca gcctatccgc ggctctgatg aagttctgtt taaggtctat    2760
tgcatggacc ccacctacac aaccattcgg gtgccagtgg ccacttcggt gaaggaagtc    2820
atcagtgcag ttgccgacaa gctgggctcc ggggagggcc tgatcatagt caagatgagt    2880
tccggaggag aaaaggtggt gctcaaacct aatgatgttt cagtatttat gacgctcacc    2940
attaatggac gcctgtttgc ttgcccgcga gagcaattcg attcactgac tcccttacca    3000
gaacaggaag gcccaactgt tggaacagtg ggaacttttg aactgatgag ctccaaagat    3060
ttagcatacc agatgacaat ttatgattgg gaactcttca actgcgtgca tgagctggag    3120
ctaatctatc acacatttgg aaggcataat tttaaaaaga ccacagcaaa cttggatttg    3180
ttcctgagga gatttaatga aattcagttt tgggtcgtca ctgagatctg cctttgttct    3240
cagctcagca agcgtgttca gctattaaaa aaatttatta agatagcagc ccactgtaag    3300
gagtataaaa atctgaattc cttttttgcc atcgtcatgg gactaagtaa cgttgctgtg    3360
agccgcttgg cactaacgtg ggagaaactg ccaagcaagt tcaagaagtt ctatgcggag    3420
tttgaaagtt taatggaccc ttcaaggaac cacagggcct acaggctgac agtagctaag    3480
ctggaacctc ctctcatccc cttcatgcct ttgctcatta agatatgac atttactcat    3540 gagggggaaca agacgttcat tgacaatcta gtaaactttg aaaaaatgcg catgattgca    3600
aatacggcca aacagtgag atactacagg agccaaccct tcaatcctga tgcagctcaa    3660
gctaataaga accatcagga tgtccggagt tatgtacggc aattaaatgt gattgacaac    3720
cagagaactt tatcacagat gtcacacaga ttagagcctc gtcgacca    3768
```

<210> SEQ ID NO 74
<211> LENGTH: 881
<212> TYPE: PRT
<213> ORGANISM: Homo sapiens

<400> SEQUENCE: 74

```
Met Val Leu Arg Arg Met His Arg Pro Arg Ser Cys Ser Tyr Gln Leu
1               5                   10                  15

Leu Leu Glu His Gln Arg Pro Ser Cys Ile Gln Gly Leu Arg Trp Thr
            20                  25                  30

Pro Leu Thr Asn Ser Glu Glu Ser Leu Asp Phe Ser Glu Ser Leu Glu
        35                  40                  45

Gln Ala Ser Thr Glu Arg Val Leu Arg Ala Gly Arg Gln Leu His Arg
    50                  55                  60

His Leu Leu Ala Thr Cys Pro Asn Leu Ile Arg Asp Arg Lys Tyr His
65                  70                  75                  80

Leu Arg Leu Tyr Arg Gln Cys Cys Ser Gly Arg Glu Leu Val Asp Gly
                85                  90                  95

Ile Leu Ala Leu Gly Leu Gly Val His Ser Arg Ser Gln Val Val Gly
            100                 105                 110

Ile Cys Gln Val Leu Leu Asp Glu Gly Ala Leu Cys His Val Lys His
        115                 120                 125

Asp Trp Ala Phe Gln Asp Arg Asp Ala Gln Phe Tyr Arg Phe Pro Gly
    130                 135                 140

Pro Glu Pro Glu Pro Val Gly Thr His Glu Met Glu Glu Leu Ala
145                 150                 155                 160

Glu Ala Val Ala Leu Leu Ser Gln Arg Gly Pro Asp Ala Leu Leu Thr
                165                 170                 175

Val Ala Leu Arg Lys Pro Pro Gly Gln Arg Thr Asp Glu Glu Leu Asp
```

```
            180                 185                 190
Leu Ile Phe Glu Glu Leu Leu His Ile Lys Ala Val Ala His Leu Ser
        195                 200                 205
Asn Ser Val Lys Arg Glu Leu Ala Ala Val Leu Leu Phe Glu Pro His
        210                 215                 220
Ser Lys Ala Gly Thr Val Leu Phe Ser Gln Asp Lys Gly Thr Ser
225                 230                 235                 240
Trp Tyr Ile Ile Trp Lys Gly Ser Val Asn Val Val Thr His Gly Lys
                245                 250                 255
Gly Leu Val Thr Thr Leu His Glu Gly Asp Asp Phe Gly Gln Leu Ala
            260                 265                 270
Leu Val Asn Asp Ala Pro Arg Ala Ala Thr Ile Ile Leu Arg Glu Asp
        275                 280                 285
Asn Cys His Phe Leu Arg Val Asp Lys Gln Asp Phe Asn Arg Ile Ile
        290                 295                 300
Lys Asp Val Glu Ala Lys Thr Met Arg Leu Glu Glu His Gly Lys Val
305                 310                 315                 320
Val Leu Val Leu Glu Arg Ala Ser Gln Gly Ala Gly Pro Ser Arg Pro
                325                 330                 335
Pro Thr Pro Gly Arg Asn Arg Tyr Thr Val Met Ser Gly Thr Pro Glu
            340                 345                 350
Lys Ile Leu Glu Leu Leu Leu Glu Ala Met Gly Pro Asp Ser Ser Ala
        355                 360                 365
His Asp Pro Thr Glu Thr Phe Leu Ser Asp Phe Leu Leu Thr His Arg
        370                 375                 380
Val Phe Met Pro Ser Ala Gln Leu Cys Ala Ala Leu Leu His His Phe
385                 390                 395                 400
His Val Glu Pro Ala Gly Gly Ser Glu Gln Arg Ser Thr Tyr Val
                405                 410                 415
Cys Asn Lys Arg Gln Gln Ile Leu Arg Leu Val Ser Gln Trp Val Ala
            420                 425                 430
Leu Tyr Gly Ser Met Leu His Thr Asp Pro Val Ala Thr Ser Phe Leu
        435                 440                 445
Gln Lys Leu Ser Asp Leu Val Gly Arg Asp Thr Arg Leu Ser Asn Leu
        450                 455                 460
Leu Arg Glu Gln Trp Pro Glu Arg Arg Cys His Arg Leu Glu Asn
465                 470                 475                 480
Gly Cys Gly Asn Ala Ser Pro Gln Met Lys Ala Arg Asn Leu Pro Val
                485                 490                 495
Trp Leu Pro Asn Gln Asp Glu Pro Leu Pro Gly Ser Ser Cys Ala Ile
            500                 505                 510
Gln Val Gly Asp Lys Val Pro Tyr Asp Ile Cys Arg Pro Asp His Ser
        515                 520                 525
Val Leu Thr Leu Gln Leu Pro Val Thr Ala Ser Val Arg Glu Val Met
        530                 535                 540
Ala Ala Leu Ala Gln Glu Asp Gly Trp Thr Lys Gly Gln Val Leu Val
545                 550                 555                 560
Lys Val Asn Ser Ala Gly Asp Ala Ile Gly Leu Gln Pro Asp Ala Arg
                565                 570                 575
Gly Val Ala Thr Ser Leu Gly Leu Asn Glu Arg Leu Phe Val Val Asn
            580                 585                 590
Pro Gln Glu Val His Glu Leu Ile Pro His Pro Asp Gln Leu Gly Pro
        595                 600                 605
```

```
Thr Val Gly Ser Ala Glu Gly Leu Asp Leu Val Ser Ala Lys Asp Leu
    610                 615                 620

Ala Gly Gln Leu Thr Asp His Asp Trp Ser Leu Phe Asn Ser Ile His
625                 630                 635                 640

Gln Val Glu Leu Ile His Tyr Val Leu Gly Pro Gln His Leu Arg Asp
                645                 650                 655

Val Thr Thr Ala Asn Leu Glu Arg Phe Met Arg Arg Phe Asn Glu Leu
            660                 665                 670

Gln Tyr Trp Val Ala Thr Glu Leu Cys Leu Cys Pro Val Pro Gly Pro
        675                 680                 685

Arg Ala Gln Leu Leu Arg Lys Phe Ile Lys Leu Ala Ala His Leu Lys
    690                 695                 700

Glu Gln Lys Asn Leu Asn Ser Phe Phe Ala Val Met Phe Gly Leu Ser
705                 710                 715                 720

Asn Ser Ala Ile Ser Arg Leu Ala His Thr Trp Glu Arg Leu Pro His
                725                 730                 735

Lys Val Arg Lys Leu Tyr Ser Ala Glu Arg Leu Leu Asp Pro Ser
            740                 745                 750

Trp Asn His Arg Val Tyr Arg Leu Ala Leu Ala Lys Leu Ser Pro Pro
        755                 760                 765

Val Ile Pro Phe Met Pro Leu Leu Leu Lys Asp Met Thr Phe Ile His
    770                 775                 780

Glu Gly Asn His Thr Leu Val Glu Asn Leu Ile Asn Phe Glu Lys Met
785                 790                 795                 800

Arg Met Met Ala Arg Ala Ala Arg Met Leu His His Cys Arg Ser His
                805                 810                 815

Asn Pro Val Pro Leu Ser Pro Leu Arg Ser Arg Val Ser His Leu His
            820                 825                 830

Glu Asp Ser Gln Val Ala Arg Ile Ser Thr Cys Ser Glu Gln Ser Leu
        835                 840                 845

Ser Thr Arg Ser Pro Ala Ser Thr Trp Ala Tyr Val Gln Gln Leu Lys
    850                 855                 860

Val Ile Asp Asn Gln Arg Glu Leu Ser Arg Leu Ser Arg Glu Leu Glu
865                 870                 875                 880

Pro

<210> SEQ ID NO 75
<211> LENGTH: 381
<212> TYPE: PRT
<213> ORGANISM: Homo sapiens

<400> SEQUENCE: 75

Met Glu Ser Gly Ser Thr Ala Ala Ser Glu Glu Ala Arg Ser Leu Arg
1               5                   10                  15

Glu Cys Glu Leu Tyr Val Gln Lys His Asn Ile Gln Ala Leu Leu Lys
                20                  25                  30

Asp Ser Ile Val Gln Leu Cys Thr Ala Arg Pro Glu Arg Pro Met Ala
            35                  40                  45

Phe Leu Arg Glu Tyr Phe Glu Arg Leu Glu Lys Glu Glu Ala Lys Gln
        50                  55                  60

Ile Gln Asn Leu Gln Lys Ala Gly Thr Arg Thr Asp Ser Arg Glu Asp
65                  70                  75                  80

Glu Ile Ser Pro Pro Pro Pro Asn Pro Val Val Lys Gly Arg Arg Arg
                85                  90                  95
```

```
Arg Gly Ala Ile Ser Ala Glu Val Tyr Thr Glu Asp Ala Ala Ser
                100                 105                 110

Tyr Val Arg Lys Val Ile Pro Lys Asp Tyr Lys Thr Met Ala Ala Leu
            115                 120                 125

Ala Lys Ala Ile Glu Lys Asn Val Leu Phe Ser His Leu Asp Asp Asn
        130                 135                 140

Glu Arg Ser Asp Ile Phe Asp Ala Met Phe Ser Val Ser Phe Ile Ala
145                 150                 155                 160

Gly Glu Thr Val Ile Gln Gln Gly Asp Glu Gly Asp Asn Phe Tyr Val
                165                 170                 175

Ile Asp Gln Gly Glu Thr Asp Val Tyr Val Asn Asn Glu Trp Ala Thr
            180                 185                 190

Ser Val Gly Glu Gly Gly Ser Phe Gly Glu Leu Ala Leu Ile Tyr Gly
        195                 200                 205

Thr Pro Arg Ala Ala Thr Val Lys Ala Lys Thr Asn Val Lys Leu Trp
210                 215                 220

Gly Ile Asp Arg Asp Ser Tyr Arg Arg Ile Leu Met Gly Ser Thr Leu
225                 230                 235                 240

Arg Lys Arg Lys Met Tyr Glu Glu Phe Leu Ser Lys Val Ser Ile Leu
                245                 250                 255

Glu Ser Leu Asp Lys Trp Glu Arg Leu Thr Val Ala Asp Ala Leu Glu
            260                 265                 270

Pro Val Gln Phe Glu Asp Gly Gln Lys Ile Val Val Gln Gly Glu Pro
        275                 280                 285

Gly Asp Glu Phe Phe Ile Ile Leu Glu Gly Ser Ala Ala Val Leu Gln
290                 295                 300

Arg Arg Ser Glu Asn Glu Glu Phe Val Glu Val Gly Arg Leu Gly Pro
305                 310                 315                 320

Ser Asp Tyr Phe Gly Glu Ile Ala Leu Leu Met Asn Arg Pro Arg Ala
                325                 330                 335

Ala Thr Val Val Ala Arg Gly Pro Leu Lys Cys Val Lys Leu Asp Arg
            340                 345                 350

Pro Arg Phe Glu Arg Val Leu Gly Pro Cys Ser Asp Ile Leu Lys Arg
        355                 360                 365

Asn Ile Gln Gln Tyr Asn Ser Phe Val Ser Leu Ser Val
370                 375                 380

<210> SEQ ID NO 76
<211> LENGTH: 184
<212> TYPE: PRT
<213> ORGANISM: Homo sapiens

<400> SEQUENCE: 76

Met Arg Glu Tyr Lys Leu Val Phe Leu Gly Ser Gly Val Gly Lys
1               5                   10                  15

Ser Ala Leu Thr Val Gln Phe Val Gln Gly Ile Phe Val Glu Lys Tyr
            20                  25                  30

Asp Pro Thr Ile Glu Asp Ser Tyr Arg Lys Gln Val Glu Val Asp Ala
        35                  40                  45

Gln Gln Cys Met Leu Glu Ile Leu Asp Thr Ala Gly Thr Glu Gln Phe
    50                  55                  60

Thr Ala Met Arg Asp Leu Tyr Met Lys Asn Gly Gln Gly Phe Ala Leu
65                  70                  75                  80

Val Tyr Ser Ile Thr Ala Gln Ser Thr Phe Asn Asp Leu Gln Asp Leu
                85                  90                  95
```

```
Arg Glu Gln Ile Leu Arg Val Lys Asp Thr Asp Val Pro Met Ile
            100                 105                 110

Leu Val Gly Asn Lys Cys Asp Leu Glu Asp Glu Arg Val Val Gly Lys
            115                 120                 125

Glu Gln Gly Gln Asn Leu Ala Arg Gln Trp Asn Asn Cys Ala Phe Leu
    130                 135                 140

Glu Ser Ser Ala Lys Ser Lys Ile Asn Val Asn Glu Ile Phe Tyr Asp
145                 150                 155                 160

Leu Val Arg Gln Ile Asn Arg Lys Thr Pro Val Pro Gly Lys Ala Arg
                165                 170                 175

Lys Lys Ser Ser Cys Gln Leu Leu
            180
```

<210> SEQ ID NO 77
<211> LENGTH: 239
<212> TYPE: PRT
<213> ORGANISM: Artificial Sequence
<220> FEATURE:
<223> OTHER INFORMATION: Synthetic

<400> SEQUENCE: 77

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```